US006878705B2

(12) United States Patent
Cudahy et al.

(10) Patent No.: US 6,878,705 B2
(45) Date of Patent: Apr. 12, 2005

(54) 4-OXO-4,7-DIHYDROFURO[2,3-B]PYRIDINE-5-CARBOXAMIDE ANTIVIRAL AGENTS

(75) Inventors: Michele M. Cudahy, Plainwell, MI (US); Mark E. Schnute, Kalamazoo, MI (US); Steven P. Tanis, Kalamazoo, MI (US); William R. Perrault, Kalamazoo, MI (US); Paul Matthew Herrinton, Portage, MI (US); Sajiv K. Nair, Portage, MI (US)

(73) Assignee: Pfizer, Bridgewater, NJ (US)

( * ) Notice: Subject to any disclaimer, the term of this patent is extended or adjusted under 35 U.S.C. 154(b) by 0 days.

(21) Appl. No.: 10/345,062

(22) Filed: Jan. 14, 2003

(65) Prior Publication Data

US 2004/0259907 A1 Dec. 23, 2004

Related U.S. Application Data

(60) Provisional application No. 60/348,718, filed on Jan. 14, 2002.

(51) Int. Cl.[7] ............... A61K 31/4355; A61K 31/5377; A61K 31/497; C07D 491/048; A61P 31/22
(52) U.S. Cl. .................... 514/233.8; 514/302; 514/266; 514/258; 514/256; 514/255.05; 544/277; 544/284; 544/127; 544/335; 544/405; 546/116
(58) Field of Search ......................... 546/116; 544/277, 544/284, 127, 335, 405; 514/302, 266, 258, 233.8, 256, 255.05

(56) References Cited

U.S. PATENT DOCUMENTS

| | | | | |
|---|---|---|---|---|
| 4,125,611 | A | 11/1978 | Yamade et al. | 424/246 |
| 4,145,418 | A | 3/1979 | Kuwada et al. | 424/246 |
| 4,767,766 | A | 8/1988 | Baker et al. | 514/301 |
| 4,877,793 | A | 10/1989 | Davies | 514/301 |
| 4,959,363 | A | 9/1990 | Wentland | 514/235.2 |
| 5,155,115 | A | 10/1992 | Suzuki et al. | 514/301 |
| 5,219,864 | A | 6/1993 | Suzuki et al. | 514/301 |
| 5,352,685 | A | 10/1994 | Maruyama et al. | 514/301 |
| 5,593,943 | A | 1/1997 | Nuebling et al. | 504/221 |
| 5,817,819 | A | 10/1998 | Furuya et al. | 546/114 |
| 6,239,142 | B1 | 5/2001 | Schnute et al. | 514/301 |
| 6,620,810 | B2 | 9/2003 | Thorarensen | 514/233.8 |

FOREIGN PATENT DOCUMENTS

| | | | | |
|---|---|---|---|---|
| DE | 4227747 | 2/1994 | ......... | C07D/487/04 |
| EP | 0046990 | 3/1982 | ......... | C07D/495/04 |
| EP | 0269295 | 6/1988 | ......... | C07D/495/04 |
| EP | 0443568 | 8/1991 | ......... | C07D/495/04 |
| EP | 505058 | 9/1992 | ......... | C07D/495/04 |
| EP | 0560348 | 9/1993 | ......... | C07D/519/00 |
| GB | 1062840 | 3/1967 | .......... | C07D/27/56 |
| GB | 2289276 | 11/1995 | ....... | C07D/491/048 |
| JP | 46-032198 | 9/1970 | | |
| JP | 57116077 | 7/1982 | ......... | C07D/495/04 |
| JP | 57142985 | 9/1982 | ......... | C07D/495/04 |
| JP | 07076586 | 3/1995 | ....... | C07D/491/048 |
| JP | 8143573 | 6/1996 | ......... | C07D/519/00 |
| JP | 08301849 | 11/1996 | ......... | C07D/217/26 |
| JP | 9208496 | 8/1997 | .......... | A61K/47/40 |
| WO | WO-92/03427 | 3/1992 | ......... | C07D/307/82 |
| WO | WO-95/28405 | 10/1995 | ......... | C07D/495/04 |
| WO | WO-96/18616 | 6/1996 | ......... | C07D/213/75 |
| WO | WO-96/18617 | 6/1996 | ......... | C07D/213/75 |
| WO | WO-97/40846 | 11/1997 | .......... | A61K/38/09 |
| WO | WO-98/11073 | 3/1998 | ......... | C07D/215/48 |
| WO | WO-99/32450 | 7/1999 | ......... | C07D/215/56 |
| WO | WO-99/62908 | 12/1999 | ......... | C07D/495/04 |
| WO | WO-00/07595 | 2/2000 | .......... | A61K/31/47 |
| WO | WO-00/40561 | 7/2000 | ......... | C07D/215/16 |
| WO | WO-00/40563 | 7/2000 | ......... | C07D/215/56 |
| WO | WO-00/53610 | 9/2000 | ......... | C07D/513/04 |
| WO | WO-00/76990 | 12/2000 | ......... | C07D/307/78 |
| WO | WO-01/37824 | 5/2001 | ......... | A61K/31/315 |
| WO | WO-01/58898 | 8/2001 | ......... | C07D/453/02 |
| WO | WO-03/020729 | 3/2003 | ......... | C07D/495/04 |

OTHER PUBLICATIONS

The Merck Manual. Eleventh Edition (1966), pp. 212–213.*

Blaskiewicz, P., et al., "Thienopyridinonecarboxylic Acid Derivatives", *Chemical Abstracts*, Abstract of German Patent No. 2,447,477, Abstract No. 85:46627 (1976), 1 p.

El–Abadelah, Mustafa M., et al., "Synthesis and Chiroptical Properties of Some N–(2–Chloro–7–cyclopropyl–4, 7–dihydro–4–oxo–thieno[2,3–b]pyridine–5–carbonyl) L–α–Amino Esters", *Z. Naturforsch.* (1977), pp. 419–426.

Elliott, Richard L., et al., "The Preparation of 2–(Heterocyclyl)thieno[3,2–b]pyridine Derivatives", *Tetrahedron*, vol. 43 (1987), pp. 3295–3302.

Goerlitzer, K., et al., "Gyrase inhibitors; Part 3.: Synthesis and reactions of ethyl 1,4–dihydro–4–oxo[1]benzothieno[3, 2–b]pyridine–3–carboxylate", *Pharmazie*, vol. 55 (2000), pp. 595–600.

(Continued)

*Primary Examiner*—Evelyn Mei Huang
(74) *Attorney, Agent, or Firm*—Schwegman, Lundberg, Woessner & Kluth, P.A.

(57) ABSTRACT

The invention provides a compound of formula I:

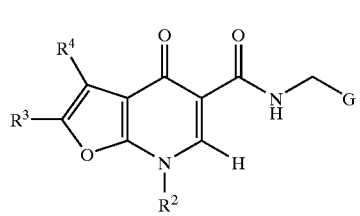

wherein G, R², R³, and R⁴ have any of the values defined in the specification, or a pharmaceutically acceptable salt thereof, as well as processes and intermediates useful for preparing such compounds or salts, and methods of treating a herpesvirus infection using such compounds or salts.

83 Claims, No Drawings

OTHER PUBLICATIONS

Nishikawa, Yoshinori, et al., "Synthesis and Antiallergic Activity of N-[4-(4-Diphenylmethyl-1-piperazinyl)butyl]-1,4-dihydro-4-oxopyridine-3-carboxamides", *Chem. Pharm. Bull.*, vol. 37 (1989), pp. 1256-1259.

Patani, G. A., et al., "Bioisosterism: A Rational Approach in Drug Design", *Chemical Reviews*, 96(8) (1996), pp. 3147-3176.

Thornber, C. W., "Isosterism and Molecular Modification in Drug Design", *Chemical Society Reviews*, 8(4) (1979), pp. 563-580.

*Database Crossfire Beilstein, vol. 26, No. 1,* Beilstein Institut zur Foerderung der chemischen Wissenschaften, Frankfurt am Main, DE Datebase Accession No. 4321837, (1991), 3-11.

*Database Crossfire Beilstein, vol. 21,* Beilstein Institut zur Foerderung der chemischen Wissenschaften, Frankfurt am Main, DE Datebase Accession No. 4381517, (1984), 785-790.

Vaillancourt, V. A., et al., "Naphthalene carboxamides as inhibitors of human cytomegalovirus DNA polymerase", *Bioorganic & Medicinal Chemistry Letters, vol. 10, No. 18,* (Sep. 2000), 2079-2081.

\* cited by examiner

4-OXO-4,7-DIHYDROFURO[2,3-B]PYRIDINE-5-CARBOXAMIDE ANTIVIRAL AGENTS

RELATED APPLICATIONS

This application claims priority to U.S. Provisional Patent Application Ser. No. 60/348,718 filed Jan. 14, 2002.

FIELD OF THE INVENTION

The present invention provides 4-oxo-4,7-dihydrofuro[2,3-b]pyridine-5-carboxamides derivatives that are useful as antivirals, for example, as agents against viruses of the herpes family.

BACKGROUND OF THE INVENTION

The herpesviruses comprise a large family of double stranded DNA viruses. They are also a source of the most common viral illnesses in man. Eight of the herpes viruses, herpes simplex virus types 1 and 2 (HSV-1 and HSV-2), varicella zoster virus (VZV), human cytomegalovirus (HCMV), Epstein-Barr virus (EBV), and human herpes viruses 6, 7, and 8 (HHV-6, HHV-7, and HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causative agent of chicken pox and shingles. EBV causes infectious mononucleosis. It can also cause lymphomas in immunocompromised patients and has been associated with Burkitt's lymphoma, nasopharyngeal carcinoma, post-transplant lymphoproliferative disease (PTLD), and Hodgkins disease. HHV-6 is the causative agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

Infection by or reactivation of herpesviruses is associated with several cardiovascular diseases or conditions in the host such as atherosclerosis and restenosis resulting in inflammation of coronary vessel walls. It is thought that in many patients suffering from restenosis following coronary atherectomy viral infection particularly by CMV plays an important role in the proliferation of the disease. Atherosclerosis is believed to be associated with the overall infectious disease burden in the host and particularly by the herpesviruses such as HSV, CMV, and EBV.

Infection in the animal population (livestock and companion) by strains of herpesviruses is endemic including cattle (Bovine herspesvirus 1–5, BHV), sheep (Ovine herpesvirus 1 and 2), dog (Canine herpesvirus 1), horse (Equine herpesvirus 1–8, EHV), cat (Feline herpesvirus 1, FHV), swine (pseudorabies virus, PRV), and many species of fowl. In the case of bovine herpesvirus infection, animals may suffer from ocular, respiratory, or digestive disorders. Pseudorabies is an extremely contagious viral pathogen infecting several species such as cattle, horses, dogs, cats, sheep, and goats leading to rapid death. The virus is benign in adult swine, however, it remains contagious and leads to high mortality in pigs under three weeks. Infection of horses by equine herpesvirus may lead to neurological syndromes, respiratory disease, and neonatal disease. Herpesvirus infection in cats leads to the disease known as feline viral rhinotracheitis (FVR) which is characterized by rhinitis, tracheitis, laryngitis, and conjunctivitis.

Information Disclosure

JP 08301849 discloses heterocyclic carboxamide compounds which are reported to be useful as tachykinin receptor antagonists.

U.S. Pat. No. 6,239,142 discloses compounds having a thieno[2,3-b]pyridine core which are reported to be useful for the treatment of herpesvirus infections.

U.S. Pat. No. 5,593,943 discloses compounds which are reported to be useful as herbicides.

WO 00/76990 discloses a preparative process for pyridine intermediates.

GB 2289276 discloses a preparative process for pyridine compounds.

WO 92/03427 discloses pyridine compounds which are reported to be useful for treating osteoporosis.

JP 07076586 discloses pyridine compounds reported to be useful for treating osteoporosis.

WO 99/32450 discloses compounds with a 4-hydroxyquinoline core which are reported to be useful in the treatment of herpesvirus infections.

WO 00/40561 discloses compounds with a 4-oxo-1,4-dihydroquinoline core which are reported to be useful for the treatment of herpesvirus infections.

Despite the above teachings, there still exists a need for compounds with desirable antiviral activity.

SUMMARY OF THE INVENTION

The present invention provides a compound of formula I:

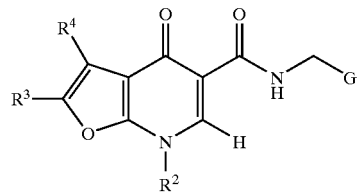

I wherein:
G is phenyl substituted with from one to five $R^1$ substituents;
each $R^1$ is independently
  (a) Cl,
  (b) Br,
  (c) F,
  (d) cyano,
  (e) $C_{1-7}$alkyl, optionally substituted by fluoro, or
  (f) $NO_2$;
$R^2$ is
  (a) H,
  (b) $R^5$,
  (c) $NR^7R^8$,
  (d) $SO_2R^9$, or
  (e) $OR^9$;
$R^3$ is
  (a) H,
  (b) halo,
  (c) aryl,
  (d) $S(O)_mR^6$, (e) (C=O)$R^6$,
(f) (C=O)OH
(g) (C=O)$OR^9$,
(h) cyano,
(i) het, wherein the het is bound via a carbon atom,
(j) $OR^{12}$;
(k) $NR^7R^8$
(l) $SR^{12}$,
(m) $C_{1-7}$alkyl which is optionally partially unsaturated and optionally substituted by the group W-A or one or more $R^{10}$ substituents, or
(n) $C_{3-8}$cycloalkyl which is optionally partially unsaturated and optionally substituted by one or more $R^{10}$, or substituted by one or more $C_{1-7}$alkyl which $C_{1-7}$alkyl is optionally substituted by one or more $R^{10}$;

W is
(a) het,
(b) aryl, or
(c) $C_{3-8}$cycloalkyl, optionally substituted by $OR^{11}$ or oxo (C=O);

A is $C_{1-7}$alkyl substituted by one or more $R^{10}$;

$R^4$ is
(a) H,
(b) halo, or
(c) $C_{1-7}$alkyl optionally substituted by halo;

$R^4$ together with $R^3$ may form a saturated carbocyclic or heterocyclic ring which may be optionally substituted by $OR^{12}$, $SR^{12}$, $NR^7R^8$, or $C_{1-7}$alkyl which $C_{1-7}$alkyl is optionally substituted by one or more $R^{10}$ substituents;

$R^5$ is
(a) $(CH_2CH_2O)_iR^{11}$,
(b) het, wherein the het is bound via a carbon atom,
(c) aryl,
(d) $C_{1-7}$alkyl which is optionally partially unsaturated and is optionally substituted by one or more $R^{10}$ substituents, or
(e) $C_{3-8}$cycloalkyl which is optionally partially unsaturated and is optionally substituted by one or more $R^{10}$ or $C_{1-7}$alkyl substituents which $C_{1-7}$alkyl are optionally substituted by $R^{10}$;

$R^6$ is
(a) $C_{1-7}$alkyl optionally substituted by aryl, het, $OR^{11}$, $SR^{11}$, $NR^{11}R^{11}$, halo, or $C_{3-8}$cycloalkyl which $C_{3-8}$cycloalkyl is optionally substituted by $OR^{11}$,
(b) $C_{3-8}$cycloalkyl which is optionally partially unsaturated and is optionally substituted by one or more halo, $OR^{11}$, $SR^{11}$, or $NR^{11}R^{11}$ substituents,
(c) $NR^7R^8$,
(d) aryl, or
(e) het, wherein the het is bound via a carbon atom;

$R^7$ and $R^8$ are independently
(a) H,
(b) aryl,
(c) $C_{1-7}$alkyl which is optionally partially unsaturated and is optionally substituted by one or more $NR^{11}R^{11}$, $OR^{12}$, $SR^{12}$, $S(O)_mR^9$, $P(=O)(OR^{12})(R^{12})$, $CONR^{11}R^{11}$, $CO_2R^{11}$, (C=O)$R^9$, het, aryl, cyano, or halo substituents,
(d) $C_{3-8}$cycloalkyl which is optionally partially unsaturated and is optionally substituted by one or more halo, $OR^{11}$, $SR^{11}$, oxo, or $NR^{11}R^{11}$ substituents,
(e) (C=O)$R^9$,
(f) $SO_2R^9$, or
(g) $R^7$ and $R^8$ together with the nitrogen to which they are attached form a bet;

$R^9$ is
(a) aryl,
(b) bet,
(c) $C_{3-8}$cycloalkyl, or
(d) $C_{1-7}$alkyl which is optionally partially unsaturated and is optionally substituted by one or more $NR^{11}R^{11}$, $OR^{12}$, $SR^{12}$, halo, $CONR^{11}R^{11}$, $CO_2R^{11}$, het, or aryl substituents;

$R^{10}$ is
(a) $OR^{12}$,
(b) $SR^{12}$,
(c) $NR^7R^8$,
(d) halo,
(e) $CONH_2$,
(f) $CONHR^9$,
(g) $CONR^9R^9$,
(l) $CO_2H$,
(i) $CO_2R^9$,
(j) het, wherein the bet is bound via a carbon atom,
(k) aryl,
(l) cyano,
(m) nitro,
(n) oxo,
(o) $SO_mR^6$, or
(p) $P(=O)(OR^{12})(R^{12})$;

$R^{11}$ is
(a) H, or
(b) $C_{1-7}$alkyl;

$R^{12}$ is
(a) H,
(b) aryl,
(c) het, wherein the het is bound through a carbon atom,
(d) $C_{1-7}$alkyl which is optionally partially unsaturated and is optionally substituted by one or more aryl, het, $OR^{11}$, $SR^{11}$, $NR^{11}R^{11}$, halo, or $C_{3-8}$cycloalkyl substituents and which $C_{3-8}$cycloalkyl is optionally substituted by $OR^{11}$, or
(e) $C_{3-8}$cycloalkyl which is optionally partially unsaturated and is optionally substituted by one or more halo, $OR^{11}$, $SR^{11}$, or $NR^{11}R^{11}$ substituents, $R^{13}$ is
(a) H,
(b) halo,
(c) $OR^{11}$,
(d) $SR^{11}$,
(e) $NR^{11}R^{11}$,
(f) phenyl, optionally substituted by halo, $C_{1-7}$alkyl, or $C_{1-7}$alkoxy,
(g) cyano,
(h) nitro,
(i) $CONR^{11}R^{11}$,
(j) $CO_2R^{11}$,
(k) $S(O)_mNR^{11}R^{11}$,
(l) $NR^{11}$—C(=O)—$R^{11}$,
(m) $C_{1-7}$alkyl which is optionally partially unsaturated and is optionally substituted by one or more $R^{15}$, or (n) $C_{3-8}$cycloalkyl which is optionally partially unsaturated and is optionally substituted by one or more oxo, halo, $OR^{11}$, $SR^{11}$, $C_{1-7}$alkyl, or $NR^{11}R^{11}$ substituents, $R^{14}$ is
(a) H
(b) $C_{1-4}$alkyl, optionally substituted by fluoro,
(c) phenyl, optionally substituted by halo, $C_{1-7}$alkyl, or $C_{1-7}$alkoxy, or
(d) $-(CH_2CH_2O)_mR^{11}$;

$R^{15}$ is
(a) phenyl, optionally substituted by halo, $C_{1-7}$alkyl, or $C_{1-7}$alkoxy,
(b) $C_{3-8}$cycloalkyl, optionally substituted by $OR^{11}$
(c) $OR^{11}$,
(d) $SR^{11}$,
(e) $NR^{11}R^{11}$,
(f) 4-morpholine,
(g) $CO_2R^{11}$,
(h) $CONR^{11}R^{11}$,
(i) oxo,
(j) halo;

each i is independently 2, 3, or 4;
each n is independently 1, 2, 3, 4 or 5;
each m is independently 1 or 2;
wherein any aryl other than G is optionally substituted with one or more $R^{13}$ substituents or any two adjacent $R^{13}$ substituents taken together constitute a group of the formula $-O(CH_2)_mO-$; and
wherein any het is optionally substituted with one or more oxo (=O), oxime (=N—$OR^{11}$), or $R^{13}$ substituents; or
a pharmaceutically acceptable salt thereof.

In another aspect, the present invention also provides:
  a pharmaceutical composition comprising a compound of formula I, or a pharmaceutically acceptable salt thereof, and a pharmaceutically acceptable excipient (the composition preferably comprises an effective antiviral amount of the compound or salt);
  a method of treating a herpesviral infection, comprising administering to a mammal (e.g. a human) in need of such treatment, a compound of formula I or a pharmaceutically acceptable salt thereof;
  a method of treating atherosclerosis or restenosis comprising administering to a mammal (e.g. a human) in need of such treatment, a compound of formula I or a pharmaceutically acceptable salt thereof;
  a method for inhibiting a viral DNA polymerase, comprising contacting (in vitro or in vivo) the polymerase with an effective inhibitory amount of a is compound of formula I, or a pharmaceutically acceptable salt thereof.
  a compound of formula I or a pharmaceutically acceptable salt thereof for use in medical treatment (e.g. the treatment of a herpesviral infection or the treatment of atherosclerosis or restenosis);
  the use of a compound of formula I or a pharmaceutically acceptable salt thereof to prepare a medicament for treating a herpesviral infection in a mammal (e.g. a human);
  the use of a compound of formula I or a pharmaceutically acceptable salt thereof to prepare a medicament for treating atherosclerosis or restenosis in a mammal (e.g. a human); and
  the use of a compound of formula I or a pharmaceutically acceptable salt thereof to prepare a medicament for inhibiting a viral DNA polymerase in a mammal (e.g. a human).

The invention also provides novel intermediates and processes disclosed herein that are useful for preparing compounds of formula I, including the generic and specific intermediates as well as the synthetic processes described in the Charts and Examples herein.

DETAILED DESCRIPTION OF THE INVENTION

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

"Aryl" denotes a phenyl radical or an ortho-fused bicyclic carbocyclic radical having about nine to ten ring atoms in which at least one ring is aromatic.

"Het" is a 4–16 membered saturated or unsaturated monocyclic, bicyclic, or tricyclic ring system having 1, 2, 3, or 4 heteroatoms, such as oxygen (—O—), sulfur (—S—), oxygenated sulfur such as sulfinyl (S=O) and sulfonyl $(S(=O)_2)$, or nitrogen, or an N-oxide thereof. Het includes "heteroaryl", which encompasses a radical attached via a ring carbon of a monocyclic aromatic ring containing five or six ring atoms consisting of carbon and 1, 2, 3, or 4 heteroatoms, such as non-peroxide oxygen (—O—), sulfur (—S—), oxygenated sulfur such as sulfinyl (S=O) and sulfonyl $(S(=O)_2)$, or nitrogen N(X) wherein X is absent or is H, O, $C_{1-4}$alkyl, phenyl or benzyl, as well as a radical of an ortho-fused bicyclic heterocycle of about eight to ten ring atoms derived there from, particularly a benz-derivative or one derived by fusing a propylene, trimethylene, or tetramethylene diradical thereto. When heteroaryl is an ortho-fused benz-derivative it can be attached via any atom in an aromatic ring (e.g. an atom of the benz-ring).

"Partially unsaturated", for example, a $C_{1-7}$alkyl which is optionally partially unsaturated, means the named substituent has one or more unsaturations, such as one or more double bonds, one or more triple bonds, or both.

"Optional" or "optionally" mean that the subsequently described event or condition may but need not occur, and that the description includes instances where the event or condition occurs and instances in which it does not. For example, "optionally substituted" means that the named substituent may be present but need not be present, and the description includes situations where the named substituent is included and situations where the named substituent is not included.

"Mammal" denotes humans and animals. Animals specifically refer to, for example, food animals or companion animals.

The terms "include", "for example", "such as", and the like are used illustratively and are not intended to limit the present invention.

The indefinite articles "a" and "an" mean "at least one" or "one or more" when used in this application, including the claims, unless specifically indicated otherwise.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art. In particular, it is understood that compounds of formula I wherein $R^2$ is hydrogen can exist in the corresponding tautomeric "enol" form, such as formula III, and that such tautomers are included as compounds of the invention.

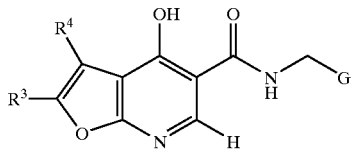

III

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours, "rt" for room temperature, and "rac" for racemic mixture).

Specific and preferred values listed below for radicals, substituents, and ranges, are for illustration only; they do not exclude other defined values or other values within defined ranges for the radicals and substituents. The compounds of the invention include compounds of formula I having any combination of the values, specific values, more specific values, and preferred values described herein.

Specifically, $C_{1-7}$alkyl can be methyl, ethyl, propyl, isopropyl, butyl, iso-butyl, sec-butyl, pentyl, 3-pentyl, hexyl, or heptyl; $C_{3-8}$cycloalkyl can be cyclopropyl, cyclobutyl, cyclopentyl, cyclohexyl, cycloheptyl, or cyclooctyl; $C_{1-7}$alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; $C_{1-7}$alkanoyl can be acetyl, propanoyl, butanoyl, pentanoyl, 4-methylpentanoyl, hexanoyl, or heptanoyl; aryl can be phenyl, indenyl, or naphthyl.

When $C_{1-7}$alkyl is partially unsaturated, it can specifically be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, or 5-hexynyl.

A specific value for "Het" is a four-(4), five-(5), six-(6), or seven-(7) membered saturated or unsaturated monocyclic, bicyclic, or tricyclic ring system having 1, 2, 3, or 4 heteroatoms, such as oxygen (—O—), sulfur (—S—), oxygenated sulfur such as sulfinyl (S=O) and sulfonyl (S(=O)$_2$), or nitrogen, and which ring system is optionally fused to a benzene ring or an N-oxide thereof. Another specific value for "Het" is a five-(5), six-(6), or seven-(7) membered saturated or unsaturated ring containing 1, 2, 3, or 4 heteroatoms, for example, non-peroxide oxygen (—O—), sulfur (—S—), oxygenated sulfur such as sulfinyl (S=O) and sulfonyl (S(—O)$_2$), or nitrogen; as well as a radical of an ortho-fused bicyclic heterocycle of about eight to twelve ring atoms derived there from, particularly a benz-derivative or one derived by fusing a propylene, trimethylene, tetramethylene or another monocyclic het diradical thereto.

A more specific value for "het" is 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl, 5-isothiazolyl, 1,3,4-oxadiazole, 4-oxo-2-thiazolinyl, 5-methyl-1,3,4-thiadiazol-2-yl, thiazoledione, 1,2,3,4-thiatriazole, 1,2,4-dithiazolone, phthalimide, quinolinyl, morpholinyl, thiomorpholinyl, piperidinyl, piperizinyl, benzoxazoyl, diazinyl, triazinyl, quinoxalinyl, naphthyridinyl, azetidinyl, pyrrolidinyl, hydantoinyl, oxathiolanyl, dioxolanyl, imidazolidinyl, or azabicyclo[2.2.1]heptyl, or a corresponding N-oxide.

A specific value for "Heteroaryl" is 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 4,5-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 7-oxo-2-isoindolyl, 1-purinyl, 3-isothiazolyl, 4-isothiazolyl and 5-isothiazolyl, 1,3,4-oxadiazole, 4-oxo-2-thiazolinyl, 5-methyl-1,3,4-thiadiazol-2-yl, thiazoledione, 1,2,3,4-thiatriazole, 1,2,4-dithiazolone, 2-quinazolinyl, or 3-purinyl, or a corresponding N-oxide.

Each of these moieties may be substituted.

A specific value for $R^1$ is F, Cl, or cyano.

Another specific value for $R^1$ is Cl.

Another specific value for $R^1$ is 4-Cl.

Another specific value for $R^1$ is 4-F.

Another specific value for $R^1$ is $C_{1-7}$alkyl.

A specific value for G is phenyl substituted with one $R^1$.

Another specific value for G is phenyl substituted with two $R^1$.

Another specific value for G is phenyl substituted with three $R^1$.

Another specific value for G is 4-chlorophenyl.

Another specific value for G is 4-fluorophenyl.

Another specific value for G is 3,4-dichlorophenyl.

Another specific value for G is 3,4-difluorophenyl.

Another specific value for G is 2,4-dichlorophenyl.

Another specific value for G is 2,4-difluorophenyl.

Another specific value for G is 4-chloro-2-fluorophenyl.

Another specific value for G is 2-chloro-4-fluorophenyl.

Another specific value for G is 3,4,5-trifluorophenyl.

Another specific value for G is 4-bromophenyl.

Another specific value for G is 4-methylphenyl.

Another specific value for G is 4-cyanophenyl.

Another specific value for G is 4-nitrophenyl.

Another specific value for G is 4-trifluoromethylphenyl.

Another specific value for G is 4-chloro-2-methylphenyl.

A specific value for $R^2$ is H.

Another specific value for $R^2$ is $R^8$.

Another specific value for $R^2$ is $NR^7R^8$.

Another specific value for $R^2$ is $SO_2R^9$.

Another specific value for $R^2$ is $OR^9$.

Another specific value for $R^2$ is $C_{1-7}$alkyl which is optionally partially unsaturated and is optionally substituted with one or more $R^{10}$ substituents.

Another specific value $R^2$ is $C_{1-7}$alkyl which is substituted with one or two hydroxy.

Another specific value $R^2$ is $C_{1-7}$alkyl which is substituted with $NR^7R^8$.

Another specific value for $R^2$ is methyl.

Another specific value for $R^2$ is ethyl.

Another specific value for $R^2$ is propyl.

Another specific value for $R^2$ is cyclopropyl.

Another specific value for $R^2$ is phenyl.

Another specific value for $R^2$ is 2-pyridyl.

Another specific value for $R^2$ is 2-phenylethyl.

Another specific value for $R^2$ is 2-(diethylamino)ethyl.

A specific value for $R^3$ is H.

Another specific value for $R^3$ is halo.

Another specific value for $R^3$ is aryl.

Another specific value for $R^3$ is het, wherein the het is bound to the furo ring via a carbon atom.

Another specific value for $R^3$ is cyano.

Another specific value for $R^3$ is $S(O)_mR^6$, $OR^{12}$, $NR^7R^8$, or $SR^{12}$.

Another specific value for $R^3$ is $(C=O)R^6$, $(C=O)OH$, or $(C=O)OR^9$.

Another specific value for $R^3$ is $(C=O)NR^7R^8$.

Another specific value for $R^3$ is $C_{3-8}$cycloalkyl which is optionally partially unsaturated and optionally substituted by one or more $R^{10}$, or substituted by one or more $C_{1-7}$alkyl which $C_{1-7}$alkyl is optionally substituted by one or more $R^{10}$.

Another specific value for $R^3$ is $C_{1-7}$alkyl which is optionally partially unsaturated and optionally substituted by one or more $R^{10}$ substituents.

Another specific value for $R^3$ is $C_{1-7}$alkyl which comprises one triple bond and is optionally substituted by one or more $R^{10}$ substituents.

Another specific value for $R^3$ is 3-hydroxy-1-propynyl.

Another specific value for $R^3$ is $C_{1-7}$alkyl which comprises one double bond and is optionally substituted by one or more $R^{10}$ substituents.

Another specific value for $R^3$ is $C_{1-7}$alkyl substituted by one or more $R^{10}$ substituents Another specific value for $R^3$ is 3-hydroxypropyl.

Another specific value for $R^3$ is tetrahydro-2H-pyran-4-yl-methyl.

Another specific value for $R^3$ is $C_{1-7}$alkyl substituted by either an aryl or a het substituent, and one or more $OR^{11}$ substituents.

Another specific value for $R^3$ is $CH_2OR^{12}$.

Another specific value for $R^3$ is $CH_2OR^{12}$ where $R^{12}$ is $C_{1-7}$alkyl substituted by either an aryl or a het substituent, and one or more $OR^{11}$ substituents.

Another specific value for $R^3$ is $CH_2NR^7R^8$.

Another specific value for $R^3$ is $CH_2NHSO_2R^9$.

Another specific value for $R^3$ is 4-morpholinomethyl.

Another specific value for $R^3$ is $CH_2NR^7R^8$ where $R^7$ is $C_{1-7}$alkyl, and $R^8$ is $C_{1-7}$alkyl which is optionally partially unsaturated and is optionally substituted by one or more $NR^{11}R^{11}$, $OR^{12}$, $SR^{12}$, $S(O)R^9$, $P(=O)(OR^{12})(R^{12})$, $CONR^{11}R^{11}$, $CO_2R^{11}$, $(C=O)R^9$, het, aryl, cyano, or halo substituents.

Another specific value for $R^3$ is $CH_2NR^7R^8$ where $R^7$ is methyl, and $R^8$ is $C_{1-7}$alkyl substituted with aryl or het, and one or more $OR^{12}$ substituents.

Another specific value for $R^3$ is (N-(2-furyl-2-hydroxyethyl)-N-methyl-amino)methyl.

Another specific value for $R^3$ is (N-(2-hydroxy-2-phenylethyl)-N-methyl-amino)methyl.

Another specific value for $R^3$ is (N-(2-hydroxy-2-(3-methoxyphenyl)-ethyl)-N-methylamino)methyl.

Another specific value for $R^3$ is (N-(2-(4-fluorophenyl)-2-hydroxyethyl)-N-methylamino)methyl.

Another specific value for $R^3$ is (N-(2-(4-chlorophenyl)-2-hydroxyethyl)-N-methylamino)methyl.

Another specific value for $R^3$ is (N-(2-hydroxy-2-(pyridin-2-yl)ethyl)-N-methylamino)methyl.

Another specific value for $R^3$ is (Ar(2-hydroxy-2-(pyridin-3-yl)ethyl)-N-methylamino)methyl.

Another specific value for $R^3$ is (N-(2-hydroxy-2-(pyridin-4-yl)ethyl)-N-methylamino)methyl.

Another specific value for $R^3$ is (N-(2-hydroxy-2-(5-methyl-2-furyl)-ethyl)-N-methylamino)methyl.

Another specific value for $R^3$ is (N-(2-(3-furyl)-2-hydroxyethyl)-N-methylamino)methyl.

Another specific value for $R^3$ is (N-(2-hydroxy-2-(2,4,6-trifluorophenyl)-N-methylamino)methyl.

Another specific value for $R^3$ is (N-(2-(1-benzofuran-2-yl)-2-hydroxy-ethyl)-N-methylamino)methyl.

Another specific value for $R^3$ is (N-(2-hydroxy-2-(thien-2-yl)ethyl)-N-methylamino)methyl.

Another specific value for $R^3$ is (N-(2-hydroxy-2-quinolin-2-ylethyl)-N-methylamino)methyl.

Another specific value for $R^3$ is (N-(2-hydroxy-2-(1-methyl-1H-pyrrol-2-yl)ethyl)-N-methylamino)methyl.

Another specific value for $R^3$ is (N-(2-(5-cyanothien-2-yl)-2-hydroxy-ethyl)N-methylamino)methyl.

Another specific value for $R^3$ is (N-(2-hydroxy-2-(1,3-thiazol-2-yl)ethyl)-N-methylamino)methyl.

Another specific value for $R^3$ is (N-(2-hydroxy-2-(5-phenyl-2-furyl)-ethyl)-N-methylamino)methyl.

Another specific value for $R^3$ is (N-(2-(4,5-dimethyl-2-furyl)-2-hydroxy-ethyl)-N-methylamino)methyl.

Another specific value for $R^3$ is (N-(2-hydroxy-2-pyrazin-2-ylethyl)-N-methylamino)methyl.

Another specific value for $R^3$ is (N-(2-hydroxy-2-pyrimidin-2-ylethyl)-N-methylamino)methyl.

Another specific value for $R^3$ is $CH_2NR^7R^8$ where $R^7$ is methyl, and $R^9$ is $C_{1-7}$alkyl substituted with $SR^2$, and one or more $OR^{12}$ substituents.

Another specific value for $R^3$ is $CH_2NR^7R^8$ where $R^7$ is methyl, and $R^8$ is $C_{1-7}$alkyl substituted with $S(O)_mR^9$, and one or more $OR^{12}$ substituents.

Another specific value for $R^3$ is (4-chlorophenyl)methylaminocarbonyl.

Another specific value for $R^3$ is $S(O)_mR^6$.

Another specific value for $R^3$ is propylsulfonyl.

Another specific value for $R^3$ is $C_{1-7}$alkyl substituted by the group W-A.

A specific value for W is pyrrolidine.

Another specific value for W is morpholine.

Another specific value for W is piperidine.

Another specific value for W is piperazine.

Another specific value for W is aryl.

Another specific value for W is $C_{3-8}$cycloalkyl.

A specific value for A is $C_{1-4}$alkyl substituted by either an aryl or a het substituent, and one or more $OR^{11}$ substituents.

A specific value for $R^4$ is H.

Another specific value for $R^4$ is halo.

Another specific value for $R^4$ is $C_{1-7}$alkyl optionally substituted by halo.

Another specific value for $R^4$ is where $R^4$ together with $R^3$ form a saturated carbocyclic or heterocyclic ring which is optionally substituted by $OR^2$, $SR^2$, $NR^7R^8$, or $C_{1-7}$alkyl which $C_{1-7}$alkyl is optionally substituted by one or more $R^{10}$ substituents.

Another specific value for $R^4$ is methyl.

A specific value for $R^5$ is $(CH_2CH_2O)_iR^{11}$.

Another specific value for $R^5$ is $C_{1-7}$alkyl which is optionally partially unsaturated and is optionally substituted by one or more $R^{10}$ substituents.

Another specific value for $R^5$ is $C_{3-8}$cycloalkyl which is optionally partially unsaturated and optionally substituted by one or more $R^{10}$ substituents or $C_{1-7}$alkyl substituents which $C_{1-7}$alkyl is optionally substituted by $R^{10}$.

Another specific value for $R^5$ is het, wherein the het is bound via a carbon atom.

Another specific value for $R^5$ is aryl.

Another specific value for $R^5$ is methyl.

Another specific value for $R^5$ is ethyl.

A specific value of $R^{16}$ is aryl.

Another specific value of $R^{16}$ is phenyl, optionally substituted by one or more $R^{13}$.

Another specific value of $R^{16}$ is phenyl.

Another specific value of $R^{16}$ is 2-cyanophenyl, 3-cyanophenyl, 4-cyanophenyl, 3-bromophenyl, 4-bromophenyl, 2-chlorophenyl, 3-chlorophenyl, 4-chlorophenyl, 2-hydroxyphenyl, 3-hydroxyphenyl, 4-hydroxyphenyl, 2-methoxyphenyl, 3-methoxyphenyl, 4-methoxyphenyl, 2-methylphenyl, 3-methylphenyl, 4-methylphenyl, 2-ethylphenyl, 3-ethylphenyl, 4-ethylphenyl, 2-trifluoromethylphenyl, 3-trifluoromethylphenyl, 4-trifluoromethylphenyl, 2-nitrophenyl, 3-nitrophenyl, 4-nitrophenyl, 4-phenoxyphenyl, 3-phenoxyphenyl, 3-(4-chlorophenoxy)phenyl, 34-methoxyphenoxy)phenyl, 3-(4-methylphenoxy)phenyl, 3,4-dibromophenyl, 2-chloro-5-trifluoromethylphenyl, 3,5-dibromophenyl, 3,5-dibromo-6-methoxyphenyl, 3,5-di(trifluoromethyl)phenyl, 3-cyano-4-fluorophenyl, 3-bromo-4-fluorophenyl, 2-bromophenyl, 3-bromo-6-fluorophenyl, 4-bromo-6-fluorophenyl, 3-bromo-6-hydroxyphenyl, 3-bromo-4-methoxyphenyl, 4-(1H-imidazol-1-yl)phenyl, 3, bromo-6-methoxyphenyl, 4-nitrophenyl, 4-chloro-5-fluorophenyl, 2-chloro-6-fluorophenyl, 2-chloro-4-fluorophenyl, 2-fluoro-4-methoxyphenyl, 4-hydroxy-5-methoxyphenyl, 4-(acetylamino)phenyl, 3-(acetylamino)phenyl, 4-hydroxy-5-methylphenyl, 2-thiomethylphenyl, 3-fluoro-2-methylphenyl, 2-trifluoromethoxyphenyl, 3-trifluoromethoxyphenyl, 4-trifluoromethoxyphenyl, 4-hydroxymethylphenyl, 3-hydroxymethylphenyl, 2-hydroxymethylphenyl, 4-aminophenyl, 3-aminophenyl, 2-fluoro-4-trifluoromethylphenyl, 2-methyl-4-methoxyphenyl, 4-dimethylaminophenyl, 2,3-dimethylphenyl, 2,4-dimethylphenyl, 3,4-dimethylphenyl, 3,5-dimethylphenyl, 4-hydroxy-5-methoxyphenyl, 4-(2-hydroxyethoxy)phenyl, 4-morpholin-4-ylphenyl, 1,1'-biphenyl-4-yl, 1,1'-biphenyl-3-yl, 2-fluorophenyl, 3-fluorophenyl, 4-fluorophenyl, 2,3-difluorophenyl, 3,4-difluorophenyl, 2,6-difluorophenyl, 2,5-difluorophenyl, 2,4-difluorophenyl, 3,5-difluorophenyl, 2,3,4-trifluorophenyl, 3,4,5-trifluorophenyl, 2,4,6-trifluorophenyl, 2,3,6-trifluorophenyl, 2,3,5-trifluorophenyl, or 2,3,4,5,6-pentafluorophenyl.

Another specific value of $R^{16}$ is 4-hydroxyphenyl, 4-chlorophenyl, 4-fluorophenyl, 4-bromophenyl, 4-methylphenyl, 4-trifluoromethylphenyl, 3-chlorophenyl, 3-fluorophenyl, 3-bromophenyl, 3-methylphenyl, 3-methoxyphenyl, 3-trifluoromethylphenyl, 3-cyanophenyl, 2-chlorophenyl, 2-fluorophenyl, 2-bromophenyl, 2-methylphenyl, 2-methoxyphenyl, 2-trifluoromethylphenyl, 4-(hydroxymethyl)phenyl, 4-(NN-dimethylaminomethyl)phenyl, 2,3,4,5,6-pentafluorophenyl, or 2,4,6-trifluorophenyl.

Another specific value of $R^{16}$ is naphthyl, optionally substituted by one or more $R^3$.

Another specific value of $R^{16}$ is 1-naphthyl or 2-naphthyl.

Another specific value of $R^{16}$ is het.

Another specific value of $R^{16}$ is heteroaryl.

Another specific value of $R^{16}$ is phenyl, fused to a pyridine or furan ring, optionally substituted with one or more $R^{13}$.

Another specific value of $R^{16}$ is a five-(5) membered heteroaryl.

Another specific value of $R^{16}$ is 2-furyl, 3-furyl, thien-2-yl, thien-3-yl, 1H-pyrrol-2-yl, 1H-pyrrol-3-yl, 1H-imidazol-4-yl, 1H-imidazol-2-yl, 1,3-thiazol-2-yl, 1H-pyrazol-5-yl, 1-methyl-1H-pyrrol-2-yl, 1-ethyl-1H-pyrrol-2-yl, 1-propyl-1H-pyrrol-2-yl, 1-methyl-1H-imidazol-4-yl, 1-methyl-1H-imidazol-2-yl, 1-ethyl-1H-imidazol-4-yl, or 1-ethyl-1H-imidazol-2-yl.

Another specific value of $R^{16}$ is 5-methyl-2-furyl, 2,5-dimethyl-3-furyl, 4,5-dimethyl-2-furyl, 4-methyl-2-furyl, 5-hydroxymethyl-2-furyl, 5-((dimethylamino)methyl)-2-furyl, 5-ethyl-2-furyl, 5-bromo-2-furyl, 4,5-dibromo-2-furyl, 5-chloro-2-furyl, 5-phenyl-2-furyl, 4-phenyl-2-furyl, 5-(2-chlorophenyl)-2-furyl, 5-(3-chlorophenyl)-2-furyl, 5-(4-chlorophenyl)-2-furyl, 5-(2,4-dichlorophenyl)-2-furyl, 5-(2,5-dichlorophenyl)-2-furyl, 5-(2,4,6-trichlorophenyl)-2-furyl, 5-cyanothien-2-yl, 4-bromothien-2-yl, or 5-chlorothien-2-yl.

Another specific value of $R^{16}$ is a five-(5) membered heteroaryl which is fused to a benzene or pyridine ring.

Another specific value of $R^{16}$ is benzofuran-2-yl, benzofuran-3-yl, benzothien-2-yl, benzothien-3-yl, 1H-indol-3-yl, 1H-indol-2-yl, 1,3-benzo thiazol-2-yl, furo[2,3-b]pyridin-2-yl, furo[2,3-c]pyridin-2-yl, furo[3,2-c]pyridin-2-yl, furo[3,2-b]pyridin-2-yl, furo[2,3-b]pyridin-3-yl, furo[2,3-c]pyridin-3-yl, furo[3,2-c]pyridin-3-yl, furo[3,2-b]pyridin-3-yl, 1-methyl-1H-indol-2-yl, or 1-ethyl-1H-indol-2-yl.

Another specific value of $R^{16}$ is 3-chloro-1-benzofuran-2-yl, 2-phenyl-1H-indol-3-yl, 2-(4-fluorophenyl)-1H-indol-3-yl, 5-fluoro-1H-indol-3-yl, 2-methyl-1H-indol-3-yl, 5-methyl-1H-indol-3-yl, 6-methyl-1H-indol-3-yl, 7-methyl-1H-indol-3-yl, 3-methyl-1-benzothien-2-yl, 3-phenyl-1H-pyrazol-4-yl, or 1,3-dimethyl-1H-pyrazol-4-yl.

Another specific value of $R^{16}$ is a six-(6) membered heteroaryl having one (1) or two (2) nitrogen atoms.

Another specific value of $R^{16}$ is pyridin-2-yl, pyridin-3-yl, pyridin-4-yl, pyrazin-2-yl, pyrimidin-2-yl, pyrimidin-4-yl, 2-pyridazin-3-yl, pyrimidin-5-yl, or pyridazin-4-yl.

Another specific value of $R^{16}$ is a six-(6) membered heteroaryl having one (1) or two (2) nitrogen atoms which is fused to a benzene ring.

Another specific value of $R^{16}$ is isoquinolin-3-yl, quinolin-3-yl, quinolin-2-yl, quinazolin-2-yl, quinoxalin-2-yl, cinnolin-3-yl, isoquinolin-1-yl, isoquinolin-4-yl, quinolin-4-yl, quinazolin-4-yl, phthalazin-1-yl, or cinnolin-4-yl.

Another specific value of $R^{16}$ is 2-furyl, 3-furyl, 5-methyl-2-furyl, 4,5-dimethyl-2-furyl, 5-phenyl-2-furyl, 5-(hydroxymethyl)-2-furyl, 2,5-dimethyl-3-furyl, thien-2-yl, thien-3-yl, 5-cyanothien-2-yl, 1H-pyrrol-2-yl, 1-methyl-1H-pyrrol-2-yl, 1-methyl-1H-imidazol-4-yl, 1H-imidazol-4-yl, 1,3-thiazol-2-yl, or 1H-pyrazol-5-yl.

Another specific value of $R^{16}$ is 2-furyl.

Another specific value of $R^{16}$ is 1-benzofuran-2-yl, 1-benzofuran-3-yl, 1,3-benzothiazol-2-yl, 1-benzothien-2-yl, benzothien-3-yl, 1H-indol-3-yl, or 1-methyl-1H-indol-2-yl.

Another specific value of $R^{16}$ is pyridin-2-yl, pyridin-3-yl, pyridin-4-yl, 6-methylpyridin-2-yl, pyrimidin-2-yl, or pyrazin-2-yl.

Another specific value of $R^{16}$ is pyrimidin-2-yl.

Another specific value of $R^{16}$ is pyrazin-2-yl.

Another specific value of $R^{16}$ is pyridin-2-yl.

Another specific value of $R^{16}$ is 1-quinolin-2-yl A specific value for $R^{17}$ is aryl.

Another specific value for $R^{17}$ is phenyl.

Another specific value for $R^{17}$ is $C_{1-7}$alkyl which is optionally partially unsaturated and is optionally substituted by one or more $NR^{11}R^{11}$, $OR^{12}$, or $SR^{12}$, $S(O)_m R^9$, $CONR^{12}R^{12}$, $CO_2R^{11}$, $(C=O)R^9$, het, aryl, cyano, or halo substituents.

Another specific value for $R^{17}$ is methyl.

Another specific value for $R^{17}$ is ethyl.

A specific group of compounds are compounds of formula I wherein G is phenyl substituted with one or two $R^1$ groups when $R^2$ and $R^3$ are both $C_{1-7}$alkyl which $C_{1-7}$alkyl substituents are optionally partially unsaturated and optionally substituted with one or more $R^{10}$ substituents.

Another specific group of compounds are compounds of formula I wherein G is phenyl substituted at the 4-position with $R^1$ when $R^3$ is $C_{1-7}$alkyl which $C_{1-7}$alkyl is optionally substituted by $NR^7R^8$; and $R^2$ is $CH_3$.

Another specific value for G is 4-chlorophenyl when $R^3$ is $CH_2N(CH_3)CH_2CH(OH)$aryl or $CH_2N(CH_3)CH_2CH(OH)$het, and $R^2$ is $CH_3$.

Another specific group of compounds are compounds of formula I wherein G is phenyl substituted at the 4-position with $R^1$; $R^3$ is $C_{1-7}$alkyl optionally substituted by $NR^7R^8$; $R^2$ is $CH_3$; and $R^4$ is H.

Another specific group of compounds are compounds of formula I wherein G is phenyl substituted at the 4-position with $R^1$; $R^3$ is $C_{1-7}$alkyl substituted with one $R^{10}$ wherein $R^{10}$ is $NR^7R^8$, $R^7$ is methyl, and $R^8$ is ethyl substituted with an $OR^{12}$ and an aryl or a het; $R^2$ is $CH_3$; and $R^4$ is H.

Another specific group of compounds are compounds of formula I wherein G is 4-chlorophenyl; $R^3$ is $CH_2N(CH_3)CH_2CH(OH)$aryl or $CH_2N(CH_3)CH_2CH(OH)$het; $R^2$ is $CH_3$; and $R^4$ is H.

A specific compound of the invention is compound of formula I:

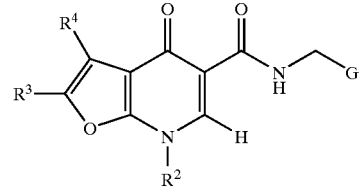

wherein:
G is phenyl substituted with from one to five $R^1$ substituents;
each $R^1$ is independently
  (a) Cl,
  (b) Br,
  (c) F,
  (d) cyano,
  (e) $C_{1-7}$alkyl, or
  (f) $NO_2$;
$R^2$ is
  (a) H,
  (b) $R^5$,
  (b) $NR^7R^8$,
  (c) $SO_2R^9$, or
  (d) $OR^9$;
$R^3$ is
  (a) H,
  (b) halo,
  (c) aryl,
  (d) $S(O)_m R^6$,
  (e) $(C=O)R^6$,
  (f) $(C=O)OH$
  (g) $(C=O)OR^9$, (h) cyano,
(i) het, wherein the het is bound via a carbon atom,
(j) $OR^{14}$,
(k) $NR^7R^8$
(l) $SR^{14}$,
(m) $NHSO_2R^{11}$,
(n) $C_{1-7}$alkyl which is optionally partially unsaturated and optionally substituted by one or more $R^{11}$ substituents, or
(o) $C_{3-8}$cycloalkyl which is optionally partially unsaturated and optionally substituted by one or more $R^{11}$, or substituted by one or more $C_{1-7}$alkyl which $C_{1-7}$alkyl is optionally substituted by one or more $R^{11}$;

$R^4$ is
(a) H,
(a) halo, or
(b) $C_{1-7}$alkyl optionally substituted by halo;
$R^4$ together with $R^3$ may form a saturated carbocyclic or heterocyclic ring which may be optionally substituted by $OR^{14}$, $SR^{14}$, $NR^7R^8$, or $C_{1-7}$alkyl which $C_{1-7}$alkyl is optionally substituted by one or more $R^{11}$ substituents;

$R^5$ is
(a) $(CH_2CH_2O)_iR^{11}$,
(b) bet, wherein the het is bound via a carbon atom,
(c) aryl,
(d) $C_{1-7}$alkyl which is optionally partially unsaturated and is optionally substituted by one or more $R^{11}$ substituents, or
(e) $C_{3-8}$cycloalkyl which is optionally partially unsaturated and is optionally substituted by one or more $R^{11}$ or $C_{1-7}$alkyl substituents which $C_{1-7}$alkyl are optionally substituted by $R^{11}$;

$R^6$ is
(a) $C_{1-7}$alkyl optionally substituted by aryl, bet, $OR^{13}$, $SR^{13}$, $NR^{13}R^{13}$, halo, or $C_{3-8}$cycloalkyl which $C_{3-8}$cycloalkyl is optionally substituted by $OR^{13}$,
(b) $C_{3-8}$cycloalkyl which is optionally partially unsaturated and is optionally substituted by one or more halo, $OR^{13}$, $SR^{13}$, or $NR^{13}R^{13}$ substituents,
(c) $NR^7R^8$,
(d) aryl, or
(e) het, wherein the het is bound via a carbon atom;

$R^7$ and $R^8$ are independently
(a) H,
(b) aryl,
(c) $C_{1-7}$alkyl which is optionally partially unsaturated and is optionally substituted by one or more $NR^{13}R^{13}$, $OR^{14}$, $SR^{14}$, $S(O)_mR^9$, $P(=O)(OR^{14})(R^{14})$, $CONR^{13}R^{13}$, $CO_2R^3$, $(C=O)R^9$, het, aryl, cyano, or halo substituents,
(c) $C_{3-8}$cycloalkyl which is optionally partially unsaturated and is optionally substituted by one or more halo, $OR^{13}$, $SR^{13}$, oxo, or $NR^{13}R^{13}$ substituents,
(d) $(C=O)R^9$, or
(e) $R^7$ and $R^8$ together with the nitrogen to which they are attached form a het;

$R^9$ is
(a) aryl,
(c) het,
(d) $C_{3-8}$cycloalkyl, or
(e) $C_{1-7}$alkyl which is optionally partially unsaturated and is optionally substituted by one or more $NR^{13}R^{13}$, $OR^{14}$, $SR^{14}$, halo, $CONR^{13}R^{13}$, $CO_2R^{13}$, het, or aryl substituents;

$R^{10}$ is
(a) H, or
(b) $C_{1-7}$alkyl optionally substituted by OH;

$R^{11}$ is
(a) $OR^{14}$,
(b) $SR^{14}$,
(c) $NR^7R^8$,
(d) halo,
(e) $CONH_2$,
(f) $CONHR^9$,
(g) $CONR^9R^9$,
(h) $CO_2H$,
(i) $CO_2R^9$,
(j) het,
(k) aryl,
(l) cyano,
(m) oxo
(n) $SO_mR^6$, or
(o) $P(=O)(OR^{14})(R^{14})$;

$R^{12}$ is
(a) H,
(b) het,
(c) aryl,
(d) $C_{3-8}$cycloalkyl optionally substituted by $R^{11}$, or
(f) $C_{1-7}$alkyl optionally substituted by $R^{11}$;

$R^{13}$ is
(a) H, or
(c) $C_{1-7}$alkyl;

$R^{14}$ is
(a) H,
(b) aryl,
(c) het, wherein the het is bound through a carbon atom,
(d) $C_{1-7}$alkyl which is optionally partially unsaturated and is optionally substituted by one or more aryl, het, $OR^{13}$, $SR^{13}$, $NR^{13}R^{13}$, halo, or $C_{3-8}$cycloalkyl substituents and which $C_{3-8}$cycloalkyl is optionally substituted by $OR^{13}$, or
(e) $C_{3-8}$cycloalkyl which is optionally partially unsaturated and is optionally substituted by one or more halo, $OR^{13}$, $SR^{13}$, or $NR^3R^{13}$ substituents;

$R^{15}$ is
(a) H,
(b) halo,
(b) $OR^{13}$,
(c) $SR^{13}$
(d) $NR^{13}R^{13}$,
(f) $O(CH_2CH_2O)_nR^{10}$,
(g) phenyl,
(h) cyano,
(i) nitro,
(j) $CONR^{13}R^{13}$,
(k) $S(O)_mNR^{13}R^{13}$,
(l) $NH-C(=O)-R^{13}$,
(m) $C_{1-7}$alkyl which is optionally partially unsaturated and is optionally substituted by one or more oxo, phenyl, 4-morpholine, $OR^{13}$, $SR^{13}$, $NR^{13}R^{13}$, halo, $CO_2R^{13}$, $CONR^{13}R^{13}$ or $C_{3-8}$cycloalkyl and which $C_{3-8}$cycloalkyl is optionally substituted by $OR^{13}$, or
(n) $C_{3-8}$cycloalkyl which is optionally partially unsaturated and is optionally substituted by one or more oxo, halo, $OR^{13}$, $SR^{13}$, $C_{1-7}$alkyl, or $NR^{13}R^{13}$ substituents, each i is independently 2, 3, or 4;
each n is independently 1, 2, 3, 4 or 5;
each m is independently 1 or 2;
wherein any aryl other than G is optionally substituted with one or more $R^{15}$ substituents; and
wherein any het is optionally substituted with one or more oxo (=O), oxime (=N—$OR^{13}$), or $R^{15}$ substituents; or a pharmaceutically acceptable salt thereof.

A specific compound of the invention is compound of formula II:

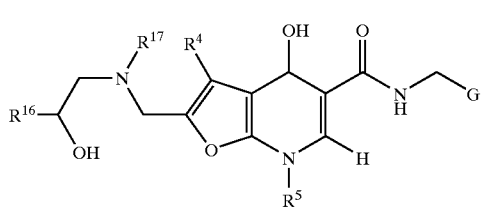

II wherein:
G is phenyl substituted with from one to five $R^1$ substituents;
each $R^1$ is independently
  (a) Cl,
  (b) Br,
  (c) F,
  (d) cyano,
  (e) $C_{1-7}$alkyl, optionally substituted by fluoro, or
  (f) $NO_2$;
$R^4$ and $R^5$ are as defined and illustrated herein;
$R^{16}$ is
  (a) aryl, or
  (b) het;
$R^7$ is
  (a) H,
  (b) aryl,
  (c) $C_{1-7}$alkyl which is optionally partially unsaturated and is optionally substituted by one or more $NR^{11}R^{11}$, $OR^{12}$, $SR^{12}$, $S(O)_mR^9$, $CONR^{12}R^{12}$, $CO_2R^{11}$, (C=O)$R^9$, het, aryl, cyano, or halo substituents,
  (d) $C_{3-8}$cycloalkyl which is optionally partially unsaturated and is optionally substituted by one or more halo, $OR^{11}$, $SR^{11}$, oxo, or $NR^{11}R^{11}$ substituents,
  (e) (C=O)$R^9$, or
  (f) $SO_2R^9$;
$R^9$ is
  (a) aryl,
  (b) het,
  (c) $C_{3-8}$cycloalkyl, or
  (d) $C_{1-7}$alkyl which is optionally partially unsaturated and is optionally substituted by one or more $NR^{11}R^{11}$, $OR^{12}$, $SR^{12}$, halo, $CONR^{11}R^{11}$, $CO_2R^{11}$, het, or aryl substituents;
$R^{11}$ is
  (a) H, or
  (b) $C_{1-7}$alkyl;
$R^{12}$ is
  (a) H,
  (b) aryl,
  (c) het, wherein the het is bound through a carbon atom,
  (d) $C_{1-7}$alkyl which is optionally partially unsaturated and is optionally substituted by one or more aryl, het, $OR^{11}$, $SR^{11}$, $NR^{11}R^{11}$, halo, or $C_{3-8}$cycloalkyl substituents and which $C_{3-8}$cycloalkyl is optionally substituted by $OR^{11}$, or
  (e) $C_{3-8}$cycloalkyl which is optionally partially unsaturated and is optionally substituted by one or more halo, $OR^{11}$, $SR^{11}$, or $NR^{11}R^{11}$ substituents,
$R^{13}$ is
  (a) H,
  (b) halo,
  (c) $OR^{14}$,
  (d) $SR^{11}$,
  (e) $NR^{11}R^{11}$,
  (f) phenyl, optionally substituted by halo, $C_{1-7}$alkyl, or $C_{1-7}$alkoxy,
  (g) cyano,
  (h) nitro,
  (i) $CONR^{11}R^{11}$,
  (j) $CO_2R^{11}$,
  (k) $S(O)_mNR^{11}R^{11}$,
  (l) $NR^{11}$—C(=O)—$R^{11}$,
  (m) $C_{1-7}$alkyl which is optionally partially unsaturated and is optionally substituted by one or more $R^{15}$, or
  (n) $C_{3-8}$cycloalkyl which is optionally partially unsaturated and is optionally substituted by one or more oxo, halo, $OR^{11}$, $SR^{11}$, $C_{1-7}$alkyl, or $NR^{11}R^{11}R^{11}$ substituents,
$R^{15}$ is
  (a) phenyl, optionally substituted by halo, $C_{1-7}$alkyl, or $C_{1-7}$alkoxy,
  (b) $C_{3-8}$cycloalkyl, optionally substituted by $OR^{11}$
  (c) $OR^{11}$,
  (d) $SR^{11}$,
  (e) $NR^{11}R^{11}$,
  (f) 4-morpholine,
  (g) $CO_2R^{11}$,
  (h) $CONR^{11}R^{11}$,
  (i) oxo,
  (j) halo;
each m is independently 1 or 2;
wherein any aryl other than G is optionally substituted with one or more $R^{13}$ substituents or any two adjacent $R^{13}$ substituents taken together constitute a group of the formula —O(CH$_2$)$_m$O—; and
wherein any het is optionally substituted with one or more oxo (=O), oxime (=N—$OR^{11}$), or $R^3$ substituents; or
a pharmaceutically acceptable salt thereof.

Another specific compound of the invention is a compound of formula II:

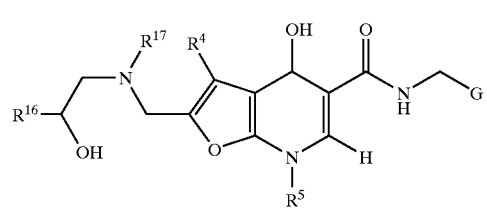

II wherein:
G is phenyl substituted with from one to five $R^1$ substituents;
each $R^1$ is independently (a) Cl,
(b) Br,
(c) F,
(d) cyano,
(e) $C_{1-7}$alkyl, or
(f) $NO_2$;
$R^4$ and $R^5$ are as defined and illustrated herein;
$R^{16}$ is
(a) aryl, or
(b) het;
$R^{17}$ is
(a) H,
(b) aryl,
(c) $C_{1-7}$alkyl which is optionally partially unsaturated and is optionally substituted by one or more $NR^{13}R^{13}$, $OR^{14}$, $SR^{14}$ $S(O)_mR^9$, $CONR^{13}R^{13}$, $CO_2R^{13}$, (C=O)$R^9$, het, aryl, cyano, or halo substituents,
(d) $C_{3-8}$cycloalkyl which is optionally partially unsaturated and is optionally substituted by one or more halo, $OR^{13}$, $SR^{13}$, oxo, or $NR^{13}R^{13}$ substituents, or
(e) (C=O)$R^9$;
$R^9$ is
(a) aryl,
(b) het,
(c) $C_{3-8}$cycloalkyl, or
(d) $C_{1-7}$alkyl which is optionally partially unsaturated and is optionally substituted by one or more $NR^{13}R^{13}$, $OR^4$, $SR^4$, halo, $CONR^{13}R^{13}$, $CO_2R^{13}$, het, or aryl substituents;
$R^{10}$ is
(a) H, or
(b) $C_{1-7}$alkyl optionally substituted by OH;
$R^{13}$ is
(a) H, or
(b) $C_{1-7}$alkyl;
$R^{14}$ is
(a) H,
(b) aryl,
(c) het, wherein the het is bound through a carbon atom,
(d) $C_{1-7}$alkyl which is optionally partially unsaturated and is optionally substituted by one or more aryl, het, $OR^{13}$, $SR^{11}$, $NR^{13}R^{13}$, halo, or $C_{3-8}$cycloalkyl substituents and which $C_{3-8}$cycloalkyl is optionally substituted by $OR^{13}$, or
(e) $C_{3-8}$cycloalkyl which is optionally partially unsaturated and is optionally substituted by one or more halo, $OR^{13}$, $SR^{13}$, or $NR^{13}R^{13}$ substituents;
$R^{15}$ is
(a) H,
(b) halo,
(c) $OR^{11}$,
(d) $SR^3$,
(e) $NR^{13}R^{13}$,
(f) $O(CH_2CH_2O)_nR^{10}$,
(g) phenyl,
(h) cyano,
(i) nitro,
(j) $CONR^{13}R^{13}$,
(k) $CO_2R^{13}$,
(k) $S(O)_mNR^{13}R^{13}$,
(m) NH—C(=O)—$R^{13}$,
(n) $C_{1-7}$alkyl which is optionally partially unsaturated and is optionally substituted by one or more oxo, phenyl, 4-morpholine, $OR^{13}$, $SR^3$, $NR^{13}R^{13}$, halo, $CO_2R^{13}$, $CONR^{13}R^{13}$, or $C_{3-8}$cycloalkyl and which $C_{3-8}$cycloalkyl is optionally substituted by $OR^{13}$, or
(o) $C_{3-8}$cycloalkyl which is optionally partially unsaturated and is optionally substituted by one or more oxo, halo, $OR^{13}$, $SR^{13}$, Cl. $_7$alkyl, or $NR^{13}R^{13}$ substituents,
each n is independently 1, 2, 3, 4 or 5;
each m is independently 1 or 2;
wherein any aryl other than G is optionally substituted with one or more $R^{15}$ substituents; and
wherein any het is optionally substituted with one or more oxo (=O), oxime (=N—$OR^{13}$), or $R^{15}$ substituents; or a pharmaceutically acceptable salt thereof A specific group of compounds of the invention are compounds of formula II wherein the carbon bearing the hydroxy group has the same absolute configuration as the same carbon in the compound of Example 4.

A specific compound of the present invention is:
N-(4-chlorobenzyl)-7-methyl-2-(4-morpholinylmethyl)-4-oxo-4,7-dihydrofuro[2,3-b]pyridine-5-carboxamide;
N-(4-chlorobenzyl)-2-(chloromethyl)-7-methyl-4-oxo-4,7-dihydrofuro[2,3-b]pyridine-5-carboxamide;
N-(4-chlorobenzyl)-2-(((2-(2-furyl)-2-hydroxyethyl)(methyl)amino)methyl)-7-methyl-4-oxo-4,7-dihydrofuro[2,3-b]pyridine-5-carboxamide;
(+)-N-(4-chlorobenzyl)-2-(((2-(2-furyl)-2-hydroxyethyl)(methyl)amino)methyl)-7-methyl-4-oxo-4,7-dihydrofuro[2,3-b]pyridine-5-carboxamide;
(−)-N-(4-chlorobenzyl)-2-(((2-(2-furyl)-2-hydroxyethyl)(methyl)amino)methyl)-7-methyl-4-oxo-4,7-dihydrofuro[2,3-b]pyridine-5-carboxamide;
N-(4-fluorobenzyl)-2-((((2R)-2-(2-furyl)-2-hydroxyethyl)(methyl)amino)methyl)-7-methyl-4-oxo-4,7-dihydrofuro[2,3-b]pyridine-5-carboxamide;
2-((((2R)-2-(2-furyl)-2-hydroxyethyl)(methyl)amino)methyl)-7-methyl-N-(4-methylbenzyl)-4-oxo-4,7-dihydroiuro[2,3-b]pyridine-5-carboxamide;
2(((2R)-2-(2-furyl)-2-hydroxyethyl)(methyl)amino)methyl)-7-methyl-N-(3,4-difluorobenzyl)-4-oxo-4,7-dihydrofuro[2,3-b]pyridine-5-carboxamide;
2-((((2R)-2-(2-furyl)-2-hydroxyethyl)(methyl)amino)methyl)-7-methyl-N-(3,4-dichlorobenzyl)-4-oxo-4,7-dihydrofuro[2,3-b]pyridine-5-carboxamide;
2-((((2R)-2-(2-furyl)-2-hydroxyethyl)(methyl)amino)methyl)-7-methyl-N-(4-bromobenzyl)-4-oxo-4,7-dibydrofuro[2,3-b]pyridine-5-carboxamide;
2-((((2R)-2-(2-furyl)-2-hydroxyethyl)(methyl)amino)methyl)-7-methyl-N-(4-trifluoromethylbenzyl)-4-oxo-4,7-dihydrofuro[2,3-b]pyridine-5-carboxamide;
N-(4-chlorobenzyl)-7-ethyl-2-(morpholin-4-ylmethyl)-4-oxo-4,7-dihydrofuron[2,3-b]pyridine-5-carboxamide;
N-(4-chlorobenzyl)-7-cyclopropyl-2-(morpholin-4-ylmethyl)-4-oxo-4,7-dihydrofuro[2,3-b]pyridine-5-carboxamide;
N-(4-chlorobenzyl)-7-propyl-2-(morpholin-4-ylmethyl)-4-oxo-4,7-dihydrofuro[2,3-b]pyridine-5-carboxamide;
N-(4-chlorobenzyl)-2-(morpholin-4-ylmethyl)-4-oxo-7-phenyl-4,7-dihydrofuro[2,3-b]pyridine-5-carboxamide;
N-(4-chlorobenzyl)-2-(morpholin-4-ylmethyl)-4-oxo-7-(2-phenylethyl)-4,7-dihydrofuro[2,3-b]pyridine-5-carboxamide;

N-(4-chlorobenzyl)-2-(morpholin-4-ylmethyl)-4-oxo-7-pyridin-2-yl-4,7-dihydrofuron[2,3-b]pyridine-5-carboxamide;

N-(4-chlorobenzyl)-7-(2-(diethylamino)ethyl)-2-(morpholin-4-ylmethyl)-4-oxo-4,7-dihydrofuro[2,3-b]pyridine-5-carboxamide;

N4-chlorobenzyl)-2-(chloromethyl)-7-ethyl-4-oxo-4,7-dihydrofuro[2,3-b]pyridine-5-carboxamide;

N-(4-chlorobenzyl)-2-(chloromethyl)-7-cyclopropyl-4-oxo-4,7-dihydrofuro[2,3-b]pyridine-5-carboxamide;

N-(4-chlorobenzyl)-2-(chloromethyl)-4-oxo-7-propyl-4,7-dihydrofilro[2,3-b]pyridine-5-carboxamide;

N-(4-chlorobenzyl)-2-(chloromethyl)-4-oxo-7-phenyl-4,7-dihydrofuro[2,3-b]pyridine-5-carboxamide;

N-(4-chlorobenzyl)-2-(chloromethyl)-4-oxo-7-(2-phenylethyl)-4,7-dihydrofuro[2,3-b]pyridine-5-carboxamide;

N-(4-chlorobenzyl)-2-(chloromethyl)-4-oxo-7-pyridin-2-yl-4,7-dihydrofuro[2,3-b]pyridine-5-carboxamide;

N-(4-chlorobenzyl)-2-(chloromethyl)-7-(2-(diethylamino)ethyl)-4-oxo-4,7-dihydrofuro[2,3-b]pyridine-5-carboxamide;

N4-chlorobenzyl)-7-ethyl-2-((((2R)-2-(2-furyl)-2-hydroxyethyl)(methyl)amino)methyl)-4-oxo-4,7-dihydrofuro[2,3-b]pyridine-5-carboxamide;

N-(4-chlorobenzyl)-7-cyclopropyl-2-((((2R)-2-(2-furyl)-2-hydroxyethyl)(methyl)amino)methyl)-4-oxo-4,7-dihydrofuro[2,3-b]pyridine-5-carboxamide;

N-(4-chlorobenzyl)-2-((((2R)-2-(2-furyl)-2-hydroxyethyl)(methyl)amino)methyl)-4-oxo-7-propyl-4,7-dihydrofuro[2,3-b]pyridine-5-carboxamide;

N-(4-chlorobenzyl)-2-((((2R)-2-(2-furyl)-2-hydroxyethyl)(methyl)amino)methyl)-4-oxo-7-phenyl-4,7-dihydrofuro[2,3-b]pyridine-5-carboxamide;

N-(4-chlorobenzyl)-2-((((2R)-2-(2-furyl)-2-hydroxyethyl)(methyl)amino)methyl)-4-oxo-7-(2-phenylethyl)-4,7-dihydrofuro[2,3-b]pyridine-5-carboxamide;

N-(4-chlorobenzyl)-2-((((2R)-2-(2-furyl)-2-hydroxyethyl)(methyl)amino)methyl)-4-oxo-7-pyridin-2-yl-4,7-dihydrofuro[2,3-b]pyridine-5-carboxamide;

N-(4-chlorobenzyl)-7-(2-(diethylamino)ethyl)-2-((((2R)-2-(2-furyl)-2-hydroxyethyl)(methyl)amino)methyl)-4-oxo-4,7-dihydrofuro[2,3-b]pyridine-5-carboxamide;

N-(4-chlorobenzyl)-2-(((2-hydroxypropyl)amino)methyl)-7-methyl-4-oxo-4,7-dihydrofuro[2,3-b]pyridine-5-carboxamide;

N-(4-chlorobenzyl)-2-(((2-hydroxypropyl)(methyl)amino)methyl)-7-methyl-4-oxo-4,7-dihydrofuro[2,3-b]pyridine-5-carboxamide;

N-(4-chlorobenzyl)-2-(((3R)-3-hydroxypyrrolidin-1-yl)methyl)-7-methyl-4-oxo-4,7-dihydrofuro[2,3-b]pyridine-5-carboxamide;

N-(4-chlorobenzyl)-2-(((2-hydroxy-2-phenylethyl)(methyl)amino)methyl)-7-methyl-4-oxo-4,7-dihydrofuro[2,3-b]pyridine-5-carboxamide;

N-(4-chlorobenzyl)-2-(((2-hydroxy-2-(4-hydroxyphenyl)ethyl)(methyl)amino)methyl)-7-methyl-4-oxo-4,7-dihydrofulro[2,3-b]pyridine-5-carboxamide;

N-(4-chlorobenzyl)-2-(((2-hydroxy-2-(3-methoxyphenyl)ethyl)(methyl)amino)methyl)-7-methyl-4-oxo-4,7-dihydrofuro[2,3-b]pyridine-5-carboxamide;

N-(4-chlorobenzyl)-2-(((2-(4-fluorophenyl)-2-hydroxyethyl)(methyl)amino)methyl)-7-methyl-4-oxo-4,7-dihydrofuro[2,3-b]pyridine-5-carboxamide;

N-(4-chlorobenzyl)-2-(((2-(4-chlorophenyl)-2-hydroxyethyl)(methyl)amino)methyl)-7-methyl-4-oxo-4,7-dihydrofuro[2,3-b]pyridine-5-carboxamide;

N-(4-chlorobenzyl)-2-(((2-hydroxy-2-pyridin-2-ylethyl)(methyl)amino)methyl)-7-methyl-4-oxo-4,7-dihydrofuro[2,3-b]pyridine-5-carboxamide;

N-(4-chlorobenzyl)-2-(((2R)-2-hydroxy-2-pyridin-2-ylethyl)(methyl)amino)methyl)-7-methyl-4-oxo-4,7-dlhydrofuro[2,3-b]pyridine-5-carboxamide;

N-(4-chlorobenzyl)-2-(((2-hydroxy-2-pyridin-3-ylethyl)(methyl)amino)methyl)-7-methyl-4-oxo-4,7-dihydrofuro[2,3-b]pyridine-5-Carboxamide;

N-(4-chlorobenzyl)-2-(((2-hydroxy-2-pyridin-4-ylethyl)(methyl)amino)-methyl-7-methyl-4-oxo-4,7-dihydrofuro[2,3-b]pyridine-5-carboxamide;

N-(4-chlorobenzyl)-2-(((2-hydroxy-2-(5-methyl-2-furyl)ethyl)(methyl)amino)methyl)-7-methyl-4-oxo-4,7-dihydrofuro[2,3-b]pyridine-5-carboxamide;

N-(4-chlorobenzyl)-2-(((2-(3-furyl)-2-hydroxyethyl)(methyl)amino)methyl)-7-methyl-4-oxo-4,7-dihydrofuro[2,3-b]pyridine-5-carboxamide;

N-(4-chlorobenzyl)-2-(((2-hydroxy-2-(2,4,6-trifluorophenyl)ethyl)(methyl)amino)methyl)-7-methyl-4-oxo-4,7-dihydrofuro[2,3-b]pyridine-5-carboxamide;

2-(((2-(1-benzofuran-2-yl)-2-hydroxyethyl)(methyl)amino)methyl)-N-(4-chlorobenzyl)-7-methyl-4-oxo-4,7-dihydrofuro[2,3-b]pyridine-5-carboxamide;

N-(4-chlorobenzyl)-2-(((2-hydroxy-2-thien-2-ylethyl)(methyl)amino)methyl)-7-methyl-4-oxo-4,7-dihydrofuro[2,3-b]pyridine-5-carboxamide;

N-(4-chlorobenzyl)-2-(((2-hydroxy-2-quinolin-2-ylethyl)(methyl)amino)methyl)-7-methyl-4-oxo-4,7-dihydrofuro[2,3-b]pyridine-5-carboxamide;

N-(4-chlorobenzyl)-2-(((2-hydroxy-2-(1-methyl-1H-pyrrol-2-yl)ethyl)(methyl)amino)methyl)-7-methyl-4-oxo-4,7-dihydrofuro[2,3-b]pyridine-5-carboxamide;

N-(4-chlorobenzyl)-2-(((2-(5-cyanothien-2-yl)-2-hydroxyethyl)(methyl)amino)methyl)-7-methyl-4-oxo-4,7-dihydrofuro[2,3-b]pyridine-5-carboxamide;

N-(4-chlorobenzyl)-2-(((2-hydroxy-2-(1,3-thiazol-2-yl)ethyl)(methyl)amino)methyl)-7-methyl-4-oxo-4,7-dihydrofuro[2,3-b]pyridine-5-carboxamide;

N-(4-chlorobenzyl)-2-(((2-hydroxy-2-(5-phenyl-2-furyl)ethyl)(methyl)amino)methyl)-7-methyl-4-oxo-4,7-dihydrofuro[2,3-b]pyridine-5-carboxamide;

N(4-chlorobenzyl)-2-(((2-(4,5-dimethyl-2-furyl)-2-hydroxyethyl)(methyl)amino)methyl)-7-methyl-4-oxo-4,7-dihydrofuro[2,3-b]pyridine-5-carboxamide;

(+)-N-(4-chlorobenzyl)-2-(((2-hydroxy-2-pyrazin-2-ylethyl)(methyl)amino)methyl)-7-methyl-4-oxo-4,7-dihydrofuro[2,3-b]pyridine-5-carboxamide;

(+)-N-(4-chlorobenzyl)-2-(((2-hydroxy-2-pyrimidin-2-ylethyl)(methyl)amino)methyl)-7-methyl-4-oxo-4,7-dihydrofuro[2,3-b]pyridine-5-carboxamide;

N-(4-chlorobenzyl)-2-(((3-hydroxy-2-phenylpropyl)(methyl)amino)methyl)-7-methyl-4-oxo-4,7-dihydrofuro[2,3-b]pyridine-5-carboxamide;

N-(4-chlorobenzyl)-2-(((2R*)-2-((S*)-hydroxy(phenyl)methyl)pyrrolidin-1-yl)methyl)-7-methyl-4-oxo-4,7-dihydrofuro[2,3-b]pyridine-5-carboxamide;

N-(4-chlorobenzyl)-2-(((2R*)-2-((R*)-2-furyl(hydroxy)methyl)-pyrrolidin-1-yl)methyl)-7-methyl-4-oxo-4,7-dihydrofuro[2,3-b]pyridine-5-carboxamide;

N-(4-chlorobenzyl)-2-(((2R)-2-((R)-hydroxy(pyridin-2-yl)methyl)-pyrrolidin-1-yl)methyl)-7-methyl-4-oxo-4,7-dihydrofuro[2,3-b]pyridine-5-carboxamide;

N-(4-chlorobenzyl)-7-methyl-2-((methylamino)methyl)-4-oxo-4,7-dihydrofuro[2,3-b]pyridine-5-carboxamide;

N-(4-chlorobenzyl)-2-(((3-chloro-2-hydroxypropyl)amino)methyl)-7-methyl-4-oxo-4,7-dihydrofuro[2,3-b]pyridine-5-carboxamide;

N-(4-chlorobenzyl)-2-(((2-hydroxy-3-((2-methoxyphenyl)thio)propyl)(methyl)amino)methyl)-7-methyl-4-oxo-4,7-dihydrofuro[2,3-b]pyridine-5-carboxamide;

2-(((3-((5-amino-1,3,4-thiadiazol-2-yl)thio)-2-hydroxypropyl)(methyl)amino)methyl)-N-(4-chlorobenzyl)-7-methyl-4-oxo-4,7-dihydrofuro[2,3-b]pyridine-5-carboxamide;

2-(((3-((3-amino-1H-1,2,4-triazol-5-yl)thio)-2-hydroxypropyl)(methyl)amino)methyl)-N-(4-chlorobenzyl)-7-methyl-4-oxo-4,7-dihydrofuro[2,3-b]-pyridine-5-carboxamide;

2-(((3-((4-aminopyrimidin-2-yl)thio)-2-hydroxypropyl)(methyl)amino)methyl)-N-4-chlorobenzyl)-7-methyl-4-oxo-4,7-dihydrofuro[2,3-b]-pyridine-5-carboxamide;

N-(4-chlorobenzyl)-2-(((2-hydroxy-3-((3-methoxyphenyl)thio)propyl)(methyl)amino)methyl)-7-methyl-4-oxo-4,7-dihydrofuro[2,3-b]pyridine-5-carboxamide;

N-(4-chlorobenzyl)-2-(((2-hydroxy-3-((4-methoxyphenyl)thio)propyl)(methyl)amino)methyl)-7-methyl-4-oxo-4,7-dihydrofuro[2,3-b]pyridine-5-carboxamide;

2-((3-(((5-(((4-chlorobenzyl)amino)carbonyl)-7-methyl-4-oxo-4,7-dihydrofuro[2,3-b]pyridin-2-yl)methyl)(methyl)amino)-2-hydroxypropyl)thio)benzoic acid;

2-((3-(((5-(((4-chlorobenzyl)amino)carbonyl)-7-methyl-4-oxo-4,7-dihydrofuro[2,3-b]pyridin-2-yl)methyl)(methyl)amino)-2-hydroxypropyl)thio)nicotinic acid;

N-(4-chlorobenzyl)-2-(((2-hydroxy-3-((4-oxo-3,4-dihydroquinazolin-2-yl)thio)propyl)(methyl)amino)methyl)-7-methyl-4-oxo-4,7-dihydrofuro[2,3-b]-pyridine-5-carboxamide;

2-(((3-((6-amino-1,3-benzothiazol-2-yl)thio)-2-hydroxypropyl)(methyl)amino)methyl)-N-(4-chlorobenzyl)-7-methyl-4-oxo-4,7-dihydrofuro[2,3-b]-pyridine-5-carboxamide;

N-(4-chlorobenzyl)-2-(((2-hydroxy-3-(9H-purin-6-ylthio)propyl)(methyl)amino)methyl)-7-methyl-4-oxo-4,7-dihydrofuro[2,3-b]pyridine-5-carboxamide;

2-(((3-(benzylthio)-2-hydroxypropyl)(methyl)amino)methyl)-N-(4-chlorobenzyl)-7-methyl-4-oxo-4,7-dihydrofuro[2,3-b]pyridine-5-carboxamide;

N-(4-chlorobenzyl)-2-(((3-((4-chlorobenzyl)thio)-2-hydroxypropyl)(methyl)amino)methyl)-7-methyl-4-oxo-4,7-dihydrofuro[2,3-b]pyridine-5-carboxamide;

N-(4-chlorobenzyl)-2-(((2-hydroxy-3-((4-methoxybenzyl)thio)propyl)(methyl)amino)methyl)-7-methyl-4-oxo-4,7-dihydrofuro[2,3-b]pyridine-5-carboxamide;

N-(4-chlorobenzyl)-7-methyl-4-oxo-4,7-dihydrofuro[2,3-b]pyridine-5-carboxamide;

2-bromo-N-(4-chlorobenzyl)-7-methyl-4-oxo-4,7-dihydrofuro[2,3-b]-pyridine-5-carboxamide;

N-(4-chlorobenzyl)-2-(3-hydroxyprop-1-ynyl)-7-methyl-4-oxo-4,7-dihydrofuro[2,3-b]pyridine-5-carboxamide;

N-(4-chlorobenzyl)-2-(3-hydroxypropyl)-7-methyl-4-oxo-4,7-dihydrofuro[2,3-b]pyridine-5-carboxamide;

N-(4-chlorobenzyl)-2-(4-hydroxybut-1-ynyl)-7-methyl-4-oxo-4,7-dihydrofuro[2,3-b]pyridine-5-carboxamide;

N-(4-chlorobenzyl)-2-(4-hydroxybutyl)-7-methyl-4-oxo-4,7-dihydrofuro[2,3-b]pyridine-5-carboxamide;

N-(4-chlorobenzyl)-2-(5-hydroxypent-1-ynyl)-7-methyl-4-oxo-4,7-dihydrofuro[2,3-b]pyridine-5-carboxamide;

N-(4-chlorobenzyl)-2-(5-hydroxypentyl)-7-methyl-4-oxo-4,7-dihydrofuro[2,3-b]pyridine-5-carboxamide;

N-(4-chlorobenzyl)-2-(3-hydroxy-3-phenylprop-1-ynyl)-7-methyl-4-oxo-4,7-dihydrofuro[2,3-b]pyridine-5-carboxamide;

N-(4-chlorobenzyl)-2-(3-hydroxy-3-phenylpropyl)-7-methyl-4-oxo-4,7-dihydrofuro[2,3-b]pyridine-5-carboxamide;

N-(4-chlorobenzyl)-2-(4-hydroxy 4-phenylbut-1-ynyl)-7-methyl-4-oxo-4,7-dihydrofuro[2,3-b]pyridine-5-carboxamide;

N-(4-chlorobenzyl)-2-(4-hydroxy-4-phenylbutyl)-7-methyl-4-oxo-4,7-dihydrofuro[2,3-b]pyridine-5-carboxamide;

N-(4-chlorobenzyl)-2-(4-(2-furyl)-4-hydroxybut-1-ynyl)-7-methyl-4-oxo-4,7-dihydrofuro[2,3-b]pyridine-5-carboxamide;

N-(4-chlorobenzyl)-2-(42-furyl)-4-hydroxybutyl)-7-methyl-4-oxo-4,7-dihydrofuro[2,3-b]pyridine-5-carboxamide;

N-(4-chlorobenzyl)-2-(4-hydroxy-4-pyridin-3-ylbut-1-ynyl)-7-methyl-4-oxo-4,7-dihydrofuro[2,3-b]pyridine-5-carboxamide;

N-(4-chlorobenzyl)-2-(4-hydroxy-4-pyridin-3-ylbutyl)-7-methyl-4-oxo-4,7-dihydrofuro[2,3-b]pyridine-5-carboxamide;

N-(4-chlorobenzyl)-2-(4-hydroxy-4-pyridin-2-ylbut-1-ynyl)-7-methyl-4-oxo-4,7-dihydrofuro[2,3-b]pyridine-5-carboxamide;

N-(4-chlorobenzyl)-2-(4-hydroxy-4-pyridin-2-ylbutyl)-7-methyl-4-oxo-4,7-dihydrofuro[2,3-b]pyridine-5-carboxamide;

N-(4-chlorobenzyl)-2-(ethoxymethyl)-7-methyl-4-oxo-4,7-dihydrofuro[2,3-b]pyridine-5-carboxamide;

N-(4-chlorobenzyl)-2-(hydroxymethyl)-7-methyl-4-oxo-4,7-dihydrofuro[2,3-b]pyridine-5-carboxamide;

N-(4-chlorobenzyl)-2-((((2S)-2-hydroxy-2-phenylethyl)oxy)methyl)-7-methyl-4-oxo-4,7-dihydrofuro[2,3-b]pyridine-5-carboxamide; or N-((4-chlorophenyl)methyl)-5(4-chlorophenyl)methylaminocarbonyl)-4-hydroxyfuro[2,3-b]pyridine-2-carboxamide.

The present invention includes a pharmaceutically acceptable salt of any of the above mentioned compounds.

Specifically, the invention provides the synthetic processes and intermediates described in Preparations and examples hereinbelow.

The following Charts A-AA describe the preparation of the compounds of the present invention. All of the starting materials are prepared by procedures described in these charts or by procedures analogous thereto, which would be well known to one of ordinary skill in organic chemistry. All of the final compounds of the present invention are prepared by procedures described in these charts, by procedures analogous thereto, or by procedures which are known to one of ordinary skill in organic chemistry. All of the variables used in the charts are as defined below or as in the claims.

As described in Chart A, amine A.2 can be prepared by reduction of 5-nitro-2-furonitrile (A.1). Compound A.2 can then be heated with, for example, diethyl ethoxymethylenemalonate followed by thermolysis in diphenyl ether to yield the ester A.4. Compound A.4 can be alkylated at the ring nitrogen, for example, by treatment with an optionally substituted alkyl halide or alkyl sulfonate ester in the presence of a base (e.g. potassium carbonate) or by reaction with an optionally substituted alkanol under Mitsunobu conditions to afford compounds of the general formula A.5 where R is a subset of $R^5$. Treatment of compounds of the formula A.5 with, for example, Raney Nickel yields aldehyde compounds of the general formula A.6. Compounds of the formula A.6 can undergo reductive amination with amines ($HNR^7R^8$) to yield derivatives of the general formula A.7 which can then be condensed with a benzylamine (e.g. 4-chlorobenzylamine, 4-bromobenzylamine, or 4-fluorobenzylamine) at high temperature to afford the corresponding amides of the general formula A.8. Alternatively, ester A.7 can be saponified to afford the corresponding acid which can then be coupled with a benzylamine mediated by 1,1'-carbonyldiimidazole (or other suitable carboxylic acid activating agent) to likewise provide amides of the general formula A.8.

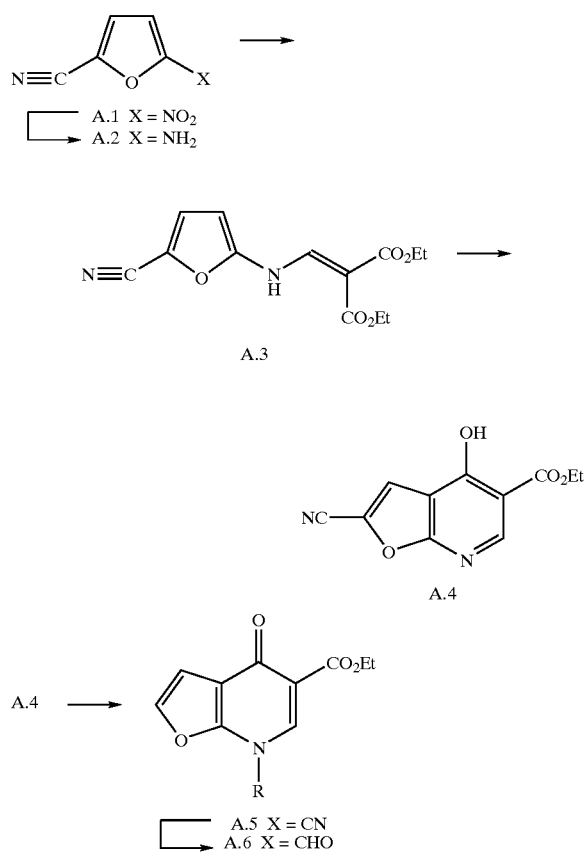

CHART A

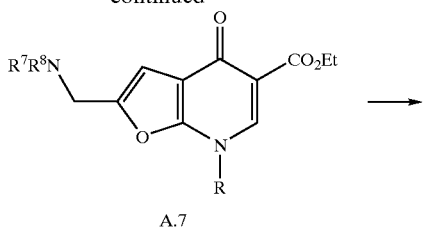

A.6 →

A.7

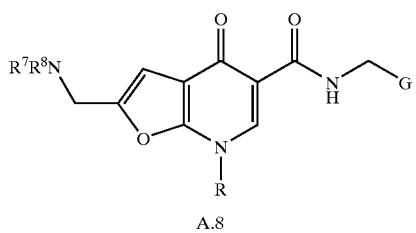

A.8

As described in Chart B, compounds of the formula B.1 are treated with a primary or secondary amine ($R^7R^8NH$) and specifically amines of the formula $R^{16}CH(OH)CH_2NH(R^{17})$ (Chart C) in the presence of a non-nucleophilic base (e.g. diisopropylethylamine or potassium carbonate) in a polar solvent (e.g. DMF or acetonitrile) to afford products of the formula B.2 or C.1. It would be understood by those skilled in the art that in some cases transient protection of hydroxyl and other Lewis basic or acidic functionality present in the amine $R^7R^8NH$ or $R^{16}CH(OH)CH_2NH(R^{17})$ may be required to facilitate the coupling described in Chart B or Chart C for which procedures are well established (Greene, T. W.; Wuts, P. G. M. *Protective Groups in Organic Synthesis*, 1999).

CHART B

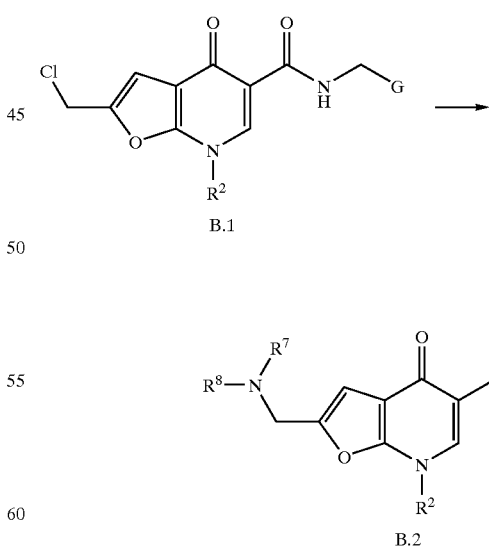

CHART C

B.1 →

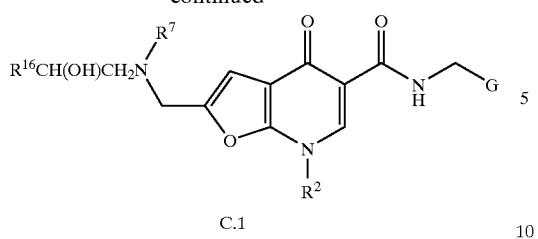

C.1

Alternatively, compounds of Formula (I) and Formula (II) are prepared as described in Chart D. Compounds of the formula B.1 are treated with a primary amine such as of the formula $R^{16}CH(OH)CH_2NH_2$ in the presence of a non-nucleophilic base (e.g. diisopropylethylamine) in a polar solvent (e.g. DMF) to afford products of the formula D.1. The resulting secondary amine is then alkylated by reactions generally known by those skilled in the art such as (1) the reaction of D.1 with a corresponding alkylhalide, dialkylsulfonate, or alkylarylsulfonate or (2) the reaction of D.1 with an aldehyde (e.g. formaldehyde or acetaldehyde) in the presence of a reducing agent (e.g. sodium cyanoborohydride or sodium triacetoxyborohydride) to afford compounds of the general formula C.1.

CHART D

B.1 ⟶

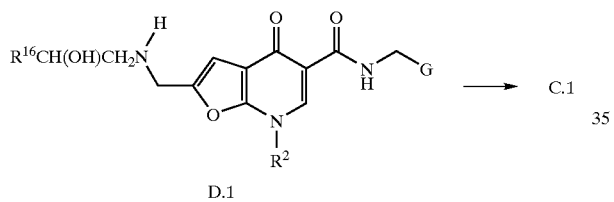

D.1 ⟶ C.1

Alternatively, compounds of Formula (I) and Formula (II) are prepared as described in Chart E. Compounds of the formula B.1 are treated with an alkyl primary amine (e.g. methylamine or ethylamine) in the presence of a non-nucleophilic base (e.g. diisopropylethylamine) or in the presence of a large excess of the respective primary amine in a polar solvent (e.g. DMF, tetrahydrofuran, acetonitrile, methanol, or ethanol) to afford products of the formula E.1. The resulting secondary amine is then treated with an electrophile either of the formula $R^{16}CH(OH)CH_2X$ (where X is Cl, Br) in the presence of a non-nucleophilic base (e.g. diisopropylethylamine) in a polar solvent (e.g. DMF) or with an epoxide to afford products of the formula C.1. Alternatively, compounds of the formula E.1 are alkylated with 2-haloketones of the formula $R^{16}C(O)CH_2X$ (where X is Cl, Br) according to Chart F to afford products of the formula F.1. The resulting amino ketones are then reduced with an appropriate achiral or chirally-modified reducing agent (e.g. $NaBH_4$ or diisopinocamphenylchloroborane) to provide compounds of the formula C.1. Alternatively, compounds of the formula E.1 are treated with sulfonic acid chlorides, carboxylic acid chlorides, carboxylic acid anhydrides, or other suitably activated carboxylic acid derivative according to Chart G to provide carboxamides (X=C(=O)) or sulfonamides ($X=SO_2$) of the formula G.1.

CHART E

B.1 ⟶

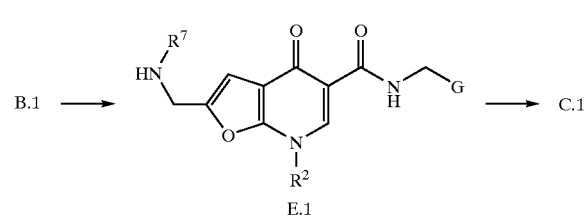

E.1

CHART F

E.1 ⟶

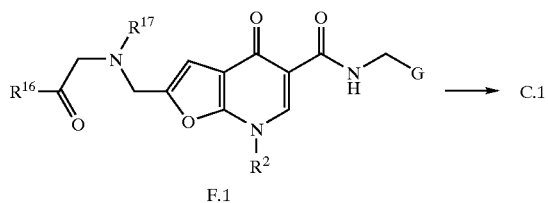

F.1 ⟶ C.1

CHART G

E.1 ⟶

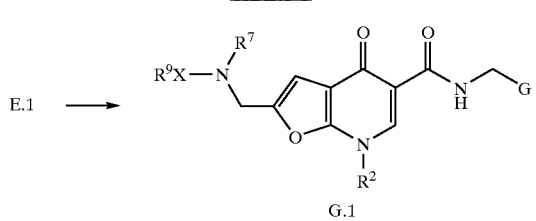

G.1

Thioether derivatives of Formula (I) may be prepared as described in Chart H. Secondary amines of the formula E.1 are reacted with epi-chlorohydrin to afford alkyl chlorides of the formula H.1. In a similar fashion, longer chain haloalkylepoxides (e.g., 2-(2-bromoethyl)oxirane or 2-(3-bromopropyl)oxirane) react with E.1 to afford oxiranes of the formula H.2 (n=2–5). Treatment of either H.1 or H.2 with thiols of the formula $R^{12}SH$ in the presence of a non-nucleophilic base (e.g. diisopropylethylamine) in a polar solvent (e.g. ethanol) affords thioether derivatives of the formula H.3 (k=1–5). It is understood by those skilled in the art of organic synthesis that the precursor oxiranes may be employed in racemic or scalemic form to afford products H.3 in racemic or scalemic forms, respectively. Compounds of the formula H.3 may be oxidized with an appropriate oxidizing reagent (e.g. m-chloroperbenzoic acid) according to Chart I to provide sulfoxides (m=1) and sulfones (m=2) of the formula I.1 (k=1–5).

CHART H

E.1 ⟶

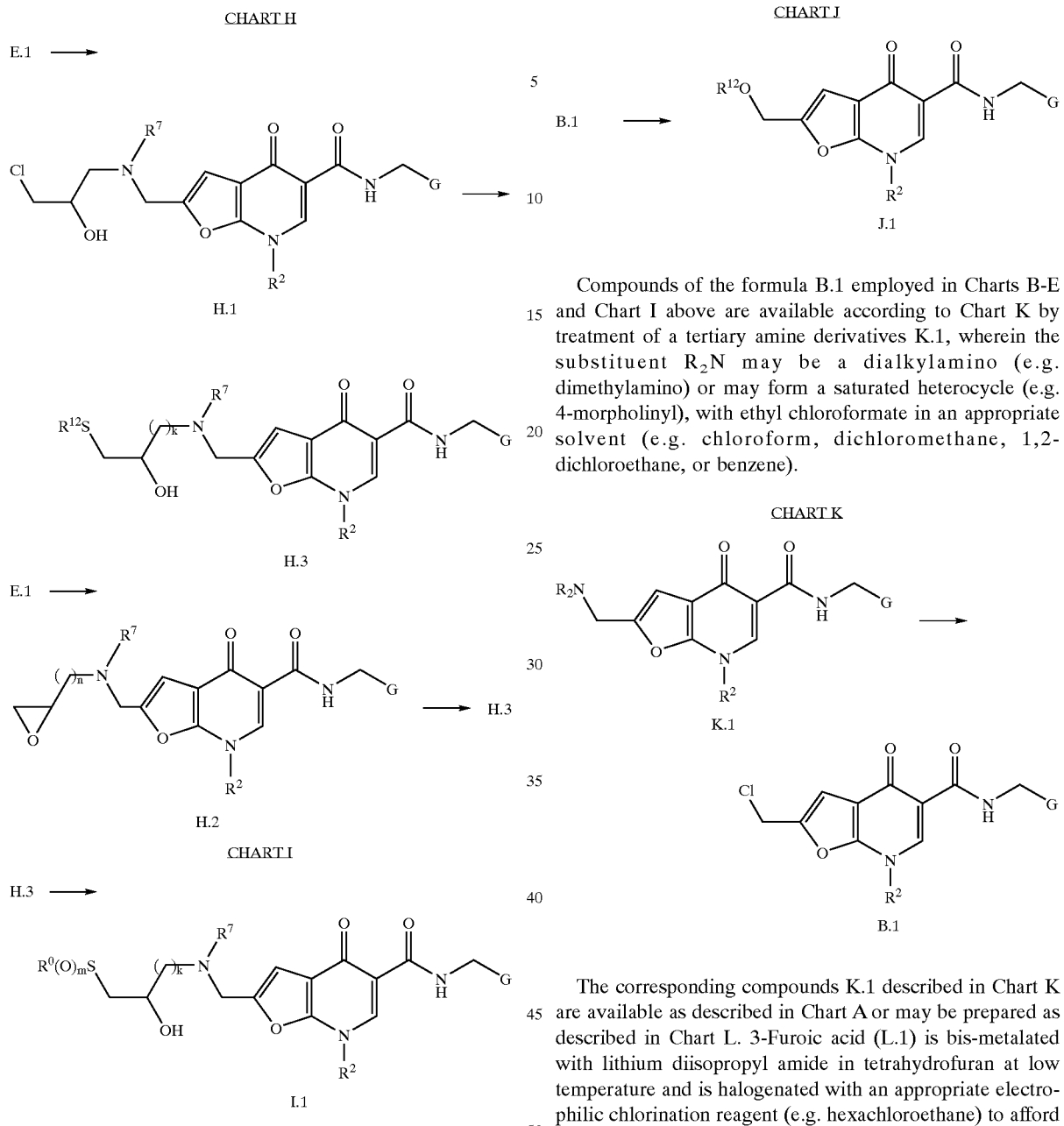

Compounds of Formula (I) may also be prepared according to Chart J. Compounds of the formula B.1 may be converted to the corresponding alcohols J.1 ($R^{12}$=H) by heating a solution in a polar solvent (e.g. DMF) containing alkali (aqueous potassium hydroxide or sodium bicarbonate). Alcohol solutions (e.g. ethanol or methanol) of B.1 may be treated with a solution of potassium hydroxide to afford alkyl ethers J.1 (e.g. $R^{12}$=methyl or ethyl). Ether derivatives J.1 wherein $R^{12}$ is $C_{1-7}$alkyl or $C_{3-8}$cycloalkyl optionally substituted in accordance to described herein including at least on hydroxy group are prepared by the treatment of B.1 with a corresponding diol in the presence of dibutyltin oxide and cesium fluoride in a polar solvent (e.g. DMF) (Nagashima, N.; Ohno, M. *Chem. Pharm. Bull.* 1991, 39, 1972–1982).

Compounds of the formula B.1 employed in Charts B-E and Chart I above are available according to Chart K by treatment of a tertiary amine derivatives K.1, wherein the substituent $R_2N$ may be a dialkylamino (e.g. dimethylamino) or may form a saturated heterocycle (e.g. 4-morpholinyl), with ethyl chloroformate in an appropriate solvent (e.g. chloroform, dichloromethane, 1,2-dichloroethane, or benzene).

The corresponding compounds K.1 described in Chart K are available as described in Chart A or may be prepared as described in Chart L. 3-Furoic acid (L.1) is bis-metalated with lithium diisopropyl amide in tetrahydrofuran at low temperature and is halogenated with an appropriate electrophilic chlorination reagent (e.g. hexachloroethane) to afford the carboxylic acid L.2. The acid is then converted to the corresponding imidazolide in-situ which is coupled with potassium ethyl malonate in the presence of a magnesium salt (e.g. $MgCl_2$) and a tertiary amine base (e.g. triethylamine) to provide ester L.3. Compound L.3 is then refluxed in a mixture of acetic anhydride and triethylorthoformate to afford an intermediate enol ether which is then condensed with a compound of the formula $R^2NH_2$, followed by treatment with a base (e.g. potassium tert-butoxide) to provide a compound of the formula L.4. The reagent employed in this step according to the formula $R^2NH_2$ may be primary amines, anilines, or aminoheterocycles (e.g. methylamine, ethylamine, propylamine, cyclopropylamine, phenethylamine, 3-amino-1-propanol, 5-amino-1-pentanol, aniline, 2-aminopyridine, or N,N-diethylethylenediamine). Other reagents of the formula $R^2NH_2$ include hydrazines (e.g. 1,1-dimethylhydrazine, 4-aminomorpholine, or 1-aminopiperidine), primary sulfonamides (e.g. methanesulfonamide or benzenesulfonamide), or alkoxyamines (e.g. methoxyamine or O-(tert-butyl)hydroxylamine). Condensation of L.4 with an iminium ion such as 4-methylenemorpholin-4-ium chloride ($R_2N$=mopholinyl) or dimethyl-(methylene)ammonium iodide (R=methyl) affords a tertiary amine of the formula L.5. The resulting ester is then treated with a benzylamine (e.g. 4-chlorobenzylamine, 4-fluorobenzylamine, or 4-bromobenzylamine) either in methanol with sodium methoxide as catalyst or in ethylene glycol with heating to afford carboxamides of the formula L.6.

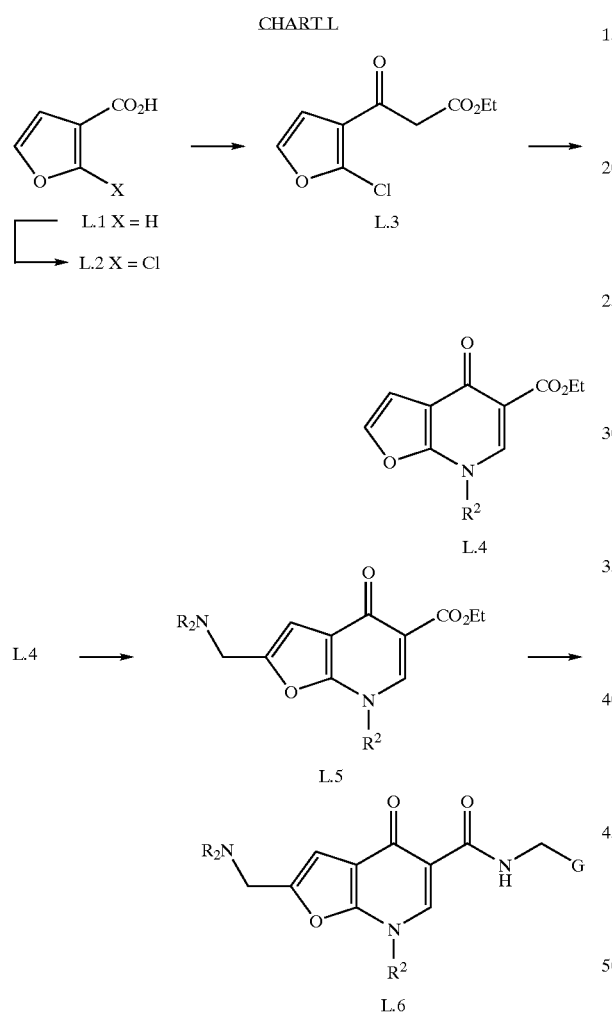

The amine ($R^7R^8NH$) in Chart B and specifically amines of the formula $R^{16}CH(OH)CH_2NH(R^{17})$ employed in Chart C may be commercially available, can be prepared by procedures know to those skilled in the art, or can be prepared by methods illustrated in Charts M-S. As shown in Chart M, commercially available methylketones M.1 can be halogenated (X=Cl, Br) to provide the haloketones of the formula M.2. The resulting haloketones can be reduced to yield the corresponding halohydrins M.3 employing either achiral (e.g. $NaBH_4/CeCl_3$) or chiral reduction conditions (e.g. Hamada, T.; Torii, T.; Izawa, K.; Noyori, R.; Ikariya, T. Org. Lett. 2002, 4, 4373–4376). The resulting halohydrin is then treated with a primary amine (e.g. methylamine or ethylamine) to afford amines of the formula M.5.

Alternatively, the haloketones can be treated directly with the primary amine (e.g. methylamine or ethylamine) to provide an aminoketone M.4 which can then be reduced under achiral or chiral reduction conditions (Ohkuma, T.; Ishii, D.; Takeno, H.; Noyori, R. J. Am. Chem. Soc. 2000, 122, 6510–6511; Kawamoto, A.; Wills, M. Tetrahedron. Asymmetry 2000, 11, 3257–3261) to afford compounds of the formula M.5. In this case, the basic nitrogen may require transient protection (e.g. tert-butylcarbamate) to facilitate the reduction. The precursor N-Boc aminoketones N.2 may be prepared as described in Chart N in which a Weinreb amide derivative ($Y=N(CH_3)(OCH_3)$), prepared by methods well know in the literature, e.g. Sibi, M. Org. Prep. Proc. Int. 1993, 25, 15–40) is reacted with metalated tert-butyl dimethylcarbamate in the presence of tetramethylethylenediamine at low temperature. Other compounds of the formula N.1 which also undergo this reaction include carboxamides wherein Y=4-morpholine and thiol esters (e.g. Y=SPh).

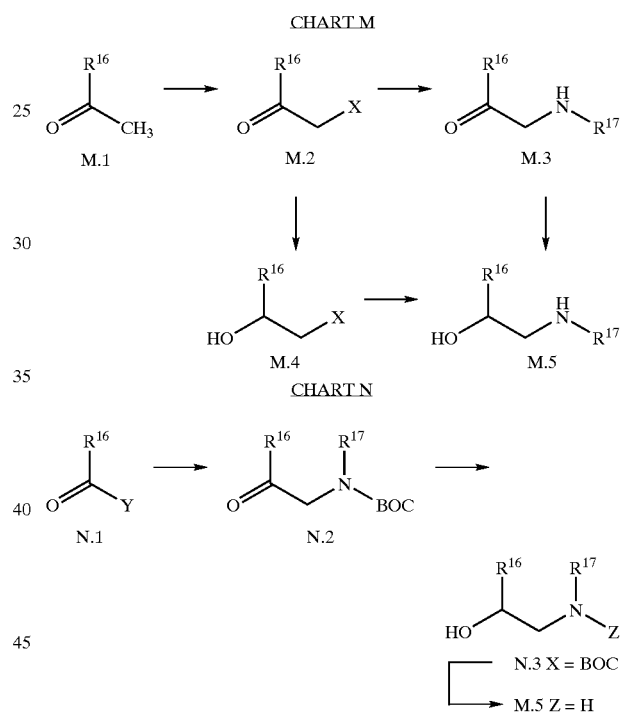

Alternatively, as shown in Chart O specific amines of the formula $R^{16}C(OH)CH_2NH(R^{17})$ can be prepared from carboxaldehydes O.1 which are commercially available or prepared by methods known to those skilled in the art. Epoxidation of O.1 with a sulfonium ylide (e.g. trimethylsulfonium iodide) affords epoxides of the formula O.2. Treatment of the epoxides with a primary amine (e.g. methylamine or ethylamine) provides compounds of the formula M.5.

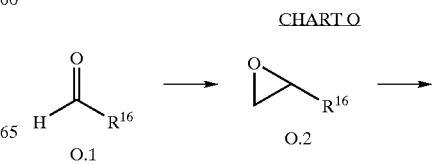

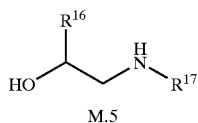

M.5

As shown in Chart P, specific amines of the formula $R^{16}R^{18}C(OH)CH_2NH(R^{17})$ (wherein $R^{18}$ is H or $C_{1-3}$alkyl optionally substituted with one or more hydroxy) are also prepared from carbonyl derivatives P.1 by the reaction with metalated tert-butyl dimethylcarbamate in the presence of tetramethylethylenediamine at low temperature to afford the BOC-protected amino alcohol P.2. Subsequent cleavage under acidic conditions (e.g. trifluoroacetic acid or hydrochloric acid) or oxazolidinone cyclization under basic conditions (e.g. sodium hydride) followed by basic hydrolysis provides compounds of the formula P.3. In cases where $R^{18}$ is $C_{1-3}$alkyl substituted with one or more hydroxy, the hydroxyl group is transiently protected using common protecting groups (Greene, T. W.; Wuts, P. G. M. *Protective Groups in Organic Synthesis*, 1999) and then deprotected either prior to or after coupling as described in Chart B.

CHART P

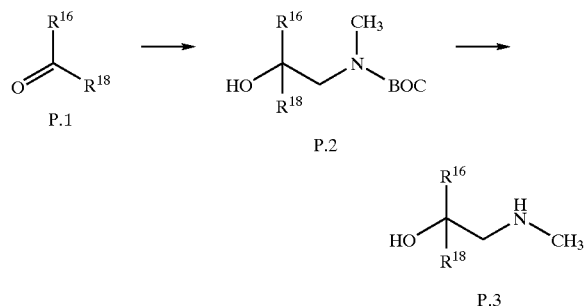

In cases where the $R^{18}$ substituent of the amine $R^{16}R^{18}C(OH)CH_2NH(R^{17})$ is methyl or ethyl, the amine may be prepared as described in Chart Q. The olefin Q.1 is reacted with N-bromosuccinimide in an ether solvent employing a catalytic amount sulfuric acid to afford the bromohydrin Q.2. The resulting bromohydrin is then treated with a primary amine (e.g. methylamine or ethylamine) to afford amines of the formula Q.3.

CHART Q

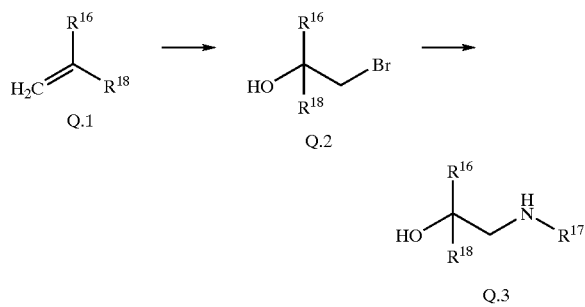

Specific amines of the formula $R^{16}CH(OH)CH_2NH(CH_3)$ are also available from primary amines of the formula $R^{16}CH(OH)CH_2NH_2$ according to methods described in Chart R.1. An amino alcohol of the formula R.1 is treated with dimethyl carbonate and potassium tert-butoxide to afford an oxazolidinone of the formula R.2. The resulting oxazolidinone is subsequently hydrolyzed in the presence of aqueous alkali (e.g. potassium hydroxide) to provide an amino alcohol of the formula R.3.

CHART R

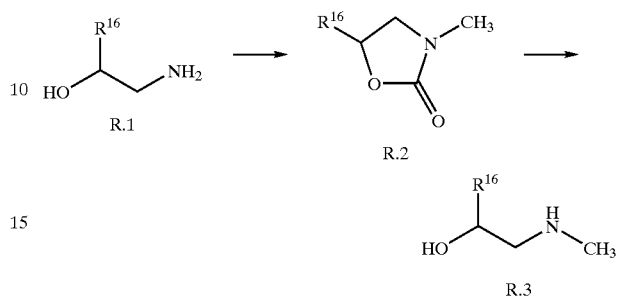

Specific secondary amines utilized in Chart B of the formula H-W-A (wherein W is a saturated heterocycle containing nitrogen) or in which the substituent $NR^7R^8$ forms a heterocyclic ring are prepared according to literature procedures or adaptations there of, Chart S. Amines of the formula S.1 may be prepared by procedures described by Cooper, G. F.; McCarthy, K. E.; Martin, M. G. *Tetrahedron Lett.* 1992, 33, 5895–5896 (a specific example of $R^{10}$ being 3,4-dimethoxyphenyl); Gaur, S. P.; Jain, P. C.; Anand, N. *Ind. J. Chem. B,* 1982, 21, 46–51 (specific examples of $R^{10}$ being phenyl, 3-methoxyphenyl, 1-naphthyl, and 2-naphthyl). Amines of the formula S.2 may be prepared by procedures described by Tsutsumi, S.; Okonogi, T; Shibahara, S.; Ohuchi, S.; Hatsushiba, E.; Patchett, A. A.; Christensen, B. G. *J. Med. Chem.* 1994, 37, 3492–3502 (specific examples of $R^{10}$ being thiazol-2-yl, thiopen-2-yl, benzothiazol-2-yl, thiazol-5-yl, imidazol-2-yl, pyridin-2-yl, pyridin-3-yl, pyrimidin-5-yl, benzoxazol-2-yl, oxazolo[4,5-b]pyridin-2-yl, thiazolin-2-yl, and thiazol-4-yl); Sanner, M. A. *Tetrahedron Lett.* 1989, 30, 1909–1912 (specific examples of $R^{10}$ being 4-fluorophenyl, 4-chlorophenyl, 4-bromophenyl, 4-methylphenyl, and 4-methoxyphenyl). Amines of formula S.3 may be prepared by procedures described by Gottlieb, L.; Meyers, A. I. *Tetrahedron Lett.* 1990, 31, 4723–4726 (a specific example of $R^{10}$ being phenyl); Kanao, M.; Hashizume, T.; Ichikawa, Y.; Irie, K.; Satoh, Y.; Isoda, S. *Chem. Pharm. Bull.* 1982, 30, 180–188 (a specific example of $R^{10}$ being 4-methoxyphenyl); Cardellini, M.; Claudi, F.; Perlini, V.; Balduini, W.; Cattabeni, F.; Cimino, M. *Farmaco Ed. Sci.* 1987, 42, 307–318 (specific examples of $R^{10}$ being 3-methoxyphenyl and 3,4-dimethoxyphenyl); Panizzon, L. *Helv. Chim. Acta* 1944, 27, 1748–1456 (a specific example of $R^{10}$ being naphth-1-yl); Seibert, R. A.; Norton, T. R.; Bensen, A. A.; Bergstrom, F. W. *J. Am. Chem. Soc.* 1946, 68, 2721–2723 (a specific example of $R^{10}$ being quinolin-2-yl). Amines of formula S.4 may be prepared by procedures described by Sanner, M. A. *Tetrahedron Lett.* 1989, 30, 1909–1912 (specific examples of $R^{10}$ being phenyl, 4-fluorophenyl, and 4-methoxyphenyl); Wollweber, H.; Hiltmann, R.; Stoepel, K.; Kroneberg, H. G. *Eur. J. Med. Chem—Chim. Therapeutica* 1980, 15, 111–117 (specific examples of $R^{10}$ being 3-methylphenyl, 4-methylphenyl, 3-methoxyphenyl, 4-chlorophenyl, and 3-chlorophenyl); Seibert, R. A.; Norton, T. R.; Bensen, A. A.; Bergstrom, F. W. *J. Am. Chem. Soc.* 1946, 68, 2721–2723 (a specific example of R10 being quinolin-3-yl); Sencar, A. E.; Sargent, H.; Mead, J. F.; Koepfli, J. B. *J. Am. Chem. Soc.* 1946, 68, 2695–2697 (a specific example of $R^{10}$ being quinolin-4-yl). Amines of the formula S.5 may be prepared by procedures described by Shawe, T. T.; Koenig, G. J., Jr.; Ross, A. A. *Syn. Commun.* 1997, 27, 1777–1782 (a specific example of $R^{10}$ being phenyl). Amines of the formula S.6 may be prepared by procedures described by Crabb, T. A.; Hall, M. J. *J. Chem. Soc., Perkin Trans.* 2, 1974, 1419–1423 (a specific example of $R^{10}$ being phenyl). Amines of the formula S.7 may be prepared by procedures described by Ohlmacht, C. J., Jr.; McLeren, F. M. *J. Heterocyclic Chem.* 1991, 28, 1219–1224 (specific examples of $R^{10}$ being phenyl, 4-methoxyphenyl, and 3-chloro-4-methoxyphenyl).

CHART S

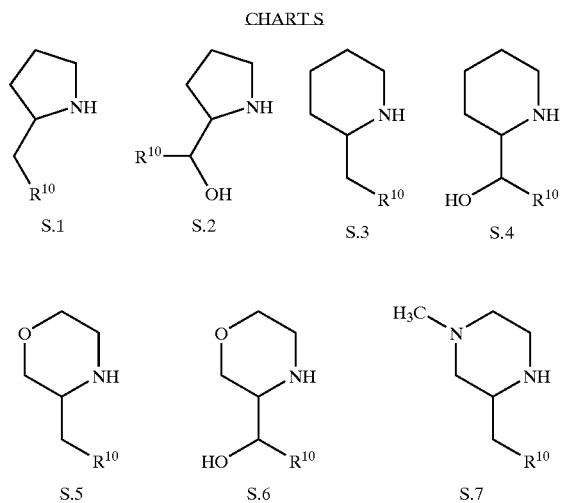

Additional specific secondary amines utilized in Chart B of the formula H-W-A (wherein W is a saturated heterocycle containing nitrogen) are prepared as described in Chart T. N-Boc-pyrrolidine (T.1) is metalated under the conditions described by Beak, P.; Lee, W. K. *J. Org. Chem.* 1993, 58, 1109–1117. The resulting anion is treated with aromatic or heteroaromatic carboxaldehydes (e.g. benzaldehyde) to afford the corresponding addition products (T.2). Deprotection employing common procedures (e.g. trifluoroacetic acid followed by neutralization) provides amino alcohols of the formula T.3.

CHART T

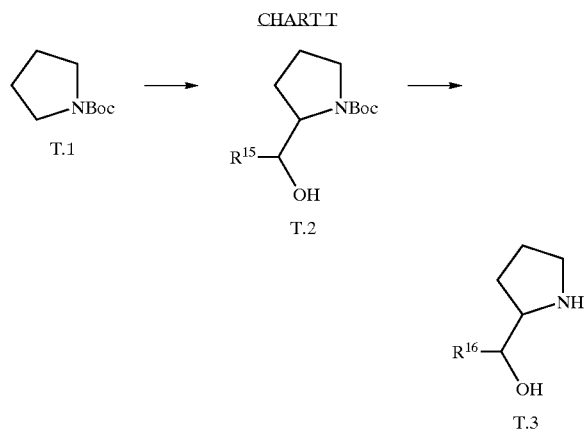

Methods to prepare primary amines of the formula $R^{16}CH(OH)CH_2NH_2$ utilized in Chart D and Chart R are well known to those skilled in the art of organic synthesis (Bergmeier, S. C. *Tetrahedron* 2000, 56, 2561–2576; Ager, D. J.; Prakash, I.; Schaad, D. R. *Chem. Rev.* 1996, 96, 835–875; Watanabe, M; Murata, K.; Ikariya, T. *J. Org. Chem.* 2002, 67, 1712–1715.).

Alternatively, compounds of the formula B.2 may be prepared according to Chart U by treatment of a tertiary amine derivatives L.5, wherein the substituent $R_2N$ may be a dialkylamino (e.g. dimethylamino) or may form a saturated heterocycle (e.g. 4-morpholinyl), with ethyl chloroformate in an appropriate solvent (e.g. chloroform, dichloromethane, 1,2-dichloroethane, or benzene) to provide alkyl chlorides U.1. Compounds of the formula U.1 are treated with a secondary amine ($R^7R^8NH$) in the presence of a non-nucleophilic base (e.g. diisopropylethylamine or potassium carbonate) in a polar solvent (e.g. DMF or acetonitrile) to afford products of the formula U.2. The resulting esters are treated with a substituted benzylamine (e.g. 4-chlorobenzylamine, 4-fluorobenzylamine, or 4-bromobenzylamine) either in methanol with sodium methoxide as catalyst or in ethylene glycol with heating to afford carboxamides of the formula B.2.

CHART U

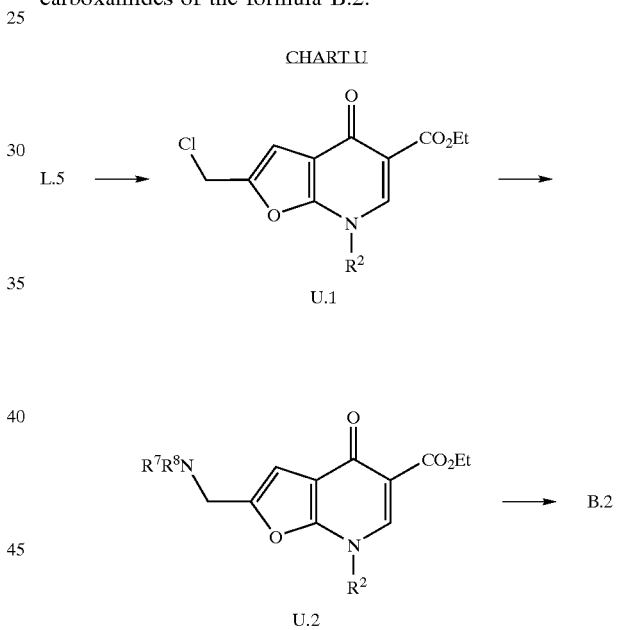

Additional compounds of Formula (I) may be prepared from compounds L.4, Chart V. Compounds of Formula (I) wherein $R^3$ is hydrogen are prepared from compounds of the formula L.4 by treatment with a substituted benzylamine (e.g. 4-chlorobenzylamine, 4-fluorobenzylamine, or 4-bromobenzylamine) either (1) in methanol with sodium methoxide as catalyst, (2) in ethylene glycol with heating, or (3) as a neat mixture at high temperature to afford carboxamides of the formula V.1. Alternatively, esters of the formula L.4 may be saponified to afford the corresponding acid which can then be coupled with a benzylamine mediated by 1,1'-carbonyldiimidazole (or other suitable carboxylic acid activating agent) to likewise provide amides of the general formula V.1. Compounds of the formula V.1 undergo halogenation when treated with N-bromosuccinimide to afford compounds of the formula V.2.

CHART V

L.4 → 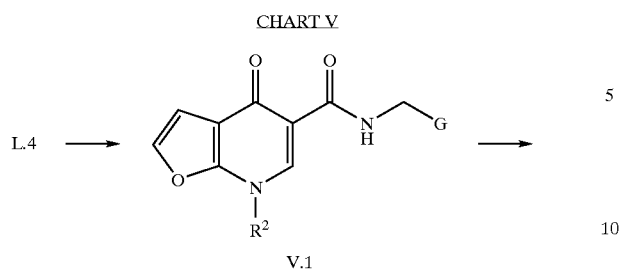

V.1

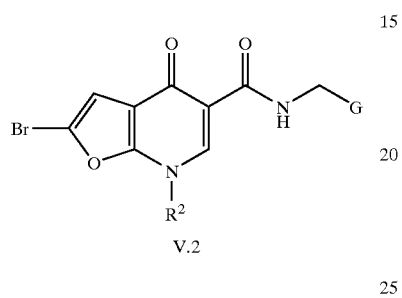

V.2

Compounds of the formula V.2 undergo transition metal mediated coupling reactions to provide compounds of Formula (I) according to Chart W. Nitrile derivatives of the formula W.1 (Y=CN) may be prepared by treatment of V.2 with a cyanide salt in the presence of a palladium catalyst (Maligres, P. E.; Waters, M. S.; Fleitz, F.; Askin, D. *Tetrahedron Lett.* 1999, 40, 8193–8195). Aryl derivatives of the formula W.1 (Y=aryl) and heteroaryl derivatives (Y=heteroaryl) may be prepared by coupling of V.2 with aryl or heteroaryl boronate, silane, or stannane derivatives in the presence of a palladium catalyst according to procedures commonly known to those skilled in the art of organic synthesis (Miyaura, N. *Cross-Coupling Reactions: A Practical Guide,* 2002). Heteroatom substituted derivatives of the formula W.1 such as ethers (Y=OR$^{12}$), thioethers (Y=SR$^{12}$), or amines (Y=NR$^7$R$^8$) may likewise be prepared through commonly employed palladium mediated conditions (Prim, D.; Campagne, J-M.; Joseph, D.; Andrioletti, B. *Tetrahedron* 2002, 58, 2041–2075). The resulting thioether derivatives may be further oxidized to the corresponding sulfoxide (Y=S(O)R$^6$) or sulfone (Y=S(O)$_2$R$^6$) by contact with an appropriate oxidizing agent (e.g. m-chloroperbenzoic acid). Carboxamide derivatives of the formula W.1 (Y=N(R$^7$)(C=O)R$^9$) may be prepared by treatment of V.2 with carboxamides in the presence of copper catalysts (Klapars, A.; Huang, X.; Buchwald, S. L. *J. Am. Chem. Soc.* 2002, 124, 7421–7428). Compounds of the formula V.2 undergo palladium mediated carbonylation according to Chart X when treated with carbon monoxide in the presence of a nucleophile to afford compounds of the formula X.1 including carboxylic acids (X=OH, nucleophile =H$_2$O), carboxylic acid esters (X=OR$^9$, nucleophile=alcohols of the formula R$^9$OH), and carboxamides (X=NR$^7$R$^8$, nucleophile=amines of the formula HNR$^7$R$^8$).

CHART W

V.2 → 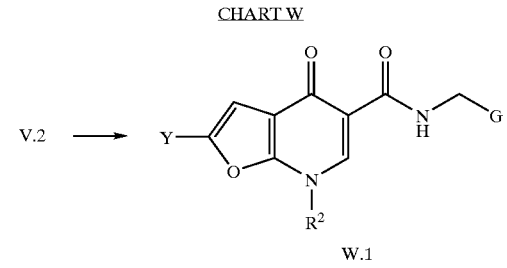

W.1

CHART X

V.2 → 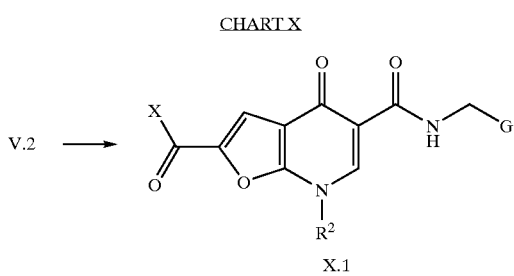

X.1

Symmetrical bis-amide derivatives wherein R$_3$ is C(O)NHCH$_2$G are prepared as shown in Chart Y. Compound Y.1 (Bhupathy, M. et al., *J. Heterocyclic Chem.* 1995, 32, 1283) can be condensed with a benzylamine (e.g. 4-chlorobenzylamine, 4-bromobenzylanine, or 4-fluorobenzylamine) at high temperature to afford compounds of the general formula Y.2 wherein G is as defined herein.

CHART Y

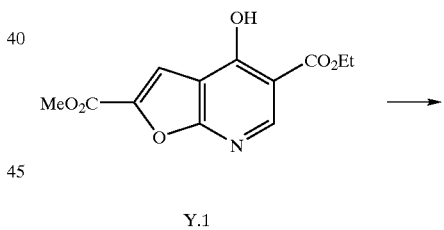

Y.1

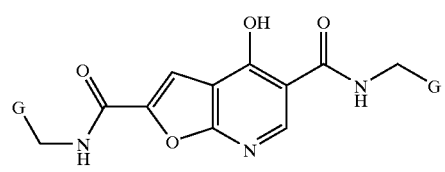

Y.2

Compounds of the formula V.2 also undergo coupling reactions according to Chart Z with an electron-rich acetylene (e.g. propargyl alcohol) catalyzed by PdCl$_2$(PPh$_3$)$_2$ and copper(I) iodide either in diethylamine or in a mixture of DMF and triethylamine to provide the corresponding alkynyl derivative Z.1. Saturation of the alkyne by hydrogenation catalyzed by reagents such as palladium on carbon in an appropriate solvent (e.g. methanol, ethanol tetrahydrofuran) affords alkyl derivatives of formula Z.2 wherein the group $CH_2CH_2Z$ embodies the substituent $C_{1-7}$alkyl optionally substituted by $R^{10}$. Hydrogenation of Z.1 employing a suitable poisoned catalyst provides compounds of the formula Z.3 bearing a carbon—carbon double bond.

CHART Z

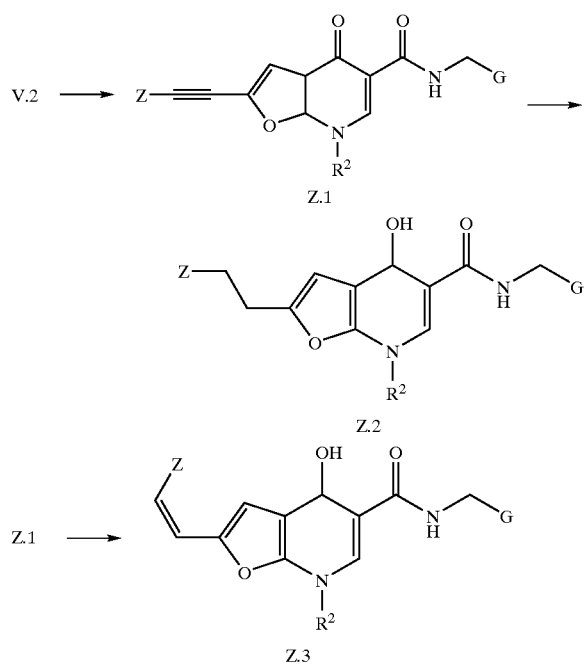

Compounds of the formula V.2 may also undergo palladium-mediated alpha-substitution to enolates and other stabilized carbanions according to Chart AA to afford AA.1 wherein Y includes hydrogen, alkyl, or aryl, or both Y substituents form a cycloalkyl or het ring, and Z includes nitro, cyano, $C(=O)OR^9$, $C(=O)H$, $C(=O)(C_{1-5}alkyl)$, $C(=O)(aryl)$, or $C(=O)NR^9R^9$. In cases where Z is attached to Y, the stabilized carbanion may be a carbocyclic or heterocyclic ring system (e.g. cyclohexanone). Methods to effect said coupling are analogous to those reported in the literature, for example, Terao, Y.; Fukuoka, Y.; Satoh, T.; Miura, M.; Nomura; M. Tetrahedron Lett. 2002, 43, 101–104; Vogl, E. M.; Buchwald, S. L. J. Org. Chem. 2002, 67, 106–111; Culkin, D. A.; Hartwig, J. F. J. Am. Chem. Soc. 2002, 124, 9330–9331; Moradi, W. A.; Buchwald; S. L. J. Am. Chem. Soc. 2001, 123, 7996–8002; Fox, J. M.; Huang, X.; Chieffi, A.; Buchwald, S. L. J. Am. Chem. Soc. 2000, 122, 1360–1370; Lee, S.; Hartwig, J. F. J. Org. Chem. 2001, 66, 3402–3415.

CHART AA

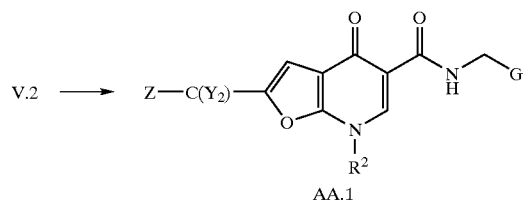

The compounds of Formula (I) or Formula (II) may be prepared as single enantiomer or as a mixture of individual enantiomers which includes racemic mixtures. Methods to obtain preferentially a single enantiomer from a mixture of individual enantiomers or a racemic mixture are well known to those ordinarily skilled in the art of organic chemistry. Such methods include but are not limited to preferential crystallization of diastereomeric salts (e.g. tartrate or camphor sulfonate), covalent derivatization by a chiral, non-racemic reagent followed by separation of the resulting diastereomers by common methods (e.g. crystallization, chromatographic separation, or distillation) and chemical reversion to scalemic compound, Simulated Moving Bed technology, or high/medium-pressure liquid chromatography employing a chiral stationary phase (Eliel, E. L. Stereochemistry of Organic Compounds, 1994; Subramanian, G. Chiral Separation Techniques. A Practical Approach, 2001). These techniques may be performed on the final compounds of Formula (I), Formula (II), or on any intermediates to compounds of Formula (I) or Formula (II) which bear a stereogenic center. Also, to facilitate separation by any of the methods described above, the compounds of Formula (I), Formula (II), or any intermediates to the compounds of Formula (I) or Formula (II) which bear a stereogenic center may be transiently reacted with an achiral reagent, separated, and then reverted to scalemic compound by standard synthetic techniques.

The invention also provides a process for making tert-butyl (1-(pyrimidin-2-yl)ethanon-2-yl)(methyl)carbamate comprising: reacting tert-butyldimethylcarbamate with a suitable alkyl lithium (e.g. sec-butyl lithium) in an ethereal solvent, treating with a magnesium salt (e.g. magnesium bromide), treating with N-methoxy-N-methylpyrimidine-2-carboxamide, 4-(pyrimidin-2-ylcarbonyl)morpholine, or S-phenyl pyrimidine-2-carbothioate, and treating with an aqueous acid to provide tert-butyl (1-(pyrimidin-2-yl) ethanon-2-yl)(methyl)carbamate.

The invention also provides the compound tert-butyl (1-(pyrimidin-2-yl)ethanon-2-yl)(methyl)carbamate.

The invention also provides method for preparing a compound of formula B.1

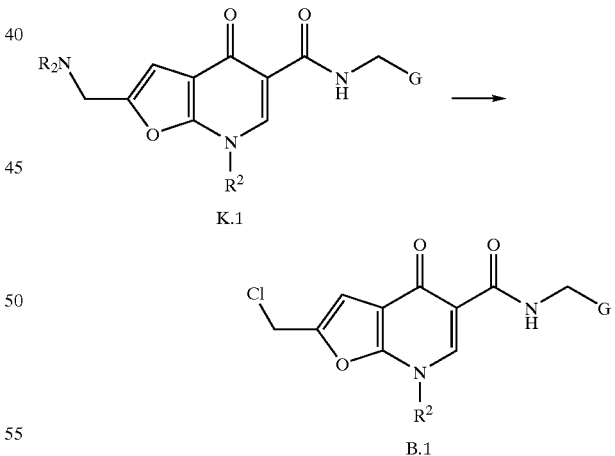

wherein $R^2$ and G have any of the values or specific values defined herein, comprising treating a corresponding compound of formula K.1, wherein $R_2N$ is dialkylamino or forms a saturated heterocycle, with ethyl chloroformate in a suitable solvent.

The invention also provides the compound ethyl 3-(2-chloro-3-furyl)-3-oxopropanoate.

The invention also provides the compound ethyl 7-methyl-4-oxo-4,7-dihydrofuro[2,3-b]pyridine-5-carboxylate.

The invention also provides the compound ethyl 7-methyl-2-(morpholin-4-ylmethyl)-4-oxo-4,7-dihydrofuro[2,3-b]pyridine-5-carboxylate.

The invention also provides the compound N-(4-chlorobenzyl)-7-methyl-2-(4-morpholinylmethyl)-4-oxo-4,7-dihydrofuro[2,3-b]pyridine-5-carboxamide.

The invention also provides the compound N-(4-chlorobenzyl)-2-(chloromethyl)-7-methyl-4-oxo-4,7-dihydrofuro[2,3-b]pyridine-5-carboxamide.

The invention also provides a method of preparing (1R)-2-(methylamino)-1-pyridin-2-ylethanol (2S)-2-(6-methoxy-2-naphthyl)propanoic acid salt comprising selectively crystallizing a mixture of (S)-Naproxen and 2-(methylamino)-1-pyridin-2-ylethanol.

The invention also provides the compound (1R)-2-(methylamino)-1-pyridin-2-ylethanol (2S)-2-(6-methoxy-2-naphthyl)propanoic acid salt.

The invention also provides the compound: (a) 2-(methylamino)-1-pyridin-2-ylethanol; (b) 2-(methylamino)-1-(2,4,6-trifluorophenyl)ethanol; (c) 2-(methylamino)-1-(1-methyl-1H-pyrrol-2-yl)ethanol; (d) 2-(methylamino)-1-(5-phenyl-2-furyl)ethanol; (e) 1-(4,5-dimethyl-2-furyl)-2-(methylamino)ethanol; or (f) (1R)-2-(methylamino)-1-pyrimidin-2-ylethanol; or a salt thereof.

The invention also provides a method for preparing a compound of formula L.6 as shown in Chart L, wherein $R^2$ and G have any of the values or specific values defined herein, and wherein each R is independently $C_{1-7}$alkyl or $R_2N$ taken together form a het, comprising treating a corresponding ester of formula L.5 with the requisite amine to provide the compound of formula L.6; and optionally further comprising preparing the compound of formula L.5 from a corresponding compound of formula L.4 by condensation with the requisite iminium ion; and optionally, further comprising preparing the compound of formula L.4 from a corresponding compound of formula L.3 by treating with acetic anhydride and triethylorthoformate followed by the requisite amine of formula $R^2NH_2$, and then a base; and optionally further comprising preparing the compound of formula L.3 from a corresponding acid of formula L.2 by conversion of the acid to the corresponding imidazolide and coupling with an ethyl malonate salt in the presence of a magnesium salt to provide the compound of formula L.3; and optionally, further comprising preparing the acid of formula L.2 from a corresponding compound acid of formula L.1 by bis-metalating the compound of formula L.1 and treating the bis-metalated compound with a chlorinating reagent.

The invention also provides a method for preparing a compound of formula L.4 as shown in Chart L, wherein $R^2$ has any of the values or specific values defined herein, comprising treating a compound of formula L.3 with acetic anhydride and triethylorthoformate followed by the requisite amine of formula $R^2NH_2$, and then a base.

The invention also provides a compound of formula L.4 as shown in Chart L, wherein $R^2$ is methyl, cyclopropyl, phenyl, 2-pyridyl, phenethyl, or 2-(N,N-dimethylamino)ethyl.

The invention also provides a compound of formula L.5 as shown in Chart L, wherein $R^2$ is methyl, ethyl, cyclopropyl, phenyl, 2-pyridyl, phenethyl, or 2-(N,N-dimethylamino)ethyl; and each R is independently $C_{1-7}$alkyl or $R_2N$ taken together form a het.

The invention also provides a compound of formula L.6 as shown in Chart L, wherein $R^2$ is methyl, ethyl, cyclopropyl, phenyl, 2-pyridyl, phenethyl, or 2-(N,N-dimethylamino)ethyl; and each R is independently $C_{1-7}$alkyl or $R_2N$ taken together form a het.

The compounds of formula I can be used in the native form or as a salt. In cases where forming a stable nontoxic salt is desired, administration of the compound as a pharmaceutically acceptable salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, ketoglutarate, glycerophosphate, and like salts. Suitable inorganic salts may also be formed, including hydrochloride, hydrobromide, sulfate, nitrate, bicarbonate, carbonate, and like salts. Alkali metal (for example, sodium, potassium or lithium) or alkaline earth metal (for example calcium) salts of carboxylic acids can also be made.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, hydrobromide, sulfate, nitrate, bicarbonate, and carbonate salts.

Pharmaceutically acceptable salts may be obtained using standard procedures well known in the art, for example, by reacting a sufficiently basic compound such as an amine with a suitable acid affording a physiologically acceptable anion. Alkali metals, for example, sodium, potassium or lithium, or alkaline earth metal salts, for example calcium, of carboxylic acids can also be made.

Compounds of the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally, for example, by intravenous, intraperitoneal or intramuscular injection, topically, parenterally, orally, rectally, transmucosally, or intestinally depending on whether the preparation is used to treat internal or external viral infections. Parenteral administrations include indirect injections to generate a systemic effect or direct injections to the afflicted area. Examples of parenteral administrations are subcutaneous, intravenous, intramuscular, intradermal, intrathecal, intraocular, intranasal, intravetricular injections or infusions techniques. The rectal administration includes the form of suppositories. The transmucosal administration includes nasal aerosol or inhalation applications. Preferred routes of administration are oral and parenteral. Additionally, the compounds may be delivered using a sustained-release system. Various sustained-release materials have been established and are well known by those skilled in the art. Sustained-release capsules may, depending on their chemical nature, release the compounds for 24 or for hours up to several days. Additionally, the compounds may be delivered using a sustained-release system. Various sustained-release materials have been established and are well known by those skilled in the art. Sustained-release capsules may, depending on their chemical nature, release the compounds for 24 or for hours up to several days.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid. Topical administrations include the treatment of infectious areas or organs readily accessible by local application, such as, for example, eyes, ears including external and middle ear infections, vaginal, open wound, or skin including the surface skin and the underneath dermal structures. It also includes transdermal delivery to generate a systemic effect.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and is additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157), and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1,000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1,000 mg per unit dose.

For parenteral administration or for administration as drops, as for eye infections, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula I in a liquid composition, such as a lotion, will be from about 0.1–25 wt-%, preferably from about 0.5–10 weight percent. The concentration in a semi-solid or solid composition such as a gel or a powder will be about 0.1–5 weight percent, preferably about 0.5–2.5 weight percent.

The exact regimen for administration of the compounds and compositions disclosed herein will necessarily be dependent upon the needs of the individual subject being treated, the type of treatment and, of course, the judgment of the attending practitioner.

The antiviral activity of a compound of the invention can be determined using pharmacological models which are well known to the art, or using Test A described below.

The compounds of formula I and pharmaceutically acceptable salts thereof are useful as antiviral agents. Thus, they are useful to combat viral infections in mammals, including man and animals. The compounds are generally active against herpes viruses, and are particularly useful against the varicella zoster virus, the Epstein-Barr virus, the herpes simplex virus, the human herpes virus type 8 (HHV-8) and the cytomegalovirus (CMV). The compounds of the present invention may also be useful for the treatment of herpesvirus infections in mammals, for example, illnesses caused by bovine herpesvirus 1–5 (BHV), ovine herpesvirus 1 and 2, Canine herpesvirus 1, equine herpesvirus 1–8 (EHV), feline herpesvirus 1 (FHV), and pseudorabies virus (PRV).

The compounds of the present invention may also useful for the treatment of several cardiovascular diseases such as atherosclerosis and restenosis. These diseases have been connected with inflammation of coronary vessel walls resulting from infection or reactivation of herpesviruses.

While many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

Test A.

The HCMV polymerase assay is performed using a scintillation proximity assay (SPA) as described in several references, such as N.D. Cook, et al., Pharmaceutical Manufacturing International, pages 49–53 (1992); K. Takeuchi, Laboratory Practice, September issue (1992); and U.S. Pat. No. 4,568,649 (1986), which are incorporated by reference herein. Reactions are performed in 96-well plates. The assay is conducted in 100 µl volume with 5.4 mM HEPES (pH 7.5), 11.7 mM KCl, 4.5 mM MgCl$_2$, 0.36 mg/ml BSA, and 90 nM $^3$H-dTTP. Assays are run with and without CHAPS, (3-[(3-cholamidopropyl)-dimethyl-ammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 µg/ml BSA, and 0.01% sodium azide. The HCMV polymerase, which is expressed in recombinant baculovirus-infected SF-9 cells and purified according to literature procedures, is added at 10% (or 10 µl) of the final reaction volume, i.e., 100 µl. Compounds are diluted in 50% DMSO and 10 µl are added to each well. Control wells contain an equivalent concentration of DMSO. Unless noted otherwise, reactions are initiated via the addition of 6 nM biotinylated poly (dA)-oligo (dT) template/primer to reaction mixtures containing the enzyme, substrate, and compounds of interest. Plates are incubated in a 25° C. or 37° C. water bath and terminated via the addition of 40 µL/reaction of 0.5 M EDTA (pH 8) per well. Reactions are terminated within the timeframe during which substrate incorporation is linear and varied depending upon the enzyme and conditions used, i.e., 30 min. for HCMV polymerase. Streptavidin-SPA beads (10 µL, 20 mg/ml in PBS/10% glycerol) are added following termination of the reaction. Plates are incubated 10 min. at 37° C., then equilibrated to room temperature, and counted on a Packard Topcount. Linear regressions are performed and IC$_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DOT) is added to the polymerase buffer. Also, a different lot of CMV polymerase is used, which appears to be more active resulting in a more rapid polymerase reaction. Representative compounds of formula I that were tested were found to be active in this assay.

Description of the Preferred Embodiments

Preparation 1. 5-Amino-2-furonitrile.

A solution of 5-nitro-2-furonitrile (10.0 g) in methanol (150 mL) was hydrogenated over 5% Pd/CaCO$_3$ (2.00 g) at 40 p.s.i. for 18 h. The reaction mixture was filtered through a Celite pad and the filtrate was concentrated in vacuo. The resulting oil was purified by column chromatography (CH$_2$Cl$_2$) to yield 3.60 g of the title compound as a yellow oil. Physical characteristics. $^1$H NMR (300 MHz, DMSO-d$_6$) δ 7.34, 6.76, 5.07; $^{13}$C NMR (DMSO-d$_6$) δ 161.9, 128.0, 114.0, 113.0, 82.8; HRMS (FAB) m/z 109.0402 (M+H)$^+$.

Preparation 2. Diethyl 2-(((Cyano-2-furyl)amino) methylene)malonate.

5-Amino-2-furonitrile (Preparation 1, 3.505 g) was combined with diethylethoxymethylene malonate (6.4 mL) and heated to 135° C. for 3 h. The reaction mixture was cooled to room temperature and the resulting solid was triturated with diethyl ether to yield 5.18 g of the title compound as a pale yellow solid. Physical characteristics. $^1$H NMR (300 MHz, DMSO-d$_6$) δ 11.20, 8.15, 7.62, 6.29, 4.254.11, 1.31–1.21; $^{13}$C NMR (DMSO-d$_6$) δ 165.8, 164.3, 151.7, 146.8, 126.9, 118.6, 112.1, 97.3, 93.5, 60.1, 59.9, 14.1, 14.0; MS (ESI+) m/z. 279 (M+H)$^+$; HRMS (FAB) m/z 279.0979 (M+H)$^+$.

Preparation 3. Ethyl 2-Cyano-4-hydroxyfuro[2,3-b] pyridine-5-carboxylate.

Diethyl 2-(((5-cyano-2-furyl)amino)methylene)malonate (Preparation 2, 5.14 g) was combined with diphenyl ether (60 mL), degassed and then heated to reflux for 15 minutes. The reaction mixture was allowed to cool for several minutes and then poured into hexanes. The resulting solid was filtered to give 3.569 g of the title compound as a tan solid.

Physical characteristics. M.p. 147–151° C.; $^1$H NMR (300 MHz, DMSO-d$_6$) δ 8.81, 8.28, 4.40, 1.35; $^{13}$C NMR (DMSO-d$_6$)δ 166.1, 164.3, 162.2, 124.4, 117.9, 111.3, 109.4, 107.6, 61.4, 13.9; MS (ESI+) m/z 233 (M−H)$^+$; Anal. Found: C, 56.76; H, 3.33; N, 12.26.

Preparation 4. Ethyl 2-Cyano-7-methyl-4-oxo-4,7-dihydrofuro[2,3-b]-pyridine-5-carboxylate.

Ethyl 2-cyano-4-hydroxyfuro[2,3-b]pyridine-5-carboxylate (Preparation 3, 0.500 g) was dissolved in DMF (20 mL). Potassium carbonate (0.594 g) was added followed by the addition of iodomethane (0.16 mL). The reaction mixture was stirred at room temperature for 18 h and was then poured into water (90 mL). The aqueous layer was extracted with CH$_2$Cl$_2$ (4×100 mL). The combined organic layers were dried (MgSO$_4$), filtered, and concentrated in vacuo. The resulting solid was purified by column chromatography (CH$_2$Cl$_2$, CH$_2$Cl$_2$/methanol, 99/1; 95/5) to yield 0.303 g of the title compound as a yellow solid. Physical characteristics. M.p. 208–210° C. (dec); $^1$H NMR (300 MHz, DMSO-d$_6$) δ 8.48, 8.17, 4.24, 3.85, 1.27; MS (ESI−) m/z 245 (M−H)$^-$; HRMS (FAB) m/z 247.0726 (M+H)$^+$.

Preparation 5. Ethyl 2-Formyl-7-methyl-4-oxo-4,7-dihydrofuro[2,3-b]-pyridine-5-carboxylate.

Ethyl 2-cyano-7-methyl-4-oxo-4,7-dihydrofuro[2,3-b]pyridine-5-carboxylate (Preparation 4, 0.870 g) was dissolved in a mixture of water (7 mL), acetic acid (7 mL), and pyridine (7 mL). Sodium hypophosphite (0.749 g) was added followed by addition of Raney-Ni. The reaction mixture was stirred at 60° C. for 1 h. The mixture was allowed to cool to room temperature and was then filtered through Celite. The filtrate was concentrated in vacuo and was then diluted with water (20 mL). The aqueous layer was extracted with CH$_2$Cl$_2$ (4×50 mL). The combined organic layers were washed with saturated aqueous sodium bicarbonate (50 mL), and the aqueous layer was back extracted with CH$_2$Cl$_2$ (2×50 mL). The combined organic layers were dried (MgSO$_4$), filtered, and concentrated in vacuo to yield 0.65 g of the title compound as a yellow solid. Physical characteristics. M.p. 176–195° C. (dec); $^1$H NMR (300 MHz, DMSO-d$_6$) δ 9.64, 8.48, 8.03, 4.24, 3.86, 1.28; $^{13}$C NMR (DMSO-d$_6$) δ 178.3, 170.5, 163.9, 155.4, 147.9, 145.2, 120.8, 116.2, 114.1, 60.1, 14.1; MS (ESI−) m/z 248 (M−H)$^-$; HRMS (FAB) m/z 250.0721 (M+H)$^+$.

Preparation 6. Ethyl 7-Methyl-4-oxo-2-(4-morpholinylmethyl)4,7-dihydrofuro[2,3-b]pyridine-5-carboxylate.

Ethyl 2-formyl-7-methyl-4-oxo-4,7-dihydrofuro[2,3-b]pyridine-5-carboxylate (Preparation 5, 0.603 g) was suspended in 1,2-dichloroethane (20 mL). Acetic acid (0.14 mL), morpholine (0.23 mL), and sodium triacetoxy borohydride (0.769 g) were added. The reaction mixture was stirred at room temperature for 1 h. A 1 N sodium hydroxide solution (2.4 mL) was added, and the mixture was stirred for 5 minutes. The organic layer was removed, and the aqueous layer was diluted with water and extracted with CH$_2$Cl$_2$ (4×40 mL). Additional material was recovered from the aqueous layer by adjusting it to pH 8 with a 10% aqueous sodium hydroxide solution and extracting with CH$_2$Cl$_2$ (3×20 mL). The combined organic layers were dried (MgSO$_4$), filtered, and concentrated in vacuo. The resulting solid was purified by column chromatography (CH$_2$Cl$_2$/methanol, 98/2; 97/3; 95/5) to yield 0.372 g of the title compound as a pale yellow solid. Physical characteristics. M.p. 136–140° C.; $^1$H NMR (300 MHz, CDCl$_3$) δ 8.09, 6.89, 4.40, 3.88, 3.74, 3.50, 2.54, 1.22; $^3$C NMR (CDCl$_3$)δ 171.5, 165.4, 152.7, 149.2, 142.1, 116.8, 115.6, 107.6, 66.7, 61.1, 55.1, 53.2, 37.6, 14.4; MS (ESI+) m/z 321 (M+H)$^+$; HRMS (FAB) m/z 321.1453 (M+H)$^+$.

Preparation 7. 2-Chloro-3-furoic acid.

A solution of diisopropylamine (713 mL) in dry THF (5.1 L) was cooled to less than −50° C. A solution of 2.5 M n-butyl lithium in hexanes (2033 ml) was added over about 40 min maintaining the temperature below −50° C. A solution of 3-furoic acid (285 g) in dry THF (1742 ml) was added maintaining the temperature below −70° C. The solution was stirred at below −70° C. for 40 min and then a solution of hexachloroethane (662 g) in dry THF (1017 ml) was added maintaining the temperature below −70° C. The solution was stirred for 3 h at below −70° C. and then was allowed to warm to room temperature overnight. The reaction mixture was quenched with water (10.9 L). The aqueous layer was separated and extracted with MTBE (5.8 L). The water layer was then acidified with 2 N HCl to a pH=1–2 (2.15 L). The product was extracted into ethyl acetate (2×3.8 L) and then the solvent was removed in vacuo to provide a light gray solid. Recrystallization from water (7522 ml) on the steam bath with decantation from dark insolubles provided 233 g of the title compound as pale tan crystals on cooling to 0–5° C. overnight, filtering, washing with cold water, and drying (vacuum oven, 40° C.). Physical characteristics. $^1$H NMR (400 MHz, CDCl$_3$) δ 12.15, 6.82, 7.34; $^{13}$C NMR (100 MHz, CDCl$_3$) δ 167.6, 143.7, 141.9, 112.6, 109.8.

Preparation 8. Ethyl 3-(2-Chloro-3-furyl)-3-oxopropanoate.

A solution of 2-chloro-3-furoic acid (Preparation 7, 228.0 g) in dry THF (373 mL) was added over about 30 min to a slurry of N-carbonyldiimidazole (278.3 g) in dry THF (2280 mL). The slurry became a solution as the mixture was stirred over 2 h. In a separate reaction vessel, a slurry of potassium ethyl malonate (530.5 g) and dry acetonitrile (4560 ml) was cooled to 10–15° C. Triethylamine (435 ml) was then added. Solid anhydrous magnesium chloride (370 g) was added portionwise maintaining the reaction temperature below 25° C. The resulting slurry was stirred at room temperature for 2.5 h and then the previously prepared imidazolide solution was added via cannula maintaining the temperature below 25° C. The slurry was stirred overnight at room temperature. The solvent was removed on the rotary evaporator and the residue was treated with 0.5 N HCl (9.3 liters) and toluene (4.6 liters) to dissolve the solids. The aqueous layer was extracted with toluene (1.9 liters) and the combined organic layers were washed with saturated aqueous sodium bicarbonate (1.9 liters). The solvent was removed on a rotary evaporator (30 mm/40° C. bath) to provide 317.9 g of the title compound as a brown oil consisting of a mixture of two tautomers. Physical characteristics. $^1$H NMR (400 MHz, CDCl$_3$) δ 12.5, 7.34, 6.84, 6.70, 5.62, 4.23, 3.88, 1.29.

Preparation 9. Ethyl 7-Methyl-4-oxo-4,7-dihydrofuro[2,3-b]pyridine-5-carboxylate.

A mixture of ethyl 3-(2-chloro-3-furyl)-3-oxopropanoate (Preparation 8, 607.0 g), triethylorthoformate (932.2 ml), and acetic anhydride (925.4 ml) was heated to reflux (118–119° C.) while volatiles were condensed into a receiver. After 3 h, volatiles were removed by distillation under high vacuum at pot temperatures up to about 65° C. to afford a black oil. The resulting oil was dissolved in THF (1.26 L) and a 2 M solution of methylamine in THF (1.5 L) was added maintaining the temperature around 25° C. with a cooling bath. The mixture was allowed to stir overnight at room temperature and was then cooled to −10° C. A 1.0 M solution of potassium 1-butoxide in THF (3.08 L) was added slowly maintaining the temperature below 0° C. The reaction mixture was warmed to 3540° C. for about 1 h. The reaction mixture was concentrated by rotary evaporation and then partitioned between saturated aqueous NH$_4$Cl and $CH_2Cl_2$. The aqueous layer was extracted with $CH_2Cl_2$ (4×3.5 L). The combined organic layers were concentrated, redissolved in $CH_2Cl_2$, and filtered. The resulting filtrate was concentrated to afford 418.4 g of the title compound as a waxy brown solid. Physical characteristics. $^1$H NMR (400 MHz, $CDCl_3$) δ 8.09, 7.33, 7.03, 4.36, 3.86, 1.39; $^{13}$C NMR (100 MHz, $CDCl_3$) δ 171.7, 165.3, 152.9, 142.3, 139.8, 116.6, 114.8, 108.2, 60.9, 37.4, 14.3.

Preparation 10. Ethyl 7-Methyl-2-(morpholin-4-ylmethyl)-4-oxo-4,7-dihydrofuro[2,3-b]pyridine-5-carboxylate.

A solution of ethyl 7-methyl-4-oxo-4,7-dihydrofuro[2,3-b]pyridine-5-carboxylate (Preparation 9, 417.8 g) in anhydrous acetonitrile (2.95 liters) was added to 4-methylenemorpholin-4-ium chloride (320.1 g). The slurry was stirred for three days at room temperature. The reaction was quenched by adding saturated aqueous $Na_2CO_3$ (1.5 L) and then acetonitrile was removed by rotary evaporation. The aqueous residue was diluted with additional saturated aqueous $Na_2CO_3$ (3.5 L) and extracted with $CH_2Cl_2$ (6×2.85 L). The combined organic layers were concentrated, redissolved into $CH_2Cl_2$ (approximately 150 mL), and triturated with hexanes (7.2 L). The slurry was stirred vigorously for 48 h and then filtered. The solids were washed with hexanes (3×1.7 L) and dried in a vacuum oven (30° C., overnight) to afford 494.1 g of the title compound as a tan solid. Physical characteristics. $^1$H NMR (400 MHz, $CDCl_3$) δ 8.07, 6.86, 4.36, 3.87, 3.72, 3.59, 2.51, 1.38; $^{13}$C NMR (100 MHz, $CDCl_3$) δ 171.4, 165.3, 152.7, 149.4, 142.0, 116.7, 115.5, 107.3, 66.7, 60.9, 55.1, 53.2, 37.5, 14.3.

EXAMPLE 1

N-(4-Chlorobenzyl)-7-methyl-2-(4-morpholinylmethyl)-4-oxo-4,7-dihydrofuro[2,3-b]pyridine-5-carboxamide.

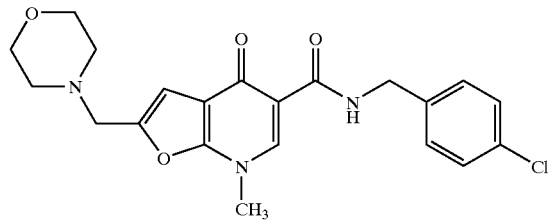

Procedure A. A mixture of ethyl 7-methyl-4-oxo-24-morpholinylmethyl)-4,7-dihydrofuro[2,3-b]pyridine-5-carboxylate (Preparation 6, 0.302 g) and 4-chlorobenzylamine (1.14 mL) was heated to 190° C. for 1.5 h. The reaction mixture was cooled to room temperature and toluene was added. The resulting solid was filtered and recrystallized from acetonitrile to yield 0.278 g of the title compound as a white solid. Physical characteristics. M.p. 211–212° C.; $^1$H NMR (300 MHz, $CDCl_3$) δ 10.64, 8.46, 7.33–7.27, 6.87, 4.64, 3.94, 3.75, 3.64, 2.54; $^3$C NMR ($CDCl_3$) δ 173.7, 164.8, 153.2, 150.2, 141.0, 137.3, 132.8, 128.9, 128.6, 116.8, 114.9, 106.8, 66.7, 55.1, 53.2, 42.5, 37.9; MS (ESI+) m/z 416 (M+H)$^+$; Anal. Found: C, 60.46; H, 5.37; N, 10.13; Cl, 8.45.

Procedure B. A mixture of ethyl 7-methyl-2-(morpholin-4-ylmethyl)-4-oxo-4,7-dihydrofuro[2,3-b]pyridine-5-carboxylate (Preparation 10, 492.5 g), dry methanol (6.15 L), a 25% solution of sodium methoxide in methanol (33.5 ml), and 4-chlorobenzylamine (435.4 g) was heated to 55–60° C. for 4 days. The resulting slurry was cooled to 0–5° C. overnight, filtered, rinsed with cold methanol (2×3 L), and dried in a vacuum oven (55° C., overnight) to afford 483.2 g of the title compound as an off-white solid. Physical characteristics. $^1$H NMR (400 MHz, $CDCl_3$) δ 10.62, 8.44, 7.28, 6.85, 4.62, 3.92, 3.72, 3.62, 2.52; $^{13}$C NMR (100 MHz, $CDCl_3$) a 173.6, 164.7, 153.1, 150.2, 141.0, 137.3, 132.7, 128.8, 128.6, 116.7, 114.8, 106.7, 66.7, 55.1, 53.2, 42.5, 37.7. Anal. Found: C, 60.37; H, 5.39; N, 10.00.

EXAMPLE 2

N(4-Chlorobenzyl)-2-(chloromethyl)-7-methyl-4-oxo-4,7-dihydrofuro[2,3-b]pyridine-5-carboxamide.

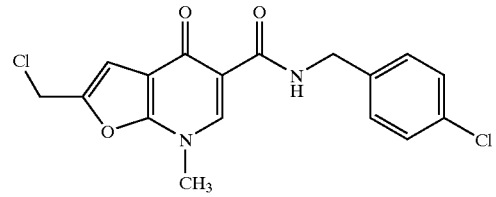

Ethyl chloroformate (150.1 ml) was added to a suspension of N-(4-chlorobenzyl)-7-methyl-2-(4-morpholinylmethyl)-4-oxo-4,7-dihydrofuro[2,3-b]pyridine-5-carboxamide (Example 1, 262.0 g) and $CH_2Cl_2$ with very low water content (2.63 L). The slurry was warmed to 39–40° C. After 2 h, the reaction mixture was cooled to room temperature and ethyl ether (2.63 L) was added. The mixture was stirred overnight, filtered, was washed with ethyl ether (3×2 L), and dried in a vacuum oven (40° C.) to afford 221.8 g of the title compound as a colorless solid. Physical characteristics. $^1$H NMR (400 MHz, TFA-d) δ 11.50, 8.94, 7.23, 4.64, 4.27; $^{13}$C NMR (100 MHz, TFA-d) δ 167.3, 165.2, 155.8, 155.1, 140.4, 134.2, 132.7, 128.4, 128.3, 113.5, 110.6, 103.8, 43.4, 38.9, 33.8. Anal. Found: C, 55.89; H, 3.69; N, 7.60; Cl, 18.98.

Preparation 11. 2-Furoyl bromide.

Bromine (6.5 mL) was added dropwise over 1 h to a solution of 2-acetylfuran (11.0 g) in dioxane/$Et_2O$ (1/2, 60 mL) at 0° C. (internal). The reaction mixture was then allowed to warm to room temperature and was stirred for 2 h. A saturated ammonium chloride solution (70 mL) was added. The organic layer was removed, and the aqueous layer was extracted with diethyl ether (2×50 mL). The combined organic layers were dried ($MgSO_4$), filtered, and concentrated in vacuo. The resulting solid was purified by column chromatography (hexanes/$CH_2Cl_2$, 70/30) to yield 7.996 g of the title compound as a yellow oil. Physical characteristics. $^1$H NMR (400 MHz, DMSO-d$_6$) δ 8.09, 7.66–7.64, 6.79–6.77, 4.65.

Preparation 12. rac-1(2-Furyl)-2-methylamino)ethanol.

A solution of 2-furoyl bromide (Preparation 11, 7.50 g) in methanol (40 mL) was added dropwise to a 2.0 M solution of methylamine in methanol (198 mL) at 0° C. (internal). The reaction mixture was stirred at 0° C. for 30 min. A solution of sodium borohydride (2.25 g) in water (40 mL) was then added dropwise. The reaction mixture was stirred at 0° C. for 30 min and then quenched with a 2 N HCl solution (to pH 34). The reaction mixture was concentrated in vacuo to remove methanol and was then poured into cold EtOAc (200 mL)/2 N NaOH (100 mL). The organic layer was removed. The aqueous layer was adjusted to pH 12 with a 2 N NaOH solution and extracted with EtOAc (3×200 mL). The combined organic layers were dried ($MgSO_4$), filtered, and concentrated in vacuo. The resulting brown oil was purified by column chromatography ($CHCl_3$/methanol, 95/5; CHCl₃/methanol/NH₄OH, 90/10/1) to yield 2.06 g of the title compound as a brown oil. Physical characteristics. ¹H NMR (400 MHz, DMSO-d₆) δ 7.56, 6.39–6.37, 6.26–6.25, 5.15, 4.624.58, 2.77–2.66, 2.33; MS (ESI+) m/z 142 (M+H)⁺.

Preparation 13. (5R)-5-(2-Furyl)-3-methyl-1,3-oxazolidin-2-one.

A 250 mL round-bottomed flask equipped with an overhead stirrer, reflux condenser, thermocouple and an addition funnel was charged with (R)₂-amino-1-(2-furylethanol (10 g) and potassium t-butoxide (10.6 g). Anhydrous DMF was charged at such a rate as to keep the temperature below 50° C. The reaction was heated to 80° C. (internal temp), the addition funnel was charged with dimethyl carbonate (50 mL), and the liquid was added to the reaction drop-wise. Once addition of dimethyl carbonate was complete, the temperature was raised to reflux (about 100° C.), and maintained for approximately 12 h. The reaction mixture was cooled to less than 60° C., poured into water (100 mL) and extracted with isopropyl acetate (100 mL). The layers were separated, and the water layer was extracted with additional isopropyl acetate (2×100 mL). The combined organic layers were washed with water (100 mL) and dried over sodium sulfate and magnesol for 10 min. The solids were removed via vacuum filtration, and the organic layers were concentrated in vacuo. The resulting oil was crystallized from MTBE (2 mL/g) to provide 10.25 g of the title compound. Physical characteristics. ¹H NMR (400 MHz, CDCl₃) δ 7.46, 6.49, 6.39, 5.47, 3.78, 2.97; [alpha]$_D$=−113° (CH₂Cl₂).

Preparation 14. (1R)-1-(2-Furyl)-2-(methylamino)ethanol.

A round-bottomed flask equipped with an overhead stirrer, reflux condenser and nitrogen inlet was charged with (5R)-5-(2-furyl)-3-methyl-1,3-oxazolidin-2-one (Preparation 13, 47.1 g). A 1 M solution of KOH (987 mL) was added and the resulting solution was heated at 50° C. When complete, the flask was charged with NaCl (310 g) and MTBE (470 mL). The aqueous layer was separated and further extracted twice with a solution of MTBE (470 mL) and CH₂Cl₂ (23 mL). The combined organic layers were dried (MgSO₄), filtered, and concentrated to afford 38.0 g of the title compound. Physical characteristics. ¹HNMR (400 MHz, DMSO-d₆) δ 7.52, 6.36, 6.24, 4.60, 2.71, 2.28; ¹³C NMR (100 MHz, DMSO-d₆) δ 157.0, 141.6, 110.1, 105.6, 65.2, 56.2, 35.9; [alpha]$^{32}_D$=+340 (EtOH, c=1.0).

EXAMPLE 3

N-(4-Chlorobenzyl)-2-(((22-furyl)-2-hydroxyethyl)(methyl)amino)methyl)-7-methyl-4-oxo-4,7-dihydrofuro[2,3-b]pyridine-5-carboxamide.

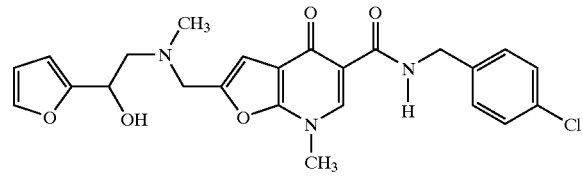

Ethyl 2-formyl-7-methyl-4-oxo-4,7-dihydrofuro[2,3-b]pyridine-5-carboxylate (Preparation 6, 0.356 g) was suspended in 1,2-dichloroethane (16 mL). The reaction mixture was cooled to 0° C. Acetic acid (0.10 mL), rac-1-(2-furyl)-2-(methylamino)ethanol (Preparation 12, 0.440 g), and sodium triacetoxy borohydride (0.497 g) were added. The reaction mixture was stirred at room temperature for 18 h. After 18 h, an additional 0.202 g of 1-(2-furyl)-2-(methylamino)ethanol, 0.10 mL acetic acid, and 0.303 g sodium triacetoxy borohydride were added. The reaction mixture was stirred at room temperature for 3 days. A 2 N sodium hydroxide solution (7 mL) was added, and the mixture was stirred for 5 minutes. An additional 20 mL water was added. The organic layer was removed, and the aqueous layer was diluted with water and extracted with CH₂Cl₂ (4×25 mL). The combined organic layers were dried (MgSO₄), filtered, and concentrated in vacuo. The resulting brown oil (0.733 g) was combined with 4-chlorobenzylamine (1.74 mL) and heated to 190° C. for 1 h. The reaction mixture was cooled to room temperature and toluene (30 mL) was added. The mixture was concentrated in vacuo and the resulting brown oil was purified by column chromatography (CH₂Cl₂; CH₂Cl₂/methanol, 99/1). The resulting gummy yellow solid was triturated with diethyl ether to yield 0.290 g of the title compound as an off-white solid. Physical characteristics. M.p. 94–101° C.; ¹H NMR (400 MHz, DMSO-d₆) δ 10.65, 8.55, 7.52–7.51, 7.41–7.32, 6.86, 6.37–6.36, 6.25–6.24, 5.24, 4.724.67, 4.55, 3.90, 3.75–3.67, 2.76–2.65, 2.28; ¹³C NMR (CDCl₃)δ 173.7, 164.7, 153.7, 153.3, 142.4, 141.2, 137.3, 132.8, 128.9, 128.7, 116.9, 114.7, 110.3, 107.2, 63.6, 60.4, 53.9, 42.6, 41.8, 37.8; MS (ESI+) m/z 470 (M+H)⁺; Anal. Found: C, 61.02; H, 5.18; N, 8.90; Cl, 7.82.

EXAMPLE 4

(+)-N-(4-Chlorobenzyl)-2-(((2-(2-furyl)-2-hydroxyethyl)(methyl)amino)methyl)-7-methyl-4-oxo-4,7-dlhydrofuro[2,3-b]pyridine-5-carboxamide.

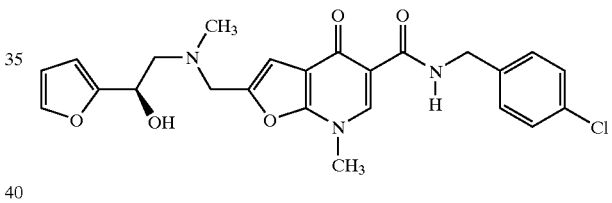

Procedure A. Racemic N-(4-chlorobenzyl)-2-(((2-(2-furyl)-2-hydroxyethyl)(methyl)amino)methyl)-7-methyl-4-oxo-4,7-dihydrofuro[2,3-b]pyridine-5-carboxamide (Example 3) was resolved preparatively on a 5×50 cm Chiralpak AD column (Chiral Technologies), at a column temperature of 30° C. The mobile phase was 50% isopropyl alcohol/50% heptane (v/v) with a flow rate of 70 mL/min. Peaks were detected by UV at 250 nm. A 250 mg sample was injected in 10 mL of 50% IPA/50% CHCl₃ (v/v). The more quickly eluting enantiomer was isolated and then further purified by column chromatography (CH₂Cl₂/methanol, 99/1, 98/2). The resulting white solid was recrystallized from ethyl acetate to yield 0.053 g of the title compound as a white solid. Physical characteristics. M.p. 93–96° C.; ¹H NMR (400 MHz, DMSO-d₆) δ 10.65, 8.54, 7.52, 7.41–7.32, 6.85, 6.37–6.36, 6.25–6.24, 5.23, 4.724.67, 4.55, 3.90, 3.75–3.67, 2.76–2.67, 2.28; MS (ESI+) m/z 470 (M+H)⁺; [alpha]$^{25}_D$=+19 (c 0.62, CH₂Cl₂); Anal. Found: C, 60.74; H, 5.17; N, 8.84; Cl, 7.48.

Procedure B. A solution of(1R)1-(2-furyl)-2-(methylamino)ethanol (Preparation 14, 13.2 g) (azeotopically dried with toluene (2×250 ml) on the rotary evaporator (30 mm/40° C.) followed by drying at high vacuum with rotation at 35° C. overnight) in anhydrous DMF (158 ml) was added via cannula to a flask containing N-(4-chlorobenzyl)-2-(chloromethyl)-7-methyl-4-oxo-4,7- dihydrofuro[2,3-b]pyridine-5-carboxamide (Example 2, 27.3 g). Diisopropylethylamine (16.3 ml) was added. The slurry was heated to 40° C. overnight. The solution was cooled to about 13° C. and water (819 ml) was added slowly with ice bath cooling. The gummy solid was stirred overnight with a mechanical stirrer to produce a filterable solid. After cooling to 3.5° C., the solids were filtered, washed with ice water (5×25 ml), and dried on a pressure filter with room temperature single-pass nitrogen overnight to constant weight. The crude product was recrystallized from EM ethyl acetate (1225 ml) on the steam bath, filtered on a medium sintered glass funnel, and the filtrate was cooled to room temperature and stored in the freezer overnight. The resulting pale yellow crystals were filtered, washed with cold ethyl acetate (2×20 ml), and dried in the vacuum oven (35° C.) to afford 20.75 g of the title compound. Physical characteristics. $^1$H NMR (400 MHz, DMSO-$d_6$) a 10.63, 8.52, 7.50, 7.35, 6.83, 6.35, 6.24, 5.20, 4.69, 4.53, 3.89, 3.70, 2.71, 2.28; $^{13}$C NMR (100 MHz, DMSO-$d_6$) δ 172.7, 164.3, 156.8, 153, 1, 151.4, 141.8, 141.6, 138.6, 131.4, 129.1, 128.4, 115.3, 113.8, 110.2, 106.0, 105.6, 64.3, 60.6, 53.2, 42.3, 41.4, 37.5; [alpha]$_D$=+18 ($CH_2Cl_2$). Anal. Found: C, 61.25; H, 5.20; N, 8.94; Cl, 7.67.

EXAMPLE 5

(−)-N-(4-Chlorobenzyl)-2-((2-(2-furyl)-2-hydroxyethyl)(methyl)amino)methyl)-7-methyl-4-oxo-4,7-dihydrofuro[2,3-b]pyridine-5-carboxamide.

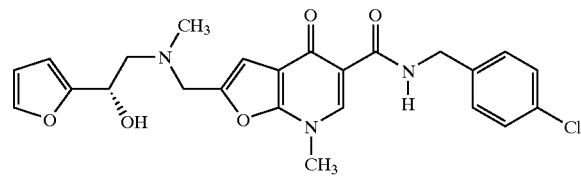

Racemic N-(4-chlorobenzyl)-2-(((2-(2-furyl)-2-hydroxyethyl)(methyl)amino)methyl)-7-methyl-4-oxo-4,7-dihydrofuro[2,3-b]pyridine-5-carboxamide (Example 3) was resolved preparatively on a 5×50 cm Chiralpak AD column (Chiral Technologies), at a column temperature of 30° C. The mobile phase was 50% isopropyl alcohol/50% heptane (v/v) with a flow rate of 70 mL/min. Peaks were detected by UV at 250 nm. A 250 mg sample was injected in 10 mL of 50% IPA/50% $CHCl_3$ (v/v). The more slowly eluting enantiomer was further purified by column chromatography ($CH_2Cl_2$/methanol, 99/1, 98/2). The resulting pale yellow solid was recrystallized from ethyl acetate to yield 0.066 g of the title compound as a white solid. Physical characteristics. M.p. 94–98° C.;

$^1$H NMR (400 MHz, DMSO-$d_6$) δ 10.65, 8.54, 7.52, 7.41–7.32, 6.85, 6.37–6.36, 6.25–6.24, 5.24, 4.72–4.67, 4.55, 3.90, 3.75–3.67, 2.76–2.67, 2.28; MS (ESI+) m/z 470 (M+H)$^+$; [alpha]$^{25}_D$=−18 (c 0.80, $CH_2Cl_2$); Anal. Found: C, 61.04; H, 5.18; N, 8.89; Cl, 7.53.
Preparation 15. Ethyl 2-(Chloromethyl)-7-methyl-4-oxo 4,7-dihydrofuro[2,3-b]pyridine-5-carboxylate.

Ethyl 7-methyl-2-(morpholin-4-ylmethyl)-4-oxo-4,7-dihydrofuro[2,3-b]-pyridine-5-carboxylate (Preparation 10, 1.0 g) was dissolved in $CHCl_3$ (50 mL). Ethylchloroformate (0.75 mL) was added, and the mixture was stirred overnight at room temperature. The mixture was diluted with diethyl ether and filtered to afford 0.65 g of the title compound as a yellow powder. Physical characteristics. M.p. 181–184° C.; $^1$H NMR (300 MHz, DMSO-$d_6$) δ 8.36, 7.04, 4.96, 4.20, 3.85, 1.27; Anal. Found: C, 53.15; H, 4.56; N, 5.32.

Preparation 16. Ethyl 2-((((2R)-2-(2-Furyl)-2-hydroxyethyl)(methyl)amino)methyl)-7-methyl-4-oxo-4,7-dihydrofuro[2,3-b]pyridine-5 carboxylate.

(1R)-1-(2-Furyl)-2-(methylamino)ethanol (2.1 g) and N,N-diisopropylethylamine (2.35 mL) were added to a solution of ethyl 2-(chloromethyl)-7-methyl-4-oxo-4,7-dihydrofuro[2,3-b]pyridine-5-carboxylate (Preparation 15, 2.0 g) in DMF (175 mL). The reaction mixture was stirred for 1 h at 70° C. The mixture was diluted with water (350 mL) and extracted with $CH_2Cl_2$ (3×350 mL). The combined organic layers were concentrated in vacuo to afford an oil. The crude product was purified by column chromatography ($CH_2Cl_2$/methanol, 95/5) to afford 1.63 g of the title compound as a yellow solid. Physical characteristics. $^1$H NMR (300 MHz, DMSO-$d_6$) δ 8.30, 7.52, 6.78, 6.37, 6.25, 5.23, 4.68, 4.21, 3.81, 3.68, 2.75–2.69, 2.27, 1.27; HRMS (ESI) m/z 375.1566 (M+H)$^+$. Anal. Found: C, 60.60; H, 5.96; N, 7.48.

General procedure for preparation of Example 6-Example 11. Ethyl 2-((((2R)-2-(2-furyl)-2-hydroxyethyl)(methyl)amino)methyl)-7-methyl-4-oxo-4,7-dihydrofuro[2,3-b]pyridine-5-carboxylate (Preparation 16, 0.25 g) was dissolved in ethylene glycol (0.5 M). A substituted benzylamine (3 equiv) was added and the mixture was stirred overnight at 130° C. The mixture was allowed to cool to room temperature and diluted with water (75 mL). After extraction with $CH_2Cl_2$ (3×5 mL), the organic layer was concentrated in vacuo. The crude product was purified by column chromatography ($CH_2Cl_2$/methanol, 97/3) and trituration with diethyl ether.

EXAMPLE 6

N-(4-Fluorobenzyl)-2-((((2R)-2-(2-furyl)-2-hydroxyethyl)(methyl)amino)methyl)-7-methyl-4-oxo-4,7-dihydrofuro[2,3-b]pyridine-5-carboxamide.

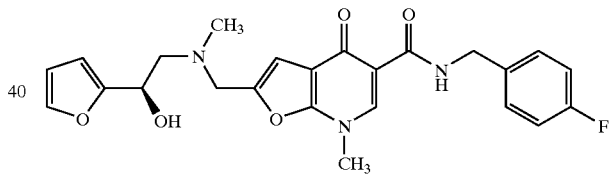

4-Fluorobenzylamine provided 35 mg of the title compound as a yellow solid. Physical characteristics. $^1$H NMR (300 MHz, DMSO-$d_6$) δ 10.54, 8.54, 7.51, 7.35–7.33, 7.19–7.13, 6.85, 6.36, 6.25, 5.28, 4.72, 4.53, 3.90, 3.70, 2.95–2.70, 2.28; HRMS (ESI) m/z 454.1786 (M+H)$^+$. Anal. Found: C, 63.43; H, 5.38; N, 9.25.

EXAMPLE 7

2-((((2R)-2-(2-Furyl)-2-hydroxyethyl)(methyl)amino)methyl)-7-methyl-N-(4-methylbenzyl)-4-oxo-4,7-dihydrofuro[2,3-b]pyridine-5-carboxamide.

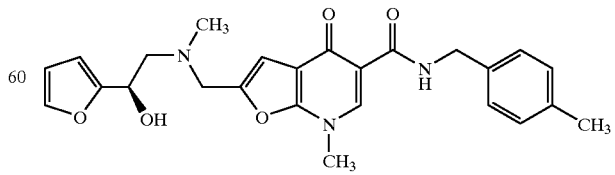

4-Methylbenzylamine provided 86 mg of the title compound as a white solid. Physical characteristics. M.p. 75–76°

C.; ¹H NMR (300 MHz, DMSO-d₆) δ 10.54, 8.54, 7.51, 7.21–7.13, 6.85, 6.36, 6.25, 5.24, 4.68, 4.50, 3.90, 3.70, 2.85–2.60, 2.28. Anal. Found: C, 66.52; H, 6.11; N, 9.31.

EXAMPLE 8

2-(((2R)-2-(2-Furyl)-2-hydroxyethyl)(methyl)amino)methyl)-7-methyl-N-(3,4-difluorobenzyl)-4-oxo-4,7-dihydrofuro[2,3-b]pyridine-5-carboxamide.

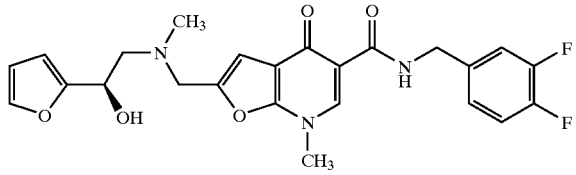

3,4-Difluorobenzylamine provided 74 mg of the title compound as a white solid. Physical characteristics. M.p. 129–130° C.; ¹H NMR (300 MHz, DMSO-d₆) δ 10.54, 8.54, 7.51, 7.43–7.33, 7.20–7.10, 6.85, 6.36, 6.25, 5.24, 4.68, 4.50, 3.90, 3.75–3.67, 2.80–2.65, 2.28. Anal. Found: C, 61.02; H, 4.96; N, 8.85.

EXAMPLE 9

2-((((2R)-2-(2-Furyl)-2-hydroxyethyl)(methyl)amino)methyl)-7-methyl-N-(3,4-dichlorobenzyl)-4-oxo-4,7-dihydrofuro[2,3-b]pyridine-5-carboxamide.

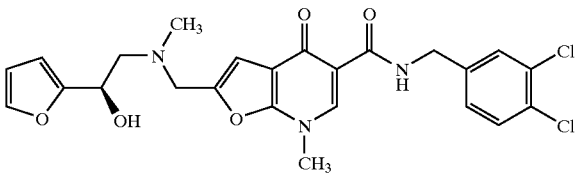

3,4-Dichlorobenzylamine provided 63 mg of the title compound as a white powder. Physical characteristics. M.p. 122–123° C.; ¹H NMR (300 MHz, DMSO-d₆) δ 10.54, 8.54, 7.61–7.51, 7.32–7.29, 6.85, 6.36, 6.25, 5.24, 4.68, 4.50, 3.90, 3.75–3.67, 2.82–2.65, 2.28. Anal. Found: C, 57.17; H, 4.60; N, 8.28.

EXAMPLE 10

2(((2R)-2-(2-Furyl)-2-hydroxyethyl)(methyl)amino)methyl)-7-methyl-N-(4-bromobenzyl)-4-oxo-4,7-dibydrofuro[2,3-b]pyridine-5-carboxamide.

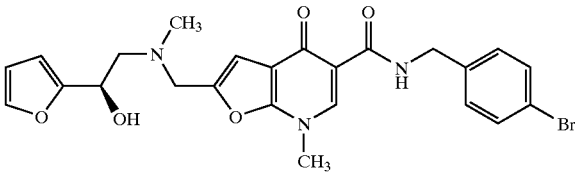

4-Bromobenzylamine hydrochloride (500 mg) was dissolved in water (25 mL) and 1 M NaOH (2 mL) was added. The mixture was extracted with CH₂Cl₂ (3×30 mL) and the combined organic layers were concentrated in vacuo to a clear oil. The resulting 4-bromobenzylamine afforded 51 mg of the title compound as a white solid. Physical characteristics. ¹H NMR (300 MHz, DMSO-d₆) δ 10.54, 8.54, 7.54–7.51, 7.29–7.26, 6.85, 6.36, 6.25, 5.24, 4.68, 4.50, 3.90, 3.75–3.67, 2.77–2.65, 2.28; HRMS (ESI) m/z 514.0994 (M+H)⁺.

EXAMPLE 11

2-((((2R)-2-(2-Furyl)-2-hydroxyethyl)(methyl)amino)methyl)-7-methyl-N-(4-trifluoromethylbenzyl)-4-oxo-4,7-dihydrofuro[2,3-b]-pyridine-5-carboxamide.

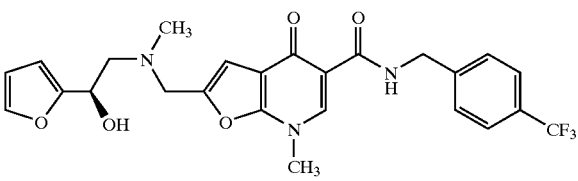

4-Trifluoromethylbenzylamine provided 105 mg of the title compound as a white solid. Physical characteristics. M.p. 113–115° C.; ¹H NMR (300 MHz, DMSO-d₆) δ 10.54, 8.54, 7.51, 7.43–7.33, 7.20–7.10, 6.85, 6.36, 6.25, 5.24, 4.68, 4.50, 3.90, 3.75–3.67, 2.80–2.65, 2.28; HRMS (ESI) m/z 504.1757 (M+H)⁺.

General procedure for Preparation 17—Preparation 23. A mixture of ethyl 3-(2-chloro-3-furyl)-3-oxopropanoate (Preparation 8, 10.0 g), triethylorthoformate (15.4 mL), and acetic anhydride (15.3 mL) was heated to 135° C. with removal of ethyl acetate distillate with a Dean-Stark trap. After 3 h, volatiles were removed at 40 Torr (100° C.) and then at 0.2 Torr (65° C., 1 h) to afford a black oil. The resulting oil was dissolved in THF (50 mL) and a corresponding amine (50.8 mmol) was added while cooling in an ice bath. The mixture was allowed to stir at room temperature for 20 h and was then cooled in an ice-brine bath. A solution of potassium tert-butoxide (1.0 M in THF, 50.8 mL) was added maintaining the internal temperature below 0° C. The mixture was allowed to warm to room temperature and was then held at 30–40° C. for 1 h. The mixture was diluted with ethyl acetate (400 mL) and sat aq. ammonium chloride (200 mL). The organic layer was washed with sat. aq. ammonium chloride (2×100 mL). The combined aqueous layers were extracted with ethyl acetate (2×100 mL). The combined organic layers were washed with brine (50 mL), dried (Na₂SO₄), and concentrated.

Preparation 17. Ethyl 7-Ethyl-4-oxo-4,7-dihydrofuro[2,3-b]pyridine-5-carboxylate.

The crude product derived from ethylamine was purified by column chromatography (CH₂Cl₂/methanol, 100/1; 50/1; 25/1). The resulting solid was recrystallized from EtOAc/hexane to afford 5.48 g as a tan solid. Physical characteristics. M.p. 117° C.; ¹H NMR (400 MHz, DMSO-d₆) δ 8.38, 7.83, 6.98, 4.27, 4.21, 1.40, 1.27; ¹³C NMR (75 MHz, DMSO-d₆) δ 170.4, 164.6, 152.5, 141.7, 141.1, 115.7, 113.7, 107.3, 59.9, 46.0, 14.7, 14.2; MS (EI) m/z 235 (M⁻).

Preparation 18. Ethyl 7-Cyclopropyl-4-oxo-4,7-dihydrofuro[2,3-b]pyridine-5-carboxylate.

The crude product derived from cyclopropylamine was triturated with diethyl ether and filtered to afford 3.58 g as a gray solid. Physical characteristics. M.p. 197–198° C.; ¹H NMR (400 MHz, DMSO-d₆) δ 8.12, 7.84, 6.97, 4.21, 3.67, 1.27, 1.16–1.08; ¹³C NMR (75 MHz, CDCl₃) δ 171.7, 165.3, 153.7, 141.9, 140.1, 116.5, 114.7, 108.0, 61.0, 32.0, 14.4, 6.8; MS (EI) m/z 247 (M+). Anal. Found: C, 63.47; H, 5.34; N, 5.69.

Preparation 19. Ethyl 4-oxo-7-propyl-4,7-dihydrofuro[2,3-b]pyridine-5-carboxylate.

The crude product derived from propylamine was purified by column chromatography ($CH_2Cl_2$/methanol, 100/1; 50/1; 25/1). The resulting oil was crystallized from EtOAc/hexane to afford 3.42 g as a yellow solid. Physical characteristics. M.p. 81–85° C.; $^1$H NMR (400 MHz, DMSO-$d_6$) δ 8.37, 7.81, 6.97, 4.24·4.17, 1.80, 1.27, 0.87; $^{13}$C NMR (75 MHz, $CDCl_3$) δ 171.8, 165.5, 152.7, 141.7, 139.8, 116.4, 115.0, 108.2, 61.0, 53.1, 23.0, 14.4, 10.8; MS (EI) m/z 249 ($M^+$).

Preparation 20. Ethyl 4-Oxo-7-phenyl-4,7-dihydrofuro[2,3-b]pyridine-5-carboxylate.

The crude product derived from aniline was purified by column chromatography ($CH_2Cl_2$/methanol, 100/1; 50/1; 25/1) to afford 1.07 g (8%) as a brown solid. Physical characteristics. M.p. 201–202° C.; $^1$H NMR (400 MHz, DMSO-$d_6$) δ 8.30, 7.77, 7.76–7.73, 7.66–7.58, 7.05, 4.22, 1.26; $^3$C NMR (75 MHz, $CDCl_3$) δ 171.8, 165.1, 151.9, 141.8, 140.0, 137.4, 130.1, 129.9, 125.1, 117.3, 114.9, 108.2, 61.2, 14.4; MS (EI) m/z 283 ($M^+$).

Preparation 21. Ethyl 4-Oxo-7-(2-phenylethyl)-4,7-dihydrofuro[2,3-b]-pyridine-5-carboxylate.

The crude product derived from phenethylamine was purified by column chromatography ($CH_2Cl_2$/methanol, 100/1; 5011; 25/1) to afford 7.48 g as a orange solid. Physical characteristics. M.p. 110–112° C.; $^1$H NMR (400 MHz, DMSO-$d_6$) δ 8.20, 7.77, 7.30–7.18, 6.94, 4.48, 4.17, 3.11, 1.24; MS (EI) m/z 311 ($M^+$). Anal. Found: C, 69.07; H, 5.60; N, 4.59.

Preparation 22. Ethyl 4-Oxo-7-pyridin-2-yl-4,7-dihydrofuro[2,3-b]pyridine-5-carboxylate.

The crude product derived from 2-aminopyridine was purified by column chromatography ($CH_2Cl_2$/methanol, 100/1; 50/1; 25/1) to afford 4.86 g as a orange solid. Physical characteristics. M.p. 187–189° C.; $^1$H NMR (400 MHz, DMSO-$d_6$)δ 8.82, 8.70, 8.17, 8.04, 7.86, 7.62, 7.08, 4.25, 1.28; $^{13}$C NMR (100 MHz, $CDCl_3$) δ 172.6, 165.2, 151.1, 149.8, 148.9, 140.0, 139.9, 139.7, 124.2, 118.1, 117.8, 115.2, 108.4, 61.5, 14.7; MS (EI) m/z 284 ($M^+$).

Preparation 23. Ethyl 7-(2-(Diethylamino)ethyl)-4-oxo-4,7-dihydrofuro[2,3-b]pyridine-5-carboxylate.

Saturated aq. ammonium chloride was replaced by sodium bicarbonate in general workup. The crude product derived from N,N-diethylethylenediamine was purified by column chromatography ($CH_2Cl_2$/methanol, 100/1; 50/1; 25/11, 10/1) to afford 6.27 g (44%) as a white solid. Physical characteristics. M.p. 108–109° C.; $^1$H NMR (400 MHz, DMSO-$d_6$) δ 8.32, 7.80, 6.96, 4.27, 4.20, 2.71, 2.43, 1.26, 0.77; $^{13}$C NMR(100 MHz, $CDCl_3$) δ 172.3, 165.8, 153.0, 143.4, 139.9, 116.0, 115.1, 108.6, 61.1, 52.4, 50.0, 47.7, 14.7, 12.5; MS (ESI+) m/z 307 $(M+H)^+$. Anal. Found: C, 62.76; H, 7.31; N, 9.06.

General procedures for Preparation 24-Preparation 30. Esters of Preparation 17-Preparation 23 were suspended in acetonitrile (0.25 M) and 4-methylenemorpholin-4-ium chloride (1.5 equiv) was added. The reaction mixture was heated to 60° C. for 3 h, allowed to cool to room temperature, and then was quenched with sat. aq. sodium carbonate (50 mL). The mixture was diluted with water (100 mL) and $CH_2Cl_2$ (300 mL). The aqueous layer was extracted with $CH_2Cl_2$ (2×100 mL). The combined organic layers were washed with brine (50 mL), dried ($Na_2SO_4$), and concentrated.

Preparation 24. Ethyl 7-Ethyl-2-(morpholin-4-ylmethyl)-4-oxo-4,7-dihydrofuro[2,3-b]pyridine-5-carboxylate.

Ethyl 7-ethyl-4-oxo-4,7-dihydrofiiro[2,3-b]pyridine-5-carboxylate (Preparation 17, 5.03 g) provided 6.18 g as a tan solid. Physical characteristics. M.p. 158–160° C.; $^1$H NMR (400 MHz, DMSO-$d_6$) δ 8.35, 6.80, 4.25, 4.20, 3.62, 3.58, 2.42, 1.39, 1.27; $^{13}$C NMR (75 MHz, $CDCl_3$) δ 171.5, 165.5, 152.3, 149.1, 140.9, 116.8, 115.7, 107.4, 66.7, 61.0, 55.0, 53.1, 46.5, 15.1, 14.4; MS (ESI+) m/z 335 $(M+H)^+$; Anal. Found: C, 60.92; H, 6.67; N, 8.41.

Preparation 25. Ethyl 7-Cyclopropyl-2-(morpholin-4-ylmethyl)-4-oxo-4,7-dihydrofuro[2,3-bipyridine-5-carboxylate.

Ethyl 7-cyclopropyl-4-oxo-4,7-dihydrofuro[2,3-b]pyridine-5-carboxylate (Preparation 18, 3.93 g) provided 4.98 g as a tan solid. Physical characteristics. M.p. 200–201° C.; $^1$H NMR (400 MHz, DMSO-$d_6$) δ 8.09, 6.79, 4.20, 3.66, 3.62, 3.58, 2.44, 1.26, 1.17–1.08; $^{13}$C NMR (75 MHz, $CDCl_3$) δ 171.5, 165.4, 153.5, 149.4, 141.6, 116.6, 115.4, 107.1, 66.8, 61.0, 54.9, 53.1, 32.1, 14.4, 6.8; MS (ESI+) m/z 347 $(M+H)^+$. Anal. Found: C, 62.08; H, 6.42; N, 8.04.

Preparation 26. Ethyl 2-(Morpholin-4-ylmethyl)-4-oxo-7-propyl-4,7-dihydrofuro[2,3-b]pyridine-5-carboxylate.

Ethyl 4-oxo-7-propyl-4,7-dihydrofuro[2,3-b]pyridine-5-carboxylate (Preparation 19, 3.02 g) provided 3.62 g as a tan solid. Physical characteristics. M.p. 129.5–130° C.; $^1$H NMR (400 MHz, DMSO-$d_6$) δ 8.34, 6.80, 4.21, 4.19, 3.61, 3.57, 2.41, 1.80, 1.27, 0.87; $^{13}$C NMR (100 MHz, $CDCl_3$) δ 171.9, 165.9, 152.8, 149.4, 141.7, 116.9, 116.0, 107.7, 67.1, 61.3, 55.3, 53.4, 53.2, 23.4, 14.7, 11.2; MS (ESI+) m/z 349 $(M+H)^+$. Anal. Found: C, 61.82; H, 6.94; N, 8.04.

Preparation 27. Ethyl 2{(Morpholin-4-ylmethyl)-4-oxo-7-phenyl-4,7-dihydrofuro[2,3-b]pyridine-5-carboxylate.

Ethyl 4-oxo-7-phenyl-4,7-dihydrofuro[2,3-b]pyridine-5-carboxylate (Preparation 20, 4.09 g) provided 3.62 g as a brown solid. Physical characteristics. M.p. 168–170° C.; $^1$H NMR (400 MHz, DMSO-$d_6$) δ 8.25, 7.75–7.58, 6.88, 4.21, 3.54, 2.37, 1.26; $^{13}$C NMR (100 MHz, $CDCl_3$) δ 171.9, 165.6, 151.9, 149.7, 141.9, 137.9, 130.5, 130.1, 125.4, 117.9, 116.0, 107.4, 67.1, 61.5, 55.2, 53.4, 14.7; MS (ESI+) m/z 383 $(M+H)^+$.

Preparation 28. Ethyl 2-(Morpholin-4-ylmethyl)-4-oxo-7-(2-phenylethyl)-4,7-dihydrofuro[2,3-b]pyridine-5-carboxylate.

Ethyl 4-oxo-7-(2-phenylethyl)-4,7-dihydrofuro[2,3-b]pyridine-5-carboxylate (Preparation 21, 6.96 g) provided 8.26 g as a tan solid. Physical characteristics. M.p. 139–140° C.; $^1$H NMR (400 MHz, DMSO-$d_6$) δ 8.18, 7.28–7.13, 6.75, 4.46, 4.17, 3.58, 3.56, 3.11, 2.40, 1.24; $^{13}$C NMR (100 MHz, $CDCl_3$) δ 171.5, 165.2, 152.2, 149.2, 141.3, 136.0, 128.9, 128.7, 127.4, 116.4, 115.6, 107.1, 66.8, 60.8, 54.9, 53.1, 52.6, 36.1, 14.3; MS (ESI+) m/z 411 $(M+H)^+$. Anal. Found: C, 66.92; H, 6.39; N, 6.80.

Preparation 29. Ethyl 2-(Morpholin-4-ylmethyl)-4-oxo-7-pyridin-2-yl-4,7-dihydrofuro[2,3-b]pyridine-5-carboxylate.

Ethyl 4-oxo-7-pyridin-2-yl-4,7-dihydrofuro[2,3-b]pyridine-5-carboxylate (Preparation 22, 4.38 g) provided 5.37 g as a tan solid. Physical characteristics. M.p. 199–199.5° C.; $^1$H NMR (400 MHz, DMSO-$d_6$) δ 8.79, 8.70, 8.19, 8.02, 7.62, 6.91, 4.25, 3.62, 3.56, 2.43, 1.28; $^{13}$C NMR (100 MHz, $CDCl_3$) δ 171.9, 164.8, 150.4, 149.4, 149.1, 148.6, 139.3, 139.2, 123.8, 117.8, 117.3, 115.5, 106.9, 66.7, 61.0, 54.9, 53.1, 14.3; MS (ESI+) m/z 384 $(M+H)^+$. Anal. Found: C, 62.46; H, 5.79; N, 10.66.

Preparation 30. Ethyl 7-(2-(Diethylamino)ethyl)-2-(morpholin-4-ylmethyl)-4-oxo-4,7-dihydrofuro[2,3-b]pyridine-5-carboxylate.

Ethyl 7-(2-(diethylamino)ethyl)-4-oxo-4,7-dihydrofuro[2,3-b]pyridine-5-carboxylate (Preparation 23, 5.77 g), with a modification to the general procedure in that after 1 h additional 4-methylenemorpholine chloride (2.55 g) was added, provided 2.42 g as a white solid. Physical characteristics. M.p. 107–109° C.; $^1$H NMR (400 MHz, DMSO-d$_6$) δ 8.29, 6.79, 4.25, 4.20, 3.60, 3.57, 2.72,2,45–2.40, 1.26, 0.78; "C NMR (100 MHz, CDCl$_3$) δ 171.6, 165.4, 152.4, 148.9, 142.6, 115.8, 115.3, 107.2, 66.8, 60.7, 55.0, 53.1, 51.9, 49.7, 47.3, 14.3, 12.1; MS (ESI+) m/z 406 (M+H)$^+$. Anal. Found: C, 62.29; H, 7.76; N, 10.40.

General procedure for preparation of Example 12-Example 18. Esters of Preparation 24-Preparation 30 were dissolved in ethylene glycol (0.5 M). 4-Chlorobenzylamine (3 equiv) was added and the mixture was stirred overnight at 130° C. The mixture was allowed to cool to room temperature and diluted with water (75 mL). The resulting precipitate was filtered on a fritted funnel.

EXAMPLE 12

N-(4-Chlorobenzyl)-7-ethyl-2-(morpholin-4-ylmethyl)-4-oxo-4,7-dihydrofuro[2,3-b]pyridine-5-carboxamide.

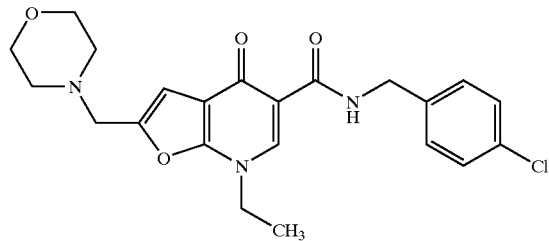

Ethyl 7-ethyl-2-morpholin-4-ylmethyl)-4-oxo-4,7-dihydrofuro[2,3-b]-pyridine-5-carboxylate (Preparation 24, 6.0 g) afforded 6.67 g as a white solid after recrystallization from EtOAc. Physical characteristics. M.p. 229–231° C.;

$^1$H NMR (300 MHz, DMSO-d$_6$) δ 10.54, 8.59, 7.41–7.31, 6.85, 4.54–4.53, 4.36–4.33, 3.64, 3.57, 2.43, 1.41. Anal. Found: C, 61.49; H, 5.69; N, 9.68; Cl, 8.37.

EXAMPLE 13

N-(4-Chlorobenzyl)-7-cyclopropyl-2-(morpholin-4-ylmethyl) 4-oxo-4,7-dihydrofuro[2,3-b]pyridine-5-carboxamide

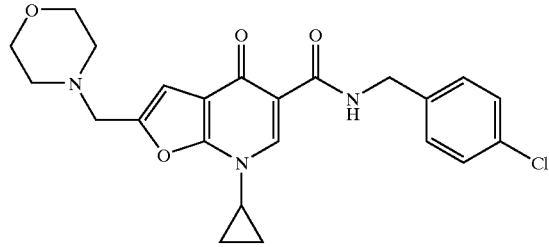

Ethyl 7-cyclopropyl-2-(morpholin-4-ylmethyl)-4-oxo-4,7-dihydrofuro[2,3-b]pyridine-5-carboxylate (Preparation 25, 4.85 g) afforded 4.5 g as a solid after recrystallization from EtOAc. Physical characteristics. M.p. 195.5–197.8° C.; $^1$H NMR (300 MHz, DMSO-d$_6$) δ 10.54, 8.35, 7.41–7.31, 6.88, 4.54–4.52, 3.83–3.72, 3.65, 3.57, 2.45, 1.17–1.15. Anal. Found: C, 62.39; H, 5.56; N, 9.44; Cl, 8.01.

EXAMPLE 14

N-(4-Chlorobenzyl)-7-propyl-2-(morpholin-4-ylmethyl)-4-oxo-4,7-dihydrofuro[2,3-b]pyridine-5-carboxamide

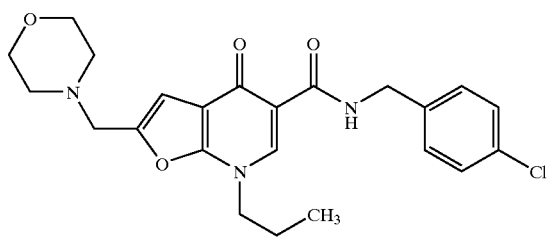

Ethyl 2-(morpholin-4-ylmethyl)-4-oxo-7-propyl-4,7-dihydrofuro[2,3-b]-pyridine-5-carboxylate (Preparation 26, 3.4 g) afforded 3.45 g as an off-white solid after recrystallization from EtOAc. Physical characteristics. M.p. 195–196° C.; $^1$H NMR (300 MHz, DMSO-d$_6$) δ 10.54, 8.57, 7.41–7.31, 6.88, 4.544.53, 4.314.27, 3.64, 3.57, 2.43, 1.86–1.78, 0.88–0.83. Anal. Found: C, 62.14; H, 5.79; N, 9.34; Cl, 8.02.

EXAMPLE 15

N-(4-Chlorobenzyl)-2-(morpholin-4-ylmethyl)-4-oxo-7-phenyl-4,7-dihydrofuro[2,3-b]pyridine-5-carboxamide.

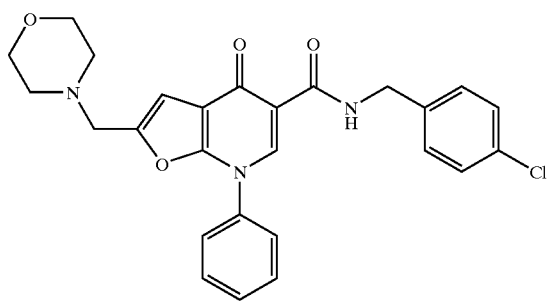

Ethyl 2-(morpholin-4-ylmethyl)-4-oxo-7-phenyl-4,7-dihydrofuro[2,3-b]-pyridine-5-carboxylate (Preparation 27, 4.7 g) afforded 4.1 g as a tan solid after recrystallization from EtOAc. Physical characteristics. M.p. 209.6–212.0° C.;. $^1$H NMR (300 MHz, DMSO-d$_6$) δ 10.54, 8.41, 7.78–7.75, 7.68–7.61, 7.42–7.31, 6.96, 4.574.55, 3.56–3.51, 2.39–2.31. Anal. Found: C, 65.36; H, 5.16; N, 8.75; Cl, 7.41.

EXAMPLE 16

N-(4-Chlorobenzyl)-2-(morpholin-4-ylmethyl)-4-oxo-7-(2-phenylethyl)-4,7-dihydrofuro[2,3-b]pyridine-5-carboxamide

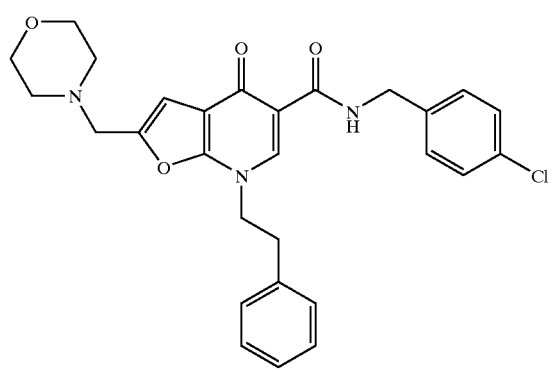

Ethyl 2-morpholin-4-ylmethyl)-4-oxo-7-(2-phenylethyl)-4,7-dihydrofuro[2,3-b]pyridine-5-carboxylate (Preparation 28, 8.0 g) afforded 8.3 g as an off-white solid after recrystallization from EtOAc. Physical characteristics. M.p. 150–153° C.; $^1$H NMR (300 MHz, DMSO-d$_6$) δ 10.54, 8.49, 7.40–7.12, 6.82, 4.58–4.48, 3.60–3.54, 3.15–3.10, 2.41–2.37; HRMS (ESI) m/z 506.1849 (M+H)$^+$.

EXAMPLE 17

N-(4-chlorobenzyl)-2-morpholin-4-ylmethyl)-4-oxo-7-pyridin-2-yl-4,7-dihydrofuro[2,3-b]pyridine-5-carboxamide

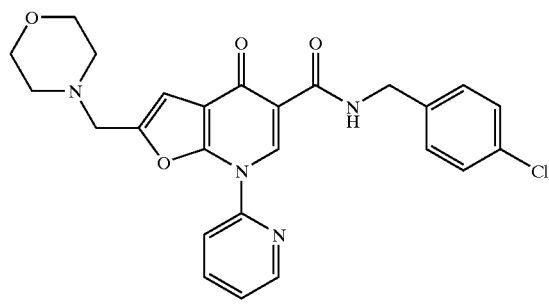

Ethyl 2(morpholin-4-ylmethyl)-4-oxo-7-pyridin-2-yl-4,7-dihydrofuro[2,3-b]pyridine-5-carboxylate (Preparation 29, 5.1 g) afforded 4.4 g as an off-white solid after recrystallization from EtOAc. Physical characteristics. M.p. 192–195° C.; $^1$H NMR (300 MHz, DMSO-d$_6$) δ 10.54, 9.08, 8.71, 8.27–8.1.8, 8.07, 8.04, 7.42–7.34, 6.98, 4.584.56, 3.65, 3.56, 2.43. Anal. Found: C, 62.57; H, 4.85; N, 11.66; Cl, 7.28.

EXAMPLE 18

N-(4-Chlorobenzyl)-7-(2-(diethylamino)ethyl)-2-morpholin-4-ylmethyl)-4-oxo-4,7-dihydrofuro[2,3-b]pyridine-5-carboxamide

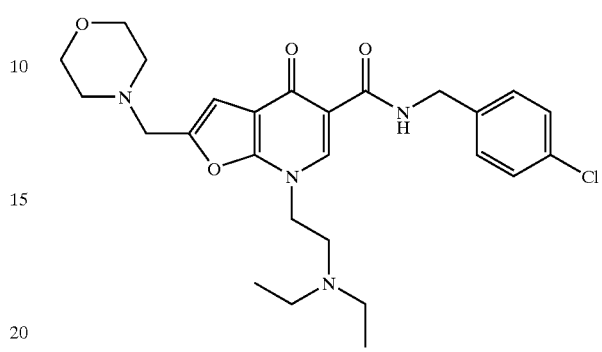

Ethyl 7-(2-(diethylamino)ethyl)-2-(morpholin-4-ylmethyl)-4-oxo-4,7-dihydrofuro[2,3-b]pyridine-5-carboxylate (Preparation 30, 2.3 g) afforded 1.4 g as a beige solid after recrystallization from EtOAc/heptanes. Physical characteristics. M.p. 131–134° C.; $^1$H NMR (300 MHz, DMSO-d$_6$) δ 10.54, 8.54, 7.41–7.32, 6.87, 4.54, 4.52, 4.374.33, 3.63, 3.58–3.55, 2.76–2.72, 2.462.39, 0.77–0.73; HRMS (ESI) m/z 501.2276 (M+H)$^+$.

General procedure for preparation of Example 19-Example 25.

Carboxamides of Example. 12-Example 18 were dissolved in CHCl$_3$ (0.0625 M). Ethylchloroformate (2.5 equiv) was added and the mixture was stirred overnight at room temperature. The mixture was concentrated to a slurry, filtered on a fritted funnel, and washed with diethyl ether and acetonitrile.

EXAMPLE 19

N-(4-Chlorobenzyl)-2-(chloromethyl)-7-ethyl-4-oxo-4,7-dihydrofuro[2,3-b]pyridine-5-carboxamide.

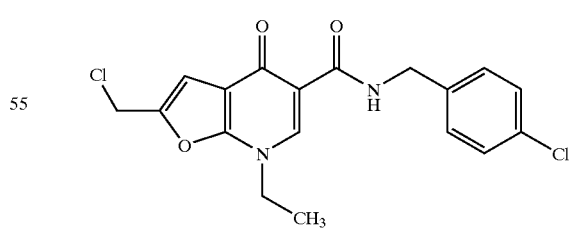

N-(4-Chlorobenzyl)-7-ethyl-2-(morpholin-4-ylmethyl)-4-oxo-4,7-dihydrofuro[2,3-b]pyridine-5-carboxamide (Example 12, 6.4 g) afforded 4.9 g as a white solid after recrystallization from acetonitrile. Physical characteristics.

M.p. 192–193° C.; ¹H NMR (300 MHz, DMSO-d₆) δ 10.54, 8.64, 7.41–7.32, 7.11, 4.99, 4.54–4.53, 4.40–4.32, 1.45–1.40. Anal. Found: C, 56.98; H, 4.26; N, 7.39, Cl, 18.64.

EXAMPLE 20

N-(4-Chlorobenzyl)-2-(chloromethyl)-7-cyclopropyl-4-oxo-4,7-dihydrofuro[2,3-b]pyridine-5-carboxamide

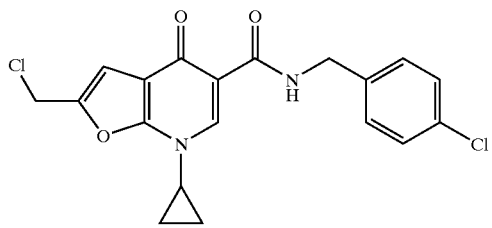

N-(4-Chlorobenzyl)-7-cyclopropyl-2-(morpholin-4-ylmethyl)-4-oxo-4,7-dihydrofuro[2,3-b]pyridine-5-carboxamide (Example 13, 4.2 g) afforded 1.9 g as a white solid after recrystallization from acetonitrile. Physical characteristics. M.p. 174–176° C.; ¹H NMR (300 MHz, DMSO-d₆) δ 10.54, 8.38, 7.41–7.31, 7.11, 5.00, 4.54–4.52, 3.85–3.68, 1.18–1.12. Anal. Found: C, 58.27; H, 4.11; N, 7.16; Cl, 17.93.

EXAMPLE 21

N-(4-Chlorobenzyl)-2-(chloromethyl)-4-oxo-7-propyl-4,7-dihydrofuro[2,3-b]pyridine-5-carboxamide.

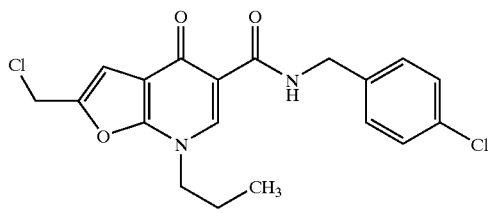

N-(4-Chlorobenzyl)-7-propyl-2-(morpholin-4-ylmethyl)-4-oxo-4,7-dihydrofuro[2,3-b]pyridine-5-carboxamide (Example 14, 3.2 g) afforded 1.8 g as a white solid after recrystallization from acetonitrile. Physical characteristics. M.p. 160–162° C.; ¹H NMR (300 MHz, DMSO-d₆) δ 10.54, 8.62, 7.41–7.32, 7.11, 4.98,4,55–4.53, 4.33–4.28, 1.92–1.79, 0,90–0.87. Anal. Found: C, 57.95; H. 4.65; N, 7.12; Cl, 17.96.

EXAMPLE 22

N-(4-Chlorobenzyl)-2-(chloromethyl)-4-oxo-7-phenyl-4,7-dihydrofuro[2,3-b]pyridine-5-carboxamide.

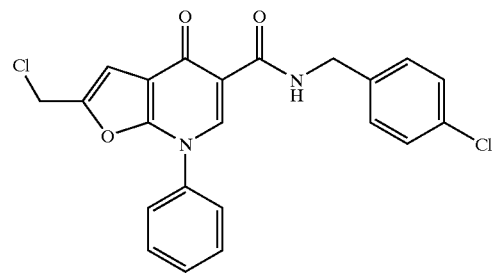

N-(4-Chlorobenzyl)-2-(morpholin-4-ylmethyl)-4-oxo-7-phenyl-4,7-dihydrofuro[2,3-b]pyridine-5-carboxamide (Example 15, 3.8 g) afforded 1.9 g as a white solid after recrystallization from acetonitrile. Physical characteristics. M.p. 207–209° C.; ¹H NMR (300 MHz, DMSO-d₆) δ 10.54, 8.44, 7.79–7.76, 7.69–7.55, 7.43–7.34, 7.19, 4.93, 4.57 4.55. Anal. Found: C, 61.88; H, 3.78; N, 6.55; Cl, 16.44.

EXAMPLE 23

N-(4-Chlorobenzyl)-2-(chloromethyl)-4-oxo-7-(2-phenylethyl)-4,7-dihydrofuro[2,3-b]pyridine-5-carboxamide

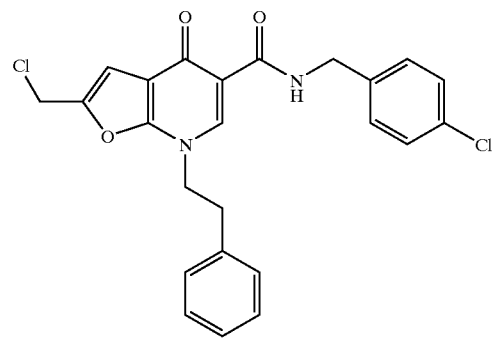

N-(4-Chlorobenzyl)-2-(morpholin-4-ylmethyl)-4-oxo-7-(2-phenylethyl)-4,7-dihydrofuro[2,3-b]pyridine-5-carboxamide (Example 16, 8.0 g) afforded 4.0 g as a white solid. Physical characteristics. M.p. 150–153° C.; ¹H NMR (300 MHz, DMSO-d₆) δ 10.54, 8.52, 7.41–7.15, 7.06, 4.91, 4.60 4.50, 3.17–3.12; Anal. Found: C, 63.19; H, 4.42; N, 6.13; Cl, 15.23.

EXAMPLE 24

N-(4-Chlorobenzyl)-2-chloromethyl)-4-oxo-7-pyridin-2-yl-4,7-dihydrofuro[2,3-b]pyridine-5-carboxamide.

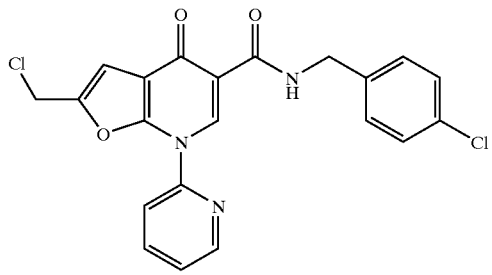

N-(4-Chlorobenzyl)-2-(morpholin-4-ylmethyl)-4-oxo-7-pyridin-2-yl-4,7-dihydrofuro[2,3-b]pyridine-5-carboxamide (Example 17, 4.0 g) afforded 2.9 g as a white solid. Physical characteristics. M.p. 224–227° C.; $^1$H NMR (300 MHz, DMSO-$d_6$) δ 10.54, 9.06, 8.74, 8.23–8.20, 8.07–8.04, 7.68–7.64, 7.42–7.35, 7.21, 4.99, 4.58–4.56.

EXAMPLE 25

N-(4-Chlorobenzyl)-2-(chloromethyl)-7-(2-(diethylamino) ethyl)-4-oxo-4,7-dihydrofuro[2,3-b]pyridine-5-carboxamide

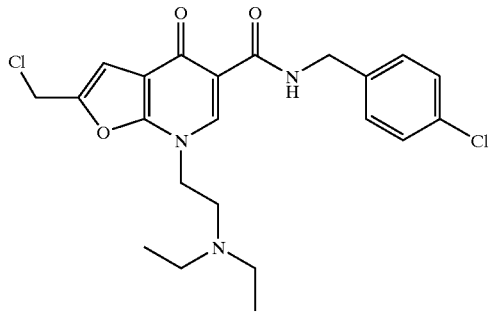

N-(4-Chlorobenzyl)-7-(2-(diethylamino)ethyl)-2-(morpholin-4-ylmethyl)-4-oxo-4,7-dihydrofuro[2,3-b]pyridine-5-carboxamide (Example 18, 1.0 g) afforded 0.62 g as a beige solid. Physical characteristics. M.p. 113–115° C.;

$^1$H NMR (300 MHz, DMSO-$d_6$) δ 10.50, 8.58, 7.42–7.33, 7.10, 4.97, 4.54–4.52, 4.36, 2.76, 2.49–2.42, 0.75.

General procedure for example 26-Example 32. Chlorides of Example 19-Example 25 (0.75 mmol) were dissolved in DMF (0.04 M). (1R)-1-(2-Furyl)-2-(methylamino)ethanol (2.0 equiv) and N,N-diisopropylethylamine (2.0 equiv) were added and the mixture was stirred for 2 h at 90° C. The mixture was diluted with water (40 mL), extracted with $CH_2Cl_2$ (3×40 mL), and concentrated.

EXAMPLE 26

N-(4-Chlorobenzyl)-7-ethyl-2(((2R)-2-(2-furyl)-2-hydroxyethyl)(methyl)amino)methyl)-4-oxo-4,7-dihydrofuro[2,3-b]pyridine-5-carboxamide.

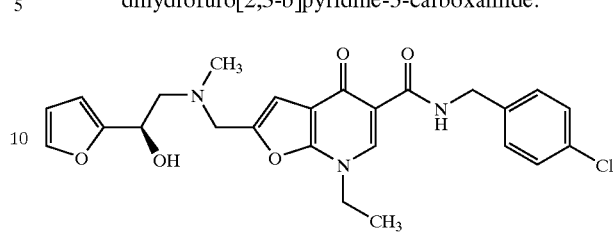

N-(4-Chlorobenzyl)-2-(chloromethyl)-7-ethyl-4-oxo-4,7-dihydrofuro[2,3-b]pyridine-5-carboxamide (Example 19). The crude product was purified by column chromatography ($CH_2Cl_2$/methanol, 98/2) and triturated with $Et_2O$ to afford 0.11 g as a white solid. Physical characteristics. $^1$H NMR (300 MHz, DMSO-$d_6$) δ 10.54, 8.59, 7.53, 7.41–7.31, 6.86, 6.38, 6.23, 5.23, 4.81–4.74, 4.55,4,39–4.32, 3.73, 2,81–2.68, 2.28, 1.43–1.37; HRMS (ESI) m/z 484.1642 (M+H)$^+$.

EXAMPLE 27

N-(4-Chlorobenzyl)-7-cyclopropyl-2-((((2R)-2-(2-furyl)-2-hydroxyethyl)(methyl)amino)methyl)-4-oxo-4,7-dihydrofuro[2,3-b]pyridine-5-carboxamide

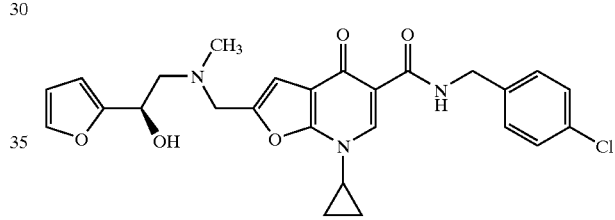

N-(4-Chlorobenzyl)-2-(chloromethyl)-7-cyclopropyl-4-oxo-4,7-dihydrofuro[2,3-b]pyridine-5-carboxamide (Example 20). The crude product was purified by column chromatography ($CH_2Cl_2$/methanol, 98/2) and triturated with $Et_2O$ to afford 0.15 g as a white solid. Physical characteristics. $^1$H NMR (306 MHz, DMSO-$d_6$) δ 10.54, 8.35, 7.54, 7.42–7.32, 6.85, 6.37, 6.29, 5.23, 4.85–4.71, 4.56, 3.79–3.70, 2.76–2.70, 2.30, 1.19–1.12; Anal. Found: C, 62.82; H, 5.24; N, 8.38; Cl, 7.20.

EXAMPLE 28

N-(4-Chlorobenzyl)-2-((((2R)-2-(2-furyl)-2-hydroxyethyl)(methyl)amino)methyl)-4-oxo-7-propyl-4,7-dihydrofuro[2,3-b]pyridine-5-carboxamide.

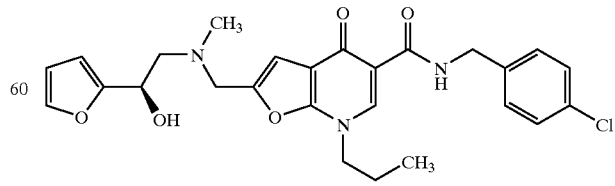

N-(4-Chlorobenzyl)-2-(chloromethyl)-4-oxo-7-propyl-4,7-dihydrofuro[2,3-b]pyridine-5-carboxamide (Example 21).

The crude product was purified by column chromatography (CH₂Cl₂/methanol, 98/2) and triturated with Et₂O to afford 0.18 g as a yellow solid. Physical characteristics. $^1$H NMR (300 MHz, DMSO-d$_6$) δ 10.52, 8.57, 7.52, 7.43–7.31, 6.86, 6.35, 6.26, 5.23–5.21, 4.76–4.63, 4.55–4.53, 4.29–4.25, 3.73, 2.80–2.68, 2.27, 1.90–1.72, 0.89–0.81; Anal. Found: C, 62.58; H, 5.75; N, 8.36; Cl, 7.04.

EXAMPLE 29

N-(4-Chlorobenzyl)-2-((((2R)-2-(2-furyl)-2-hydroxyethyl)(methyl)amino)methyl)-4-oxo-7-phenyl-4,7-dihydrofuro[2,3-b]pyridine-5-carboxamide

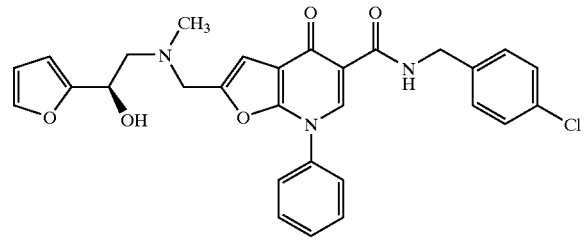

N-(4-Chlorobenzyl)-2-(chloromethyl)-4-oxo-7-phenyl-4,7-dihydrofuro[2,3-b]pyridine-5-carboxamide (Example 22). The crude product was purified by column chromatography (CH₂Cl₂/methanol, 98/2) and triturated with Et₂O to afford 0.21 g as a white solid. Physical characteristics. $^1$H NMR (300 MHz, DMSO-d$_6$) δ 10.52, 8.42, 7.77–7.73, 7.69–7.58, 7.51, 7.43–7.32, 6.94, 6.34, 6.18, 5.20–5.17, 4.70–4.61, 4.584.56, 3.66, 2.67, 2.23; Anal. Found: C, 65.51; H, 5.02; N, 7.99; Cl, 6.67.

EXAMPLE 30

N-(4-Chlorobenzyl)-2-((((2R)-2-(2-furyl)-2-hydroxyethyl)(methyl)amino)methyl)-4 oxo-7-(2-phenylethyl)-4,7-dihydrofuro[2,3-b]-pyridine-5-carboxamide.

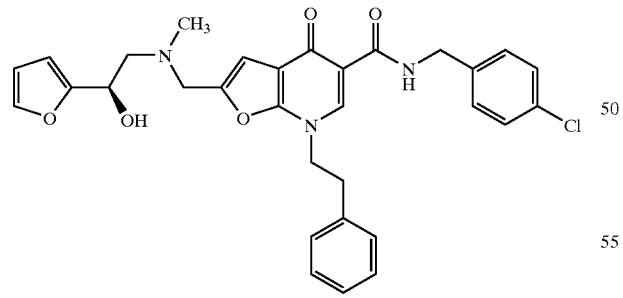

N-(4-Chlorobenzyl)-2-(chloromethyl)-4-oxo-7-(2-phenylethyl)-4,7-dihydrofuro[2,3-b]pyridine-5-carboxamide (Example 23). The crude product was purified by column chromatography (CH₂Cl₂/methanol, 98/2) and triturated with Et₂O to afford 0.18 g as a white foam. Physical characteristics: $^1$H NMR (300 MHz, DMSO-d$_6$) δ 10.54, 8.49, 7.57, 7.41–7.04, 6.81, 6.35, 6.25, 5.23, 4.764.68, 4.564.45, 3.68, 3.17–3.08, 2.78–2.70, 2.26.

EXAMPLE 31

N-(4-Chlorobenzyl)-2-((((2R)-2-(2-furyl)-2-hydroxyethyl)(methyl)amino)methyl)-4-oxo-7-pyridin-2-yl-4,7-dihydrofuro[2,3-b]-pyridine-5-carboxamide.

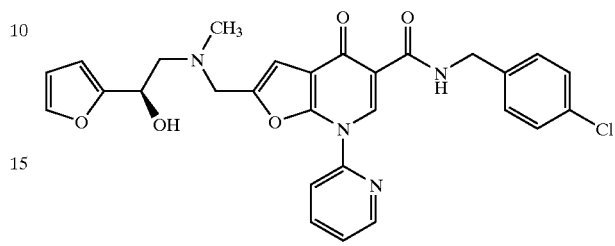

N-(4-Chlorobenzyl)-2-(chloromethyl)-4-oxo-7-pyridin-2-yl-4,7-dihydrofuro[2,3-b]pyridine-5-carboxamide (Example 24). The crude product was twice purified by column chromatography (CH₂Cl₂/methanol, 98/2) and triturated with Et₂O to afford 0.050 g as a white foam. Physical characteristics. $^1$H NMR (300 MHz, DMSO-d$_6$) δ 10.45, 9.07, 8.69–8.65, 8.15–8.05, 7.98–7.94, 7.62–7.56, 7.50, 7.43–7.33, 6.96, 6.33, 6.23, 5.23–5.21, 4.764.65, 4.58–4.56, 3.74, 3.40–3.33, 2.79–2.61, 2.28, 1.09;

EXAMPLE 32

N-(4-Chlorobenzyl)-7-(2-(diethylamino)ethyl)-2(((2R)-2-(2-furyl)-2-hydroxyethyl)(methyl)amino)methyl)-4-oxo-4,7-dihydrofuro[2,3-b]-pyridine-5-carboxamide.

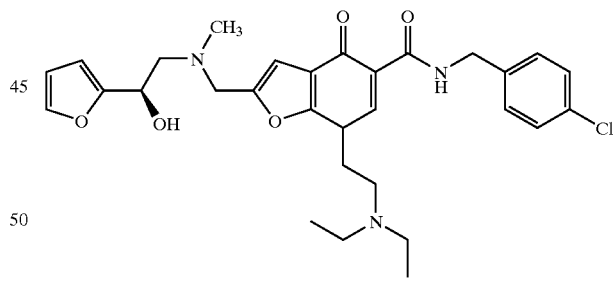

N-(4-Chlorobenzyl)-2-(chloromethyl)-7-(2-(diethylamino)ethyl)-4-oxo-4,7-dihydrofuro[2,3-b]pyridine-5-carboxamide (Example 25). The crude product was purified by column chromatography (CH₂Cl₂/methanol, 98/2) and triturated with Et₂O to afford 0.18 g as a white foam. Physical characteristics.

$^1$H NMR (300 MHz, DMSO-d$_6$) δ 10.55, 8.52, 7.53, 7.41–7.32, 6.85, 6.37, 6.26, 5.23–5.21, 4.77–4.68, 4.54–4.52, 4.32, 3.73, 2.79–2.65, 2.44–2.38, 2.27, 0.76–0.72.

EXAMPLE 33

N-(4-Chlorobenzyl)-2-(((2-hydroxypropyl)amino)methyl)-7-methyl-4-oxo-4,7-dihydrofuro[2,3-bipyridine-5-carboxamide.

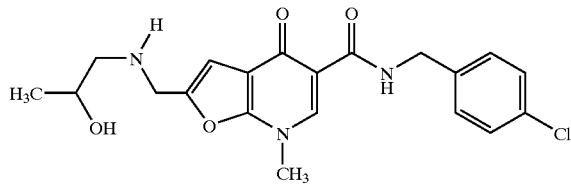

N,N-Diisopropylethylamine (1.57 mL) and 1-amino-2-propanol (0.75 mL) were added to a solution of N-(4-chlorobenzyl)-2-(chloromethyl)-7-methyl-4-oxo-4,7-dihydrofuro[2,3-b]pyridine-5-carboxamide (Example 2, 1.10 g) in DMF (60 mL). The reaction mixture was heated to 90° C. for 1 h. The mixture was allowed to cool to room temperature and was poured into water (120 mL). The resulting solid was filtered. The filtrate was extracted with $CH_2Cl_2$ (4×50 mL). The combined organic layers were dried ($MgSO_4$), filtered, and concentrated in vacuo. The resulting solid was combined with the material obtained from filtration and purified by column chromatography ($CH_2Cl_2$/methanol; 95/5, 90/10) followed by recrystallization from methanol to yield 0.762 g of the title compound as a white solid. Physical characteristics. M.p. 172–173° C.; $^1H$ NMR (400 MHz, DMSO-$d_6$) δ 10.66, 8.54, 7.41–7.32, 6.80, 4.55, 4.51, 3.93, 3.80, 3.70–3.64, 2.46–2.44, 2.15, 1.04; MS (ESI+) m/z 404 (M+H)$^+$.

EXAMPLE 34

N-(4-Chlorobenzyl)-2-(((2-hydroxypropyl)(methyl)amino)methyl)-7-methyl-4-oxo-4,7-dihydrofuro[2,3-b]pyridine-5-carboxamide.

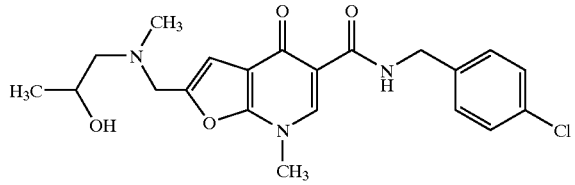

Aq. formaldehyde (0.19 mL) and sodium triacetoxy borohydride (0.526 g) were added to a suspension of N-(4-chlorobenzyl)-2-(((2-hydroxypropyl)-amino)methyl)-7-methyl-4-oxo-4,7-dihydrofuro[2,3-b]pyridine-5-carboxamide (Example 33, 0.500 g) in],2-dichloroethane (50 mL). The reaction mixture was stirred at room temperature for 18 h. A sat. aq. sodium bicarbonate solution (30 mL) was added. The aqueous layer was separated and extracted with $CH_2Cl_2$ (4×50 mL). The combined organic layers were dried ($MgSO_4$), filtered, and concentrated in vacuo. The resulting solid was purified by column chromatography ($CH_2Cl_2$/methanol; 97/3, 96/4) followed by recrystallization from ethyl acetate to yield 0.301 g of the title compound as a white solid. Physical characteristics. M.p. 152° C.; $^1H$ NMR (400 MHz, DMSO-$d_6$) δ 10.65, 8.55, 7.41–7.32, 6.87, 4.55, 4.35, 3.92, 3.80–3.73, 3.69, 2.36–2.31, 2.28–2.20, 1.04; MS (EST+) m/z 418 (M+H)$^+$.

EXAMPLE 35

N-(4-Chlorobenzyl)-2-(((3R)-3-hydroxypyrrolidin-1-yl)-methyl)-7-methyl-4-oxo-4,7-dihydrofuro[2,3-b]pyridine-5-carboxamide.

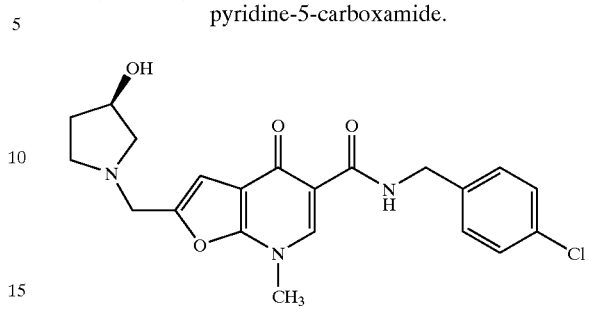

N,N-Diisopropylethylamine (0.48 mL) and N-(4-chlorobenzyl)-2-(chloromethyl)-7-methyl-4-oxo-4,7-dihydrofuro[2,3-b]pyridine-5-carboxamide (Example 2, 0.500 g) were added to a solution of (R)-3-hydroxypyrrolidine (0.22 mL) in DMF (30 mL). The reaction mixture was heated to 90° C. for 2 h. The mixture was allowed to cool to room temperature, poured into water (60 mL), and extracted with ethyl acetate (4×50 mL) then $CH_2Cl_2$ (2×50 mL). The combined organic layers were dried ($MgSO_4$), filtered, and concentrated in vacuo. The resulting solid was purified by column chromatography ($CH_2Cl_2$/methanol; 98/2, 97/3, 95/5) followed by recrystallization from ethyl acetate to yield 0.360 g of the title compound as a pale yellow solid. Physical characteristics. M.p. 189–190° C.; $^1H$ NMR (400 MHz, DMSO-$d_6$) δ 10.64, 8.54, 7.41–7.32, 6.85, 4.73, 4.55, 4.22–4.16, 3.93, 3.68, 2.78–2.74, 2.68–2.62, 2.52–2.47, 2.41–2.37, 2.02–1:94, 1.58–1.50; MS (ESI+) m/z 416 (M+H)$^+$; $[\alpha]^{25}_D$=–3 ($CH_2Cl_2$).

EXAMPLE 36

N-(4-Chlorobenzyl)-2-(((2-hydroxy-2-phenylethyl)(methyl)amino)methyl)-7-methyl-4-oxo-4,7-dihydrofuro[2,3-b]pyridine-5-carboxamide.

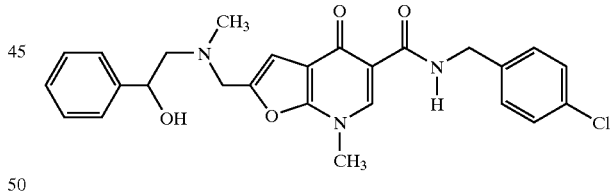

N,N-Diisopropylethylamine (0.111 mL) and (x-(methylaminomethyl)-benzyl alcohol (0.094 g) were added to a suspension of N-(4-chlorobenzyl)-2-(chloromethyl)-7-methyl-4-oxo-4,7-dihydrofuro[2,3-b]pyridine-5-carboxamide (Example 2, 0.150 g) in DMF (10 mL). The reaction mixture was heated to 90° C. for 1 h. The mixture was allowed to cool to room temperature and was poured into water (25 mL). The suspension was filtered and the resulting solid was purified by column chromatography ($CH_2Cl_2$/methanol; 99/1, 98/2) followed by recrystallization from ethyl acetate to yield 0.095 g of the title compound as a pale yellow solid. Physical characteristics. M.p. 118–121° C.; $^1H$ NMR (400 MHz, DMSO-$d_6$) δ 10.65, 8.54, 7.41–7.35, 7.32–7.25, 7.22–7.18, 6.84, 5.10, 4.734.69, 4.55, 3.89, 3.73, 2.62–2.54, 2.32; MS (ESI+) m/z 480 (M+H)$^+$. Anal. Found: C, 63.48; H, 5.56; N, 8.24; Cl, 6.94.

EXAMPLE 37

N-(4-Chlorobenzyl)-2-(((2-hydroxy-2-(4-hydroxyphenyl)-ethyl)(methyl)amino)methyl)-7-methyl-4-oxo-4,7-dihydrofuro[2,3-b]-pyridine-5-carboxamide.

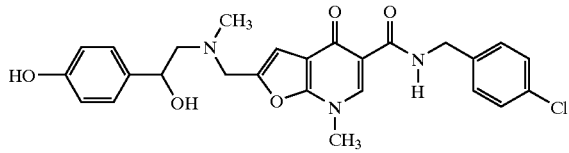

N,N-Diisopropylethylamine (0.14 mL) and N-(4-chlorobenzyl)-2-(chloromethyl)-7-methyl-4-oxo-4,7-dihydrofuro[2,3-b]pyridine-5-carboxamide (Example 2, 0.150 g) were added to a solution of synephrine (0.137 g) in DMF (10 mL). The reaction mixture was heated to 90° C. for 1 h. The mixture was allowed to cool to room temperature, poured into water (25 mL), and extracted with $CH_2Cl_2$ (4×25 mL). The combined organic layers were dried ($MgSO_4$), filtered, and concentrated in vacuo. The resulting oil was purified by column chromatography ($CH_2Cl_2$/methanol; 98/2, 97/3) followed by recrystallization from ethyl acetate/methanol to yield 0.120 g of the title compound as a white solid. Physical characteristics. M.p. 117–122° C.; $^1H$ NMR (400 MHz, DMSO-$d_6$) δ 10.65, 9.21, 8.54, 7.41–7.33, 7.09, 6.85, 6.65, 4.88, 4.614.57, 4.55, 3.89, 3.71, 2.58–2.45, 2.30; $^{13}C$ NMR (100 MHz, CDCl$_3$) δ 173.7, 164.8, 156.1, 153.2, 150.9, 141.2, 137.1, 132.9, 132.8, 128.9, 128.7, 127.4, 116.6, 115.3, 114.8, 106.6, 69.5, 64.0, 54.0, 42.6, 42.2, 37.8; MS (ESI+) m/z 496 (M+H)+

Preparation 31. rac-1-(3-Methoxyphenyl)-2-(methylamino)ethanol.

A mixture of (3-methoxyphenyl)oxirane (Perrone, R., et al., *J. Med. Chem.*, 35, 1992, 3045–3049) (3.00 g) and a 2.0 M solution of methylamine in methanol (20 mL) was heated in a sealed tube at 10° C. for 4 h. After cooling, the solvent was evaporated under reduced pressure and the residue purified by column chromatography ($CH_2Cl_2$/$CH_3OH$/TEA, 90/9/1) to yield 1.16 g of the title compound as a white solid. Physical characteristics. MS (ESI–) m/z 272 (M–H)$^-$.

Preparation 32. 2-Bromo-1-(4-fluorophenyl)ethanol.

Sodium borohydride (1.74 g) was added to a solution of 2-bromo-4'-fluoroacetophenone (10.0 g) in methanol (100 mL) at 0° C. (internal). The reaction mixture was allowed to warm to room temperature and was stirred for 1 h. A 2 N HCl solution (50 mL) was added, and the mixture was concentrated in vacuo to remove methanol. The aqueous layer was extracted with $CH_2Cl_2$ (4×50 mL), and the combined organic layers were dried ($MgSO_4$), filtered, and concentrated in vacuo. The resulting oil was purified by column chromatography (heptane/ethyl acetate, 90/10) to yield 8.96 g of the title compound as a yellow oil. Physical characteristics. $^1H$ NMR (400 MHz, DMSO-$d_6$) δ 7.46–7.41, 7.19–7.12, 5.86, 4.83–4.79, 3.67–3.64, 3.59–3.55.

Preparation 33. rac-1-(4-Fluorophenyl)-2-methylamino)ethanol.

A 2.0 M solution of methylamine in methanol (25 mL) was added to a solution of 2-bromo-1-(4-fluorophenyl)ethanol (Preparation 33, 2.19 g) in methanol (25 mL). The reaction mixture was heated to reflux for 30 min. The reaction mixture was allowed to cool to room temperature and was concentrated in vacuo. The resulting brown oil was partitioned between water (50 mL) and $CH_2Cl_2$ (50 mL). The organic layer was removed and the aqueous layer was extracted with $CH_2Cl_2$ (3×50 mL). The aqueous layer was adjusted to pH 12 with a 2 N NaOH solution and extracted with $CH_2Cl_2$ (4×50 mL). The combined organic layers were dried ($MgSO_4$), filtered, and concentrated in vacuo. The resulting oil was purified by column chromatography ($CH_2Cl_2$/methanol, 95/5) to yield 0.537 g of the title compound as a yellow solid. Physical characteristics. M.p. 72–75° C.; $^1H$ NMR (400 MHz, DMSO-$d_6$) δ 7.38–7.35, 7.15–7.10, 5.32, 4.654.62, 2.61–2.55, 2.30; MS (ESI+) m/z 170 (M+H)$^+$.

Preparation 34. 2-Bromo-1-(4-chlorophenyl)ethanol.

Sodium borohydride (1.62 g) was added to a suspension of 2-bromo-4'-chloroacetophenone (10.0 g) in methanol (100 mL) at 0° C. (internal). The reaction mixture was allowed to warm to room temperature and was stirred for 1 h. A 2 N HCl solution (50 mL) was added, and the mixture was concentrated in vacuo to remove methanol. The aqueous layer was extracted with $CH_2Cl_2$ (4×50 mL), and the combined organic layers were dried ($MgSO_4$), filtered, and concentrated in vacuo. The resulting oil was purified by column chromatography (heptane/ethyl acetate, 90/10; heptane/$CH_2Cl_2$, 1/1) to yield 7.64 g of the title compound as a white solid. Physical characteristics. M.p. 58–62° C.; $^1H$ NMR (400 MHz, DMSO-$d_6$) δ 7.44–7.38, 5.90, 4.84–4.80, 3,68–3.65, 3.60–3.55.

Preparation 35. rac-1-(4-Chlorophenyl)-2-(methylamino)ethanol.

A 2.0 M solution of methylamine in methanol (25 mL) was added to a solution of 2-bromo-1-(4-chlorophenyl)ethanol (Preparation 34, 2.16 g) in methanol (25 mL). The reaction mixture was heated to reflux for 30 min. The reaction mixture was allowed to cool to room temperature and was concentrated in vacuo. The resulting brown oil was partitioned between water (50 mL) and $CH_2Cl_2$ (50 mL). The organic layer was removed and the aqueous layer was extracted with $CH_2Cl_2$ (3×50 mL). The aqueous layer was adjusted to pH 12 with a 2 N NaOH solution and extracted with $CH_2Cl_2$ (4×50 mL). The combined organic layers were dried ($MgSO_4$), filtered, and concentrated in vacuo. The resulting oil was purified via column chromatography ($CH_2Cl_2$/methanol, 95/5) to yield 0.480 g of the title compound as a yellow solid. Physical characteristics. M.p. 75–79° C.; $^1H$ NMR (400 MHz, DMSO-$d_6$) δ 7.34, 5.34, 4.63, 2.60–2.51, 2.29; MS (ESI+) m/z 186 (M+H)$^+$.

Preparation 36. rac-2-(Methylamino)-1-pyridin-2-ylethanol.

Procedure A. A solution of 2-bromoacetylpyridine hydrobromide (Tsushima, S., et al., EP 278621, 1988) (8.87 g) in methanol (90 mL) was cooled to –10° C. (internal). A solution of sodium borohydride (1.85 g) in water (30 mL) was added dropwise over 1 h. The reaction mixture was allowed to stir for an additional 5–10 min after the addition was complete. Hydrobromic acid (48%) was added to pH 34. The reaction mixture was concentrated in vacuo to remove methanol and then poured into cold ethyl acetate (60 mL)/2 N NaOH (30 mL). The organic layer was removed, and the aqueous layer was extracted with ethyl acetate (3×60 mL). The combined organic layers were dried ($MgSO_4$), filtered, and concentrated in vacuo to yield 5.73 g of the bromohydrin as a yellow oil. The crude bromohydrin (5.00 g) was dissolved in methanol (20 mL), and a 2.0 M solution of methylamine in methanol (125 mL) was added. The reaction mixture was stirred at room temperature for 18 h and then concentrated in vacuo. The resulting orange oil was dissolved in a 2 N NaOH solution (25 mL) and extracted with $CH_2Cl_2$ (8×100 mL). The combined organic layers were dried (MgSO$_4$), filtered, and concentrated in vacuo. The resulting orange oily solid was purified via column chromatography (CHCl$_3$/methanol, 95/5, 90110; CHCl$_3$/methanol/NH$_4$OH, 90/10/1) to yield 1.324 g of the title compound as a yellow oil. Physical characteristics. $^1$H NMR (400 MHz, DMSO-d$_6$) δ 8.48–8.47, 7.79–7.75, 7.50–7.48, 7.25–7.22, 5.44, 4.694.66, 2.80–2.76, 2.64–2.59, 2.30; MS (ESI+) m/z 153 (M+H)$^+$.

Procedure B. A 3-neck, round-bottomed flask, fitted with mechanical stirring, thermocouple, addition funnel and nitrogen inlet was charged with N-bromosuccinimide (3.72 g) and water (20 mL). The resulting slurry was cooled to between 0–5° C. in an ice/water bath and acetic acid (1.32 g) was added. A solution of 2-vinyl pyridine (2.0 g) in t-butanol (3 mL) was added drop-wise keeping the temperature below 10° C. The mixture was stirred maintaining a temperature below 10° C. for 2 h. A solution of sodium hydroxide (2.7 g) in water (20 mL) was slowly added keeping the temperature below 25° C. The resulting solution was stirred for 1 h and MTBE (20 mL) was added. The aqueous layer was separated and washed with MTBE (10 mL). The combined organic layers were washed with brine and concentrated. The oil was dissolved in THF (4 mL) and the resulting solution was added drop-wise to a 40% aqueous solution of methyl amine (15 g) maintaining the temperature at 10–20° C. When complete, the mixture was concentrated and repeatedly distilled from ethanol (20 mL) to afford the title compound as an oil.

Preparation 37. (1R)-2-(Methylamino)-1-pyridin-2-ylethanol (2S)-2-(6-Methoxy-2-naphthyl)propanoic Acid Salt.

2-(Methylamino)-1-pyridin-2-ylethanol (Preparation 36, Procedure B, approximately 1.16 g) was diluted with ethanol (15 mL) and (S)-Naproxen (1.75 g) was added. The mixture was heated to 75° C. and then cooled to 40° C. The mixture was further cooled to 0–5° C. The resulting slurry was stirred for at least 1 h, filtered and washed with cold ethanol (500 mL). The product was dried (vacuum oven, 50° C.) and then recrystallized from ethanol until the desired optical purity was obtained for the title compound. Physical characteristics. $^1$H NMR (300 MHz, CDCl$_3$) δ 8.40, 8.05, 7.58, 7.40, 7.12, 7.02, 4.92, 3.87, 3.69, 3.00, 2.78, 2.23, 1.48; $^{13}$C NMR (75 MHz, CDCl$_3$)δ 181.6, 159.9, 157.2, 148.4, 138.8, 136.9, 133.2, 129.0, 128.9, 126.9, 126.6, 125.6, 122.5, 120.9, 118.5, 105.5, 69.0, 55.2, 55.0, 48.0, 33.1, 19.2. Anal. Found: C, 69.25; H, 6.89; N, 7.13.

Preparation 38. (1R)-2-(Methylamino)-1-pyridin-2-ylethanol Dihydrochloride.

(1R)-2-(Methylamino)-1-pyridin-2-ylethanol (2S)-2-(6-methoxy-2-naphthyl)propanoic acid salt (Preparation 37, 6.1 g) was slurried in water (20 mL) and concentrated hydrochloric acid (4.25 mL) was added. The resulting slurry was heated to 50° C. for 3 h and was then cooled to 30° C. The slurry was filtered and the recovered Naproxen was washed with water (10 mL). The filtrate was concentrated to approximately 7 mL volume by vacuum distillation and diluted with ethanol (50 mL). The resulting solution was then concentrated to approximately 10 mL volume and cooled to 0° C. The mixture was filtered, washed with cold ethanol (10 mL) and dried (vacuum oven, 75° C.) to provide 3.4 g of the title compound. Physical characteristics. $^1$H NMR (400 MHz, DMSO-d$_6$) δ 9.40, 8.79, 8.47, 8.04, 7.86, 5.42, 3.42, 3.23.

Preparation 39. rac-2-(Methylamino)-1-pyridin-3-ylethanol hydrobromide.

A solution of 3-bromoacetylpyridine hydrobromide (Tsushima, S., et al., EP 278621, 1988) (14.0 g) in methanol (52 mL) was cooled to –10° C. (internal).

A solution of sodium borohydride (2.92 g) in water (52 mL) was added dropwise over 45 min. The reaction mixture was allowed to stir for an additional 5–10 min after the addition was complete. Hydrobromic acid (48%) was added to pH 34. The reaction mixture was concentrated in vacuo to remove methanol and then poured into cold ethyl acetate (100 mL)/2 N NaOH (25 mL). The organic layer was removed and the aqueous layer was adjusted to pH 12 with a 2 N NaOH solution. The aqueous layer was extracted with ethyl acetate (2×100 mL). The combined organic layers were dried (MgSO$_4$), filtered, and concentrated in vacuo to yield 9.098 g of the bromohydrin as a yellow oil. The crude bromohydrin (5.00 g) was dissolved in methanol (20 mL), and a 2.0 M solution of methylamine in methanol (125 mL) was added. The reaction mixture was heated to reflux for 1 h. The reaction mixture was allowed to cool to room temperature and then concentrated in vacuo. The resulting orange oil was crystallized from methanol/ethyl acetate to yield 2.406 g of the title compound as a yellow solid. Physical characteristics. M.p. 146–170° C.; $^1$H NMR (400 MHz, DMSO-d$_6$) δ 8.62–8.61, 8.54–8.53, 8.41, 7.83–7.81, 7.45–7.42, 6.27, 5.024.99, 3.23–3.17, 3.13–3.07, 2.61; MS (ESI+) m/z 153 (M+H)$^+$.

Preparation 40. rac-2-Methylamino)-1-pyridin-4-ylethanol.

A solution of 4-bromoacetylpyridine hydrobromide (Taurins, A.; Blaga, A. J. Heterocyclic Chem., 1970, 7, 11.37–1141) (14.5 g) in methanol (150 mL) was cooled to –10° C. (internal). A solution of sodium borohydride (3.03 g) in water (50 mL) was added dropwise over 1 h. The reaction mixture was allowed to stir for an additional 5–10 min after the addition was complete. Hydrobromic acid (48%) was added to pH 34. The reaction mixture was concentrated in vacuo to remove methanol and then poured into cold ethyl acetate (100 mL)/2: N NaOH (50 mL). The organic layer was removed, dried (MgSO$_4$), filtered, and concentrated in vacuo to yield 8.406 g of the bromohydrin as a pink solid. The crude bromohydrin (5.00 g) was dissolved in methanol (20 mL), and a 2.0 M solution of methylamine in methanol (125 mL) was added. The reaction mixture was stirred at room temperature for 18 h and then concentrated in vacuo. The resulting orange oil was dissolved in water (50 mL), adjusted to pH 12 with a 2 N NaOH solution, and extracted with ethyl acetate (4×100 ml). The combined organic layers were dried (MgSO$_4$), filtered, and concentrated in vacuo. The resulting solid was purified via column chromatography (CHCl$_3$/methanol, 95/5, 90/10; CHCl$_3$/methanol/NH$_4$OH, 90/10/1) to yield 0.986 g of the title compound as a pale orange solid. Physical characteristics. M.p. 90–93° C.; $^1$H NMR (400 MHz, DMSO-d$_6$) δ 8.49, 7.35, 5.49, 4.664.63, 2.63–2.54, 2.29, 1.67; MS (ESI+) m/z 153 (M+H)$^+$.

Preparation 41. 2-Bromo-1-(5-methyl-2-furyl)ethanone.

Bromine (5.1 mL) was added dropwise over 1 h to a solution of 2-acetyl-5-methylfuran (11.0 g) in dioxane/Et$_2$O (1/2, 60 mL) at 0° C. (internal). The reaction mixture was stirred at 0° C. for 30 min and then allowed to warm to room temperature and was stirred for 18 h. The reaction mixture was cooled to 0° C. (internal), and additional bromine (1.53 mL) was added dropwise. The reaction mixture was allowed to warm to room temperature and was stirred for 1 h. A saturated ammonium chloride solution (100 mL) was added. The organic layer was removed, and the aqueous layer was extracted with Et$_2$O (2×100 mL). The combined organic layers were dried (MgSO$_4$), filtered, and concentrated in vacuo. The resulting brown solid was purified via column chromatography (hexanes/CH$_2$Cl$_2$, 70/30) to yield a yellow solid which was recrystallized from EtOAc/hexanes to yield 8.571 g of the title compound as a pale yellow solid. Physical characteristics. M.p. 60–63° C.; $^1$H NMR (400 MHz, DMSO-d$_6$) δ 7.60, 6.44, 4.58, 2.41.

Preparation 42. rac-2-Methylamino)-1-(5-methyl-2-furyl) ethanol.

A solution of 2-bromo-1-(5-methyl-2-furyl)ethanone (Preparation 41, 8.00 g) in methanol (100 mL) was added dropwise to a 2.0 M solution of methylamine in methanol (197 mL) at 0° C. (internal). The reaction mixture was stirred at 0° C. for 30 min. A solution of sodium borohydride (2.23 g) in water (40 mL) was then added dropwise. The reaction mixture was stirred at 0° C. for 1.5 h and then quenched with a 2 N HCl solution (to pH 34). The reaction mixture was concentrated in vacuo to remove methanol and then poured into cold EtOAc (200 mL)/2 N NaOH (100 mL). The organic layer was removed. The aqueous layer was adjusted to pH 12 with a 2 N NaOH solution and extracted with EtOAc (3×200 mL). The combined organic layers were dried (MgSO$_4$), filtered, and concentrated in vacuo. The resulting oil was purified by column chromatography (CHCl$_3$/methanol, 95/5, 90/10; CHCl$_3$/methanol/NH$_4$OH, 90/10/1). The resulting yellow oil was crystallized from diethyl ether to yield 1.88 g of the title compound as a yellow solid. Physical characteristics. M.p. 4045° C.; $^1$H NMR (400 MHz, DMSO-d$_6$) δ 6.11, 5.97–5.96, 5.05, 4.54–4.51, 2.72–2.65, 2.29, 2.22; MS (ESI+) m/z 156 (M+H)$^+$.

Preparation 43. rac-1-(3-Furyl)-2-(methylamino)ethanol.

Trimethylsulfonium iodide (20.4 g) and 3-furaldehyde (8.65 mL) were added to potassium hydroxide (11.2 g) and water (0.45 mL) in acetonitrile (150 mL). The reaction mixture was heated to 60° C. for 2.5 h. The reaction mixture was allowed to cool to room temperature. The precipitate was filtered off, and the filtrate was concentrated in vacuo. The resulting crude epoxide (10.747 g) was dissolved in methanol (50 mL) and added to a 2.0 M solution of methylamine in methanol (100 mL). The reaction mixture was stirred at room temperature for 3 d and then heated to reflux for 30 min. The reaction mixture was allowed to cool to room temperature and was concentrated in vacuo. The resulting brown oil was purified via column chromatography (CHCl$_3$/methanol, 95/5, 90110; CHCl$_3$/methanol/NH$_4$OH, 90/10/1) to yield 2.703 g of the title compound as a yellow oil. Physical characteristics. $^1$H NMR (400 MHz, DMSO-d$_6$) δ 7.56–7.55, 7.51, 6.44, 5.07, 4.58–4.55, 2.62–2.56, 2.30; MS (ESI+) m/z 142 (M+H)$^+$.

Preparation 44. rac-2-Methylamino)-1-(2,4,6-trifluorophenyl)ethanol.

Potassium hydroxide (7.0 g), and water (2.8 mL) were added to acetonitrile (95 mL). 2,4,6-trifluorobenzaldehyde (10.0 g) was dissolved in the acetonitrile mixture. Trimethylsulfonium iodide (12.7 g) was added, and the mixture was stirred at 60° C. for 3 h. The reaction mixture was cooled to room temperature and filtered. The retentate was washed with diethyl ether and filtered. This process was repeated until no more KI precipitated. The resulting crude epoxide was concentrated in vacuo and dissolved in a 2.0 M solution of methylamine in methanol (315 mL). The mixture was stirred at room temperature for 18 hours, then concentrated in vacuo to an orange oil. The oil was purified by column chromatography (CHCl$_3$/methanol, 95/5; CHCl$_3$/methanol/NH$_4$OH, 89/10/1, 79/20/1) to afford 1.5 g of the title compound as a yellow oil. Physical characteristics: $^1$H NMR (300 MHz, DMSO-d$_6$) δ 7.11, 5.50, 4.94, 2.90, 2.68, 2.28.

Preparation 45. rac-1-(1-Benzofuran-2-yl)-2-(methylamino) ethanol.

Potassium hydroxide (9.2 g), and water (3.7 mL) were added to acetonitrile (125 mL). Benzofuran-2-carboxaldehyde (12.0 g) was dissolved in the acetonitrile mixture. Trimethylsulfonium iodide (16.7 g) was added, and the mixture was stirred at 60° C. for 3 h. The reaction mixture was cooled to room temperature and filtered. The filtrate was washed with diethyl ether and filtered. This process was repeated until no more KI precipitated. The resulting crude epoxide was concentrated in vacuo and dissolved in a 2.0 M solution of methylamine in methanol (410 mL). The mixture was stirred at room temperature for 18 hours, then concentrated in vacuo to a brown oil. The oil was purified by column chromatography (CHCl$_3$/methanol, 95/5, 90/10; CHCl$_3$/methanol/NH$_4$OH, 89/10/1, 79/20/1) to afford 3.0 g of the title compound as an off-white solid. Physical characteristics. $^1$H NMR (300 MHz, DMSO-d$_6$) δ 7.59, 7.53, 7.24, 6.47, 5.62, 4.77, 2.83, 2.32.

Preparation 46. rac-2-(Methylamino)-1-thien-2-ylethanol.

Thiophene-2-carboxaldehyde (8.5 g) was dissolved in acetonitrile (115 mL). Trimethylsulfonium iodide (15.5 g), potassium hydroxide (8.5 g), and water (3.4 mL) were added, and the mixture was stirred at 60° C. for 3 h. The reaction mixture was cooled to room temperature and filtered. The retentate was washed with diethyl ether and filtered. This process was repeated until no more KI precipitated. The resulting crude epoxide was concentrated in vacuo and distilled using a Kugelrohr distillation apparatus (0.8 Torr, oven temperature 50° C.). The crude epoxide was dissolved in a 2.0 M solution of methylamine in methanol (152 mL). The mixture was stirred at room temperature for 18 hours, then concentrated in vacuo to a yellow oil. The oil was purified by column chromatography (CHCl$_3$/methanol, 95/5, 90/10; CHCl$_3$/methanol/NH$_4$OH, 89/10/1) to afford 1.8 g of the title compound as a yellow oil that solidifies on standing. Physical characteristics. $^1$H NMR (300 MHz, DMSO-d$_6$) δ 7.38, 6.95, 5.62, 4.86, 3.34, 2.67, 2.31.

Preparation 47. rac-2-(Methylamino)-quinolin-2-ylethanol.

Potassium hydroxide (3.21 g) and water (0.13 mL) were added to acetonitrile (50 mL). Trimethylsulfonium iodide (5.84 g) and 2-quinoline carboxaldehyde (4.50 g) were then added. The reaction mixture was heated to 60° C. for 4 h. The reaction mixture was allowed to cool to room temperature and was diluted with Et$_2$O (25 mL) The precipitate was filtered off. The filtrate was concentrated in vacuo and the residue was re-subjected to the reaction conditions above and heated to 60° C. for 1 h. The reaction mixture was allowed to cool to room temperature and was diluted with Et$_2$O (25 mL). The precipitate was filtered off and the filtrate was concentrated in vacuo. The resulting crude epoxide (5.5 g) was dissolved in methanol (20 mL) and added to a 2.0 M solution of methylamine in methanol (100 mL). The reaction mixture was heated to reflux for 1 h. The reaction mixture was allowed to cool to room temperature and concentrated in vacuo. The resulting brown oil was purified by column chromatography (CHCl$_3$/methanol, 95/5, 90/10; CHCl$_3$/methanol/NH$_4$OH, 90/10/1) to yield 1.191 g of the title compound as a yellow-green oil. Physical characteristics. $^1$H NMR (400 MHz, DMSO-d$_6$) δ 8.36–8.33, 7.98–7.94, 7.76–7.67, 7.59–7.54, 5.63, 4.884.84, 2.89–2.72, 2.32; MS (ESI+) ?/z 203 (M+H)$^+$.

Preparation 48. rac-2-(Methylamino)-1-(1-methyl-1H-pyrrol-2-yl)ethanol. 2-Chloro-1-(1-methyl-1H-pyrrol-2-yl) ethanol (Croce, P. D.; Ferraccioli, R.; Ritieni, A. *Synthesis,* 1990, 212–213) (2.05 g) was dissolved in methanol (40 mL)

and added dropwise to a 2.0 M solution of methylamine in methanol (65 mL) at 0° C. The reaction mixture was stirred at 0° C. for 1 h and then allowed to warm to room temperature. The reaction mixture was stirred at room temperature for 18 h and then cooled to 0° C. Sodium borohydride (0.738 g) in water (40 mL) was added dropwise. The reaction mixture was stirred at 0° C. for 30 min and then allowed to warm to room temperature. The reaction mixture was stirred at room temperature for 18 h. An additional 0.738 g (19.5 mmol) of sodium borohydride was added and the reaction mixture was stirred at room temperature for 18 h. The reaction was quenched with a 1 N HCl solution and then concentrated in vacuo to remove methanol. The aqueous layer was adjusted to pH 12 with a 2 N NaOH solution and extracted with $CH_2Cl_2$ (4×100 mL). The combined organic layers were dried ($MgSO_4$), filtered, and concentrated in vacuo. The resulting yellow oil was crystallized from ethyl acetate to yield 0.772 g of the title compound as a white solid. Physical characteristics. M.p. 64–66° C.; $^1$H NMR (400 MHz, DMSO-$d_6$) δ 6.63–6.62, 5.90–5.86, 5.00, 4.62–4.59, 3.59, 2.81–2.68, 2.32; MS (ESI+) m/z 155 (M+H)$^+$.

Preparation 49. 5-(Bromoacetyl)thiophene-2-carbonitrile.

Bromine (0.5 mL) was added to a solution of 2-acetyl-5-cyanothiophene (1.5 g) in a mixture of p-dioxane/ethyl ether (20 mL, 1/2, v/v). After 2 h, ice water (30 mL) was added. The solid precipitates were collected by filtration and washed with water to afford 1.4 g of the title compound as a white solid. Physical characteristics. $^1$H NMR (DMSO-$d_6$) δ 8.16, 8.11, 4.94; MS (ESI–) m/z 230 (M–H)$^-$.

Preparation 50. 5-(2-Bromo-1-hydroxyethyl)thiophene-2-carbonitrile.

A solution of $NaBH_4$ (0.46 g in 5 mL of water) was added to a suspension of 5-(bromoacetyl)thiophene-2-carbonitrile (Preparation 49, 1.85 g) in methanol (50 mL) cooled to –10° C. After 10 min, 48% aq. HBr was added to adjust the pH to 3. The reaction mixture was concentrated to approximately 25 mL before water (30 mL) was added. The mixture was extracted with dichloromethane (3×40 mL). The organic layers were combined, washed with brine, and dried ($MgSO_4$). Removal of the solvent gave 1.6 g of the title compound as an orange oil. Physical characteristics. $^1$H NMR (DMSO-$d_6$) δ 7.86, 7.23, 6.67, 5.17, 3.81, 3.68; MS (ESI–) m/z 232 (M–H)$^-$ Preparation 51. rac-5-(1-Hydroxy-2-(methylamino)ethyl) thiophene-2-carbonitrile.

A solution of methylamine (2.0 M in methanol, 80 mL) was added to a solution of 52-bromo-1-hydroxyethyl) thiophene-2-carbonitrile (Preparation 50, 1.6 g) in methanol (20 mL). The reaction mixture was stirred at room temperature overnight and then was concentrated to nearly dryness. The residue was dissolved in methanol (20 mL) and was treated with resin (2 g, BiORad AG® 50w-x2, hydrogen form, strongly acidic cation) for 4 hours. The resin was collected by filtration and washed with a large amount of methanol. The resin was washed with 10% $NH_4OH/MeOH$ (100 mL) and the solution was concentrated. The crude product was purified by flash chromatography (silica gel, 1% $NH_4OH/10\%$ MeOH/89% $CH_2Cl_2$) to yield 0.80 g of the title compound as a white solid. Physical characteristics. $^1$H NMR (DMSO-$d_6$) δ 7.81, 7.13, 6.13, 4.93, 2.72, 2.33; MS (ESI+) m/z 183 (M+H)$^+$; HRMS (FAB) m/z 183.0600 (M+H)$^+$.

Preparation 52. 2-Chloro-1-(1,3-thiazol-2-yl)ethanone.

2-(Trimethylsilyl)thiazole (4.83 g) was dissolved in $CH_2Cl_2$ (40 mL) and cooled to 0° C. Chloroacetyl chloride (5.1 mL) was added dropwise via syringe with vigorous stirring. After 4 h, sat. aq. $NaHCO_3$ solution was added until the solution was at neutral pH and the resulting mixture was extracted with $CH_2Cl_2$. The combined organics were dried ($MgSO_4$), filtered, and concentrated to afford 4.27 g of the title compound as pale yellow solid. Physical characteristics. $^1$H NMR (400 MHz, CDCl$_3$) δ 7.90–7.88, 7.65–7.64, 4.83.

Preparation 53. rac-2-(Methylamino)-1-(1,3-thiazol-2-yl) ethanol. 2-Chloro-1-(1,3-thiazol-2-yl)ethanone (Preparation 52, 0.6 g) was dissolved in methanol (4 mL) and cooled to 0° C. Sodium borohydride (0.3 g) in methanol (4 mL) stirred 1 h and was then added to the ketone dropwise. The reaction mixture was stirred at 0° C. for 30 min. and then for 1.5 h at room temperature. HCl (1 N) was added until pH 4 and then sat. aq. $NaHCO_3$ was added until neutral pH. The resulting mixture was extracted with $CH_2Cl_2$. The combined organic layers were dried ($MgSO_4$), filtered, and concentrated to provide a colorless oil. The resulting oil, methylamine (2.0 M in methanol, 30.0 mL) and NaI (45 mg) were placed in a sealed tube and heated at 60° C. for 16 h. The solution was concentrated and purified by chromatotron (2 mm silica, 99/1 to 90/10 $CH_2Cl_2$/MeOH) to provide 0.223 g of the title compound as an off-white solid. Physical characteristics. $^1$H NMR (400 MHz, DMSO-$d_6$) δ 7.81–7.80, 7.74–7.73, 6.95, 5.15–5.11, 3.33, 3.14–3.09, 2.58; MS (ESI+) m/z 159 (M+H)$^+$.

Preparation 54. rac-3-Methyl-5-(5-phenyl-2-furyl)-1,3-oxazolidin-2-one.

Boc-Dimethylamine (5.47 g) and TMEDA (9.6 mL) were dissolved in THF (160 mL). The mixture was cooled to –70° C. and sec-BuLi (1.3 M in cyclohexane, 35.7 mL) was added maintaining the temperature below 65° C. The reaction mixture was stirred at –70° C. for 1.25 h and then a solution of 5-phenylfurylcarboxaldehyde (5.0 g) in THF (20 mL) was added maintaining the temperature below 65° C. After 2 h, the mixture was allowed to warm to 0° C. and was then quenched with sat. aq. ammonium chloride (100 mL). The mixture was diluted with diethyl ether (300 mL). The aqueous layer was separated and extracted with additional diethyl ether (2×100 mL). The combined organic layers were washed with sat. aq. ammonium chloride (2×50 mL) followed by brine (50 mL), dried ($MgSO_4$), and concentrated to afford a yellow oil. The crude oil was dissolved in THF (100 mL) and sodium hydride (60% mineral oil dispersion, 2.32 g) was added. The mixture was allowed to stir at room temperature for 18 h and then with ice bath cooling was quenched with sat. aq. ammonium chloride (100 mL). The reaction mixture was diluted with diethyl ether (200 mL). The organic layer was washed with sat. aq. ammonium chloride (100 mL) followed by brine (100 mL), dried ($MgSO_4$), and concentrated to afford an oil. The crude product was purified by column chromatography (heptane/EtOAc, 4/1; 1/1) to afford 3.48 g of the title compound as a tan solid. Physical characteristics. M.p. 97–99° C.; $^1$H NMR (400 MHz, DMSO-$d_6$) δ 7.73, 7.45, 7.33, 7.00, 6.81, 5.65, 3.88, 3.82, 2.86; $^{13}$C NMR (100 MHz, CDCl$_3$) δ 158.1, 155.6, 149.4, 130.5, 129.1, 128.4, 124.4, 112.6, 106.2, 68.2, 50.9, 31.5; MS (CI) m/z 244 (MH$^+$). Anal. Found: C, 69.04; H, 5.49; N, 5.74.

Preparation 55. rac-2-(Methylamino)-1-(5-phenyl-2-furyl) ethanol.

rac-3-Methyl-5-(5-phenyl-2-furyl)-1,3-oxazolidin-2-one (Preparation 54, 2.43 g) was suspended in a solution of 1 M aq. potassium hydroxide (35 mL) and ethanol (20 mL). The mixture was heated to 50° C. for 7 h, and then was allowed to cool to room temperature. Sodium chloride was added, and the mixture was extracted with diethyl ether (4×100 mL). The organic layer was concentrated to a volume of 100 mL and then was extracted with sat. aq. ammonium chloride solution (6×50 mL). The aqueous layer was adjusted to pH 10 with solid sodium hydroxide and then extracted with diethyl ether (5×100 mL). The combined organic layers were dried ($K_2CO_3/Na_2SO_4$) and concentrated to afford an oil. The crude product was crystallized from diethyl ether/hexane to afford 1.56 g of the title compound as a white solid. Physical characteristics. M.p. 75–76° C.; $^1$H NMR (400 MHz, DMSO-$d_6$) δ 7.67, 7.41, 7.27, 6.86, 6.38, 5.42, 4.66, 2.84–2.76, 2.32; $^{13}$C NMR (100 MHz, CDCl$_3$) δ 155.4, 153.8, 131.1, 129.0, 127.7, 124.1, 108.9, 106.0, 65.8, 55.9, 36.3; MS (ESI+) m/z 218 (M+H)$^+$. Anal. Found: C, 71.54; H, 6.96; N, 6.40.

Preparation 56. rac-5-(4,5-Dimethyl-2-furyl)-3-methyl-1,3-oxazolidin-2-one.

Boc-Dimethylamine (7.6 g) and TMEDA (13.4 mL) were dissolved in THF (200 mL). The mixture was cooled to −70° C. and sec-BuLi (1.3 M in cyclohexane, 49.6 mL) was added maintaining the temperature below −65° C., The reaction mixture was stirred at −70° C. for 1.25 h and then a solution of 5-phenylfurylcarboxaldehyde (5.0 g) in THF (20 mL) was added maintaining the temperature below −65° C. After 2 h, the mixture was allowed to warm to 0° C. and was then quenched with sat. aq. ammonium chloride (100 mL). The mixture was diluted with diethyl ether (300 mL). The aqueous layer was separated and extracted with additional diethyl ether (2×100 mL). The combined organic layers were washed with sat. aq. ammonium chloride (2×50 mL) followed by brine (50 mL), dried (MgSO$_4$), and concentrated to afford a yellow oil. The crude oil was dissolved in THF (150 mL) and sodium hydride (60% mineral oil dispersion, 3.23 g) was added. The mixture was allowed to stir at room temperature for 18 h and then with ice bath cooling was quenched with sat. aq. ammonium chloride (100 mL). The reaction mixture was diluted with diethyl ether (300 mL). The organic layer was washed with sat. aq. ammonium chloride (2×100 mL) followed by brine (100 mL), dried (MgSO$_4$), and concentrated to afford an oil. The crude product was purified by column chromatography (heptane/EtOAc, 4/1; 1/1) to afford 3.46 g of the title compound as an oil. Physical characteristics. $^1$H NMR (400 MHz, DMSO-$d_6$) δ 6.44, 5.46, 3.78, 3.64, 2.80, 2.19, 1.90; $^{13}$C NMR (100 MHz, DMSO-$d_6$) δ 157.4, 148.8, 147.6, 115.1, 113.8, 67.4, 49.6, 30.9, 11.5, 9.8; MS (EI) m/z 195 (M$^+$); Anal. Found: C, 61.29; H, 6.87; N, 7.35.

Preparation 57. rac-1-(4,5-Dimethyl-2-furyl)-2-(methylamino)ethanol.

rac-5-(4,5-Dimethyl-2-furyl)-3-methyl-1,3-oxazolidin-2-one (Preparation 56, 3.23 g) was suspended in a solution of 1 M aq. potassium hydroxide (58 mL) and ethanol (10 mL). The mixture was heated to 60° C. for 3 h, and then was allowed to cool to room temperature. Sodium chloride was added, and the mixture was extracted with diethyl ether (4×100 mL). The organic layer was concentrated to a volume of 100 mL and then was extracted with sat. aq. ammonium chloride solution (6×50 mL). The aqueous layer was adjusted to pH 10 with solid sodium hydroxide and then extracted with diethyl ether (5×100 mL). The combined organic layers were dried ($K_2CO_3/Na_2SO_4$) and concentrated to afford an oil. The crude product was crystallized from hexane/EtOAc (10/1) to afford 1.04 g of the title compound as a light yellow solid. Physical characteristics. M.p. 59.50° C.; $^1$H NMR (400 MHz, DMSO-$d_6$) δ 6.00, 5.16, 4.47, 2.69, 2.64, 2.28, 2.14, 1.86; $^{13}$C NMR (100 MHz, DMSO-$d_6$) δ 151.8, 143.2, 111.7, 106.7, 62.9, 54.1, 33.8, 9.0, 7.5; MS (ESI+) m/z 170 (M+H)$^+$. Anal. Found: C, 63.63; H, 8.78; N, 8.01.

Preparation 58. 2-Bromo-1-pyrazin-2-ylethanone Hydrobromide.

A 1 L round-bottomed flask was charged with 2-acetylpyrazine (25 g), glacial acetic acid (175 mL), and a 30 wt % solution of HBr in acetic acid (40 mL). Pyridinium tribromide (70 g) was added to the mixture all at once as a solid. The slurry was allowed to stir for 1 h at room temperature. This resulting solution was poured into diethyl ether (1.5 L) giving a yellow solid which was recovered by gravity filtration, washed with CH$_3$CN (3×500 mL) and then diethyl ether (2×250 mL) to afford 34.9 g of the title compound. Physical characteristics. MS m/z 201, 202.

Preparation 59. tert-Butyl (1-(pyrazin-2-yl)ethanon-2-yl)(methyl)carbamate.

A 2 L round-bottomed flask was charged with 2-bromo-1-pyrazin-2-ylethanone hydrobromide (Preparation 58, 49.2 g) followed by THF (1 L). The resulting slurry was cooled to ca. 0–5° C. (ice bath). To this solution was added a 2 M solution of methylamine in THF (350 mL) giving rise to an exotherm with the solution reaching 15° C. After 20 minutes, (Boc)$_2$O (75 g) was added all at once as a solid at 5° C. The reaction mixture was allowed to stir for 30 min and then additional (Boc)$_2$O (10 g) was added and the reaction mixture allowed to stir for an additional 30 min at 5° C. The reaction mixture was allowed to warm to room temperature and was then filtered through a short pad of silica gel using ethyl acetate to wash the silica get. The filtrate was concentrated in vacuo. The resulting oil was purified by column chromatography (hexane/EtOAc, 9/1; 4/1) to afford 25.5 g of the title compound. Physical characteristics. $^1$H NMR (CD$_3$CN) δ 9.1, 8.78, 8.64, 4.78, 2.89, 2.86, 1.41, 1.28 ppm; MS m/z 274 (MNa$^+$)

Preparation 60. tert-Butyl (2R)-2-hydroxy-2-pyrazin-2-ylethyl(methyl)carbamate.

A 50 mL Schlenk flask was charged with [($\eta^6$C$_6$H$_6$)RuCl$_2$]$_2$ (200 mg), (R)(R)-TsDPEN (350 mg), anhydrous i-PrOH (10 mL), and triethylamine (0.35 mL). The Schlenk flask was removed from the glove box and placed on a Schlenk line, a reflux condenser attached, and the reaction mixture was heated to 75° C. for 1 h under nitrogen. The reaction was then cooled to 0° C. giving a solid which was collected by filtration. The solid was washed with diethyl ether and air-dried giving 228 mg of ($\eta^6$C$_6$H$_6$)Ru[(R,R)-TsDPEN]Cl. A solution of formic acid and triethylamine was prepared by adding triethylamine (91 g) to formic acid (65 g) cooled in an ice bath under a nitrogen atmosphere. The ice bath was removed and to this solution was added ($\eta^6$C$_6$H$_6$)Ru[(R,R)-TsDPEN]Cl (106 mg) and the solution allowed to stir at room temperature for 30 min. To this solution was added tert-butyl (1-(pyrazin-2-yl)ethanon-2-yl)(methyl)-carbamate (Preparation 59, 27.98 g) and the mixture was stirred at room temperature for 21 h. Additional ($\eta^6$C$_6$H$_6$)Ru[(R,R)-TsDPEN]Cl (110 mg) was added and the mixture stirred at room temperature for an additional 24 h. The mixture was poured into water (500 mL) and ethyl acetate (500 mL). The aqueous layer was extracted with ethyl acetate (500 mL). The combined ethyl acetate layers were extracted with 1 N aq. NaHCO$_3$ (2×250 mL), water (250 mL), and brine (250 mL). The ethyl acetate layer was then dried (MgSO$_4$), filtered, and concentrated to give 27.5 g of the title compound as a light brown oil. Physical characteristics. $^1$H NMR (CD$_3$CN) δ 8.66, 8.46, 4.91, 3.55, 3.4, 2.80, 1.34, 1.25 ppm; MS m/z 276 (MNa$^+$).

Preparation 61. (1R)-2-(Methylamino)-1-pyrazin-2-ylethanol.

A mixture of tert-butyl (2R)-2-hydroxy-2-pyrazin-2-ylethyl(methyl)-carbamate (Preparation 60, 27.5 g) and 6 N aq. HCl (105 mL) was stirred at room temperature for 20 min. The mixture was concentrated in vacuo using ethanol to azeotrope residual water. To the residue was added 20% aq. NaOH until the pH reached 11. This aqueous solution was extracted with EtOAc (2×250 mL). The pH was then adjusted to 14 and NaCl was added to saturate the aqueous layer. This was then extracted with EtOAc (2×200 mL). The combined EtOAc layers were dried ($MgSO_4$), filtered, and concentrated to afford a solid. The aqueous layer was further extracted with $CH_3CN$ (2×250 mL). The combined organic layers were dried ($MgSO_4$), filtered, and concentrated to afford a solid. The combined solids were dissolved in hot MTBE, filtered, and allowed to cool first to room temperature and then to 5° C. in the refrigerator giving 8.4 g of the title compound as yellow crystals. Physical characterists. $^1$H NMR (DMSO-$d_6$) δ 8.72, 8.51, 4.74, 2.81, 2.72, 2.26; $^{13}$C NMR (DMSO-$d_6$) δ 159.3, 144.0, 143.8, 143.5, 71.7, 58.2, 36.7; MS m/z 154 ($MH^+$).

Preparation 62. Sodium pyrimidine-2-carboxylate.

To a slurry of 2-cyanopyrimidine (50 g) in water (100 ml) at 2° C. was added a solution of sodium hydroxide (50 wt %, 45.6 g) in water (30 ml) with an exotherm to 50° C. The mixture was stirred at 55° C. for 2 h, ethanol (500 ml) was added and the mixture concentrated in vacuo to an oil. Ethanol (250 ml) was added and the mixture concentrated to a paste. Ethanol (250 ml) was added and the mixture stirred at 15–20° C. for 30 min. The precipitate was collected by vacuum filtration, washed with ethanol (100 ml) and dried in a 75° C. vacuum oven to afford 67.57 g of the title compound as a white solid. Physical characteristics. $^1$H NMR (400 MHz, $CD_3OD$) δ 7.53, 8.84; $^{13}$C NMR (100 MHz, $CD_3OD$) δ 123.7, 159.2, 163.6, 171.5.

Preparation 63. N-Methoxy-N-methylpyrimidine-2-carboxamide.

Sodium pyrimidine-2-carboxylate (Preparation 62, 154.05 g), imidazole hydrochloride (119.3 g), and 1,1-carbonyldiimidazole (195 g) was slurried in acetonitrile (700 ml). The mixture was warmed from 15° C. to 52° C. over 0.5 h. Carbon dioxide was vigorously evolved between 30 and 50° C. The mixture was stirred 1 h at 52° C. then cooled to 15° C. and N,O-dimethylhydroxylamine hydrochloride (131.90 g) was added with an exotherm to 34° C. The mixture was cooled to 14° C. and methylene chloride (300 ml) and water (500 ml) was added. The pH was adjusted from 7.6 to 1.6 with aqueous sulfuric acid (6.13 M, 226 ml). The phases were separated and the lower aqueous phase washed with methylene chloride (500 ml). To the combined organics was added water (300 ml) and the pH adjusted to 1.18 with aqueous sulfuric acid (6.13 M, 5.1 ml). The phases were separated and the organics washed with saturated aq. sodium bicarbonate (300 ml). All three aqueous phases were serial back extracted with methylene chloride (500 ml). The bicarbonate wash was back extracted with methylene chloride (500 ml). The combined organics were dried ($MgSO_4$) and concentrated in vacuo to a thin slurry. The residue was slurried in methylene chloride (200 ml) and the solids filtered off. The filtrate was concentrated to afford 160.7 g of the title compound as an oil. Physical characteristics. $^1$H NMR (400 MHz, $CDCl_3$) δ 3.38, 3.69, 7.39, 8.82; $^{13}$C NMR (100 MHz, $CDCl_3$) δ 32.05, 61.62, 121.34, 157.

Preparation 64. 4-Pyrimidin-2-ylcarbonyl)morpholine.

Following the general procedure of Preparation 63 and making non-critical variations, but substituting morpholine for N,O-dimethylhydroxylamine hydrochloride the title compound is obtained. Physical characteristics. $^1$H NMR (400 MHz, $CDCl_3$) δ 3.40, 3.69, 3.83, 7.38, 8.83;"$^3$C NMR (100 MHz, $CDCl_3$) δ 42.2, 47.1, 66.6, 66.7, 121.2, 157.4, 161.8, 165.0.

Preparation 65. S-Phenyl Pyrimidine-2-carbothioate.

Sodium pyrimidine-2-carboxylate (Preparation 62, 5.06 g), imidazole hydrochloride (4.23 g), and 1,1-carbonyldiimidazole (7.14 g) was slurried in acetonitrile (40 mL). The mixture was warmed to 52° C and stirred for 1 h. The mixture was cooled to 7° C. and thiophenol (4.52 ml, 44.0 mmol, 1.27 eq) was added. The mixture was stirred at 17° C. for 10 minutes then poured into water (25 ml). Toluene (25 ml) was added and the phases separated. The aqueous layer was extracted with toluene (2×25 ml). The combined organic layers were dried ($MgSO_4$) and then concentrated to an oil. Branched octanes (42 g) was added, the mixture seeded and the resultant slurry cooled to 0° C. The precipitate was collected by vacuum filtration, washed with branched octanes and dried in a nitrogen stream to give a solid. The solid was partitioned between toluene (44 g) and water (25 ml) at approximately 30° C. The phases were separated and the aqueous layer was extracted with toluene (3×25 ml). The combined organic layers were dried ($MgSO_4$) and then concentrated to 45 g net weight. Branched octanes (35 g) was added, the mixture seeded and the precipitate was collected by vacuum filtration, washed with branched octanes and dried in a nitrogen stream to afford 5.75 g of the title compound as a solid. Physical characteristics. $^1$H NMR (400 MHz, $CDCl_3$) δ 7.47, 7.54, 8.97; $^3$C NMR (100 MHz, $CDCl_3$) δ 123.6, 127.5, 129.3, 129.6, 134.6, 157.8, 159.1.

Preparation 66. tert-Butyl (1-(pyrimidin-2-yl)ethanon-2-yl) (methyl) carbamate.

Procedure A. To a solution of tert-butyl dimethylcarbamate (57.8 g) in N,N,N',N"-tetramethylethylenediamine (70 ml) and MTBE (485 g) was added sec-butyl lithium (1.4 M in cyclohexane, 300 ml) over 0.5 h while maintaining the temperature below −65° C. The mixture was stirred at −65° C. for 0.5 h, then magnesium bromide diethyl etherate (111.07 g) was added with an exotherm to −60° C. The resultant slurry was allowed to warm to −11° C. over 0.5 h then cooled to −72° C. The slurry was cannulated into a −72° C. solution of N-methoxy-N-methylpyrimidine-2-carboxamide (Preparation 63, 27.2 g) in methylene chloride (400 ml) with an exotherm to −60° C. and rinsed in with MTBE (25 ml). The mixture was warmed to 0° C. over 45 min then cooled to −27° C. Acetone (30.5 ml) was added. The mixture was cooled to −29° C., then a solution of acetic acid (63.7 g) in water (303 ml) was added with an exotherm to 11° C. The mixture was warmed to 20° C. and the phases separated. The organic layer was washed with saturated aq. sodium bicarbonate (250 ml) and the aqueous phases serial back extracted with MTBE (350 ml). The combined organics were dried ($MgSO_4$) and concentrated in vacuo to a net weight of 85 g. Toluene (200 ml) was added and the mixture concentrated to 128 g net weight. Branched octanes (205 g) was added to the cloud point, the mixture seeded and the product allowed to precipitate for 15 minutes with stirring. The slurry was cooled to −19° C. and the precipitate collected by vacuum filtration, washed with branched octanes (82 g) and dried in a nitrogen stream to afford 29.27 g of the title compound as a solid. Physical characteristics. $^1$H NMR (400 MHz, $CDCl_3$) δ 1.38, 1.49, 3.00, 4.83, 4.92, 7.50, 8.94; $^{13}$C NMR (100 MHz, $CDCl_3$) δ 28.11, 28.30, 35.57, 35.71, 56.11, 56.61, 79.96, 123.25, 123.36, 157.56, 157.65.

Procedure B. Following the general procedure of Preparation 66, Procedure A and making non-critical variations, but substituting 4-(pyrimidin-2-ylcarbonyl)morpholine or S-phenyl pyrimidine-2-carbothioate for N-methoxy-N-methylpyrimidine-2-carboxamide the title compound is obtained.

Preparation 67. tert-Butyl (2R)-2-hydroxy-2-pyrimidin-2-ylethyl(methyl)-carbamate.

In a glove box, triethylamine (6.6 g) was added carefully with stirring to formic acid (4.6 g) in a glass vial and stirring was continued until the mixture had cooled to room temperature. A 50 mL Schlenk flask was charged with [($\eta^6C_6H_6$)RuCl$_2$]$_2$ (200 mg), (R)(R)-TsDPEN (350 mg), anhydrous i-PrOH (10 mL), and triethylamine (0.35 mL). The Schlenk flask was removed from the glove box and placed on a Schlenk line, a reflux condenser attached, and the reaction mixture was heated to 75° C. for 1 h under nitrogen. The reaction was then cooled to 0° C. giving a solid which was collected by filtration. The solid was washed with diethyl ether and air-dried giving 228 mg of ($\eta^6C_6H_6$)Ru[(R,R)-TsDPEN]Cl. To a 50 mL RB flask in a glove box was added ($\eta^6C_6H_6$)Ru[(R,R)-TsDPEN]Cl (17 mg) followed by the mixture of the triethylamine/formic acid solution prepared above. The mixture was allowed to stir at room temperature for 20 min and tert-butyl 2-oxo-2-pyrimidin-2-ylethyl-(methyl)carbamate (Preparation 66, 1.33 g) was added. The mixture was stirred at room temperature for 17 h, poured into water (75 mL), and extracted with EtOAc (3×100 mL). The combined organic layers were washed with 1 M aq. NaHCO$_3$ (50 mL) and brine (50 mL). The organic layer was dried (MgSO$_4$), filtered, and concentrated to afford 1.17 g of the title compound as an oil. Physical characteristics. $^1$H NMR (CDCl$_3$) 8.66, 7.20, 4.95, 3.69, 3.45, 2.88, 1.30; MS m/z 276 (MNa$^+$).

Preparation 68. (1R)-2-(Methylamino)-1-pyrimidin-2-ylethanol Dihydrochloride.

A 6 N solution of aq. HCl (5 mL) was added to tert-butyl (2R)-2-hydroxy-2-pyrimidin-2-ylethyl(methyl)carbamate (Preparation 67, 1.17 g) at room temperature. After 2.5 h, reaction mixture was concentrated in vacuo using 3×10 mL portions of ethanol to assist in water removal. The oil was dissolved in ethanol, heated to ca. 50° C. and THF was added until slightly turbid at this temperature. The solution was allowed to cool to room temperature. The resulting solid was collected by filtration and washed with ethanol/THF (50150) followed by diethyl ether to afford 0.78 g of the title compound. Physical properties. $^1$H NMR (D$_2$O) 8.85, 7.62, 5.17, 3.45, 3.30, 2.63. $^{13}$C NMR (D20) 165.1, 158.3, 122.3, 68.4, 52.5, 33.6.

EXAMPLE 38

N-(4-Chlorobenzyl)-2-(((2-hydroxy-2-(3-methoxyphenyl)-ethyl)(methyl)amino)methyl)-7-methyl-4-oxo-4,7-dihydrofuro[2,3-b]-pyridine-5-carboxamide.

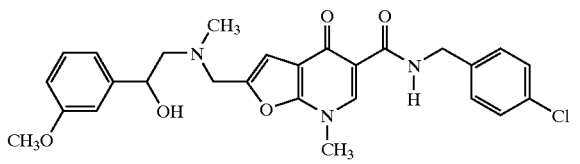

N,N-Diisopropylethylamine (0.11 mL) and 1-(3-methoxyphenyl)-2-(methylamino)ethanol (Preparation 31, 0.112 g) were added to a suspension of N-(4-chlorobenzyl)-2-(chloromethyl)-7-methyl-4-oxo-4,7-dihydrofuro[2,3-b]-pyridine-5-carboxamide (Example 2, 0.150 g) in DMF (10 mL). The reaction mixture was heated to 90° C. for 1 h. The mixture was allowed to cool to room temperature and was poured into water (25 mL). The suspension was filtered and the resulting solid was purified by column chromatography (CH$_2$Cl$_2$/methanol; 99/1, 98/2) followed by recrystallization from ethyl acetate to yield 0.102 g of the title compound as a pale yellow solid. Physical characteristics. M.p. 116–120° C.; $^1$H NMR (400 MHz, DMSO-d$_6$) δ 10.65, 8.54, 7.41–7.32, 7.18, 6.88–6.85, 6.77–6.75, 5.10, 4.704.66, 4.55, 3.89, 3.74, 3.70, 2.61, 2.33; MS (ESI+) m/z 510 (M+H)$^+$. Anal. Found: C, 63.48; H, 5.56; N, 8.24; Cl, 6.94.

EXAMPLE 39

N4-Chlorobenzyl)-2-(((2-(4-fluorophenyl)-2-hydroxyethyl)(methyl)amino)methyl)-7-methyl-4-oxo-4,7-dihydrofuro[2,3-b]pyridine-5-carboxamide.

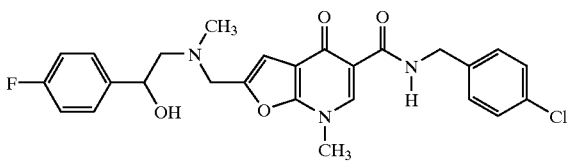

Analogous to the procedures described in Example 38, N-(4-chlorobenzyl)-2-(chloromethyl)-7-methyl-4-oxo-4,7-dihydrofuro[2,3-b]pyridine-5-carboxamide (Example 2) is treated with rac-1-(4-fluorophenyl)-2-methylamino)ethanol (Preparation 33) to afford the title compound.

EXAMPLE 40

N-(4-Chlorobenzyl)-2-(((2-(4-chlorophenyl)-2-hydroxyethyl)(methyl)amino)methyl)-7-methyl-4-oxo-4,7-dihydrofuro[2,3-b]pyridine-5-carboxamide.

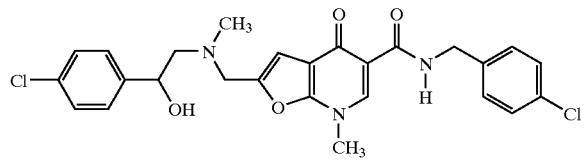

Analogous to the procedures described in Example 38, N(4-chlorobenzyl)-2-(chloromethyl)-7-methyl-4-oxo-4,7-dihydrofuro[2,3-b]pyridine-5-carboxamide (Example 2) is treated with rac-1-(4-chlorophenyl)-2-(methylamino)ethanol (Preparation 35) to afford the title compound.

EXAMPLE 41

N-(4-Chlorobenzyl)-2-(((2-hydroxy-2-pyridin-2-ylethyl)-(methyl)amino)methyl)-7-methyl-4-oxo-4,7-dihydrofuro[2,3-b]pyridine-5-carboxamide.

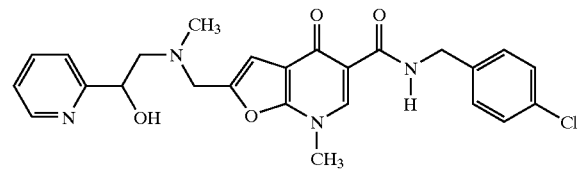

N,N-Diisopropylethylamine (0.11 mL) and rac-2-methylamino)-1-pyridin-2-ylethanol (Preparation 36, 0.094 g) were added to a suspension of N-(4-chlorobenzyl)-2-(chloromethyl)-7-methyl-4-oxo-4,7-dihydrofuro[2,3-b]-pyridine-5-carboxamide (Example 2, 0.150 g) in DMF (10 mL). The reaction mixture was heated to 90° C. for 1 h. The mixture was allowed to cool to room temperature, poured into water (25 mL), and was extracted with CH$_2$Cl$_2$ (4×25 mL). The combined organic layers were dried (MgSO$_4$), filtered, and concentrated in vacuo. The resulting solid was purified by column chromatography (CH$_2$Cl$_2$/methanol; 99/1, 98/2, 97/3, 95/5) followed by recrystallization from ethyl acetate to yield 0.082 g of the title compound as a pale yellow solid. Physical characteristics. M.p. 130–132° C.; $^1$H NMR (400 MHz, DMSO-d$_6$) δ 10.65, 8.54, 8.43–8.42, 7.76–7.73, 7.47–7.45, 7.41–7.32, 7.24–7.21, 6.83, 5.31, 4.79–4.74, 4.55, 3.89, 3.74, 2.79–2.74, 2.66–2.61, 2.33; MS (ESI+) m/z 481 (M+H)$^+$. Anal. Found: C, 62.08; H, 5.25; N, 11.57; Cl, 7.39.

EXAMPLE 42

N4-Chlorobenzyl)-2-((((2R)-2-hydroxy-2-pyridin-2-ylethyl)-(methyl)amino)methyl)-7-methyl-4-oxo-4,7-dihydrofuro[2,3-b]pyridine-5 carboxamide.

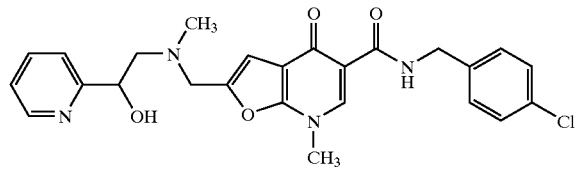

N,N-Diisopropylethylamine (0.36 mL), N-(4-chlorobenzyl)-2-(chloromethyl)-7-methyl-4-oxo-4,7-dihydrofuro[2,3-b]pyridine-5-carboxamide (Example 2, 0.500 g), and 4 Å molecular sieves (powder, 2.74 g) were added to a solution of (R)-2-(methylamino)-1-pyridin-2-ylethanol dihydrochloride (Preparation 38, 0.314 g) in DMF (30 mL). The reaction mixture was heated to 90° C. for 1.5 h. The mixture was allowed to cool to room temperature and was filtered through Celite. The Celite was washed with CH$_2$Cl$_2$. The filtrate was partitioned between water (50 mL) and CH$_2$Cl$_2$ (50 mL). The aqueous layer was separated and extracted with CH$_2$Cl$_2$ (3×50 mL). The combined organic layers were dried (MgSO$_4$), filtered, and concentrated in vacuo. The resulting solid was purified by column chromatography (CH$_2$Cl$_2$/methanol; 97/3, 96/4) followed by recrystallization from ethyl acetate to yield 0.375 g of the title compound as a pale yellow solid. Physical characteristics. M.p. 133–138° C.; $^1$H NMR (400 MHz, DMSO-d$_6$) δ 10.65, 8.54, 8.43–8.42, 7.77–7.72, 7.47, 7.41–7.32, 7.24–7.21, 6.83, 5.32, 4.79–4.75, 4.55, 3.90, 3.77–3.71, 2.79–2.75, 2.66–2.61, 2.33; $^{13}$C NMR (100 MHz, CDCl$_3$) δ 173.7, 164.8, 160.9, 153.1, 150.8, 148.7, 141.0, 137.3, 136.8, 132.8, 128.9, 128.6, 122.5, 120.4, 116.8, 114.8, 106.5, 70.3, 63.1, 54.0, 42.5, 42.1, 37.8; MS (ESI+) m/z 481 (M+H)$^+$; [alpha]D=+38° (CH$_2$Cl$_2$).

EXAMPLE 43

N-(4-Chlorobenzyl)-2-(((2-hydroxy-2-pyridin-3-ylethyl)-(methyl)amino)methyl)-7-methyl-4-oxo-4,7-dihydrofuro[2,3-b]pyridine-5-carboxamide.

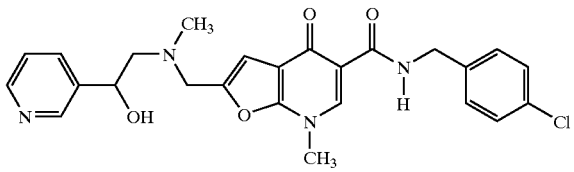

N,N-Diisopropylethylamine (0.11 mL) and 2-(methylamino)-1-pyridin-3-ylethanol (Preparation 39, 0.094 g) were added to a suspension of N-(4-chlorobenzyl)-2-(chloromethyl)-7-methyl-4-oxo-4,7-dihydrofuro[2,3-b]pyridine-5-carboxamide (Example 2, 0.150 g) in DMF (10 mL). The reaction mixture was heated to 90° C. for 1 h. The mixture was allowed to cool to room temperature, poured into water (25 mL), and was extracted with CH$_2$Cl$_2$ (4×25 mL). The combined organic layers were dried (MgSO$_4$), filtered, and concentrated in vacuo. The resulting solid was purified by column chromatography (CH$_2$Cl$_2$/methanol; 98/2, 97/3, 96/4, 95/5) followed by recrystallization from ethyl acetate to yield 0.074 g of the title compound as a pale yellow solid. Physical characteristics. M.p. 145–149° C.; $^1$H NMR (400 MHz, DMSO-d$_6$) δ 10.64, 8.54, 8.50, 8.40–8.39, 7.69–7.67, 7.41–7.33, 7.29–7.25, 6.83, 5.33, 4.77–4.73, 4.55, 3.88, 3.71, 2.67–2.55, 2.32; MS (ESI+) m/z 481 (M+H)$^+$.

EXAMPLE 44

N-(4-Chlorobenzyl)-2-(((2-hydroxy-2-pyridin-4-ylethyl)-(methyl)amino)methyl)-7-methyl-4-oxo-4,7-dibydrofuro[2,3-b]pyridine-5-carboxamide.

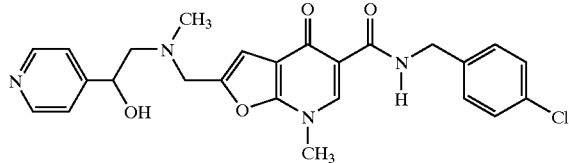

Analogous to the procedures described in Example 38, N-(4-chlorobenzyl)-2-(chloromethyl)-7-methyl-4-oxo-4,7-dlhydrofuro[2,3-b]pyridine-5-carboxamide (Example 2) is treated with rac-2-(methylamino)-1-pyridin-4-ylethanol (Preparation 40) to afford the title compound.

EXAMPLE 45

N-(4-Chlorobenzyl)-2-(((2-hydroxy-2-(5-methyl-2-furyl) ethyl)(methyl)amino)methyl)-7-methyl-4-oxo-4,7-dihydrofuro[2,3-b]-Pyridine-5-carboxamide.

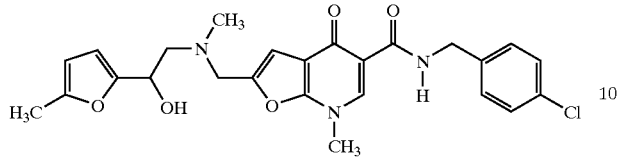

N,N-Diisopropylethylamine (0.14 mL) and N4-chlorobenzyl)-2-(chloromethyl)-7-methyl-4--oxo-4,7-dihydrofuro[2,3-b]pyridine-5-carboxamide (Example 2, 0.150 g) were added to a solution of rac-2-(methylamino)-1-(5-methyl-2-furyl)ethanol (Preparation 42, 0.127 g) in DMF (10 mL). The reaction mixture was heated to 90° C. for 1 h. The mixture was allowed to cool to room temperature and was poured into water (25 mL). The suspension was filtered and the resulting solid was purified by column chromatography ($CH_2Cl_2$/methanol, 98/2) followed by recrystallization from ethyl acetate to yield 0.128 g of the title compound as a white solid. Physical characteristics. M.p. 130–132° C.; $^1$H NMR (400 MHz, DMSO-$d_6$) δ 10.65, 8.55, 7.41–7.32, 6.85, 6.10–6.09, 5.95–5.94, 5.14, 4.644.59, 4.55, 3.91, 3.75–3.67, 2.74–2.63, 2.29, 2.18; $^{13}$C NMR (100 MHz, $CDCl_3$) δ 173.7, 164.7, 153.2, 152.2, 151.9, 150.5, 141.1, 137.3, 132.8, 128.9, 128.6, 116.8, 114.8, 108.2, 106.7, 106.1, 63.6, 60.5, 54.0, 42.5, 41.8, 37.8, 13.6; MS (ESI+) m/z 485 (M+H)$^+$.

EXAMPLE 46

N-(4-Chlorobenzyl)-2-(((2-(3-furyl)-2-hydroxyethyl)(methyl)amino)methyl)-7-methyl-4-oxo-4,7-dihydrofuro[2,3-b]pyridine-5-carboxamide.

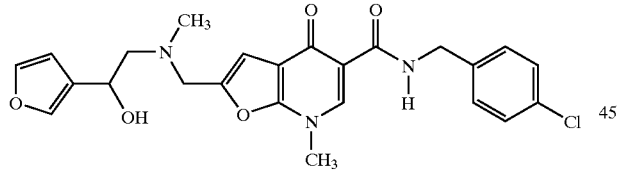

N,N-Diisopropylethylamine (0.14 mL) and N-(4-chlorobenzyl)-2-(chloromethyl)-7-methyl-4-oxo-4,7-dihydrofuro[2,3-b]pyridine-5-carboxamide (Example 2, 0.150 g) were added to a solution of rac-1-(3-furyl)-2-(methylamino)ethanol (Preparation 43, 0.116 g) in DMF (10 mL). The reaction mixture was heated to 90° C. for 1 h. The mixture was allowed to cool to room temperature and was poured into water (25 mL). The suspension was filtered and the resulting solid was purified by column chromatography ($CH_2Cl_2$/methanol, 98/2) followed by recrystallization from ethyl acetate to yield 0.102 g of the title compound as a pale yellow solid. Physical characteristics. M.p. 93–97° C.; $^1$H NMR (400 MHz, DMSO-$d_6$) δ 10.65, 8.55, 7.54–7.53, 7.41–7.32, 6.87, 6.42, 4.97, 4.694.65, 4.55, 3.91, 3.74, 2.63–2.53, 2.30; $^{13}$C NMR (100 MHz, $CDCl_3$) δ 173.7, 164.7, 153.2, 150.6, 143.4, 141.1, 139.4, 137.3, 132.8, 128.9, 126.0, 116.8, 114.7, 108.3, 106.6, 102.1, 63.2, 62.7, 54.1, 42.6, 41.8, 37.8; MS (ESI+) m/z 470 (M+H)$^+$.

EXAMPLE 47

N-(4-Chlorobenzyl)-2-(((2-hydroxy-2-(2,4,6-trifluorophenyl) ethyl)(methyl)amino)methyl)-7-methyl-4-oxo-4,7-dihydrofuro[2,3-b]-pyridine-5-carboxamide.

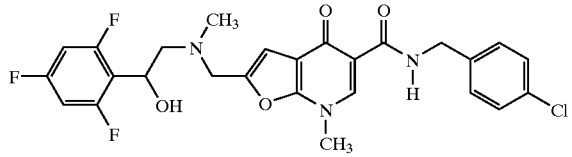

Analogous to the procedures described in Example 38, N-(4-chlorobenzyl)-2-(chloromethyl)-7-methyl-4-oxo-4,7-dihydrofuro[2,3-b]pyridine-5-carboxamide (Example 2) is treated with rac-2-(methylamino)-1-(2,4,6-trifluorophenyl) ethanol (Preparation 44) to afford the title compound.

EXAMPLE 48

2-(((2-(1-Benzofuran-2-yl)-2-hydroxyethyl)(methyl) amino)methyl)-N-4-chlorobenzyl)-7-methyl-4-oxo-4,7-dihydrofuro[2,3-b]-pyridine-5-carboxamide.

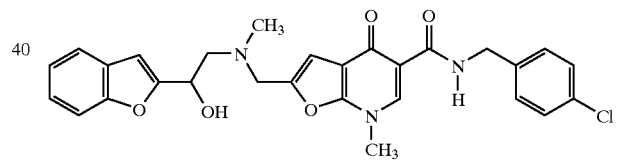

N,N-Diisopropylethylamine (0.11 mL) and rac-1-(1-benzofuran-2-yl)-2-(methylamino)ethanol (Preparation 45, 0.119 g) were added to a suspension of N-(4-chlorobenzyl)-2-(chloromethyl)-7-methyl-4-oxo-4,7-dihydrofuro[2,3-b]-pyridine-5-carboxamide (Example 2, 0.150 g) in DMF (10 mL). The reaction mixture was heated to 90° C. for 1 h. The mixture was allowed to cool to room temperature, poured into water (25 mL), and was extracted with $CH_2Cl_2$ (4×25 mL). The combined organic layers were dried ($MgSO_4$), filtered, and concentrated in vacuo. The crude product was purified by column chromatography ($CH_2Cl_2$/methanol, 98/2). The resulting solid was triturated with ethyl acetate to yield 0.137 g of the title compound as a pale yellow solid. Physical characteristics. M.p. 176–179° C.; $^1$H NMR (400 MHz, DMSO-$d_6$) δ 10.65, 8.50, 7.57–7.54, 7.41–7.33, 7.21–7.19, 6.89, 6.73, 5.55, 4.874.83, 4.56, 3.75–3.67, 2.93–2.88, 2.75–2.69, 2.33; MS (ESI+) m/z 520 (M+H)$^+$.

EXAMPLE 49

N-(4-Chlorobenzyl)-2-(((2-hydroxy-2-thien-2-ylethyl)-(methyl)amino)methyl)-7-methyl-4-oxo-4,7-dihydrofuro[2,3-b]pyridine-5-carboxamide.

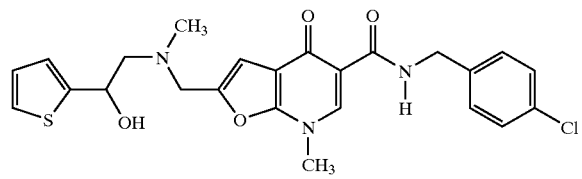

N,N-Diisopropylethylamine (0.14 mL) and N-(4-chlorobenzyl)-2-(chloromethyl)-7-methyl-4-oxo-4,7-dihydrofuro[2,3-b]pyridine-5-carboxamide (Example 2, 0.150 g) were added to a solution of rac-2-(methylamino)-1-thien-2-ylethanol (Preparation 46, 0.130 g) in DMF (10 mL). The reaction mixture was heated to 90° C. for 1 h. The mixture was allowed to cool to room temperature and was poured into water (25 mL). The suspension was filtered and the resulting solid was purified by column chromatography (CH$_2$Cl$_2$/methanol; 99/1, 98/2) followed by recrystallization from ethyl acetate to yield 0.125 g of the title compound as a white solid. Physical characteristics. M.p. 145–147° C.; $^1$H NMR (400 MHz, DMSO-d$_6$) δ 10.65, 8.54, 7.41–7.32, 6.97–6.93, 6.87, 6.42, 5.52, 4.984.93, 4.55, 3.91, 3.76, 2.70–2.60, 2.30; $^{13}$C NMR (100 MHz, CDCl$_3$) δ 168.9, 159.9, 148.3, 145.6, 140.3, 136.2, 132.4, 127.9, 124.1, 123.8, 121.8, 119.8, 119.0, 112.0, 109.9, 101.8, 61.3, 59.6, 49.2, 37.7, 37.0, 32.9; MS (ESI+) m/z 486 (M+H)$^+$.

EXAMPLE 50

N-(4-Chlorobenzyl)-2-(((2-hydroxy-2-quinolin-2-ylethyl)(methyl)amino)methyl)-7-methyl-4-oxo-4,7-dihydrofuro[2,3-b]pyridine-5-carboxamide.

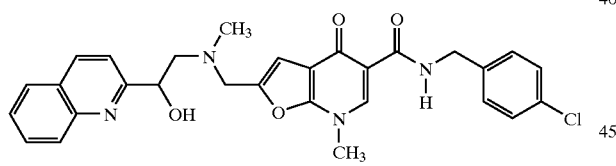

N,N-biisopropylethylamine (0.11 mL) and rac-2-(methylamino)-1-quinolin-2-ylethanol (Preparation 47, 0.125 g) were added to a suspension of N-(4-chlorobenzyl)-2-(chloromethyl)-7-methyl-4-oxo-4,7-dihydrofuro[2,3-b]pyridine-5-carboxamide (Example 2, 0.150 g) in DMF (10 mL). The reaction mixture was heated to 90° C. for 1 h. The reaction mixture was allowed to cool to room temperature, poured into water (25 mL), and was extracted with CH$_2$Cl$_2$ (4×25 mL). The combined organic layers were dried (MgSO$_4$), filtered, and concentrated in vacuo. The resulting solid was purified by column chromatography (CH$_2$Cl$_2$/methanol; 99/1, 98/2, 97/3, 9515). The product was then recrystallized from ethyl acetate and then methanol to yield 0.106 g of the title compound as a pale yellow solid. Physical characteristics. M.p. 154–159° C. (dec); $^1$H NMR (400 MHz, DMSO-d$_6$) δ 10.64, 8.48, 8.29–8.27, 7.94–7.87, 7.70–7.66, 7.62–7.60, 7.57–7.52, 7.41–7.33, 6.85, 5.53, 4.95–4.91, 4.55, 3.74, 3.74–3.72, 2.89–2.85, 2.79–2.74, 2.36; MS (ESI+) m/z 531 (M+H)$^+$.

EXAMPLE 51

N-(4-Chlorobenzyl)-2-(((2-hydroxy-2-(1-methyl-1H-pyrrol-2-yl)ethyl)(methyl)amino)methyl)-7-methyl-4-oxo-4,7-dihydrofuro[2,3-b]-pyridine-5-carboxamide.

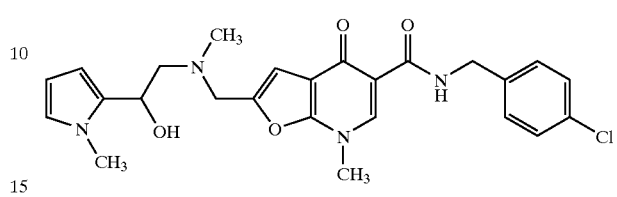

N,N-Diisopropylethylamine (0.14 mL) and N-(4-chlorobenzyl)-2-(chloromethyl)-7-methyl-4-oxo-4,7-dihydrofuro[2,3-b]pyridine-5-carboxamide (Example 2, 0.150 g) were added to a solution of rac-2-(methylamino)-1-(1-methyl-1H-pyrrol-2-yl)ethanol (Preparation 48, 0.126 g) in DMF (10 mL). The reaction mixture was heated to 90° C. for 1 h. The mixture was allowed to cool to room temperature, poured into water (25 mL), and was extracted with CH$_2$Cl$_2$ (4×25 mL). The combined organic layers were dried (MgSO$_4$), filtered, and concentrated in vacuo. The resulting oil was purified by column chromatography (CH$_2$Cl$_2$/methanol, 98/2) followed by recrystallization from ethyl acetate to yield 0.126 g the title compound as a white solid. Physical characteristics. M.p. 122–124° C. (dec); $^1$H NMR (400 MHz, DMSO-d$_6$) δ 10.65, 8.55, 7.41–7.32, 6.89, 6.61–6.60, 5.85–5.83, 4.84, 4.74–4.69, 4.55, 3.91, 3.79–3.71, 3.58, 2.79–2.70, 2.31; $^{13}$C NMR (100 MHz, CDCl$_3$) δ 173.7, 164.7, 153.2, 150.6, 141.1, 137.3, 132.8, 131.4, 128.9, 128.6, 123.4, 116.8, 114.8, 106.8, 106.6, 106.0, 61.9, 60.8, 54.3, 42.5, 41.9, 37.8, 34.1; MS (ESI+) m/z 483 (M+H)$^+$.

EXAMPLE 52

N-(4-Chlorobenzyl)-2-(((2-(5-cyanothien-2-yl)-2-hydroxyethyl)(methyl)amino)methyl)-7-methyl-4-oxo-4,7-dihydrofuro[2,3-b]-pyridine-5-carboxamide

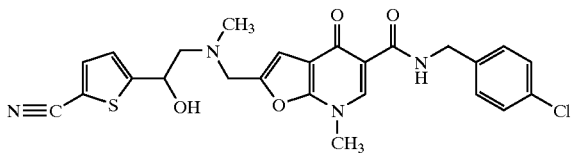

N,N-Diisopropylethylamine (0.18 mL) and N-(4-chlorobenzyl)-2-(chloromethyl)-7-methyl-4-oxo-4,7-dihydrofuro[2,3-b]pyridine-5-carboxamide (Example 2, 0.250 g) were added to a solution of rac-5-(1-hydroxy-2-(methylamino)ethyl)thiophene-2-carbonitrile (Preparation 51, 0.188 g) in DMF (15 mL). The reaction mixture was heated to 90° C. for 2 h. The mixture was allowed to cool to room temperature and was poured into water (30 mL). The suspension was filtered and the resulting solid was purified by column chromatography (CH$_2$Cl$_2$/methanol; 98/2) followed by recrystallization from ethyl acetate/methanol to yield 0.111 g of the title compound as a pale yellow solid. Physical characteristics. M.p. 190–195° C. (dec); $^1$H NMR (400 MHz, DMSO-d$_6$) δ 10.63, 8.56, 7.80, 7.41–7.32, 7.14, 6.88, 6.06, 5.01–4.97, 4.55, 3.92, 3.76, 2.69–2.64, 2.34; $^{13}$C NMR (100 MHz, CDCl$_3$) δ 173.7, 164.6, 154.3, 153.2, 150.0, 141.2, 137.4, 137.2, 132.8, 128.9, 128.7, 123.3, 116.9, 114.7, 114.3, 108.5, 106.9, 66.3, 63.9, 54.1, 42.6, 41.8, 37.8; MS (ESI+) m/z 511 (M+H)$^+$.

EXAMPLE 53

N-(4-Chlorobenzyl)-2-(((2-hydroxy-2-(1,3-thiazol-2-yl)ethyl)(methyl)amino)methyl)-7-methyl-4-oxo-4,7-dihydrofuro[2,3-b]pyridine-5-carboxamide

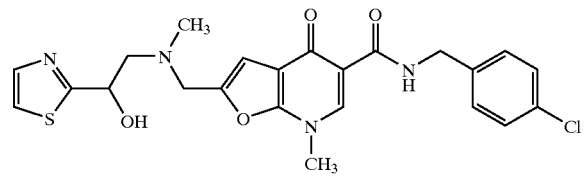

N,N-Diisopropylethylamine (0.24 mL) and N-(4-chlorobenzyl)-2-(chloromethyl)-7-methyl-4-oxo-4,7-dihydrofuro[2,3-b]pyridine-5-carboxamide (Example 2, 0.250 g) were added to a solution of rac-2-(methylamino)-1-(1,3-thiazol-2-yl)ethanol (Preparation 53, 0.217 g) in DMF (15 mL). The reaction mixture was heated to 90° C. for 2 h. The mixture was allowed to cool to room temperature, poured into water (30 mL), and was extracted with ethyl acetate (3×50 mL). The combined organic layers were washed with brine (25 mL), dried (MgSO$_4$), filtered, and concentrated in vacuo. The resulting solid was purified by column chromatography (CH$_2$Cl$_2$/methanol; 98/2, 95/5) followed by recrystallization from ethyl acetate to yield 0.120 g of the title compound as a pale yellow solid. Physical characteristics. M.p. 114–116° C.; $^1$H NMR (400 MHz, DMSO-d$_6$) δ 10.65, 8.55, 7.70, 7.61, 7.41–7.32, 6.86, 6.13, 5.034.98, 4.55, 3.91, 3.77, 2.89–2.84, 2.74–2.69, 2.35; MS (ESI+) m/z 487 (M+H)$^+$.

EXAMPLE 54

N-(4-Chlorobenzyl)-2-(((2-hydroxy-2-(5-phenyl-2-furyl)ethyl)(methyl)amino)methyl)-7-methyl-4-oxo-4,7-dihydrofuro[2,3-b]pyridine-5-carboxamide

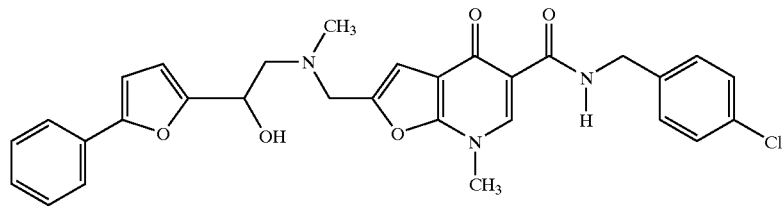

N,N-Diisopropylethylamine (0.17 mL) was added to a solution of N-(4-chlorobenzyl)-2-(chloromethyl)-7-methyl-4-oxo-4,7-dihydrofuro[2,3-b]pyridine-5-carboxamide (Example 2, 0.183 g) and rac-2-(methylamino)-1-(5-phenyl-2-furyl)ethanol (Preparation 55, 0.217 g) in DMF (15 mL). The reaction mixture was heated to 90° C. for 2 h. The mixture was allowed to cool to room temperature, poured into water (50 mL), and was extracted with ethyl acetate (3×100 mL). The combined organic layers were washed with brine (50 mL), dried (Na$_2$SO$_4$), filtered, and concentrated in vacuo. The crude product was purified by column chromatography (CH$_2$Cl$_2$/methanol, 100/1; 50/1; 25/1) and crystallized from ethyl acetate/CH$_2$Cl$_2$/diethyl ether to afford 0.22 g of the title compound as a white solid. Physical characteristics. M.p. 115–119°C.; $^1$H NMR (400 MHz, DMSO-d$_6$) δ 10.63, 8.40, 7.56, 7.42–7.30, 7.17, 6.89, 6.84, 6.37, 5.34, 4.74, 4.54, 3.80, 3.74, 3.67, 2.88, 2.68, 2.33; MS (ESI+) m/z 546 (M+H)$^+$.

EXAMPLE 55

N4-Chlorobenzyl)-2-(((2-(4,5-dimethyl-2-furyl)-2-hydroxyethyl)(methyl)amino)methyl)-7-methyl-4-oxo-4,7-dihydrofuro[2,3-b]-pyridine-5-carboxamide.

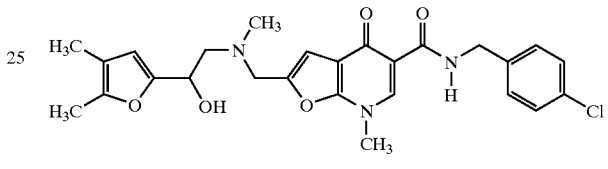

N,N-Diisopropylethylamine (0.17 mL) was added to a solution of N-(4-chlorobenzyl)-2-(chloromethyl)-7-methyl-4-oxo-4,7-dihydrofuro[2,3-b]pyridine-5-carboxamide (Example 2, 0.183 g) and rac-1-(4,5-dimethyl-2-furyl)-2-(methylamino)ethanol (Preparation 57, 0.169 g) in DMF (15 mL). The reaction mixture was heated to 90° C. for 2 h. The mixture was allowed to cool to room temperature, poured into water (50 mL), and was extracted with ethyl acetate (3×100 mL). The combined organic layers were washed with brine (50 mL), dried (Na$_2$SO$_4$), filtered, and concentrated in vacuo. The crude product was purified by column chromatography (CH$_2$Cl$_2$/methanol, 100/1; 50/1; 25/1) to afford 0.18 g of the title compound as a white solid. Physical characteristics. M.p. 140–140.5° C.; $^1$H NMR (400 MHz, DMSO-d$_6$) δ 10.65, 8.55, 7.41–7.33, 6.85, 5.99, 5.07, 4.594.54, 3.91, 3.73, 3.68, 2.69, 2.62, 2.28, 2.09, 1.84; MS (ESI+) m/z 498 (M+H)$^+$.

EXAMPLE 56

(+)-N-(4-Chlorobenzyl)-2-(((2-hydroxy-2-pyrazin-2-ylethyl)(methyl)amino)methyl)-7-methyl-4-oxo-4,7-dihydrofuro[2,3-b]pyridin-5-carboxamide.

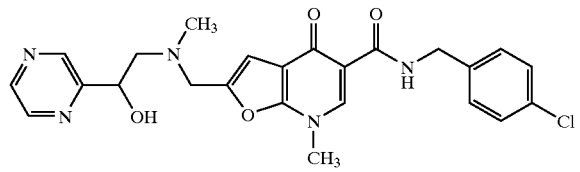

N,N-Diisopropylethylamine (0.26 mL) and (1R)-2-(methylamino)-1-pyrazin-2-ylethanol (Preparation 61, 0.230 g) were added to a solution of N-(4-chlorobenzyl)-2-(chloromethyl)-7-methyl-4-oxo-4,7-dihydrofuro[2,3-b]pyridine-5-carboxamide (Example 2, 0.365 g) in DMF (20 mL). The reaction mixture was heated to 90° C. for 1 h. The reaction mixture was allowed to cool to room temperature, poured into water (40 mL), and was extracted with $CH_2Cl_2$ (4×40 mL). The combined organic layers were washed with brine (75 mL), dried ($MgSO_4$), filtered, and concentrated in vacuo. The resulting solid was purified by column chromatography ($CH_2Cl_2$/methanol; 97/3, 96/4) followed by recrystallization from ethyl acetate to yield 0.313 g of the title compound as a white solid. Physical characteristics. M.p. 148–151° C.; $^1$H NMR (400 MHz, DMSO-$d_6$) δ 10.65, 8.70, 8.54, 8.50–8.48, 7.41–7.33, 6.81, 5.58, 4.864.79, 4.55, 3.88, 3.70, 2.86–2.81, 2.74–2.69, 2.32; MS (ESI+) m/z 482 (M+H)$^+$; [a]D=+39 ($CH_2Cl_2$)

EXAMPLE 57

(+N-(4-Chlorobenzyl)-2-(((2-hydroxy-2-pyrimidin-2-ylethyl(methyl)amino)methyl)-7-methyl-4-oxo-4,7-dihydrofuro[2,3-b]pyridine-5-carboxamide.

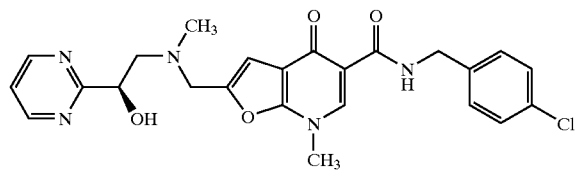

N,N-Diisopropylethylamine (0.37 mL) and N-(4-chlorobenzyl)-2-(chloromethyl)-7-methyl-4-oxo-4,7-dihydrofuro[2,3-b]pyridine-5-carboxamide (Example 2, 0.230 g) were added to a solution of (1R)-2-(methylamino)-1-pyrimidin-2-ylethanol dihydrochloride (Preparation 68, 0.200 g) in DMF (15 mL). The reaction mixture was heated to 90° C. for 1 h. The mixture was allowed to cool to room temperature, poured into water (30 mL), and was extracted with $CH_2Cl_2$ (4×30 mL). The combined organic layers were washed with brine (50 mL), dried ($MgSO_4$), filtered, and concentrated in vacuo. The resulting solid was purified by column chromatography ($CH_2Cl_2$/methanol; 98/2, 9515) followed by recrystallization from ethyl acetate to yield 0.116 g of the title compound as a white solid. Physical characteristics. M.p. 127–129° C.; $^1$H NMR (400 MHz, DMSO-$d_6$) δ 10.65, 8.73, 8.54, 7.41–7.33, 6.80, 5.30, 4.814.77, 4.55, 3.86, 3.68, 2.96–2.92, 2.73–2.69, 2.29; MS (ESI+) m/z 482 (M+H)$^+$; $[\alpha]^{25}_D$ ($CH_2Cl_2$)=+28.

Preparation 69. rac-3-Amino-2-phenylpropan-1-ol.

A 1.0 M solution of lithium aluminum hydride in THF (100 mL) was cooled to 0° C. Ethyl phenyl cyanoacetate (4.59 mL) was added dropwise. The reaction mixture was allowed to warm to room temperature and was stirred for 18 h. The reaction was quenched with water (10 mL), 1 N NaOH (10 mL), and additional water (10 mL). The aluminum salts were filtered, and the filtrate was concentrated in vacuo. The resulting oil was purified by column chromatography ($CHCl_3$, $CHCl_3$/methanol; 98/2, 95/5, $CHCl_3$/methanol/$NH_4OH$, 89/10/1) to yield 0.819 g of the title compound as a yellow oil. Physical characteristics. $^1$H NMR (400 MHz, DMSO-$d_6$) δ 7.30–7.26, 7.20–7.17, 3.67–3.62, 3.58–3.54, 2.94–2.89, 2.79–2.69.

Preparation 70. rac-Ethyl 3-Hydroxy-2-phenylpropylcarbamate.

rac-3-Amino-2-phenylpropan-1-ol (Preparation 69, 0.799 g) was dissolved in water (30 mL) and cooled to 0° C. Ethyl chloroformate (0.23 mL) was added dropwise. A 2 N NaOH solution (5.5 mL) was added followed by additional ethyl chloroformate (0.22 mL). The reaction mixture was stirred at 0° C. for 1.5 h and then at room temperature for 18 h. Additional ethyl chloroformate (0.55 mL) was added. The mixture was stirred at room temperature for 1 h and then acidified with a 1 N HCl solution. The aqueous layer was extracted with ethyl acetate (4×25 mL). The combined organic layers were dried ($MgSO_4$), filtered, and concentrated in vacuo. The resulting oil was purified by column chromatography ($CH_2Cl_2$, $CH_2Cl_2$/methanol, 99/1) to yield 0.593 g of the title compound as a yellow oil. Physical characteristics. $^1$H NMR (400 MHz, DMSO-$d_6$) δ 7.29–7.26, 7.21–7.17, 6.98, 4.62 (bs, 1H), 3.93 (q, J=7.0 Hz, 2H), 3.59–3.51, 3.35–3.29, 3.23–3.16, 2.90–2.83, 1.10; MS (ESI+) m/z 224 (M+H)$^+$.

Preparation 71. rac-3-(Methylamino)-2-phenylpropan-1-ol.

rac-Ethyl 3-hydroxy-2-phenylpropylcarbamate (Preparation 70, 0.521 g) was added dropwise to a 1.0 M solution of lithium aluminum hydride in THE (10 mL). The reaction mixture was stirred at room temperature for 18 h. The mixture was cooled to 0° C. and was quenched with water (10 mL), 1N 1 N NaOH (10 mL), and additional water (10 mL). The aluminum salts were filtered, and the filtrate was concentrated in vacuo to yield 0.375 g of the title compound as a yellow oil. Physical characteristics. $^1$H NMR (400 MHz, DMSO-$d_6$) δ 7.31–7.17, 3.66–3.61, 3.57–3.53, 2.89–2.82, 2.73–2.63, 2.25; MS (ESI+) m/z 166 (M+H)$^+$.

EXAMPLE 58

N4-Chlorobenzyl-2-((3-hydroxy-2-phenylpropyl)(methyl)amino)methyl)-7-methyl-4-oxo-4,7-dihydrofuro[2,3-b]pyridine-S carboxamide

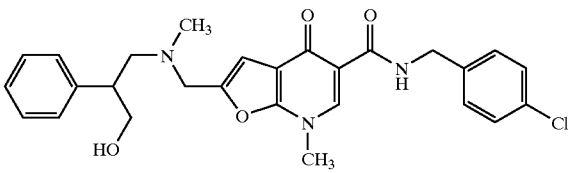

N,N-Diisopropylethylamine (0.24 mL) and N-(4-chlorobenzyl)-2-(chloromethyl)-7-methyl-4-oxo-4,7-dihydrofuro[2,3-b]pyridine-5-carboxamide (Example 2, 0.250 g) were added to a solution of rac-3-(methylamino)-2-phenylpropan-1-ol (Preparation 71, 0.226 g) in DMF (15 mL). The reaction mixture was heated to 90° C. for 2 h. The mixture was allowed to cool to room, temperature, was poured into water (30 mL), and was extracted with $CH_2Cl_2$ (4×25 mL). The combined organic layers were dried (MgSO$_4$), filtered, and concentrated in vacuo. The resulting solid was purified by column chromatography (CH$_2$Cl$_2$/methanol, 99/1) followed by recrystallization from ethyl acetate to yield 0.129 g of the title compound as a pale yellow solid. Physical characteristics. M.p. 141–148° C.; $^1$H NMR (400 MHz, DMSO-d$_6$) δ 10.65, 8.54, 7.41–7.32, 7.24–7.16, 6.81, 4.69, 4.55, 3.86, 3.67–3.52, 3.00–2.94, 2.75–2.70, 2.62–2.57, 2.23; MS (ESI+) m/z 494 (M+H)$^+$.

Preparation 72. 2-(Hydroxy(phenyl)methyl)pyrrolidine.

N-Boc-pyrrolidine (5.0 g) was dissolved in diethyl ether (60 mL) and the solution was cooled to −78° C. N,N,N',N''-Tetramethylethylenediamine (TMEDA) (4.4 mL) was added to the mixture followed by sec-butyl lithium (27.0 mL, 1.3 M in cyclohexane) maintaining the temperature below −60° C. After 2 h, benzaldehyde (3.6 mL) was added and the mixture was stirred at −70° C. for an additional 30 min. The reaction mixture was allowed to warm to room temperature and was then quenched with water and poured into EtOAc (200 mL). The separated organic layer was washed with saturated aq. ammonium chloride (3×50 mL) followed by brine (50 mL), dried (MgSO$_4$), and concentrated. The crude product was purified by column chromatography (heptane/EtOAc, 8/1; 6/1) to afford 6.3 g of N-Boc-2-(hydroxy(phenyl)methyl)-pyrrolidine as a mixture of diastereomers. The resulting N-Boc-2-(hydroxy(phenyl)methyl)pyrrolidine (5.6 g) was dissolved in dichloromethane (500 mL) and trifluoroacetic acid (60 mL) was added. The mixture was concentrated, dissolved in dichloromethane (200 mL), and washed with saturated aq. sodium bicarbonate (3×100 mL). The aqueous layers were extracted with dichloromethane (4×50 mL) and the combined organic layers were concentrated. The crude product was distilled in a Kugelrohr apparatus (150–175° C., 0.2 Torr) to afford 2.47 g of the title compound as a mixture of diastereomers. Physical characteristics. MS (ESI+) m/z 178 (M+H)$^+$.

Preparation 73. 2-Furyl(pyrrolidin-2-yl)methanol.

N-Boc-pyrrolidine (5.0 g) was dissolved in diethyl ether (60 mL) and the solution was cooled to −78° C. N,N,N',N''-Tetramethylethylenediamine (TMEDA) (4.4 mL) was added to the mixture followed by sec-butyl lithium (27.0 mL, 1.3 M in cyclohexane) maintaining the temperature below −60° C. After 2 h, 2-furaldehyde (2.9 mL) was added and the mixture was stirred at −70° C. for an additional 30 min. The reaction mixture was allowed to warm to room temperature and was then quenched with water and poured into EtOAc (200 mL). The separated organic layer was washed with saturated aq. ammonium chloride (3×50 mL) followed by brine (50 mL), dried (MgSO$_4$), and concentrated. The crude product was purified by column chromatography (heptane/EtOAc, 8/1; 5/1) to afford 4.97 g of 2-furyl(N-Boc-pyrrolidin-2-yl)methanol as a mixture of diastereomers. The resulting 2-furyl(N-Boc-pyrrolidin-2-yl)methanol (4.43 g) was dissolved in dichloromethane (200 mL) and trifluoroacetic acid (30 mL) was added. The mixture was poured into a 1 M solution of sodium hydroxide. The organic layer was separated and washed with saturated aq. sodium bicarbonate (2×100 mL). The aqueous layers were extracted with dichloromethane (4×50 mL) and the combined organic layers were concentrated. The crude product was purified by column chromatography (CH$_2$Cl$_2$/methanol/NH$_4$OH, 95/5/1; 90/10/1). The resulting oil was distilled in a Kugelrohr apparatus (175–200° C., 0.2 Torr) to afford 0.20 g of the title compound as a mixture of diastereomers. Physical characteristics. MS (ESI+) m/z 168 (M+H)$^-$.

EXAMPLE 59

N-(4-chlorobenzyl)-2-(((2R*)-2(S*)-hydroxy (phenyl)methyl)pyrrolidin-1-yl)methyl)-7-methyl-4-oxo-4,7-dihydrofuro[2,3-b]-pyridine-5-carboxamide.

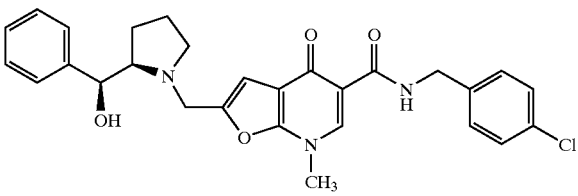

N,N-Diisopropylethylamine (0.48 mL) and N-(4-chlorobenzyl)-2-(chloromethyl)-7-methyl-4-oxo-4,7-dihydrofuro[2,3-b]pyridine-5-carboxamide (Example 2, 0.500 g) were added to a solution of 2-(hydroxy(phenyl) methyl)-pyrrolidine (Preparation 72, 0.486 g) in DMF (30 mL). The reaction mixture was heated to 90° C. for 2 h. The mixture was allowed to cool to room temperature and was poured into water (60 mL). The suspension was filtered and the resulting solid was purified by column chromatography (CH$_2$Cl$_2$/methanol; 99/1, 98/2). The less polar product was isolated and triturated with diethyl ether to yield 0.040 g of the title compound as a white solid. Physical characteristics. M.p. 141–150° C. (dec); $^1$H NMR (400 MHz, DMSO-d$_6$) δ 10.65, 8.54, 7.41–7.28, 7.22–7.19, 6.81, 4.89, 4.55, 4.574.51, 3.93, 3.82, 3.57, 2.99–2.94, 2.85–2.80, 2.48–2.41, 1.82–1.75, 1.62–1.55, 1.51–1.44; HRMS (ESI+) m/z 506.1854 (M+H)$^+$.

EXAMPLE 60

N-(4-Chlorobenzyl)-2-(((2R*)-2-((R*)-2-furyl (hydroxy)methyl)pyrrolidin-1-yl)methyl)-7-methyl-4-oxo-4,7-dihydrofuro[2,3-b]-pyridine-5-carboxamide.

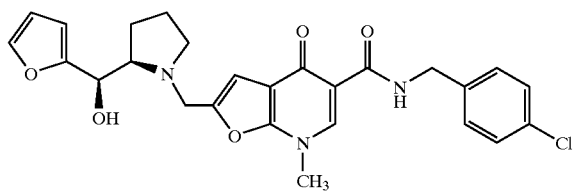

Analogous to the procedures described in Example 59, N-(4-chlorobenzyl)-2-(chloromethyl)-7-methyl-4-oxo-4,7-dihydrofuro[2,3-b]pyridine-5-carboxamide (Example 2) is treated with 2-furyl(pyrrolidin-2-yl)methanol (Preparation 73) to afford the title compound.

EXAMPLE 61

N-(4-Chlorobenzyl)-2-((2R)-2-((R)-hydroxy (pyridin-2-yl)-methyl)pyrrolidin-1-yl)methyl)-7-methyl-4-oxo-4,7-dihydrofuro[2,3-b]-pyridine-5-carboxamide.

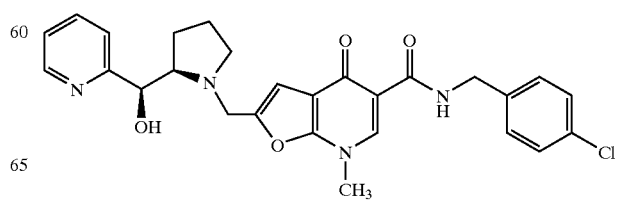

Analogous to the procedures described in Example 59, N-(4-chlorobenzyl)-2-(chloromethyl)-7-methyl-4-oxo-4,7-dihydrofuro[2,3-b]pyridine-5-carboxamide (Example 2) is treated with (R)-pyridin-2-yl((2R)-pyrrolidin-2-yl)methanol (prepared according to procedures described in Tsutsumi, S.; Okonogi, T; Shibahara, S.; Ohuchi, S.; Hatsushiba, E.; Patchett, A. A.; Christensen, B. G. J. Med. Chem. 1994, 37, 3492–3502 starting from (R)-N-Boc-prolinal) to afford the title compound.

EXAMPLE 62

N-(4-Chlorobenzyl)-7-methyl-2-((methylamino)methyl)-4-oxo-4,74-dihydrofuro[2,3-b]pyridine-5-carboxamide.

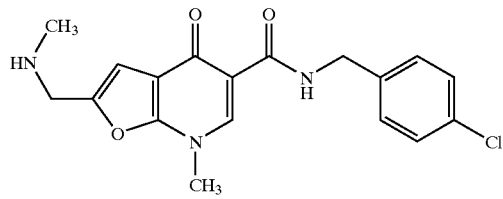

A sealed tube was charged with N-(4-chlorobenzyl)-2-(chloromethyl)-7-methyl-4-oxo-4,7-dihydrofuro[2,3-b]pyridine-5-carboxamide (Example 2, 3.74 g) and a 2 M solution of methylamine in THF (102 mL). The mixture was heated at 85° C. overnight and then was concentrated. Water (65 mL) was added and the suspension was stirred at room temperature. The suspension was extracted with CHCl$_3$ (2×). The organic layer was dried and concentrated. The crude product was purified by column chromatography (CHCl$_3$/MeOH/NH$_4$OH, 97/3/0.5%) to yield 3.21 g of the title compound. Physical characteristics. $^1$H NMR (400 MHz, DMSO-d$_6$) δ 10.66, 8.54, 7.40, 7.34, 6.80, 4.54, 3.93, 3.73, 2.29.

EXAMPLE 63

N-(4-Chlorobenzyl)-2-(((3-chloro-2-hydroxypropyl)amino)methyl)-7-methyl-4-oxo-4,7-dihydrofuro[2,3-b]pyridine-5-carboxamide.

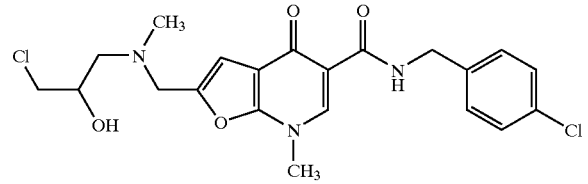

A sealed tube was charged with a mixture of N-(4-chlorobenzyl)-7-methyl-2-((methylamino)methyl)-4-oxo-4,7-dihydrofuro[2,3-b]pyridine-5-carboxamide (Example 62, 3.21 g), epi-chlorohydrin (0.90 mL), and ethanol (80 mL). The mixture was heated to 80° C. overnight and then concentrated. The crude product was purified by column chromatography (acetone/CHCl$_3$/NH$_4$OH, 1/1/0.5%) to yield 1.62 g of the title compound as a white solid. Physical characteristics. $^1$H NMR (400 MHz, DMSO-d$_6$) δ 10.65, 8.55, 7.39, 7.33, 5.08, 4.54, 3.93, 3.84, 3.75–3.65, 3.56, 2.53, 2.39, 2.28.

EXAMPLE 64

N-(4-Chlorobenzyl)-2-(((2-hydroxy-3-((2-methoxyphenyl)thio)propyl)(methyl)amino)methyl)-7-methyl-4-oxo-4,7-dihydrofuro[2,3-b]-pyridine-5-carboxamide.

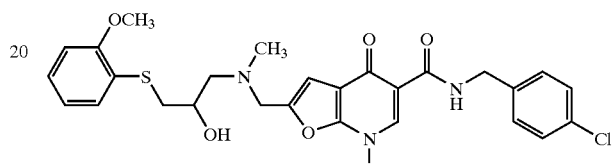

A mixture of N-(4-chlorobenzyl)-2-(((3-chloro-2-hydroxypropyl)amino)methyl)-7-methyl-4-oxo-4,7-dihydrofuro[2,3-b]pyridine-5-carboxamide (Example 63, 0.181 g), 2-methoxythiophenol (0.058 mL), and diisopropylethylamine (0.097 mL) in absolute EtOH (16 mL) was heated to reflux overnight. The reaction was poured into 50% saturated aqueous NaCl (50 mL) and extracted with CHCl$_3$. The combined organic layers were dried and concentrated. The crude product was purified by column chromatography (acetone/CHCl$_3$/NH$_4$OH; 1/2/0.5%) and triturated with Et$_2$O/hexanes. The resulting solid was collected and dried overnight to yield 0.10 g of the title compound as a white solid. Physical characteristics. M.p. 145–147° C.; $^1$H NMR (400 MHz, DMSO-d$_6$) δ 10.66, 8.52, 7.40, 7.34, 7.22, 7.13, 6.89, 4.96, 4.55, 3.84–3.64, 3.02, 2.84, 2.55, 2.44, 2.29; $^{13}$C NMR (DMSO-d$_6$) δ 174.1, 165.7, 157.4, 154.5, 152.7, 143.1, 140.0, 132.8, 130.5, 129.8, 128.1, 127.4, 126.8, 122.3, 116.6, 115.2, 112.0, 107.2, 68.8, 62.1, 56.9, 55.0, 44.3, 42.7, 38.8, 37.5. Anal. Found: C, 60.38; H, 5.56; N, 7.45.

EXAMPLE 65

2-(((3-((5-Amino-1,3,4-thiadiazol-2-yl)thio)-2-hydroxypropyl)(methyl)amino)methyl)-N-(4-chlorobenzyl)-7-methyl-4-oxo-4,7-dihydrofuro[2,3-b]pyridine-5-carboxamide.

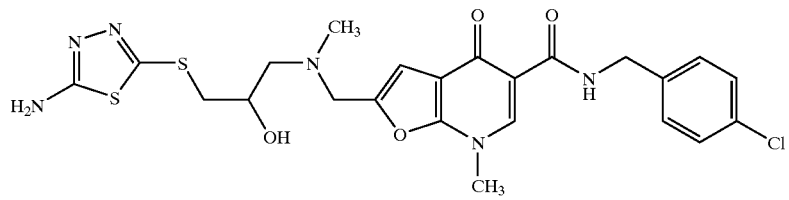

A mixture of N-(4-chlorobenzyl)-2-(((3-chloro-2-hydroxypropyl)amino)methyl)-7-methyl-4-oxo-4,7-dihydrofuro[2,3-b]pyridine-5-carboxamide (Example 63, 0.181 g), 5-amino-1,3,4-thiadiazole-2-thiol (0.064 g), and diisopropylethylamine (0.097 mL) in absolute EtOH (16 mL) was heated to reflux overnight. The reaction was poured into 50% saturated aqueous NaCl (40 mL) and extracted with CHCl₃. The organic layer was dried and concentrated. The crude product was purified by column chromatography (CHCl₃MeOH/NH₄OH, 93/7/0.5%) and triturated with Et₂O/hexanes. The resulting solid was collected and dried overnight to yield 0.087 g of the title compound as a white solid. Physical characteristics. M.p. 200–204° C.; ¹H NMR (300 MHz, DMSO-d₆) δ 10.64, 8.54, 7.39, 7.33, 7.23, 6.88, 5.11, 4.54, 3.92, 3.70, 3.29, 3.04, 2.4, 2.28; ³C NMR (DMSO-d₆) δ 172.7, 169.2, 164.3, 153.2, 151.2, 141.8, 138.6, 131.3, 129.1, 128.3, 115.2, 113.8, 105.9, 67.2, 60.6, 53.4, 42.6, 41.3, 37.5. Anal. Found: C, 50.41; H, 4.74; N, 15.06.

EXAMPLE 66

2-(((3-((3-Amino-1H-1,2,4-triazol-5-yl)thio)-2-hydroxypropyl)(methyl)amino)methyl)-N-4-chlorobenzyl)-7-methyl-4-oxo-4,7-dihydrofuro[2,3-b]pyridine-5-carboxamide.

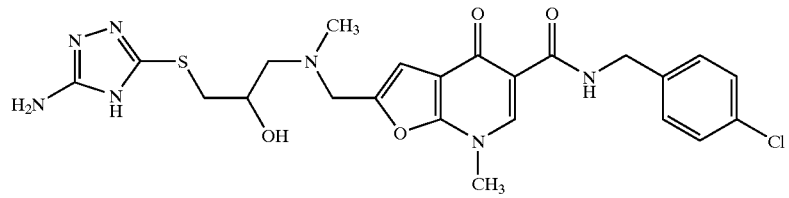

A mixture of N-(4-chlorobenzyl)-2-(((3-chloro-2-hydroxypropyl)amino)methyl)-7-methyl-4-oxo-4,7-dihydrofuro[2,3-b]pyridine-5-carboxamide (Example 63, 0.248 g), 3-amino-5-mercapto-1,2,4-triazole (0.076 g), and diisopropylethylamine (0.133 mL) in absolute EtOH (20 mL) was heated to reflux overnight. The reaction was poured into 50% saturated aqueous NaCl (50 mL) and extracted with CHCl₃. The organic layer was dried and concentrated. The crude product was purified by column chromatography (CHCl₃/MeOH/NH₄OH, 9/1/0.5%) and triturated with Et₂O/hexanes to afford the title compound. Physical characteristics. ¹H NMR (400 MHz, DMSO-d₆) δ 10.65, 8.55, 7.39, 7.34, 6.89, 6.03, 5.09, 4.54, 3.92, 3.86, 3.70, 3.20, 2.91, 2.45, 2.27.

EXAMPLE 67

2-(((3-(4-Aminopyrimidin-2-yl)thio)-2-hydroxypropyl)(methyl)amino)methyl)-N-(4-chlorobenzyl)-7-methyl-4-oxo-4,7-dihydrofuro[2,3-b]pyridine-5-carboxamide.

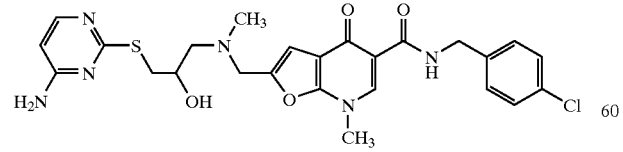

A mixture of N-(4-chlorobenzyl)-2-(((3-chloro-2-hydroxypropyl)amino)methyl)-7-methyl-4-oxo-4,7-dihydrofuro[2,3-b]pyridine-5-carboxamide (Example 63, 0.181 g), 4-amino-2-mercaptopyrimidine (0.061 g), and diisopropylethylamine (0.097 mL) in absolute EtOH (16 mL) was heated to reflux overnight. The reaction was poured into 50% saturated aqueous NaCl (50 mL) and extracted with CHCl₃. The organic layer was dried and concentrated. The crude product was purified by column chromatography (CHCl₃/MeOH/NH₄OH, 95/5/0.5%) and triturated with diethyl ether. The resulting solid was collected and dried to yield 0.135 g of the title compound as a white solid. Physical characteristics. ¹H NMR (300 MHz, DMSO-d₆) δ 10.65, 8.54, 7.86, 7.40, 7.33, 6.88, 6.11, 4.99, 4.54, 3.91, 3.87, 3.72, 3.30, 2.96, 2.46, 2.28.

EXAMPLE 68

N-(4-Chlorobenzyl)-2-(((2-hydroxy-3-(3-methoxyphenyl)thio)propyl)(methyl)amino)methyl)-7-methyl-4-oxo-4,7-dihydrofuro[2,3-b]-pyridine-5-carboxamide.

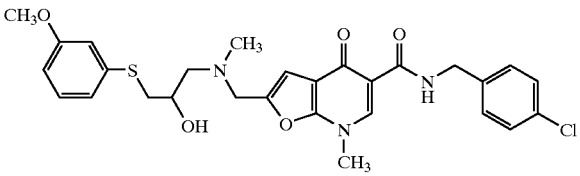

Analogous to the procedures described in Example 67, N-(4-chlorobenzyl)-2-(((3-chloro-2-hydroxypropyl)amino)methyl)-7-methyl-4-oxo-4,7-dihydrofitro[2,3-b]pyridine-5-carboxamide (Example 63) is reacted with 3-methoxythiophenol to afford the title compound.

EXAMPLE 69

N-(4-Chlorobenzyl)-2-(((2-hydroxy-3-((4-methoxyphenyl)-thio)propyl)(methyl)amino) methyl)-7-methyl-4-oxo-4,7-dihydrofuro[2,3-b]-pyridine-5-carboxamide.

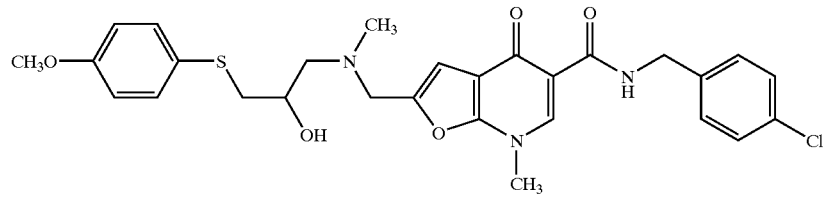

Analogous to the procedures described in Example 67, N-(4-chlorobenzyl)-2-(((3-chloro-2-hydroxypropyl)amino) methyl)-7-methyl-4-oxo-4,7-dihydrofuro[2,3-b]pyridine-5-carboxamide (Example 63) is reacted with 4-methoxythiophenol to afford the title compound.

EXAMPLE 70

2-((3-(((5-(((4-Chlorobenzyl)amino)carbonyl)-7-methyl-4-oxo-4,7-dihydrofuro[2,3-b]pyridin-2-yl) methyl)(methyl)amino)-2-hydroxypropyl)thio) benzoic acid.

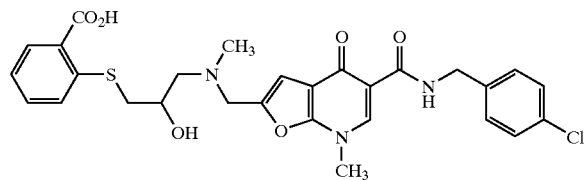

Analogous to the procedures described in Example 67, N-(4-chlorobenzyl)-2-(((3-chloro-2-hydroxypropyl)amino) methyl)-7-methyl-4-oxo-4,7-dihydrofuro[2,3-b]pyridine-5-carboxamide (Example 63) is reacted with thiosalicylic acid to afford the title compound.

EXAMPLE 71

2-((3-(((5-(((4-Chlorobenzyl)amino)carbonyl)-7-methyl-4-oxo-4,7-dihydrofuro[2,3-b]pyridin-2-yl) methyl)(methyl)amino)-2-hydroxypropyl)thio) nicotinic acid.

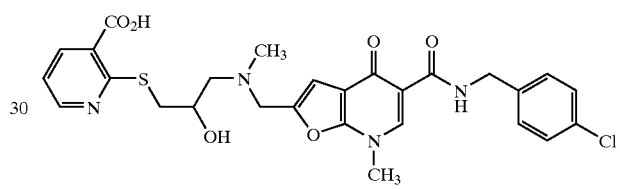

Analogous to the procedures described in Example 67, N-(4-chlorobenzyl)-0.2-(((3-chloro-2-hydroxypropyl) amino)methyl)-7-methyl-4-oxo-4,7-dihydrofuro[2,3-b] pyridine-5-carboxamide (Example 63) is reacted with 2-mercaptonicotinic acid to afford the title compound.

EXAMPLE 72

N-(4-Chlorobenzyl)-2-(((2-hydroxy-3-((4-oxo-3,4-dihydroquinazolin-2-yl)thio)propyl)(methyl)amino) methyl)-7-methyl-4-oxo-4,7-dihydrofuro[2,3-b] pyridine-5-carboxamide.

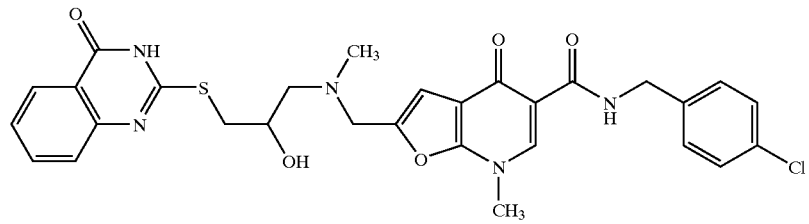

Analogous to the procedures described in Example 67, N-(4-chlorobenzyl)-2-(((3-chloro-2-hydroxypropyl)amino)methyl)-7-methyl-4-oxo-4,7-dihydrofuro[2,3-b]pyridine-5-carboxamide (Example 63) is reacted with 2-mercapto-4(3H)-quinazolinone to afford the title compound.

EXAMPLE 73

2-(((3-((6-Amino-1,3-benzothiazol-2-yl)thio)-2-hydroxypropyl)(methyl)amino)methyl)-N-(4-chlorobenzyl)-7-methyl-4-oxo-4,7-dihydrofuro[2,3-b]pyridine-5-carboxamide.

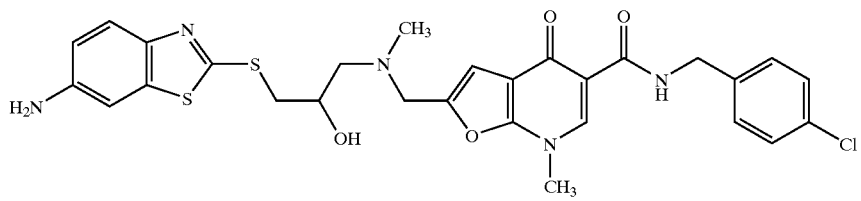

Analogous to the procedures described in Example 67, N-(4-chlorobenzyl)-2-(((3-chloro-2-hydroxypropyl)amino)methyl)-7-methyl-4-oxo-4,7-dihydrofuro[2,3-b]pyridine-5-carboxamide (Example 63) is reacted with 6-amino-2-mercaptobenzothiazole to afford the title compound.

EXAMPLE 74

N-(4-Chlorobenzyl)-2-(((2-hydroxy-3-(9H-purin-6-ylthio)propyl)(methyl)amino)methyl)-7-methyl-4-oxo-4,7-dihydrofuro[2,3-b]-pyridine-5-carboxamide.

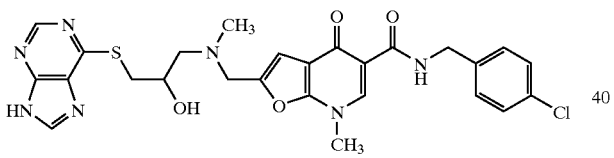

Analogous to the procedures described in Example 67, N-(4-chlorobenzyl)-2-(((3-chloro-2-hydroxypropyl)amino)methyl)-7-methyl-4-oxo-4,7-dihydrofuro[2,3-b]pyridine-5-carboxamide (Example 63) is reacted with 6-mercaptopurine to afford the title compound.

EXAMPLE 75

2-(((3-(Benzylthio)-2-hydroxypropyl)(methyl)amino)methyl)-N-(4-chlorobenzyl)-7-methyl-4-oxo-4,7-dihydrofuro[2,3-b]pyridine-5-carboxamide.

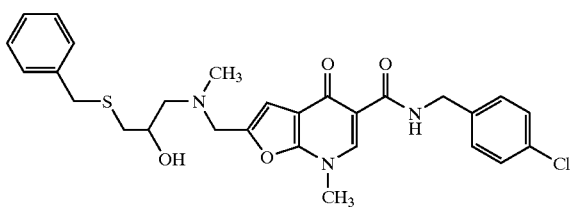

Analogous to the procedures described in Example 67, N-(4-chlorobenzyl)-2-(((3-chloro-2-hydroxypropyl)amino)methyl)-7-methyl-4-oxo-4,7-dihydrofuro[2,3-b]pyridine-5-carboxamide (Example 63) is reacted with benzyl mercaptan to afford the title compound.

EXAMPLE 76

N-(4-Chlorobenzyl)-2-(((3-((4-chlorobenzyl)thio)-2-hydroxypropyl)(methyl)amino)methyl)-7-methyl-4-oxo-4,7-dihydrofuro[2,3-b]-pyridine-5-carboxamide.

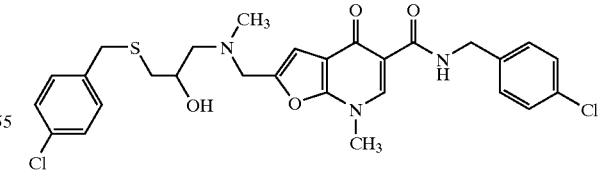

Analogous to the procedures described in Example 67, N-(4-chlorobenzyl)-2-(((3-chloro-2-hydroxypropyl)amino)methyl)-7-methyl-4-oxo-4,7-dihydrofuro[2,3-b]pyridine-5-carboxamide (Example 63) is reacted with 4-chlorobenzenemethanethiol to afford the title compound.

EXAMPLE 77

N-(4-Chlorobenzyl)-2-((2-hydroxy-3-((4-methoxybenzyl)thio)propyl)(methyl)amino)methyl)-7-methyl-4-oxo-4,7-dihydrofuro[2,3-b]-pyridine-5-carboxamide.

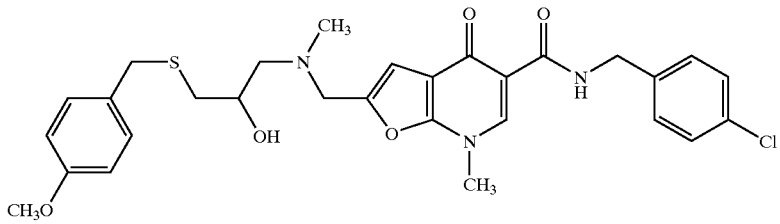

Analogous to the procedures described in Example 67, N-(4-chlorobenzyl)-2-(((3-chloro-2-hydroxypropyl)amino)methyl)-7-methyl-4-oxo-4,7-dihydrofuro[2,3-b]pyridine-5-carboxamide (Example 63) is reacted with 4-methoxy-alpha-toluenethiol to afford the title compound.

EXAMPLE 78

N-(4-Chlorobenzyl)-7-methyl-4-oxo-4,7-dihydrofuro[2,3-b]-pyridine-5-carboxamide.

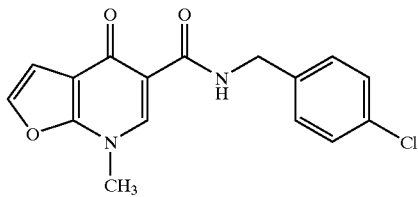

A mixture of ethyl 7-methyl-4-oxo-4,7-dihydrofuro[2,3-b]pyridine-5-carboxylate (Preparation 9, 1.00 g) and 4-chlorobenzylamine (5.5 mL) was heated to 190° C. for 1 h. The reaction mixture was allowed to cool for several minutes and toluene (50 mL) was added. The resulting off-white solid was filtered and recrystallized from ethyl acetate to yield 0.979 g (68%) of the title compound as a pale yellow solid. Physical characteristics. M.p. 197–205° C.; $^1$H NMR (400 MHz, DMSO-$d_6$) δ 10.62, 8.59, 7.92, 7.41–7.33, 7.06, 4.55, 3.94; $^{13}$C NMR (100 MHz, CDCl$_3$) δ 174.0, 164.8, 153.4, 141.4, 140.5, 137.3, 132.8, 128.9, 128.7, 116.7, 114.2, 107.9, 42.6, 37.7; MS (ESI+) m/z 317 (M+H)$^+$.

EXAMPLE 79

2-Bromo-N-(4-chlorobenzyl)-7-methyl-4-oxo-4,7-dihydrofuro[2,3-b]pyridine-5-carboxamide

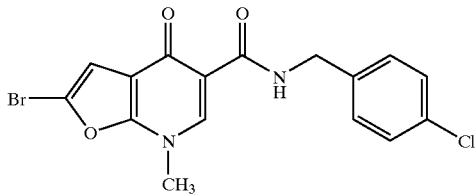

N-Bromosuccinimide (2.77 g) was added to a solution of N-(4-chlorobenzyl)-7-methyl-4-oxo-4,7-dihydrofuro[2,3-b]pyridine-5-carboxamide (Example 78, 2.46 g) in CHCl$_3$ (100 mL). The reaction mixture was heated to 50° C. for 18 h. The mixture was allowed to cool to room temperature and was washed with water (100 mL) and brine (100 mL). The organic layer was dried (MgSO$_4$), filtered, and concentrated in vacuo. The resulting solid was purified by column chromatography (CH$_2$Cl$_2$/methanol, 99/1) followed by recrystallization from ethyl acetate to yield 1.87 g (61%) of the title compound as a white solid. Physical characteristics. M.p. 232–233° C.; $^1$H NMR (400 MHz, DMSO-$d_6$) δ 10.50, 8.57, 7.41–7.32, 7.23, 4.55, 3.92; MS (EI) m/z 394 (M$^+$), 396 (M$^+$+2).

EXAMPLE 80

N-(4-Chlorobenzyl)-2-(3-hydroxyprop-1-ynyl)-7-methyl-4-oxo-4,7-dihydrofuro[2,3-h]pyridine-5-carboxamide

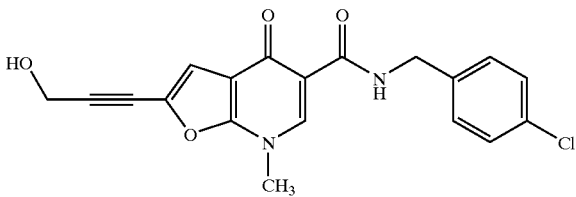

2-Bromo-N-(4-chlorobenzyl)-7-methyl-4-oxo-4,7-dihydrofuro[2,3-b]-pyridine-5-carboxamide (Example 79, 1.00 g) was suspended in diethylamine (40 mL). CuI (0.145 g), Pd(PPh$_3$)$_2$Cl$_2$ (0.091 g), and then propargyl alcohol (0.21 mL) were added. The reaction mixture was stirred at room temperature for 18 h and was then partitioned between CH$_2$Cl$_2$ (100 mL) and water (100 mL). The aqueous layer was separated and extracted with CH$_2$Cl$_2$ (3×100 mL). The combined organic layers were washed with a sat. aq. ammonium chloride solution (100 mL), dried (MgSO$_4$), filtered, and concentrated in vacuo. The solid was purified by column chromatography (CH$_2$Cl$_2$/methanol; 99/1, 98/2) followed by recrystallization from methanol to yield 0.321 g of the title compound as a pale yellow solid. Physical characteristics. M.p. 245–248° C. (dec); $^1$H NMR (400 MHz, DMSO-$d_6$) δ 10.49, 8.61, 7.41–7.39, 7.34–7.32, 5.55, 4.55, 3.93; MS (EI) m/z 370 (M+).

EXAMPLE 81

N-(4-Chlorobenzyl)-2-(3-hydroxypropyl)-7-methyl-4-oxo-4,7-dihydrofuro[2,3-b]pyridine-5-carboxamide

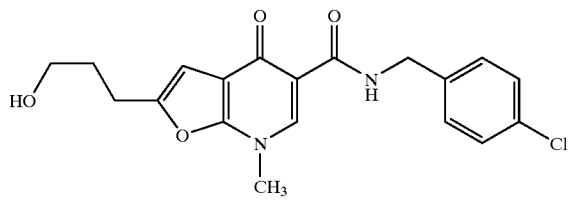

N-(4-Chlorobenzyl)-2-(3-hydroxyprop-1-ynyl)-7-methyl-4-oxo-4,7-dihydrofuro[2,3-b]pyridine-5-carboxamide (Example 80, 0.300 g) was dissolved in ethanol (150 mL) with heating and then allowed to cool to room temperature.

The mixture was the hydrogenated over 10% Pd/C (0.090 g) at 35 psi for 2 h. The reaction mixture was filtered through a Celite pad and the pad was washed with $CH_2Cl_2$ (150 mL). The filtrate was concentrated in vacuo. The resulting solid was purified by column chromatography ($CH_2Cl_2$/methanol, 98/2) followed by recrystallization from ethyl acetate to yield 0.037 g of the title compound as a white solid. Physical characteristics. $^1$H NMR (400;MHz, DMSO-$d_6$) δ 10.69, 8.51, 7.41–7.25, 6.68, 4.58, 4.54, 3.92, 3.49–3.45, 2.78, 1.84–1.77; MS (ESI+) m/z 375 (M+H)$^+$.

EXAMPLE 82

N-(4-Chlorobenzyl)-2-(4-hydroxybut-1-ynyl)-7-methyl-4-oxo-4,7-dihydrofuro[2,3-b]pyridine-5-carboxamide.

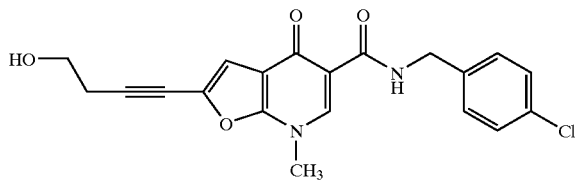

2-Bromo-N-(4-chlorobenzyl)-7-methyl-4-oxo-4,7-dihydrofuro[2,3-b]-pyridine-5-carboxamide (Example 79, 0.100 g) was suspended in a mixture of triethylamine (2.5 mL) and DMF (0.5 mL). CuI (0.006 g), Pd(PPh$_3$)$_2$Cl$_2$ (0.017 g), and then 3-butyn-1-ol (0.038 mL) were added. The mixture was stirred at room temperature for 30 min and then was partitioned between $CH_2Cl_2$ (10 mL) and water (10 mL). The aqueous layer was separated and was extracted with $CH_2Cl_2$ (3×10 mL). The combined organic layers were washed with a sat. aq. ammonium chloride solution (10 mL), dried (MgSO$_4$), filtered, and concentrated in vacuo. The resulting solid was purified by column chromatography ($CH_2Cl_2$/methanol; 99/1, 98/2) followed by recrystallization from ethyl acetate to yield 0.035 g of the title compound as a pale yellow solid. Physical characteristics. M.p. 242–243° C. (dec); $^1$H NMR (400 MHz, DMSO-$d_6$) δ 10.51, 8.59, 7.41–7.32, 7.21, 5.01, 4.55, 3.92, 3.61, 2.67; MS (ESI+) m/z 385 (,M+H)$^+$.

EXAMPLE 83

N-(4-Chlorobenzyl)-2-(4-hydroxybutyl)-7-methyl-4-oxo-4,7-dihydrofuro[2,3-b]pyridine-5-carboxamide

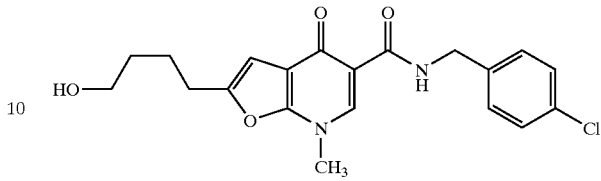

N-(4-Chlorobenzyl)-2-(4-hydroxybut-1-ynyl)-7-methyl-4-oxo-4,7-dihydrofuro[2,3-b]pyridine-5-carboxamide (Example 82, 0.219 g) was dissolved in ethanol (50 mL) with heating and then allowed to cool to room temperature. The mixture was hydrogenated over 10% Pd/C (0.065 g) at 35 psi for 2 h. The reaction mixture was filtered through a Celite pad and the pad was washed with $CH_2Cl_2$ (75 mL). The filtrate was concentrated in vacuo. The resulting solid was purified by column chromatography ($CH_2Cl_2$/methanol, 98/2) to yield 0.190 g of the title compound as a pale yellow solid. Physical characteristics. M.p. 157–160° C.; $^1$H NMR (400 MHz, DMSO-$d_6$) δ 10.69, 8.52, 7.41–7.32, 6.67, 4.55, 4.43, 3.92, 3.45–3.41, 2.74, 1.73–1.65, 1.53–1.46; $^3$C NMR (100 MHz, CDCl$_3$) δ 173.6, 165.0, 155.3, 152.6, 140.4, 137.4, 132.8, 128.9, 128.6, 127.5, 116.5, 115.2, 102.7, 62.2, 43.2, 42.5, 37.7, 31.9, 27.8, 23.9; MS (ESI+) m/z 389 (M+H)$^+$.

EXAMPLE 84

N-(4-Chlorobenzyl)$_{2,5}$-hydroxypent-1-ynyl)-7-methyl-4-oxo-4,7?dlhydrofuro[2,3-b]pyridine-5-carboxamide.

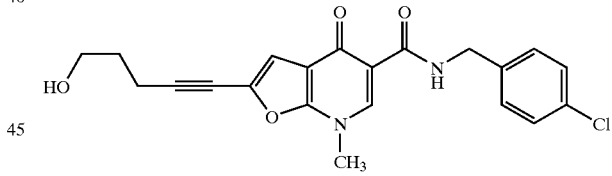

2-Bromo-N-(4-chlorobenzyl)-7-methyl-4-oxo-4,7-dihydrofuro[2,3-b]-pyridine-5-carboxamide (Example 79, 0.593 g) was suspended in a mixture of triethylamine (15 mL) and DMF (3 mL). CuI (0.086 g), Pd(PPh$_3$)$_2$C]$_2$ (0.053 g), and then 4-pentyn-1-ol (0.20 mL) were added. The reaction mixture was stirred at room temperature for 18 h and was then partitioned between $CH_2Cl_2$ (50 mL) and water (50 mL). The aqueous layer was separated and was extracted with ($CH_2Cl_2$ (3×50 mL). The combined organic layers were washed with a sat. aq. ammonium chloride solution (50 mL), dried (MgSO$_4$), filtered, and concentrated in vacuo. The resulting solid was purified by column chromatography ($CH_2Cl_2$/methanol; 99/1, 98/2) followed by recrystallization from ethyl acetate to yield 0.161 g of the title compound as a pale yellow solid. Physical characteristics. M.p. 215–219° C. (dec); $^1$H NMR (400 MHz, DMSO-$d_6$) δ 10.51, 8.59, 7.41–7.32, 7.21, 4.60, 4.55, 3.92, 3.52–3.48, 2.58, 1.74–1.67; MS (ESI+) m/z 399 (M+H)$^+$.

EXAMPLE 85

N-(4-Chlorobenzyl)-2-(5-hydroxypentyl)-7-methyl-4-oxo-4,7-dihydrofuro[2,3-b]pyridine-5-carboxamide

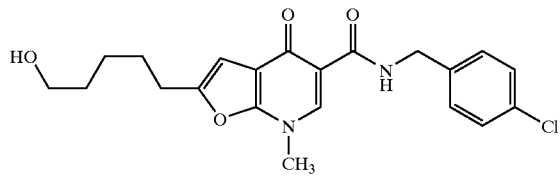

N-(4-Chlorobenzyl)-2-(5-hydroxypent-1-ynyl)-7-methyl-4-oxo-4,7-dihydrofuro[2,3-b]pyridine-5-carboxamide (Example 84, 0.125 g) was dissolved in ethanol (40 mL) with heating and then allowed to cool to room temperature. The mixture was hydrogenated over 10% Pd/C (0.038 g) at 35 psi for 2 h. The reaction mixture was filtered through a Celite pad and the pad was washed with $CH_2Cl_2$ (75 mL). The filtrate was concentrated in vacuo and then resubjected to the reaction conditions for 1 h. The resulting solid was purified by column chromatography ($CH_2Cl_2$/methanol, 98/2) followed by recrystallization from ethyl acetate to yield 0.061 g of the title compound as a white solid. Physical characteristics. M.p. 151–152° C.; $^1H$ NMR (400 MHz, DMSO-$d_6$) δ 10.69, 8.51, 7.41–7.32, 6.67, 4.54, 4.37, 3.92, 3.41–3.37, 2.73, 1.68–1.63, 1.49–1.42, 1.40–1.33; MS (ESI+) m/z 403 (M+H)$^+$.

EXAMPLE 86

N-(4-chlorobenzyl)-2-(3-hydroxy-3-phenylprop-1-ynyl)-7-methyl-4-oxo-4,7-dihydrofuro[2,3-b]pyridine-5-carboxamide.

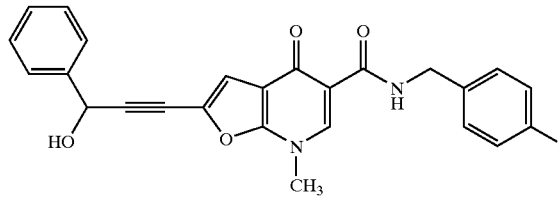

2-Bromo-N-(4-chlorobenzyl)-7-methyl-4-oxo-4,7-dihydrofuro[2,3-b]-pyridine-5-carboxamide (Example 79, 0.593 g) was suspended in a mixture of triethylamine (15 mL) and DMF (3 mL). CuI (0.029 g), Pd(PPh$_3$)$_2$Cl$_2$ (0.105 g), and then 1-phenyl-2-propyn-1-ol (0.36 mL) were added. The reaction mixture was stirred at room temperature for 30 min and then was partitioned between $CH_2Cl_2$ (50 mL) and water (50 mL). The aqueous layer was separated and then extracted with $CH_2Cl_2$ (3×50 mL). The combined organic layers were washed with a sat. aq. ammonium chloride solution (100 mL), dried (MgSO$_4$), filtered, and concentrated in vacuo. The resulting solid was purified by column chromatography ($CH_2Cl_2$/methanol; 99/1, 98/2) followed by recrystallization from methanol to yield 0.260 g of the title compound as a yellow solid. Physical characteristics. M.p. 209–211° C. (dec); $^1H$ NMR (400 MHz, DMSO-$d_6$) δ 10.48, 8.60, 7.53–7.51, 7.43–7.32, 6.43, 5.73, 4.55, 3.91; MS (ESI+) m/z 447 (M+H)$^+$.

EXAMPLE 87

N-(4-Chlorobenzyl)-2-(3-hydroxy-3-phenylpropyl)-7-methyl-4-oxo-4,7-dihydrofuro[2,3-bipyridine-5-carboxamide.

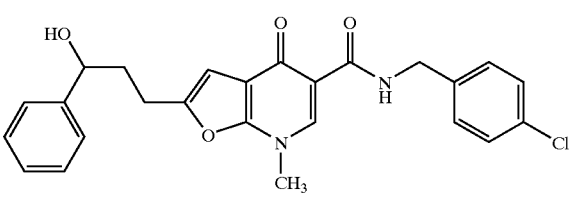

N-(4-Chlorobenzyl)-2-(3-hydroxy-3-phenylprop-1-ynyl)-7-methyl-4-oxo-4,7-dihydrofuro[2,3-b]pyridine-5-carboxamide (Example 86, 0.200 g) was dissolved in ethanol (60 mL) with heating and then allowed to cool to room temperature. The mixture was hydrogenated over 10% Pd/C (0.060 g) at 35 psi for 2 h. The reaction mixture was filtered through a Celite pad and the pad was washed with $CH_2Cl_2$ (50 mL). The filtrate was concentrated in vacuo. The resulting solid was purified by column chromatography ($CH_2Cl_2$/methanol; 99/1, 98/2) to yield 0.039 g of the title compound as a pale yellow solid. Physical characteristics. $^1H$ NMR (400 MHz, DMSO-$d_6$) δ 10.68, 8.51,7,40–7.30, 6.68, 5.39, 4.64–4.59, 4.54, 3.91, 2.81–2.76, 2.00–1.94; MS (ESI+) m/z 451 (M+H)$^+$.

EXAMPLE 88

N-(4-Chlorobenzyl)-2-(4-hydroxy-4-phenylbut-1-ynyl)-7-methyl-4-oxo-4,7-dihydrofuro[2,3-b]pyridine-5-carboxamide.

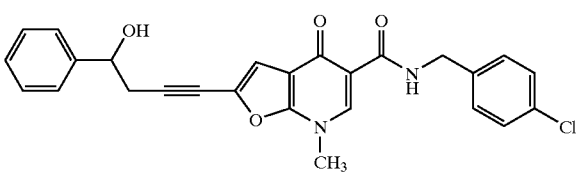

2-Bromo-N-(4-chlorobenzyl)-7-methyl-4-oxo-4,7-dlhydrofuro[2,3-b]-pyridine-5-carboxamide (Example 79, 0.593 g) was suspended in a mixture of triethylamine (15 mL) and DMF (3 mL). CuI (0.029 g), Pd(PPh$_3$)$_2$Cl$_2$ (0.105 g), and then 1-phenyl-3-butyn-1-ol (0.36 mL) were added. The reaction mixture was stirred at room temperature for 20 min and then was partitioned between $CH_2Cl_2$ (50 mL) and water (50 mL). The aqueous layer was separated and extracted with $CH_2Cl_2$ (3×50 mL). The combined organic layers were washed with a sat. aq. ammonium chloride solution (100 mL), dried (MgSO$_4$), filtered and concentrated in vacuo. The resulting solid was purified by column chromatography ($CH_2Cl_2$/methanol; 99/1, 98/2) followed by recrystallization from methanol to yield 0.275 g of the title compound as a yellow solid. Physical characteristics. M.p. 202–203° C. (dec); $^1H$ NMR (400 MHz, DMSO-$d_6$) δ 10.50, 8.58, 7.44–7.25, 7.15, 5.73, 4.85–4.81, 4.55, 3.91, 2.89; MS (ESI+) m/z 461 (M+H)$^+$.

EXAMPLE 89

N-(4-Chlorobenzyl)-2-(4-hydroxy-4-phenylbutyl)-7-methyl-4-oxo-4,7-dihydrofuro[2,3-b]pyridine-5-carboxamide

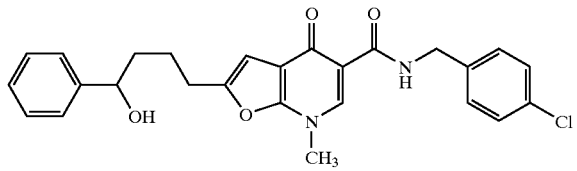

N-(4-Chlorobenzyl)-2-(4-hydroxy-4-phenylbut-1-ynyl)-7-methyl-4-oxo-4,7-dihydrofuro[2,3-b]pyridine-5-carboxamide (Example 88, 0.200 g) was dissolved in ethanol (60 mL) with heating and then allowed to cool to room temperature. The mixture was hydrogenated over 10% Pd/C (0.060 g) at 35 psi for 1.5 h. The reaction mixture was filtered through a Celite pad and the pad was washed with $CH_2Cl_2$ (60 mL). The filtrate was concentrated in vacuo. The resulting solid was purified by column chromatography ($CH_2Cl_2$/methanol; 99/1, 98/2) followed by recrystallization from ethyl acetate to yield 0.008 g of the title compound as a yellow solid. Physical characteristics. $^1$H NMR (400 MHz, DMSO-$d_6$) δ 10.68, 8.51, 7.40–7.30, 6.64, 5.20, 4.58 4.53, 4.54, 3.90, 2.75–2.72, 1.76–1.64; MS (ESI+) m/z 465 (M+H)$^+$.

Preparation 74. 1(2-Furyl)but-3-yn-1-ol.

Magnesium (0.333 g) was added to a flame-dried flask under nitrogen. Diethyl ether (6 mL) was added followed by a crystal of iodine and $HgCl_2$ (4.31 mg). Proparyl bromide (80% wt. in toluene, 1.39 mL) in diethyl ether (2 mL) was then added dropwise. The reaction mixture was stirred at room temperature for 1 h and then cooled to 0° C. 2-Furaldehyde (0.83 mL) in THF (5 mL) was added. The reaction was allowed to warm to room temperature and was stirred for 2 h. The reaction mixture was poured into a cold saturated aq. ammonium chloride solution (25 mL). The aqueous layer was separated and extracted with diethyl ether (4×10 mL). The combined organic layers were washed with a saturated aq. ammonium chloride solution (25 mL) and brine (25 mL), dried ($MgSO_4$), filtered, and concentrated in vacuo. The resulting oil was purified by column chromatography ($CH_2Cl_2$/heptane, 1/1) to yield 0.547 g of the title compound as a yellow oil. Physical characteristics. $^1$H NMR (400 MHz, $CDCl_3$) δ 7.40–7.39, 6.35, 4.89, 2.79–2.77, 2.09–2.07.

EXAMPLE 90

N-(4-Chlorobenzyl)-2-(4-(2-furyl)-4-hydroxybut-1-ynyl)-7-methyl-4-oxo-4,7-dihydrofuro[2,3-b]pyridine-5-carboxamide.

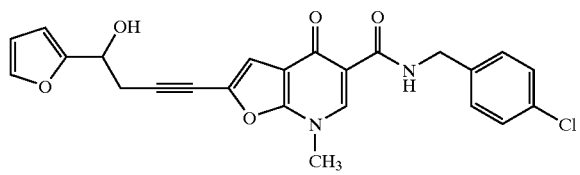

Analogous to the procedures described in Example 88, 2-bromo-N-(4-chlorobenzyl)-7-methyl-4-oxo-4,7-dihydrofuro[2,3-b]pyridine-5-carboxamide (Example 79) is treated with 1-(2-furyl)but-3-yn-1-ol (Preparation 74) to afford the title compound.

EXAMPLE 91

N-(4-Chlorobenzyl)-2-(4-(2-furyl)-4-hydroxybutyl)-7-methyl-4-oxo-4,7-dihydrofuro[2,3-b]pyridine-5-carboxamide.

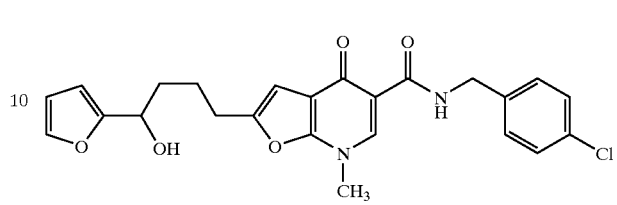

Analogous to the procedures described in Example 89, hydrogenation of N-(4-chlorobenzyl)-2-(4-(2-furyl)-4-hydroxybut-1-ynyl)-7-methyl-4-oxo-4,7-dihydrofuro[2,3-b]pyridine-5-carboxamide (Example 90) affords the title compound.

Preparation 75. 1-(Pyridin-3-yl)but-3-yn-1-ol.

Magnesium (0.666 g) was added to a flame-dried flask under nitrogen. Diethyl ether (12 mL) was added followed by a crystal of iodine and $HgCl_2$ (9 mg). Proparyl bromide (80% wt. in toluene, 2.77 mL) in diethyl ether (4 mL) was then added dropwise. The reaction mixture was stirred at room temperature for 1 h and then cooled to 0° C. 3-Pyridine carboxaldehyde (1.89 mL) in THF (10 mL) was added. The reaction was allowed to warm to room temperature, and an additional 20 mL of THF was added. After 2 b, the reaction mixture was poured into a cold saturated aq. ammonium chloride solution (50 mL). The aqueous layer was separated and extracted with diethyl ether (4×25 mL). The combined organic layers were washed with a saturated aq. ammonium chloride solution (50 mL) and brine (50 mL), dried ($MgSO_4$), filtered, and concentrated in vacuo. The resulting oil was purified by column chromatography ($CH_2Cl_2$/methanol; 9911, 9812) to yield 0.912 g of the title compound as an orange oil. Physical characteristics. $^1$H NMR (400 MHz, DMSO-$d_6$) δ 8.58–8.57, 8.48–8.45, 7.80–7.76, 7.41–7.34, 5.70, 4.78 4.73, 2.77–2.75, 2.60–2.53.

EXAMPLE 92

N-(4-Chlorobenzyl)-2-(4-hydroxy-4-pyridin-3-ylbut-1-ynyl)-7-methyl-4-oxo-4,7-dihydrofuro[2,3-b]pyridine-5-carboxamide.

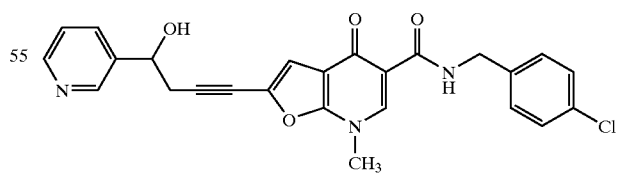

Analogous to the procedures described in Example 88, 2-bromo-N-(4-chlorobenzyl)-7-methyl-4-oxo-4,7-dihydrofuro[2,3-b]pyridine-5-carboxamide (Example 79) is treated with 1-(pyridin-3-yl)but-3-yn-1-ol (Preparation 75) to afford the title compound.

EXAMPLE 93

N-(4-Chlorobenzyl)-2-(4-hydroxy-4-pyridin-3-ylbutyl)-7-methyl-4-oxo-4,7-dihydrofuro[2,3-b]pyridine-5-carboxamide.

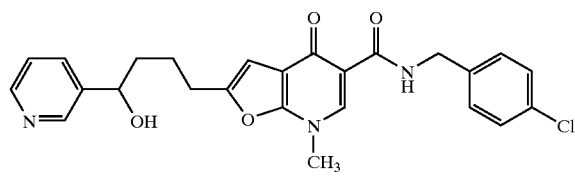

Analogous to the procedures described in Example 89, hydrogenation of N-(4-chlorobenzyl)-2-(4-hydroxy-4-pyridin-3-ylbut-1-ynyl)-7-methyl-4-oxo-4,7-dihydrofuro[2,3-b]pyridine-5-carboxamide (Example 92) affords the title compound.

Preparation 76. 1-(Pyridin-2-yl)but-3-yn-1-ol.

Magnesium (0.681 g) was added to a flame-dried flask under nitrogen. Diethyl ether (12 mL) was added followed by a crystal of iodine and $HgCl_2$ (9 mg). Proparyl bromide (80% wt. in xylene, 2.89 mL) in diethyl ether (4 mL) was then added dropwise. The reaction mixture was stirred at room temperature for 1 h and then cooled to 0° C. 2-Pyridine carboxaldehyde (1.91 mL) in THF (10 mL) was added. The reaction was allowed to warm to room temperature, and an additional 10 mL of THF was added. The reaction mixture was stirred at to room temperature for 2 h and was then poured into a cold saturated aq. ammonium chloride solution (50 mL). The aqueous layer was separated and extracted with diethyl ether (4×25 mL). The combined organic layers were washed with a saturated aq. ammonium chloride solution (50 mL) and a brine. (50 mL), dried ($MgSO_4$), filtered, and concentrated in vacuo. The resulting oil was purified by column chromatography ($CH_2Cl_2$/methanol, 99/1) to yield 1.763 g of the title compound as a brown oil. Physical characteristics. $^1H$ NMR (400 MHz, DMSO-$d_6$) δ 8.51–8.48, 7.81–7.77, 7.56–7.50, 7.30–7.25, 5.71, 4.74 4.70, 2.75–2.67, 2.58–2.52; MS (ESI+) m/z 148 (M+H)$^+$.

EXAMPLE 94

N-(4-Chlorobenzyl)-2-(4-hydroxy-4-pyridin-2-ylbut-1-ynyl)-7-methyl-4-oxo-4,7-dihydrofuro[2,3-b]pyridine-5-carboxamide.

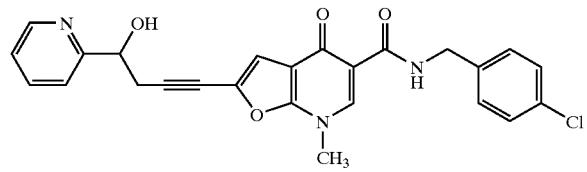

Analogous to the procedures described in Example 88, 2-bromo-N-(4-chlorobenzyl)-7-methyl-4-oxo-4,7-dihydrofuro[2,3-b]pyridine-5-carboxamide (Example 79) is treated with 1-(pyridin-2-yl)but-3-yn-1-ol (Preparation 76) to afford the title compound.

EXAMPLE 95

N-(4-Chlorobenzyl)-24-hydroxy-4-pyridin-2-ylbutyl)-7-methyl-4-oxo-4,7-dihydrofuro[2,3-b]pyridine-5-carboxamide.

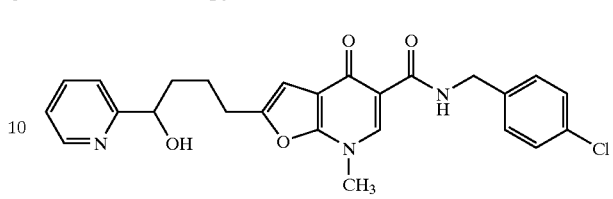

Analogous to the procedures described in Example 89, hydrogenation of N-(4-Chlorobenzyl)-2-(4-hydroxy-4-pyridin-2-ylbut-1-ynyl)-7-methyl-4-oxo-4,7-dihydrofuro[2,3-b]pyridine-5-carboxamide (Example 94) affords the title compound.

EXAMPLE 96

N-(4-Chlorobenzyl)-2-ethoxymethyl)-7-methyl-4-oxo-4,7-dihydrofuro[2,3-b]pyridine-5-carboxamide

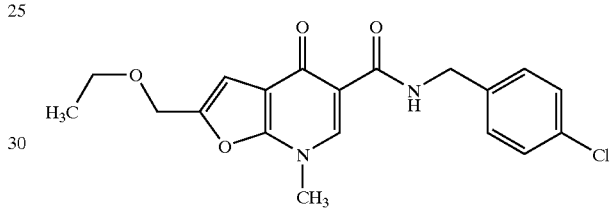

N-(4-Chlorobenzyl)-2-(chloromethyl)-7-methyl-4-oxo-4,7-dihydrofuro[2,3-b]pyridine-5-carboxamide (Example 2, 1.83 g) was suspended in hot ethanol (200 mL) at 60° C. A solution of potassium hydroxide (0.32 g) in aq. ethanol (95%, 25 mL) was added. The mixture was allowed to cool to room temperature and stir for 18 h. The reaction mixture was partially concentrated and diluted with water (100 mL). The resulting precipitate was filtered, washed with water followed by diethyl ether, and recrystallized from acetonitrile to afford 0.555 g of the title compound as a light yellow solid. Physical characteristics. M.p. 211–212° C.; $^1H$ NMR (300 MHz, DMSO-$d_6$) δ 10.60, 8.57, 7.41–7.32, 7.01, 4.54, 4.51, 3.94, 3.51, 1.14; MS (EI) m/z 374 (M+).

EXAMPLE 97

N-(4-Chlorobenzyl)-2-(hydroxymethyl)-7-methyl-4-oxo-4,7-dihydrofuro[2,3-b]pyridine-5-carboxamide.

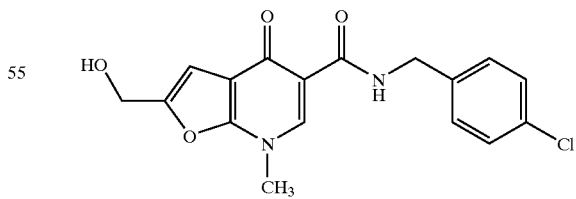

A solution of 2 N aq. sodium hydroxide (2.5 mL) was added to a solution of N-(4-chlorobenzyl)-2-(chloromethyl)-7-methyl-4-oxo-4,7-dihydrofuro[2,3-b]-pyridine-5-carboxamide (Example 2, 1.83 g) in DMF (40 mL). The mixture was heated and a sat. aq. sodium bicarbonate solution (10 mL) was added. The reaction mixture was allowed to cool to room temperature, was poured into water, and extracted with EtOAc (3×100 mL). The combined organic layers were concentrated. The crude product was purified by column chromatography (CH$_2$Cl$_2$/methanol, 100/1; 50/1; 20/1; 15/1) to afford 0.258 g of the title compound as a yellow solid. Physical characteristics. M.p. 229–230° C.; $^1$H NMR (300 MHz, DMSO-d$_6$) δ 10.63, 8.56, 7.42–7.32, 6.85, 5.53, 4.54, 4.51, 3.94; MS (EI) m/z 346 (M+).

EXAMPLE 98

N(4-Chlorobenzyl)-2-((((2S)-2-hydroxy-2-phenylethyl)oxy)methyl)-7-methyl-4-oxo-4,7-dihydrofuro[2,3-b]pyridine-5-carboxamide.

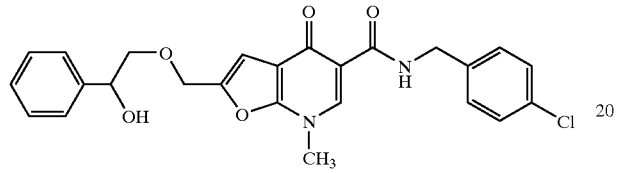

A mixture of (S)-1-phenyl-1,2-ethanediol (91 mg) and dibutyl tinoxide (164 mg) in toluene (3 mL) was refluxed for 3 h with azeotropic removal of water. The solvent was removed in vacuo and the resulting solid dried (0.1 Torr, 2 h). Cesium fluoride (190 mg) was added followed N4-chlorobenzyl)-2-(chloromethyl)-7-methyl-4-oxo-4,7-dihydrofuro[2,3-b]pyridine-5-carboxamide (Example 2,400 mg) and DMF (5 mL). The mixture was stirred at room temperature for 20 h. The reaction mixture was poured into water (25 mL) and extracted with CH$_2$Cl$_2$ (3×50 mL). The combined organic layers were concentrated. The crude product was purified by column chromatography (CH$_2$Cl$_2$/methanol, 100/1; 50/1; 25/1) and then crystallized from EtOAc/hexane to afford the title compound. Physical characteristics. $^1$H NMR (400 MHz, DMSO-d$_6$) δ 10.60, 8.57, 7.41–7.21, 7.01, 5.42, 4.73, 4.58, 4.54, 3.92, 3.58–3.50.

EXAMPLE 99

N-((4-Chlorophenyl)methyl)-5-((4-chlorophenyl)methylaminocarbonyl)-4-hydroxyfuro[2,3-b]pyridine-2-carboxamide.

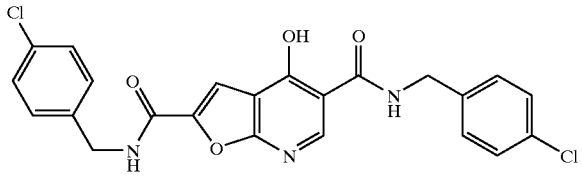

A mixture of furopyridine-2-carboxylic acid methyl ester (Bhupathy, M., et al., *J. Heterocyclic Chem.* 1995, 32, 1283) (0.305 g) and 4-chlorobenzylamine (1.40 mL) were stirred at 190° C. for 1 h. The mixture was then allowed to cool to room temperature and was then diluted with toluene. The resulting precipitate was filtered and washed with toluene followed by hexanes. The crude product was recrystallized (acetic acid/water) and purified by column chromatography (CH$_2$Cl$_2$/methanol, 9/1). The resulting solid was triturated with diethyl ether to yield 0.100 g of the title compound as a white solid. Physical characteristics. M.p. 230–245° C.; $^1$H NMR (300 MHz, DMSO-d$_6$) δ 10.43, 9.20, 8.66, 7.95, 7.52–7.33, 4.52, 4.44; $^{13}$C NMR (75 MHz, CF$_3$CO$_2$D) δ 184.5, 179.3, 170.9, 167.7, 160.5, 151.9, 147.3, 147.2, 146.3, 146.0, 141.5, 129.5, 128.2, 126.1, 125.8, 124.4, 122.8, 122.7, 122.0, 56.4, 56.2; HRMS (FAB) m/z 470.0684 (M+H)$^+$.

All cited publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

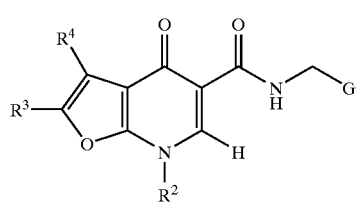

wherein:

G is phenyl substituted with from one to five R$^1$ substituents;

each R$^1$ is independently
(a) Cl,
(b) Br,
(c) F,
(d) cyano,
(e) C$_{1-7}$alkyl, optionally substituted by fluoro, or
(f) NO$_2$;

R$^2$ is
(a) H,
(b) R$^5$,
(c) NR$^7$RS
(d) SO$_2$R$^9$, or
(e) OR$^6$;

R$^3$ is
(a) H,
(b) halo,
(c) aryl,
(d) S(O)$_m$R$^6$,
(e) (C=O)R$^6$,
(f) (C=O)OH
(g) (C=O)OR$^9$,
(h) cyano,
(i) het, wherein the het is bound via a carbon atom,
(j) OR$^{12}$,
(k) NR$^7$R$^8$
(l) SR
(m) C$_{1-7}$alkyl which is optionally partially unsaturated and optionally substituted by the group W-A or one or more R$^{10}$ substituents, or
(n) C$_{3-8}$cycloalkyl which is optionally partially unsaturated and optionally substituted by one or more R$^{10}$, or substituted by one or more C$_{1-7}$alkyl which C$_{1-7}$alkyl is optionally substituted by one or more R$^{10}$;

W is
(a) het,
(b) aryl, or
(c) C$_{3-8}$cycloalkyl, optionally substituted by OR$^{11}$ or oxo (C=O);

A is C$_{1-7}$alkyl substituted by one or more R$^{10}$;

$R^4$ is
- (a) H,
- (b) halo, or
- (c) $C_{1-7}$alkyl optionally substituted by halo;

$R^5$ is
- (a) $(CH_2CH_2O)_iR^{11}$,
- (b) het, wherein the het is bound via a carbon atom,
- (c) aryl,
- (d) $C_{1-7}$alkyl which is optionally partially unsaturated and is optionally substituted by one or more $R^{10}$ substituents, or
- (e) $C_{3-8}$cycloalkyl which is optionally partially unsaturated and is optionally substituted by one or more $R^{10}$ or $C_{1-7}$alkyl substituents which $C_{1-7}$alkyl are optionally substituted by $R^{10}$;

$R^6$ is
- (a) $C_{1-7}$alkyl optionally substituted by aryl, het, $OR^{11}$, $SR^{11}$, $NR^{11}R^{11}$, halo, or $C_{3-8}$cycloalkyl which $C_{3-8}$cycloalkyl is optionally substituted by $OR^{11}$,
- (b) $C_{3-8}$cycloalkyl which is optionally partially unsaturated and is optionally substituted by one or more halo, $OR^{11}$, $SR^{11}$, or $NR^{11}R^{11}$ substituents,
- (c) $NR^7R^8$,
- (d) aryl, or
- (e) het, wherein the het is bound via a carbon atom;

$R^7$ and $R^8$ are independently
- (a) H,
- (b) aryl,
- (c) $C_{1-7}$alkyl which is optionally partially unsaturated and is optionally substituted by one or more $NR^{11}R^{11}$, $OR^{12}$, $SR^{12}$, $S(O)_mR^9$, $P(=O)(OR^{12})(R^{12})$, $CONR^{11}R^{11}$, $CO_2R^{11}$, $(C=O)R^9$, het, aryl, cyano, or halo substituents,
- (d) $C_{3-8}$cycloalkyl which is optionally partially unsaturated and is optionally substituted by one or more halo, $OR^{11}$, $SR^{11}$, oxo, or $NR^{11}R^{11}$ substituents,
- (e) $(C=O)R^9$,
- (f) $SO_2R^9$, or
- (g) $R^7$ and $R^8$ together with the nitrogen to which they are attached form a het;

$R^9$ is
- (a) aryl,
- (b) het;
- (c) $C_{3-8}$cycloalkyl, or
- (d) $C_{1-7}$alkyl which is optionally partially unsaturated and is optionally substituted by one or more $NR^{11}R^{11}$, $OR^{12}$, $SR^{12}$, halo, $CONR^{11}R^{11}$, $CO_2R^{11}$, het, or aryl substituents;

$R^{10}$ is
- (a) $OR^{11}$,
- (b) $SR^{12}$,
- (c) $NR^7R^8$,
- (d) halo,
- (e) $CONH_2$,
- (f) $CONHR^9$,
- (g) $CONR^9R^9$,
- (h) $CO_2H$,
- (i) $CO_2R^9$,
- (j) het, wherein the het is bound via a carbon atom,
- (k) aryl,
- (l) cyano,
- (m) nitro,
- (n) oxo,
- (o) $SO_mR^6$, or
- (p) $P(=O)(OR^{12})(R^{12})$;

$R^{11}$ is
- (a) H, or
- (b) $C_{1-7}$alkyl;

$R^{12}$ is
- (a) H,
- (b) aryl,
- (c) het, wherein the het is bound through a carbon atom,
- (d) $C_{1-7}$alkyl which is optionally partially unsaturated and is optionally substituted by one or more aryl, het, $OR^{11}$, $SR^{11}$, $NR^{11}R^{11}$, halo, or $C_{3-8}$cycloalkyl substituents and which $C_{3-8}$cycloalkyl is optionally substituted by $OR^{11}$, or
- (e) $C_{3-8}$cycloalkyl which is optionally partially unsaturated and is optionally substituted by one or more halo, $OR^{11}$, $SR^{11}$, or $NR^{11}R^{11}$ substituents, $R^{13}$ is
- (a) H,
- (b) halo,
- (c) $OR^{14}$,
- (d) $SR^{11}$,
- (e) $NR^{11}R^{11}$,
- (f) phenyl, optionally substituted by halo, $C_{1-7}$alkyl, or $C_{1-7}$alkoxy,
- (g) cyano,
- (h) nitro,
- (i) $CONR^{11}R^{11}$,
- (j) $CO_2R^{11}$,
- (k) $S(O)_mNR^{11}R^{11}$,
- (l) $NR^{11}—C(=O)—R^{11}$,
- (m) $C_{1-7}$alkyl which is optionally partially unsaturated and is optionally substituted by one or more $R^{15}$, or
- (n) $C_{3-8}$cycloalkyl which is optionally partially unsaturated and is optionally substituted by one or more oxo, halo, $OR^{11}$, $SR^{11}$, $C_{1-7}$alkyl, or $NR^{11}R^{11}$ substituents, $R^{14}$ is
- (a) H
- (b) $C_{1-4}$alkyl, optionally substituted by fluoro,
- (c) phenyl, optionally substituted by halo, $C_{1-7}$alkyl, or $C_{1-7}$alkoxy, or
- (d) $—(CH_2CH_2O)_mR^{11}$;

$R^5$ is
- (a) phenyl, optionally substituted by halo, $C_{1-7}$alkyl, or $C_{1-7}$alkoxy,
- (b) $C_{3-8}$cycloalkyl, optionally substituted by $OR^{11}$
- (c) $OR'''$,
- (d) $SR^{11}$,
- (e) $NR^{11}R^1$,
- (f) 4-morpholine,
- (g) $CO_2R^{11}$,
- (h) $CONR^{11}R^{11}$,
- (i) oxo,
- (j) halo;

each i is independently 2, 3, or 4;
each n is independently 1, 2, 3, 4 or 5;
each m is independently 1 or 2;
wherein any aryl other than G is optionally substituted with one or more $R^{13}$ substituents and any two adjacent $R^{13}$ substituents taken together constitute a group of the formula $(CH_2)_mO—$; and
wherein any het is optionally substituted with one or more oxo $(=O)$, oxime $(=N—OR^{11})$, or $R^{13}$ substituents; or
a pharmaceutically acceptable salt thereof.

2. The compound of claim 1 wherein $R^1$ is F, Cl, or cyano.
3. The compound of claim 1 wherein $R^1$ is Cl.
4. The compound of claim 1 wherein $R^1$ is F.

5. The compound of claim 1 wherein $R^1$ is $C_{1-7}$alkyl.

6. The compound of claim 1 wherein G is phenyl substituted with one, two, or three $R^1$ groups.

7. The compound of claim 1 wherein G is 4-chlorophenyl, 4-fluorophenyl, 3,4-dichlorophenyl, 3,4-difluorophenyl, 2,4-dichlorophenyl, 2,4-difluorophenyl, 4-chloro-2-fluorophenyl, 2-chloro-4-fluorophenyl, 3,4,5-trifluorophenyl, 4-bromophenyl, 4-methylphenyl, 4-cyanophenyl, 4-nitrophenyl, 4-trifluorophenyl, or 4-chloro-2-methylphenyl.

8. The compound of claim 1 wherein G is 4-chlorophenyl.

9. The compound of claim 1 wherein G is 4-fluorophenyl.

10. The compound of claim 1 wherein $R^2$ is $C_{1-7}$alkyl which is optionally partially unsaturated and is optionally substituted with one or more $R^{10}$ substituents.

11. The compound of claim 1 wherein $R^2$ is methyl.

12. The compound of claim 1 wherein $R^2$ is ethyl or cyclopropyl.

13. The compound of claim 1 wherein $R^2$ is $R^5$.

14. The compound of claim 1 wherein $R^3$ is $C_{1-7}$alkyl which is optionally partially unsaturated and optionally substituted by the group W-A or one or more $R^{10}$ substituents.

15. The compound of claim 1 wherein $R^3$ is $C_{1-7}$alkyl substituted by either an aryl or a het substituent, and one or more $OR^{11}$ substituents.

16. The compound of claim 1 wherein $R^3$ is $CH_2OR^{12}$ wherein $R^{12}$ is $C_{1-7}$alkyl substituted by either an aryl or a het substituent, and one or more $OR^{11}$ substituents.

17. The compound of claim 1 wherein $R^3$ is $CH_2NR^7R^8$.

18. The compound of claim 17 wherein $R^7$ is $C_{1-7}$alkyl, and $R^8$ is $C_{1-7}$alkyl which is optionally partially unsaturated and is optionally substituted by one or more $NR^{11}R^{11}$, $OR^{12}$, $SR^{12}$, $S(O)_mR^9$, $P(=O)(OR^{12})(R^{12})$, $CONR^{11}R^{11}$, $CO_2R^{11}$, $(C=O)R^9$, het, aryl, cyano, or halo substituents.

19. The compound of claim 17 wherein $R^7$ is methyl, and $R^8$ is $C_{1-7}$alkyl substituted with aryl or het, and one or more $OR^{12}$ substituents.

20. The compound of claim 17 wherein $R^7$ is methyl, and $R^8$ is $C_{1-7}$alkyl substituted with $SR^{12}$, and one or more $OR^{12}$ substituents.

21. The compound of claim 1 wherein $R^3$ is $C_{1-7}$alkyl substituted by the group W-A.

22. The compound of claim 21 wherein A is $C_{1-4}$alkyl substituted by either an aryl or a het substituent, and one or more $OR^{11}$ substituents.

23. The compound of claim 21 or claim 22 wherein W is morpholine.

24. The compound of claim 21 or claim 22 wherein W is pyrrolidine.

25. The compound of claim 1 wherein $R^4$ is H.

26. The compound of claim 1 wherein G is 4-chlorophenyl; $R^3$ is $CH_2N(CH_3)CH_2CH(OH)$aryl or $CH_2N(CH_3)CH_2CH(OH)$het; $R^2$ is methyl; and $R^4$ is H.

27. A compound of formula II:

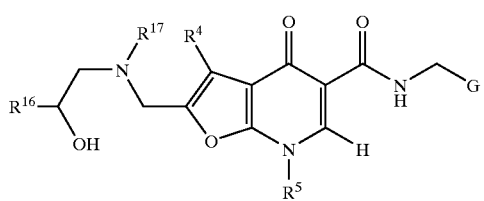

II wherein

G is phenyl substituted with from one to five $R^1$ substituents;

$R^4$ is
(a) H,
(b) halo, or
(c) $C_{1-7}$alkyl optionally substituted by halo;

$R^5$ is
(a) $(CH_2CH_2O)_iR^{11}$,
(b) het, wherein the het is bound via a carbon atom,
(c) aryl,
(d) $C_{1-7}$alkyl which is optionally partially unsaturated and is optionally substituted by one or more $R^{10}$ substituents, or
(e) $C_{3-8}$cycloalkyl which is optionally partially unsaturated and is optionally substituted by one or more $R^{10}$ or $C_{1-7}$alkyl substituents which $C_{1-7}$alkyl are optionally substituted by $R^{10}$;

$R^{16}$ is
(a) aryl, or
(b) het; and $R^{17}$ is
(a) H,
(b) aryl,
(c) $C_{1-7}$alkyl which is optionally partially unsaturated and is optionally substituted by one or more $NR^{11}R^{11}$, $OR^{12}$, or $SR^{12}$, $S(O)_mR^9$, $CONR^{12}R^{12}$, $CO_2R^{11}$, $(C=O)R^9$, het, aryl, cyano, or halo substituents,
(d) $C_{3-8}$cycloalkyl which is optionally partially unsaturated and is optionally substituted by one or more halo, $OR^{11}$, $SR^{11}$, oxo, or $NR^{11}R^{11}$ substituents,
(e) $(C=O)R^9$, or
(f) $SO_2R^9$;

or a pharmaceutically acceptable salt thereof.

28. The compound of claim 27 wherein $R^{16}$ is aryl.

29. The compound of claim 27 wherein $R^{16}$ is phenyl, optionally substituted by one or more $R^{13}$.

30. The compound of claim 27 wherein $R^{16}$ is phenyl.

31. The compound of claim 27 wherein $R^{16}$ is naphthyl, optionally substituted by one or more $R^{13}$.

32. A compound of claim 27 wherein $R^{16}$ is quinolyl, isoquinolyl, or benzofuranyl, optionally substituted with one or more $R^{13}$.

33. The compound of claim 27 wherein $R^{16}$ is 4-hydroxyphenyl, 4-chlorophenyl, 4-fluorophenyl, 4-bromophenyl, 4-methylphenyl, 4-trifluoromethylphenyl, 3-chlorophenyl, 3-fluorophenyl, 3-bromophenyl, 3-methylphenyl, 3-methoxyphenyl, 3-trifluoromethylphenyl, 3-cyanophenyl, 2-chlorophenyl, 2-fluorophenyl, 2-bromophenyl, 2-methylphenyl, 2-methoxyphenyl, 2-trifluoromethylphenyl, 4-(hydroxymethyl)phenyl, 4-(N,N-dimethylaminomethyl) phenyl, 2,3,4,5,6-pentafluorophenyl, 2,4,6-trifluorophenyl.

34. The compound of claim 27 wherein $R^{16}$ is 1-naphthyl or 2-naphthyl.

35. The compound of claim 27 wherein $R^{16}$ is het.

36. The compound of claim 27 wherein $R^{16}$ is heteroaryl.

37. The compound of claim 27 wherein $R^{16}$ is a five-membered heteroaryl.

38. The compound of claim 27 wherein $R^{16}$ is a five-membered heteroaryl that is fused to a benzene or pyridine ring.

39. The compound of claim 27 wherein $R^{16}$ is a six-membered heteroaryl having one (1) or two (2) nitrogen atoms.

40. The compound of claim 27 wherein $R^{16}$ is a six-membered heteroaryl having one (1) or two (2) nitrogen atoms that is fused to a benzene ring.

41. The compound of claim 27 wherein $R^{16}$ is 2-furyl, 3-furyl, 5-methyl-2-furyl, 4,5-dimethyl-2-furyl, 5-phenyl-2- furyl, 5-(hydroxymethyl)-2-furyl, 2,5-dimethyl-3-furyl, thien-2-yl, thien-3-yl, 5-cyanothien-2-yl, 1H-pyrrol-2-yl, 1-methyl-1H-pyrrol-2-yl, 1-methyl-1H-imidazol-4-yl, 1H-imidazol-4-yl, 1,3-thiazol-2-yl, or 1H-pyrazol-5-yl.

42. The compound of claim 27 wherein $R^{16}$ is 2-furyl.

43. The compound of claim 27 wherein $R^{16}$ is 1-benzofuran-2-yl, 1-benzofuran-3-yl, 1,3-benzothiazol-2-yl, 1-benzothien-2-yl, benzothien-3-yl, 1H-indol-3-yl, or 1-methyl-1H-indol-2-yl.

44. The compound of claim 27 wherein $R^{16}$ is pyridin-2-yl, pyridin-3-yl, pyridin-4-yl, 6-methylpyridin-2-yl, pyrimidin-2-yl, or pyrazin-2-yl.

45. The compound of claim 27 wherein $R^{16}$ is pyrimidin-2-yl.

46. The compound of claim 27 wherein $R^{16}$ is pyrazin-2-yl.

47. The compound of claim 27 wherein $R^{16}$ is pyridin-2-yl.

48. The compound of claim 27 wherein $R^{16}$ is 1-quinolin-2-yl.

49. The compound of claim 27 wherein $R^{17}$ is $C_{1-7}$alkyl which is optionally partially unsaturated and is optionally substituted by one or more $NR^{11}R^{11}$, $OR^{12}$, or $SR^{12}$, $S(O)_m R^9$, $CONR^{12}R^{12}$, $CO_2R^{11}$, $(C=O)R^9$, het, aryl, cyano, or halo substituents.

50. The compound of claim 27 wherein $R^{17}$ is methyl.
51. The compound of claim 27 wherein $R^{17}$ is ethyl.
52. The compound of claim 27 wherein $R^{17}$ is aryl.
53. The compound of claim 27 wherein $R^{17}$ is phenyl.
54. The compound of claim 217 wherein $R^4$ is H.
55. The compound of claim 27 wherein $R^4$ is halo.
56. The compound of claim 27 wherein $R^4$ is $C_{1-7}$alkyl optionally substituted by halo.
57. The compound of claim 27 wherein $R^4$ is methyl.
58. The compound of claim 27 wherein $R^5$ is $(CH_2CH_2O)_nR^{11}$ or $C_{1-7}$alkyl which is optionally partially unsaturated and is optionally substituted by one or more $R^{10}$ substituents.
59. The compound of claim 27 wherein $R^5$ is het, wherein the het is bound via a carbon atom.
60. The compound of claim 27 wherein $R^5$ is aryl.
61. The compound of claim 27 wherein $R^5$ is $C_{3-8}$cycloalkyl which is optionally partially unsaturated and is optionally substituted by one or more $R^{10}$ or $C_{1-7}$alkyl substituents which $C_{1-7}$alkyl are optionally substituted by $R^{10}$.
62. The compound of claim 27 wherein $R^5$ is methyl.
63. The compound of claim 27 wherein $R^5$ is ethyl.
64. The compound:
  (a) N-(4-chlorobenzyl)-7-methyl-2-(4-morpholinylmethyl)-4-oxo-4,7-dihydrofluro[2,3-b]pyridine-5-carboxamide; [b]pyridine-5-carboxamide;
  (b) N-(4-chlorobenzyl)-2-(chloromethyl)-7-methyl-4-oxo-4,7-dihydrofuro[2,3-b]pyridine-5-carboxamide;
  (c) N-(4-chlorobenzyl)-2-(((2(2-furyl)-2-hydroxyethyl)(methyl)amino)methyl)-7-methyl-4-oxo-4,7-dihydrofuiro[2,3-b]pyridine-5-carboxamide; methyl)-7-methyl-4-oxo-4,7-dlhydrofuro[2,3-b]pyridine-5-carboxamide;
  (d) (+)-N-(4-chlorobenzyl)-2-(((2-(2-furyl)-2-hydroxyethyl)(methyl)amino)-methyl)-7-methyl-4-oxo-4,7-dihydrofuro[2,3-b]pyridine-5-carboxamide;
  (e) (−)-N-(4-chlorobenzyl)-2-(((2-(2-furyl)-2-hydroxyethyl)(methyl)-amino)methyl)-7-methyl-4-oxo-4,7-dihydrofuro[2,3-b]pyridine-5-carboxamide;
  (f) N-(4-fluorobenzyl)-2-((((2R)-2-(2-furyl)-2-hydroxyethyl)(methyl)amino)-methyl)-7-methyl-4-oxo-4,7-dihydrofuro[2,3-b]pyridine-5-carboxamide;
  (g) 2-((((2R)-2-(2-furyl)-2-hydroxyethyl)(methyl)amino)methyl)-7-methyl-N-(4-methylbenzyl)-4-oxo-4,7-dlhydrofuiro[2,3-b]pyridine-5-carboxamide;
  (3,4-dichlorobenzyl)-4-oxo-4,7-dihydrofluro[2,3-b]pyridine-5-carboxamide;
  (h) 2-((((2R)-2-(2-furyl)-2-hydroxyethyl)(methyl)amino)methyl)-7-methyl-N-(4-methylbenzyl)-4-oxo-4,7-dihydroiuro[2,3-b]pyridine-5-carboxamide;
  (i) 2(((2R)-2-(2-furyl)-2-hydroxyethyl)(methyl)amino)methyl)-7-methyl-N-(3,4-difluorobenzyl)-4-oxo-4,7-dihydrofuro[2,3-b]pyridine-5-carboxamide;
  (j) 2-((((2R)-2-(2-furyl)-2-hydroxyethyl)(methyl)amino)methyl)-7-methyl-N-(4-bromobenzyl)-4-oxo-4,7-dihydrofuro[2,3-b]pyridine-5-carboxamide;
  (k) 2-((((2R)-2-(2-furyl)-2-hydroxyethyl)(methyl)amino)methyl)-7-methyl-N-(4-trifluoromethylbenzyl)-4-oxo-4,7-dihydrofuro[2,3-b]pyridine-5-carboxamide;
  (l) N-(4-chlorobenzyl)-7-ethyl-2-(morpholin-4-ylmethyl)-4-oxo-4,7-dihydrofuro[2,3-b]pyridine-5-carboxamide;
  (m) N-(4-chlorobenzyl)-7-cyclopropyl-2-(morpholin-4-ylmethyl)-4-oxo-4,7-dihydrofuro[2,3-b]pyridine-5-carboxamide;
  (n) N-(4-chlorobenzyl)-7-propyl-2-(morpholin-4-ylmethyl)-4-oxo-4,7-dihydrofuro[2,3-b]pyridine-5-carboxamide;
  (o) N-(4-chlorobenzyl)-2-(morpholin-4-ylmethyl)-4-oxo-7-phenyl-4,7-dihydrofuLro[2,3-b]pyridine-5-carboxamide;
  (p) N-(4-chlorobenzyl)-2-(morpholin-4-ylmethyl)-4-oxo-7-(2-phenylethyl)-4,7-dihydrofuro[2,3-b]pyridine-5-carboxamide;
  (q) N-(4-chlorobenzyl)-2-(morpholin-4-ylmethyl)-4-oxo-7-pyridin-2-yl-4,7-dihydrofuro[2,3-b]pyridine-5-carboxamide;
  (r) N-(4-chlorobenzyl)-7-(2-(diethylamino)ethyl)-2-(morpholin-4-ylmethyl)-4-oxo-4,7-dihydrofuro[2,3-b]pyridine-5-carboxamide;
  (s) N-(4-chlorobenzyl)-2-(chloromethyl)-7-ethyl-4-oxo-4,7-dihydroftro[2,3-b]pyridine-5-carboxamide;
  (t) N-(4-chlorobenzyl)-2-(chloromethyl)-7-cyclopropyl-4-oxo-4,7-dihydrofuro[2,3-b]pyridine-5-carboxamide;
  (u) N-(4-chlorobenzyl)-2-(chloromethyl)-4-oxo-7-propyl-4,7-dihydrofiio[2,3-b]pyridine-5-carboxamide;
  (v) N-(4-chlorobenzyl)-2-(chloromethyl)-4-oxo-7-phenyl-4,7-dihydrofiiro[2,3-b]pyridine-5-carboxamide;
  (w) N-(4-chlorobenzyl)-2-(chloromethyl)-4-oxo-7-(2-phenylethyl)-4,7-dihydrofuro[2,3-b]pyridine-5-carboxamide;
  (x) N-(4-chlorobenzyl)-2-(chloromethyl)-4-oxo-7-pyridin-2-yl-4,7-dihydrofilro[2,3-b]pyridine-5-carboxamide;
  (y) N-(4-chlorobenzyl)-2-(chloromethyl)-7-(2-(diethylamino)ethyl)-4-oxo-4,7-dihydrofuro[2,3-b]pyridine-5-carboxamide;
  (z) N-(4-chlorobenzyl)-7-ethyl-2-((((2R)-2-(2-furyl)-2-hydroxyethyl)(methyl)amino)methyl)-4-oxo-4,7-dihydrofuro[2,3-b]pyridine-5-carboxamide;
  (aa) N-(4-chlorobenzyl)-7-cyclopropyl-2-((((2R)-2-(2-furyl)-2-hydroxyethyl)(methyl)amino)methyl)-4-oxo-4,7-dihydrofuro[2,3-b]pyridine-5-carboxamide;
  (bb) N-(4-chlorobenzyl)-2-((((2R)-2-(2-furyl)-2-hydroxyethyl)(methyl)amino)methyl)-4-oxo-7-propyl-4,7-dihydrofitro[2,3-b]pyridine-5-carboxamide;
  (cc) N4-chlorobenzyl)-2-((((2R)-2-(2-furyl)-2-hydroxyethyl)(methyl)amino)methyl)-4-oxo-7-phenyl-4,7-dihydrofuro[2,3-b]pyridine-5-carboxamide;

(dd) N-(4-chlorobenzyl)-2-((((2R)-2-(2-furyl)-2-hydroxyethyl)(methyl)amino)methyl)-4-oxo-7-(2-phenylethyl)-4,7-dihydrofuro[2,3-b]pyridine-5-carboxamide;

(ee) N-(4-chlorobenzyl)-2-((((2R)-2-(2-furyl)-2-hydroxyethyl)(methyl)amino)methyl)-4-oxo-7-pyridin-2-yl-4,7-dihydrofuro[2,3-b]pyridine-5-carboxamide;

(ff) N-(4-chlorobenzyl)-7-(2-(diethylamino)ethyl)-2-((((2R)-2-(2-furyl)-2-hydroxyethyl)(methyl)amino)methyl)-4-oxo-4,7-dihydrofuro[2,3-b]pyridine-5-carboxamide;

(gg) N-(4-chlorobenzyl)-2-(((2-hydroxypropyl)amino)methyl)-7-methyl-4-oxo-4,7-dihydrofuro[2,3-b]pyridine-5-carboxamide;

(hh) N-(4-chlorobenzyl)-2-(((2-hydroxypropyl)(methyl)amino)methyl)-7-methyl-4-oxo-4,7-dihydrofuro[2,3-b]pyridine-5-carboxamide;

(ii) N-(4-chlorobenzyl)-2-(((3R)-3-hydroxypyrrolidin-1-yl)methyl)-7-methyl-4-oxo-4,7-dihydrofuro[2,3-b]pyridine-5-carboxamide;

(jj) N-(4-chlorobenzyl)-2-(((2-hydroxy-2-phenylethyl)(methyl)amino)methyl)-7-methyl-4-oxo-4,7-dihydrofuro[2,3-b]pyridine-S-carboxamide;

(kk) N-(4-chlorobenzyl)-2-(((2-hydroxy-2-(4-hydroxyphenyl)ethyl)-(methyl)amino)methyl)-7-methyl-4-oxo-4,7-dihydrofuro[2,3-b]pyridine-5-carboxamide;

(ll) N-(4-chlorobenzyl)-2-(((2-hydroxy-2-(3-methoxyphenyl)ethyl)(methyl)amino)methyl)-7-methyl-4-oxo-4,7-dihydrofuro[2,3-b]pyridine-5-carboxamide;

(mm) N-(4-chlorobenzyl)-2-(((2-(4-fluorophenyl)-2-hydroxyethyl)(methyl)amino)methyl)-7-methyl-4-oxo-4,7-dihydrofuro[2,3-b]pyridine-5-carboxamide;

(nn) N-(4-chlorobenzyl)-2-(((2-(4-chlorophenyl)-2-hydroxyethyl)(methyl)amino)methyl)-7-methyl-4-oxo-4,7-dihydrofuro[2,3-b]pyridine-5-carboxamide;

(oo) N-(4-chlorobenzyl)-2-(((2-hydroxy-2-pyridin-2-ylethyl)(methyl)amino)methyl)-7-methyl-4-oxo-4,7-dihydrofuro[2,3-b]pyridine-5-carboxamide;

(pp) N-(4-chlorobenzyl)-2(((2R)-2-hydroxy-2-pyridin-2-ylethyl)(methyl)amino)methyl)-7-methyl-4-oxo-4,7-dihydrofuro[2,3-b]pyridine-5-carboxamide;

(qq) N-(4-chlorobenzyl)-2((2-hydroxy-2-pyridin-3-ylethyl)(methyl)amino)methyl)-7-methyl-4-oxo-4,7-dihydrofuro[2,3-b]pyridine-5-carboxamide;

(rr) N-(4-chlorobenzyl)-2((2-hydroxy-2-pyridin-4-ylethyl)(methyl)amino)methyl)-7-methyl-4-oxo-4,7-dihydrofuro[2,3-b]pyridine-5-carboxamide;

(ss) N-(4-chlorobenzyl)-2((2-hydroxy-2-(5-methyl-2-furyl)ethyl)-(methyl)amino)methyl)-7-methyl-4-oxo-4,7-dihydrofuro[2,3-b]pyridine-5-carboxamide;

(tt) N-(4-chlorobenzyl)-2-(((2-(3-f)iry)-2-hydroxyethyl)(methyl)amino)ᵣ ethyl)-7-methyl-4-oxo-4,7-dihydrofuro[2,3-b]pyridine-5-carboxamide;

(uu) N-(4-chlorobenzyl)-2-(((2-hydroxy-2-(2,4,6-trifluorophenyl)-ethyl)(methyl)amino)methyl)-7-methyl-4-oxo-4,7-dihydrofuro[2,3-b]pyridine-5-carboxamide;

(vv) 2-(((2-(1-benzofuran-2-yl)-2-hydroxyethyl)(methyl)amino)methyl)-N-(4-chlorobenzyl)-7-methyl-4-oxo-4,7-dihydrofuro[2,3-b]pyridine-5-carboxamide;

(ww) N-(4-chlorobenzyl)-2-(((2-hydroxy-2-thien-2-ylethyl)(methyl)amino)methyl)-7-methyl-4-oxo-4,7-dihydrofuro[2,3-b]pyridine-5-carboxamide;

(xx) N-(4-chlorobenzyl)-2-(((2-hydroxy-2-quinolin-2-ylethyl)(methyl)amino)methyl)-7-methyl-4-oxo-4,7-dihydrofuro[2,3-b]pyridine-5-carboxamide;

(yy) N-(4-chlorobenzyl)-2-(((2-hydroxy-2-(1-methyl-1H-pyrrol-2-yl)ethyl)-(methyl)amino)methyl)-7-methyl-4-oxo-4,7-dihydrofuro[2,3-b]pyridine-5-carboxamide;

(zz) N-(4-chlorobenzyl)-2-(((2-(5-cyanothien-2-yl)-2-hydroxyethyl)(methyl)amino)methyl)-7-methyl-4-oxo-4,7-dihydrofuro[2,3-b]pyridine-5-carboxamide;

(aaa) N-(4-chlorobenzyl)-2-(((2-hydroxy-2-(1,3-thiazol-2-yl)ethyl)(methyl)amino)methyl)-7-methyl-4-oxo-4,7-dihydrofuro[2,3-b]pyridine-5-carboxamide;

(bbb) N-(4-chlorobenzyl)-2-(((2-hydroxy-2-(5-phenyl-2-furyl)ethyl)(methyl)amino)methyl)-7-methyl-4-oxo-4,7-dihydrofuro[2,3-b]pyridine-5-carboxamide;

(ccc) N-(4-chlorobenzyl)-2-(((2-(4,5-dimethyl-2-furyl)-2-hydroxyethyl)(methyl)amino)methyl)-7-methyl-4-oxo-4,7-dihydrofuro[2,3-b]pyridine-5-carboxamide;

(ddd) (+)-N-(4-chlorobenzyl)-2-(((2-hydroxy-2-pyrazin-2-ylethyl)(methyl)amino)methyl)-7-methyl-4-oxo-4,7-dihydrofuro[2,3-b]pyridine-5-carboxamide;

(eee) (+N-(4-chlorobenzyl)-2-(((2-hydroxy-2-pyrimidin-2-ylethyl)(methyl)amino)methyl)-7-methyl-4-oxo-4,7-dihydrofuro[2,3-b]pyridine-5-carboxamide;

(fff) N-(4-chlorobenzyl)-2-(((3-hydroxy-2-phenylpropyl)(methyl)amino)methyl)-7-methyl-4-oxo-4,7-dihydrofuiro[2,3-b]pyridine-5-carboxamide;

(ggg) N-(4-chlorobenzyl)-2-(((2R*)-2-((S*)-hydroxy(phenyl)methyl)pyridin-1-yl)methyl)-7-methyl-4-oxo-4,7-dihydrofuro[2,3-b]pyridine-5-carboxamide;

(hhh) N-(4-chlorobenzyl)-2-(((2R*)-2-((R*)-2-furyl(hydroxy)methyl)pyrrolidin-1-yl)methyl)-7-methyl-4-oxo-4,7-dihydrofuro[2,3-b]pyridine-5-carboxamide;

(iii) N-(4-chlorobenzyl)-2-(((2R)-2-((R)-hydroxy(pyridin-2-yl)methyl)pyrrolidin-1-yl)methyl)-7-methyl-4-oxo-4,7-dihydrofuro[2,3-b]pyridine-5-carboxamide;

(jjj) N-(4-chlorobenzyl)-7-methyl-2-((methylamino)methyl)-4-oxo-4,7-dihydrofuro[2,3-b]pyridine-5-carboxamide;

(kkk) N-(4-chlorobenzyl)-2-(((3-chloro-2-hydroxypropyl)amino)methyl)-7-methyl-4-oxo-4,7-dihydrofuiro[2,3-b]pyridine-5-carboxamide;

(lll) N-(4-chlorobenzyl)-2-(((2-hydroxy-3-((2-methoxyphenyl)thio)propyl)(methyl)amino)methyl)-7-methyl-4-oxo-4,7-dihydrofiaro[2,3-b]pyridine-5-carboxamide;

(mmm) 2-(((3-((5-amino-1,3,4-thiadiazol-2-yl)thio)-2-hydroxypropyl)(methyl)amino)methyl)-N-(4-chlorobenzyl)-7-methyl-4-oxo-4,7-dihydrofuro[2,3-b]pyridine-S-carboxamide;

(nnn) 2((3-((3-amino-1H-1,2,4-triazol-5-yl)thio)-2-hydroxypropyl)(methyl)amino)methyl)-N-(4-chlorobenzyl)-7-methyl-4-oxo-4,7-dihydrofuro[2,3-b]pyridine-5-carboxamide;

(ooo) 2-(((3-((4-aminopyrimidin-2-yl)thio)-2-hydroxypropyl)(methyl)amino)methyl)-N-(4-chlorobenzyl)-7-methyl-4-oxo-4,7-dihydrofuro[2,3-b]pyridine-5-carboxamide;

(ppp) N-(4-chlorobenzyl)-2-(((2-hydroxy-3-((3-methoxyphenyl)thio)propyl)(methyl)amino)methyl)-7-methyl-4-oxo-4,7-dihydrofiiro[2,3-b]pyridine-5-carboxamide;

(qqq) N-(4-chlorobenzyl)-2-(((2-hydroxy-3-((4-methoxyphenyl)thio)propyl)(methyl)amino)methyl)-7-methyl-4-oxo-4,7-dihydrofuro[2,3-b]pyridine-5-carboxamide;

(rrr) 2-((3-(((5-(((4-chlorobenzyl)amino)carbonyl)-7-methyl-4-oxo-4,7-dihydrofuro[2,3-b]pyridin-2-yl)methyl)(methyl)amino)-2-hydroxypropyl)thio)benzoic acid;

(sss) 2-((3-(((5-(((4-chlorobenzyl)amino)carbonyl)-7-methyl-4-oxo-4,7-dihydrofuro[2,3-b]pyridin-2-yl)methyl)(methyl)amino)-2-hydroxypropyl)thio)nicotinic acid;

(ttt) N-(4-chlorobenzyl)-2((2-hydroxy-3-((4-oxo-3,4-dihydroquinazolin-2-yl)thio)propyl)(methyl)amino)methyl)-7-methyl-4-oxo-4,7-dihydrofuro[2,3-b]pyridine-5-carboxamide;

(uuu) 2-(((3-((6-amino-1,3-benzothiazol-2-yl)thio)-2-hydroxypropyl)(methyl)amino)methyl)-N-(4-chlorobenzyl)-7-methyl-4-oxo-4,7-dihydrofuro[2,3-b]pyridine-5-carboxamide;

(vvv) N-(4-chlorobenzyl)-2-(((2-hydroxy-3-(9H-purin-6-ylthio)propyl)(methyl)amino)methyl)-7-methyl-4-oxo-4,7-dihydrofuro[2,3-b]pyridine-5-carboxamide;

(www) 2-(((3-(benzylthio)-2-hydroxypropyl)(methyl)amino)methyl)-N-(4-chlorobenzyl)-7-methyl-4-oxo-4,7-dihydrofuro[2,3-b]pyridine-5-carboxamide;

(xxx) N-(4-chlorobenzyl)-2-(((3-((4-chlorobenzyl)thio)-2-hydroxypropyl)(methyl)amino)methyl)-7-methyl-4-oxo-4,7-dihydrofuro[2,3-b]pyridine-5-carboxamide;

(yyy) N-(4-chlorobenzyl)-2-(((2-hydroxy-3-((4-methoxybenzyl)thio)propyl)(methyl)amino)methyl)-7-methyl-4-oxo-4,7-dihydrofuro[2,3-b]pyridine-5-carboxamide;

(zzz) N-(4-chlorobenzyl)-7-methyl-4-oxo-4,7-dihydrofuro[2,3-b]pyridine-5-carboxamide;

(aaaa) 2-bromo-N-(4-chlorobenzyl)-7-methyl-4-oxo-4,7-dihydrofuro[2,3-b]pyridine-5-carboxamide;

(bbbb) N-(4-chlorobenzyl)-2-(3-hydroxyprop-1-ynyl)-7-methyl-4-oxo-4,7-dihydrofuro[2,3-b]pyridine-5-carboxamide;

(cccc) N-(4-chlorobenzyl)-2-(3-hydroxypropyl)-7-methyl-4-oxo-4,7-dihydrofuro[2,3-b]pyridine-5-carboxamide;

(dddd) N-(4-chlorobenzyl)-2-(4-hydroxybut-1-ynyl)-7-methyl-4-oxo-4,7-dihydrofuro[2,3-b]pyridine-5-carboxamide;

(eeee) N-(4-chlorobenzyl)-2-(4-hydroxybutyl)-7-methyl-4-oxo-4,7-dihydiofuro[2,3-b]pyridine-5-carboxamide;

(ffff) N-(4-chlorobenzyl)-2-(5-hydroxypent-1-ynyl)-7-methyl-4-oxo-4,7-dihydrofuro[2,3-b]pyridine-5-carboxamide;

(gggg) N-(4-chlorobenzyl)-2-(5-hydroxypentyl)-7-methyl-4-oxo-4,7-dihydrofuro[2,3-b]pyridine-5-carboxamide;

(hhhh) N-(4-chlorobenzyl)-2-(3-hydroxy-3-phenylprop-1-ynyl)-7-methyl-4-oxo-4,7-dihydrofuro[2,3-b]pyridine-5-carboxamide;

(iiii) N-(4-chlorobenzyl)-2-(3-hydroxy-3-phenylpropyl)-7-methyl-4-oxo-4,7-dihydrofuro[2,3-b]pyridine-5-carboxamide;

(jjjj) N-(4-chlorobenzyl)-2-(4-hydroxy-4-phenylbut-1-ynyl)-7-methyloxo-4,7-dihydrofuro[2,3-b]pyridine-5-carboxamide;

(kkkk) N-(4-chlorobenzyl)-2-(4-hydroxy-4-phenylbutyl)-7-methyl-4-oxo-4,7-dihydrofuro[2,3-b]pyridine-5-carboxamide;

(llll) N-(4-chlorobenzyl)-2-(4-(2-furyl)-4-hydroxybut-1-ynyl)-7-methyl-4-oxo-4,7-dihydrofuro[2,3-b]pyridine-5-carboxamide;

(mmmm) N-(4-chlorobenzyl)-24-(2-furyl)-4-hydroxybutyl)-7-methyl-4-oxo-4,7-dihydrofuro[2,3-b]pyridine-5-carboxamide;

(nnnn) N-(4-chlorobenzyl)-2-(4-hydroxy-4-pyridin-3-ylbut-1-ynyl)-7-methyl-4-oxo-4,7-dihydrofuro[2,3-b]pyridine-5-carboxamide;

(oooo) N-(4-chlorobenzyl)-2-(4-hydroxy-4-pyridin-3-ylbutyl)-7-methyl-4-oxo-4,7-dihydrofuro[2,3-b]pyridine-5-carboxamide;

(pppp) N-(4-chlorobenzyl)-2-(4-hydroxy-4-pyridin-2-ylbut-1-ynyl)-7-methyl-4-oxo-4,7-dihydrofuro[2,3-b]pyridine-5-carboxamide;

(qqqq) N-(4-chlorobenzyl)-2-(4-hydroxy-4-pyridin-2-ylbutyl)-7-methyl-4-oxo-4,7-dihydrofuro[2,3-b]pyridine-5-carboxamide;

(rrrr) N-(4-chlorobenzyl)-2-(ethoxymethyl)-7-methyl-4-oxo-4,7-dihydro'furo[2,3-b]pyridine-5-carboxamide;

(ssss) N-(4-chlorobenzyl)-2-(hydroxymethyl)-7-methyl-4-oxo-4,7-dihydrofuro[2,3-b]pyridine-5-carboxamide;

(tttt) N-(4-chlorobenzyl)-2-((((2S)-2-hydroxy-2-phenylethyl)oxy)methyl)-7-methyl-4-oxo-4,7-dihydrofuro[2,3-b]pyridine-5-carboxamide;

(uuuu) N-((4-chlorophenyl)methyl)-5-((4-chlorophenyl)methylaminocarbonyl)-4-hydroxyfiro[2,3-b]pyridine-2-carboxamide; or a pharmaceutically acceptable salt thereof.

65. The compound:

(a) N-(4-chlorobenzyl)-2-(((2-(2-furyl)-2-hydroxyethyl)(methyl)amino)methyl)-7-methyl-4-oxo-4,7-dihydrofuro[2,3-b]pyridine-5-carboxamide;

(b) (+)-N-(4-chlorobenzyl)-2-(((2-(2-furyl)-2-hydroxyethyl)(methyl)amino)methyl)-7-methyl-4-oxo-4,7-dihydrofuro[2,3-b]pyridine-5-carboxamide;

(c) (−)-N-(4-chlorobenzyl)-2-(((2-(2-furyl}2-hydroxyethyl)(methyl)amino)methyl)-7-methyl-4-oxo-4,7-dihydrofuro[2,3-b]pyridine-5-carboxamide;

(d) N-(4-fluorobenzyl)-2-((((2R)-2-(2-furyl)-2-hydroxyethyl)(methyl)amino)methyl)-7-methyl-4-oxo-4,7-dihydrofuro[2,3-b]pyridine-5-carboxamide;

(e) 2-((((2R)-2-(2-furyl)-2-hydroxyethyl)(methyl)amino)methyl)-7-methyl-N-(4-methylbenzyl)-4-oxo-4,7-dihydrofuiro[2,3-b]pyridine-5-carboxamide;

(f) 2-((((2R)-2-(2-furyl)-2-hydroxyethyl)(methyl)amino)methyl)-7-methyl-N-(3,4-difluorobenzyl)-4-oxo-4,7-dihydrofuro[2,3-b]pyridine-5-carboxamide;

(g) 2-((((2R)-2-(2-furyl)-2-hydroxyethyl)(methyl)amino)methyl)-7-methyl-N-(3,4-dichlorobenzyl)-4-oxo-4,7-dihydrofuro[2,3-b]pyridine-5-carboxamide;

(h) 2-((((2R)-2-(2-furyl)-2-hydroxyethyl)(methyl)amino)methyl)-7-methyl-N-(4-bromobenzyl)-4-oxo-4,7-dihydrofuro[2,3-b]pyridine-5-carboxamide;

(i) 2-((((2R)-2-(2-furyl)-2-hydroxyethyl)(methyl)amino)methyl)-7-methyl-N-(4-trifluoromethylbenzyl)-4-oxo-4,7-dihydrofuio[2,3-b]pyridine-5-carboxamide;

(j) N-(4-chlorobenzyl)-7-ethyl-2-((((2R)-2-(2-furyl)-2-hydroxyethyl)(methyl)amino)methyl)-4-oxo-4,7-dihydrofuro[2,3-b]pyridine-5-carboxamide;

(k) N-(4-chlorobenzyl)-7-cyclopropyl-2-((((2R)-2-(2-furyl)-2-hydroxyethyl)(methyl)amino)methyl)-4-oxo-4,7-dihydrofuro[2,3-b]pyridine-5-carboxamide;

(l) N-(4-chlorobenzyl)-2-((((2R)-2-(2-furyl)-2-hydroxyethyl)(methyl)amino)methyl)-4-oxo-7-propyl-4,7-dihydrofuro[2,3-b]pyridine-5-carboxamide;

(m) N-(4-chlorobenzyl)-2-((((2R)-2-(2-furyl)-2-hydroxyethyl)(methyl)amino)methyl)-4-oxo-7-phenyl-4,7-dihydrofuro[2,3-b]pyridine-5-carboxamide;

(n) N-(4-chlorobenzyl)-2-((((2R)-2-(2-furyl)-2-hydroxyethyl)(methyl)amino)methyl)-4-oxo-7-(2-phenylethyl)-4,7-dihydrofuro[2,3-b]pyridine-5-carboxamide;

(o) N-(4-chlorobenzyl)-2-((((2R)-2-(2-furyl)-2-hydroxyethyl)(methyl)amino)methyl)-4-oxo-7-pyridin-2-yl-4,7-dihydrofuro[2,3-b]pyridine-5-carboxamide;

(p) N-(4-chlorobenzyl)-72-(diethylamino)ethyl)-2-((((2R)-2-(2-furyl)-2-hydroxyethyl)(methyl)amino)methyl)-4-oxo-4,7-dihydrofuro[2,3-b]pyridine-5-carboxamide;

(q) N-(4-chlorobenzyl)-2-(((2-hydroxypropyl)(methyl)amino)methyl)-7-methyl-4-oxo-4,7-dihydrofuro[2,3-b]pyridine-5-carboxamide;

(r) N-(4-chlorobenzyl)-2-(((3R)-3-hydroxypyrrolidin-1-yl)methyl)-7-methyl-4-oxo-4,7-dihydrofuro[2,3-b]pyridine-5-carboxamide;

(s) N-(4-chlorobenzyl)-2-(((2-hydroxy-2-phenylethyl)(methyl)amino)methyl)-7-methyl-4-oxo-4,7-dihydrofuro[2,3-b]pyridine-5-carboxamide;

(t) N-(4-chlorobenzyl)-2-(((2-hydroxy-2-(4-hydroxyphenyl)ethyl)-(methyl)amino)methyl)-7-methyl-4-oxo-4,7-dihydrofuro[2,3-b]pyridine-5-carboxamide;

(u) N-(4-chlorobenzyl)-2-(((2-hydroxy-2-(3-methoxyphenyl)ethyl)-(methyl)amino)methyl)-7-methyl-4-oxo-4,7-dihydrofuro[2,3-b]pyridine-5-carboxamide;

(v) N-(4-chlorobenzyl)-2-(((2-(4-fluorophenyl)-2-hydroxyethyl)(methyl)amino)methyl)-7-methyl-4-oxo-4,7-dihydrofuro[2,3-b]pyridine-5-carboxamide;

(w) N-(4-chlorobenzyl)-2-(((2-(4-chlorophenyl)-2-hydroxyethyl)(methyl)amino)methyl)-7-methyl-4-oxo-4,7-dihydrofuro[2,3-b]pyridine-5-carboxamide;

(x) N-(4-chlorobenzyl)-2-(((2-hydroxy-2-pyridin-2-ylethyl)(methyl)amino)methyl)-7-methyl-4-oxo-4,74-ihydrofuro[2,3-b]pyridine-5-carboxamide;

(y) N-(4-chlorobenzyl)-2-((((2R)-2-hydroxy-2-pyridin-2-ylethyl)(methyl)amino)methyl)-7-methyl-4-oxo-4,7-dihydrofuro[2,3-b]pyridine-5-carboxamide;

(z) N-(4-chlorobenzyl)-2-(((2-hydroxy-2-pyridin-3-ylethyl)(methyl)amino)methyl)-7-methyl-4-oxo-4,7-dihydrofuro[2,3-b]pyridine-5-carboxamide;

(aa) N-(4-chlorobenzyl)-2-(((2-hydroxy-2-pyridin-4-ylethyl)(methyl)amino)methyl)-7-methyl-4-oxo-4,7-dihydrofuro[2,3-b]pyridine-5-carboxamide;

(bb) N-(4-chlorobenzyl)-2-(((2-hydroxy-2-(5-methyl-2-furyl)ethyl)(methyl)amino)methyl)-7-methyl-4-oxo-4,7-dihydrofuro[2,3-b]pyridine-5-carboxamide;

(cc) N-(4-chlorobenzyl)-2-(((2-(3-furyl)-2-hydroxyethyl)(methyl)amino)methyl)-7-methyl-4-oxo-4,7-dihydrofuro[2,3-b]pyridine-5-carboxamide;

(dd) N-(4-chlorobenzyl)-2-(((2-hydroxy-2-(2,4,6-trifluorophenyl)ethyl)-(methyl)amino)methyl)-7-methyl-4-oxo-4,7-dihydrofuro[2,3-b]pyridine-5-carboxamide;

(ee) 2-(((21-benzofuran-2-yl)-2-hydroxyethyl)(methyl)amino)methyl)-N-(4-chlorobenzyl)-7-methyl-4-oxo-4,7-dihydrofuro[2,3-b]pyridine-5-carboxamide;

(ff) N-(4-chlorobenzyl)-2-(((2-hydroxy-2-thien-2-ylethyl)(methyl)amino)methyl)-7-methyl-4-oxo-4,7-dihydrofuro[2,3-b]pyridine-5-carboxamide;

(gg) N-(4-chlorobenzyl)-2-(((2-hydroxy-2-quinolin-2-ylethyl)(methyl)amino)methyl)-7-methyl-4-oxo-4,7-dihydrofuro[2,3-b]pyridine-5-carboxamide;

(hh) N-(4-chlorobenzyl)-2-(((2-hydroxy-2-(1-methyl-1H-pyrrol-2-yl)ethyl)-(methyl)amino)methyl)-7-methyl-4-oxo-4,7-dihydrofuro[2,3-b]pyridine-5-carboxamide;

(ii) N-(4-chlorobenzyl)-2-(((2-(5-cyanothien-2-yl)-2-hydroxyethyl)(methyl)amino)methyl)-7-methyl-4-oxo-4,7-dihydrofuro[2,3-b]pyridine-5-carboxamide;

(jj) N-(4-chlorobenzyl)-2-(((2-hydroxy-2-(1,3-thiazol-2-yl)ethyl)(methyl)-amino)methyl)-7-methyl-4-oxo-4,7-dibydrofiuro[2,3-b]pyridine-5-carboxamide;

(kk) N-(4-chlorobenzyl)-2-(((2-hydroxy-2-(5-phenyl-2-furyl)ethyl)(methyl)amino)methyl)-7-methyl-4-oxo-4,7-dihydrofuro[2,3-b]pyridine-5-carboxamide;

(ll) N-(4-chlorobenzyl)-2-(((2-(4,5-dimethyl-2-furyl)-2-hydroxyethyl)(methyl)amino)methyl)-7-methyl-4-oxo-4,7-dihydrofuro[2,3-b]pyridine-5-carboxamide;

(mm) (+)-N-(4-chlorobenzyl)-2-(((2-hydroxy-2-pyrazin-2-ylethyl)(methyl)amino)methyl)-7-methyl-4-oxo-4,7-dihydrofuro[2,3-b]pyridine-5-carboxamide;

(nn) (+)-N-(4-chlorobenzyl)-2-(((2-hydroxy-2-pyrimidin-2-ylethyl)(methyl)amino)methyl)-7-methyl-4-oxo-4,7-dihydrofuro[2,3-b]pyridine-5-carboxamide;

(oo) N-(4-chlorobenzyl)-2-(((3-hydroxy-2-phenylpropyl)(methyl)amino)methyl)-7-methyl-4-oxo-4,7-dihydrofuro[2,3-b]pyridine-5-carboxamide;

(pp) N-(4-chlorobenzyl)-2-(((2R*)-2-((S*)-hydroxy(phenyl)methyl)pyrrolidin-1-yl)methyl)-7-methyl-1-oxo-4,7-dihydrofuro[2,3-b]pyridine-5-carboxamide;

(qq) N-(4-chlorobenzyl)-2-(((2R*)-2-((R*)-2-furyl(hydroxy)methyl)pyrrolidin-1-yl)methyl)-7-methyl-4-oxo-4,7-dihydrofuro[2,3-b]pyridine-5-carboxamide;

(rr) N-(4-chlorobenzyl)-2-(((2R)-2-((R)-hydroxy(pyridin-2-yl)methyl)pyrrolidin-1-yl)methyl)-7-methyl-4-oxo-4,7-dihydrofuiro[2,3-b]pyridine-5-carboxamide;

(ss) N-(4-chlorobenzyl)-2-(((2-hydroxy-3-((2-methoxyphenyl)thio)propyl)(methyl)amino)methyl)-7-methyl-4-oxo-4,7-dihydrofuro[2,3-b]pyridine-5-carboxamide;

(tt) 2-(((3-((5-amino-1,3,4-thiadiazol-2-yl)thio)-2-hydroxypropyl)(methyl)amino)methyl)-N-(4-chlorobenzyl)-7-methyl-4-oxo-4,7-dihydrofurb[2,3-b]pyridine-5-carboxamide;

(uu) 2-(((3-((3-amino-1H-1,2,4-triazol-5-yl)thio)-2-hydroxypropyl)(methyl)amino)methyl)-N-(4-chlorobenzyl)-7-methyl-4-oxo-4,7-dihydrofuro[2,3-b]pyridine-5-carboxamide;

(vv) 2-(((3-((4-aminopyrimidin-2-yl)thio)-2-hydroxypropyl)(methyl)amino)methyl)-N-(4-chlorobenzyl)-7-methyl-4-oxo-4,7-dihydrofuro[2,3-b]pyridine-5-carboxamide;

(ww) N-(4-chlorobenzyl)-2((2-hydroxy-3-((3-methoxyphenyl)thio)propyl)(methyl)amino)methyl)-7-methyl-4-oxo-4,7-dihydrofuro[2,3-b]pyridine-5-carboxamide;

(xx) N-(4-chlorobenzyl)-2-(((2-hydroxy-3-((4-methoxyphenyl)thio)propyl)(methyl)amino)methyl)-7-methyl-4-oxo-4,7-dihydrofuro[2,3-b]pyridine-5-carboxamide;

(yy) 2-((3-(((5-(((4-chlorobenzyl)amino)carbonyl)-7-methyl-4-oxo-4,7-dihydrofuro[2,3-b]pyridin-2-yl)methyl)(methyl)amino)-2-hydroxypropyl)thio)benzoic acid;

(zz) 2-((3-(((5-(((4-chlorobenzyl)amino)carbonyl)-7-methyl-4-oxo-4,7-dihydrofuro[2,3-b]pyridin-2-yl)methyl)(methyl)amino)-2-hydroxypropyl)thio)nicotinic acid;

(aaa) N-(4-chlorobenzyl)-2-(((2-hydroxy-3-((4-oxo-3,4-dihydroquinazolin-2-yl)thio)propyl)(methyl)amino)methyl)-7-methyl-4-oxo-4,7-dihydrofuro[2,3-b]pyridine-5-carboxamide;

(bbb) 2-(((3-((6-amino-1,3-benzothiazol-2-yl)thio)-2-hydroxypropyl)(methyl)amino)methyl)-N-(4-chlorobenzyl)-7-methyl-4-oxo-4,7-dihydrofuro[2,3-b]pyridine-5-carboxamide;

(ccc) N-(4-chlorobenzyl)-2-(((2-hydroxy-3-(9H-purin-6-ylthio)propyl)(methyl)amino)methyl)-7-methyl-4-oxo-4,7-dihydrofuro[2,3-b]pyridine-5-carboxamide;

(ddd) 2-(((3-(benzylthio)-2-hydroxypropyl)(methyl)amino)methyl)-N-(4-chlorobenzyl)-7-methyl-4-oxo-4,7-dihydrofuro[2,3-b]pyridine-5-carboxamide;

(eee) N4-chlorobenzyl)-2-(((3-((4-chlorobenzyl)thio)-2-hydroxypropyl)(methyl)amino)methyl)-7-methyl-4-oxo-4,7-dihydrofuro[2,3-b]pyridine-5-carboxamide;

(fff) N-(4-chlorobenzyl)-2-(((2-hydroxy-3-((4-methoxybenzyl)thio)propyl)(methyl)amino)methyl)-7-methyl-4-oxo-4,7-dihydrofuro[2,3-b]pyridine-5-carboxamide;

(ggg) N-(4-chlorobenzyl)-2-(3-hydroxyprop-1-ynyl)-7-methyl-4-oxo-4,7-, dihydrofuro[2,3-b]pyridine-5-carboxamide;

(hhh) N-(4-chlorobenzyl)-2-(3-hydroxypropyl)-7-methyl-4-oxo-4,7-dihydrofuro[2,3-b]pyridine-5-carboxamide;

(iii) N-(4-chlorobenzyl)-2-(4-hydroxybut-1-ynyl)-7-methyl-4-oxo-4,7-dihydrofuro[2,3-b]pyridine-5-carboxamide;

(jjj) N-(4-chlorobenzyl)-2-(4-hydroxybutyl)-7-methyl-4-oxo-4,7-dihydrofuro[2,3-b]pyridine-5-carboxamide;

(kkk) N-(4-chlorobenzyl)-2-(5-hydroxypentyl)-7-methyl-4-oxo-4,7-dihydrofuro[2,3-b]pyridine-5-carboxamide;

(lll) N-(4-chlorobenzyl)-2-(3-hydroxy-3-phenylpropyl)-7-methyl-4-oxo-4,7-dihydrofuro[2,3-b]pyridine-5-carboxamide;

(mmm) N-(4-chlorobenzyl)-2-(4-hydroxy-4-phenylbutyl)-7-methyl-4-oxo-4,7-dihydrofuro[2,3-b]pyridine-5-carboxamide;

(nnn) N-(4-chlorobenzyl)-2-(4-(2-furyl)-4-hydroxybutyl)-7-methyl-4-oxo-4,7-dihydrofuro[2,3-b]pyridine-5-carboxamide;

(ooo) N-(4-chlorobenzyl)-2-(4-hydroxy-4-pyridin-3-ylbutyl)-7-methyl-4-oxo-4,7-dihydrofuro[2,3-b]pyridine-5-carboxamide;

(ppp) N-(4-chlorobenzyl)-2-(4-hydroxy-4-pyridin-2-ylbutyl)-7-methyl-4-oxo-4,7-dihydrofuro[2,3-b]pyridine-5-carboxamide; or (qqq) N-(4-chlorobenzyl)-2-(((((2S)-2-hydroxy-2-phenylethyl)oxy)methyl)-7-methyl-4-oxo-4,7-dihydrofuro[2,3-b]pyridine-5-carboxamide; or a pharmaceutically acceptable salt thereof.

66. The compound:

(a) N-(4-chlorobenzyl)-2-(((2-(2-furyl)-2-hydroxyethyl)(methyl)amino)methyl)-7-methyl-4-oxo-4,7-dihydrofuro[2,3-b]pyridine-5-carboxamide;

(b) (+)-N-(4-chlorobenzyl)-2-((((2-(2-furyl)-2-hydroxyethyl)(methyl)amino)methyl)-7-methyl-4-oxo-4,7-dihydrofuro[2,3-b]pyridine-5-carboxamide;

(c) N-(4-fluorobenzyl)-2-(((((2R)-2-(2-furyl)-2-hydroxyethyl)(methyl)amino)methyl)-7-methyl-4-oxo-4,7-dihydrofuro[2,3-b]pyridine-S-carboxamide;

(d) 2-((((2R)-2-(2-furyl)-2-hydroxyethyl)(methyl)amino)methyl)-7-methyl-N-(3,4-difluorobenzyl)-4-oxo-4,7-dihydrofuro[2,3-b]pyridine-5-carboxamide;

(e) 2-((((2R)-2-(2-furyl)-2-hydroxyethyl)(methyl)amino)methyl)-7-methyl-N-(3,4-dichlorobenzyl)-4-oxo-4,7-dihydrofuro[2,3-b]pyridine-5-carboxamide;

(f) 2-((((2R)-2-(2-furyl)-2-hydroxyethyl)(methyl)amino)methyl)-7-methyl-N-(4-bromobenzyl)-4-oxo-4,7-dihydromfi[2,3-b]pyridine-5-carboxamide;

(g) N-(4-chlorobenzyl)-7-ethyl-2-((((2R)-2-(2-furyl)-2-hydroxyethyl)(methyl)amino)methyl)-4-oxo-4,7-dihydrofuro[2,3-b]pyridine-5-carboxamide;

(h) N-(4-chlorobenzyl)-7-cyclopropyl-2-((((2R)-2-(2-furyl-2-hydroxyethyl)(methyl)amino)methyl)-4-oxo-4,7-dihydrofuro[2,3-b]pyridine-5-carboxamide;

(i) N-(4-chlorobenzyl)-2-(((((2R)-2-(2-furyl)-2-hydroxyethyl)(methyl)amino)methyl)-4-oxo-7-propyl-4,7-dihydrofuro[2,3-b]pyridine-5-carboxamide;

(j) N-(4-chlorobenzyl)-2-(((((2R)-2-(2-furyl)-2-hydroxyethyl)(methyl)amino)methyl)-4-oxo-7-phenyl-4,7-dihydrofuro[2,3-b]pyridine-5-carboxamide;

(k) N-(4-chlorobenzyl)-2-(((((2R)-2-(2-furyl)-2-hydroxyethyl)(methyl)-amino)methyl)-4-oxo-7-(2-phenylethyl)-4,7-dihydrofuro[2,3-b]pyridine-5-carboxamide;

(l) N-(4-chlorobenzyl)-2-(((((2R)-2-(2-furyl)-2-hydroxyethyl)(methyl)amino)methyl)-4-oxo-7-pyridin-2-yl-4,7-dihydrofuro[2,3-b]pyridine-5-carboxamide;

(m) N-(4-chlorobenzyl)-2-(((2-hydroxy-2-phenylethyl)(methyl)amino)methyl)-7-methyl-4-oxo-4,7-dihydrofuro[2,3-b]pyridine-5-carboxamide;

(n) N-(4-chlorobenzyl)-2-(((2-hydroxy-2-(4-hydroxyphenyl)ethyl)-(methyl)amino)methyl)-7-methyl-4-oxo-4,7-dihydrofuro[2,3-b]pyridine-5-carboxamide;

(o) N-(4-chlorobenzyl)-2-(((2-hydroxy-2-(3-methoxyphenyl)ethyl)-(methyl)amino)methyl)-7-methyl-4-oxo-4,7-dihydrofuro[2,3-b]pyridine-5-carboxamide;

(p) N-(4-chlorobenzyl)-2-(((2-hydroxy-2-pyridin-2-ylethyl)(methyl)amino)methyl)-7-methyl-4-oxo-4,7-dihydrofuro[2,3-b]pyridine-5-carboxamide;

(q) N-(4-chlorobenzyl)-2-((((2R)-2-hydroxy-2-pyridin-2-ylethyl)(methyl)amino)methyl)-7-methyl-4-oxo-4,7-dihydrofuro[2,3-b]pyridine-5-carboxamide;

(r) N-(4-chlorobenzyl)-2-(((2-hydroxy-2-pyridin-3-ylethyl)(methyl)amino)methyl)-7-methyl-4-oxo-4,7-dihydrofuro[2,3-b]pyridine-5-carboxamide;

(s) N-(4-chlorobenzyl)-2-(((2-hydroxy-2-(5-methyl-2-furyl)ethyl)(methyl)amino)methyl)-7-methyl-4-oxo-4,7-dihydrofuro[2,3-b]pyridine-5-carboxamide;

(t) N-(4-chlorobenzyl)-2-(((2-(3-furyl)-2-hydroxyethyl)(methyl)amino)methyl)-7-methyl-4-oxo-4,7-dihydrofuro[2,3-b]pyridine-5-carboxamide;

(u) 2-(((21-benzofuran-2-yl)-2-hydroxyethyl)(methyl)amino)methyl)-N-(4-chlorobenzyl)-7-methyl-4-oxo-4,7-dihydrofuro[2,3-b]pyridine-5-carboxamide;

(v) N-(4-chlorobenzyl)-2-(((2-hydroxy-2-thien-2-ylethyl)(methyl)amino)methyl)-7-methyl-4-oxo-4,7-dihydrofuiro[2,3-b]pyridine-5-carboxamide;

(w) N-(4-chlorobenzyl)-2-(((2-hydroxy-2-quinolin-2-ylethyl)(methyl)amino)methyl)-7-methyl-4-oxo-4,7-dihydrofuro[2,3-b]pyridine-5-carboxamide;

(x) N-(4-chlorobenzyl)-2-(((2-hydroxy-2-(1-methyl-1H-pyrrol-2-yl)ethyl)(methyl)amino)methyl)-7-methyl-4-oxo-4,7-dihydrofuro[2,3-b]pyridine-5-carboxamide;

(y) N-(4-chlorobenzyl)-2-(((2-(5-cyanothien-2-yl)-2-hydroxyethyl)(methyl)amino)methyl)-7-methyl-4-oxo-4,7-dihydrofuro[2,3-b]pyridine-5-carboxamide;

(z) N-(4-chlorobenzyl)-2-(((2-hydroxy-2-(1,3-thiazol-2-yl)ethyl)(methyl)amino)methyl)-7-methyl-4-oxo-4,7-dihydrofuro[2,3-b]pyridine-5-carboxamide;

(aa) N-(4-chlorobenzyl)-2-(((2-hydroxy-2-(5-phenyl-2-furyl)ethyl)(methyl)amino)methyl)-7-methyl-4-oxo-4,7-dihydrofuro[2,3-b]pyridine-5-carboxamide;

(bb) N-(4-chlorobenzyl)-2-(((2-(4,5-dimethyl-2-furyl)-2-hydroxyethyl)(methyl)amino)methyl)-7-methyl-4-oxo-4,7-dihydrofuro[2,3-b]pyridine-5-carboxamide;

(cc) (+)-N-(4-chlorobenzyl)-2-(((2-hydroxy-2-pyrazin-2-ylethyl)(methyl)amino)methyl)-7-methyl-4-oxo-4,7-dihydrofuro[2,3-b]pyridine-5-carboxamide;

(dd) (+)-N-(4-chlorobenzyl)-2-(((2-hydroxy-2-pyrimidin-2-ylethyl)(met hyl)-amino)methyl)-7-methyl-4-oxo-4,7-dihydrofuro[2,3-b]pyridine-5-carboxamide;

(ee) N-(4-chlorobenzyl)-2-(((2R*)-2-((S*)-hydroxy(phenyl)methyl)pyrrolidin-1-yl)methyl)-7-methyl-4-oxo-4,7-dihydrofuro[2,3-b]pyridine-5-carboxamide;

(ff) N-(4-chlorobenzyl)-2-(((2-hydroxy-3-((2-methoxyphenyl)thio)propyl)(methyl)amino)methyl)-7-methyl-4-oxo-4,7-dihydrofuro[2,3-b]pyridine-5-carboxamide; or (gg) N-(4-chlorobenzyl)-2-(4-hydroxybutyl)-7-methyl-4-oxo-4,7-dihydrofuro[2,3-b]pyridine-5-carboxamide; or a pharmaceutically acceptable salt thereof.

67. The compound (+)-N-(4-chlorobenzyl)-2-(((2-(2-furyl)-2-hydroxyethyl)(methyl)amino)methyl)-7-methyl-4-oxo-4,7-dihydrofuro[2,3-b]pyridine-5-carboxamide, or a pharmaceutically acceptable salt thereof.

68. A pharmaceutical composition comprising a compound of claim 1 and a pharmaceutically acceptable excipient.

69. A method of treating a herpesviral infection in a mammal, comprising:
administering to a mammal in need of such treatment an effective amount of a compound of claim 1.

70. The method of claim 69 wherein the mammal is a human, or a food or companion animal.

71. The method of claim 69 wherein the mammal is a human.

72. The method of claim 69 wherein the mammal is a food or companion animal.

73. The method of claim 69 wherein the compound is administered in an amount of from about 0.1 to about 300 mg/kg of body weight.

74. The method of claim 69 wherein the compound is administered in an amount of from about 1 to about 30 mg/kg of body weight.

75. The method of claim 69 wherein the herpesviral infection is herpes simplex virus type 1, herpes simplex virus type 2, varicella zoster virus, human cytomegalovirus, Epstein-Barr virus, human herpes virus 6, human herpes virus 7, or human herpes virus 8.

76. The method of claim 69 wherein the herpesviral infection is human cytomegalovirus.

77. The method of claim 69 wherein the compound is administered orally, parenterally or topically.

78. A method of treating atherosclerosis or restenosis associated with a herpesviral infection comprising administering to a mammal in need thereof a compound of claim 1.

79. A method for inhibiting a viral DNA polymerase, comprising contacting the polymerase in vitro with an effective inhibitory amount of a compound of claim 1.

80. A method for preparing a compound of formula B.1

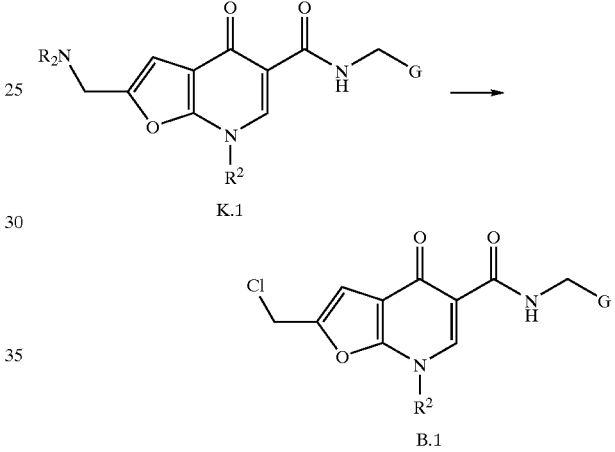

K.1

B.1 wherein $R^2$ and G have any of the values defined in claim 1, comprising treating a corresponding compound of formula K.1, wherein $R_2N$ is dialkylamino or forms a saturated heterocycle, with ethyl chloroformate in a suitable solvent.

81. The compound N-(4-chlorobenzyl)-7-methyl-2-(4-morpholinylmethyl)-4-oxo-4,7-dihydrofuro[2,3-b]pyridine-5-carboxamide.

82. The compound of claim 1 wherein $R^3$ is $CH_2Cl$, morpholinomethyl, or N-methylaminomethyl.

83. The compound N-(4-chlorobenzyl)-2-(chloromethyl)-7-methyl-4-oxo-4,7-dihydrofuro[2,3-b]pyridine-5-carboxamide.

* * * * *